(12) United States Patent
Bowman et al.

(10) Patent No.: US 11,447,810 B2
(45) Date of Patent: Sep. 20, 2022

(54) COMPOSITIONS AND METHODS FOR THE PRODUCTION OF COMPOUNDS

(71) Applicant: Ginkgo Bioworks, Inc., Boston, MA (US)

(72) Inventors: Brian R. Bowman, New Rochelle, NY (US); Joshua A. V. Blodgett, Webster Groves, MO (US); Gregory L. Verdine, Boston, MA (US); Daniel C. Gray, Medford, MA (US); Jay P. Morgenstern, Boston, MA (US); Lucy Foulston, Medford, MA (US); Keith Robison, Andover, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 29 days.

(21) Appl. No.: 17/163,016

(22) Filed: Jan. 29, 2021

(65) Prior Publication Data

US 2021/0238646 A1 Aug. 5, 2021

Related U.S. Application Data

(62) Division of application No. 16/093,074, filed as application No. PCT/US2017/027215 on Apr. 12, 2017, now Pat. No. 10,907,188.

(60) Provisional application No. 62/321,439, filed on Apr. 12, 2016.

(51) Int. Cl.
| | |
|---|---|
| *C12N 15/52* | (2006.01) |
| *C12P 35/00* | (2006.01) |
| *C07K 14/36* | (2006.01) |
| *C12N 15/76* | (2006.01) |

(52) U.S. Cl.
CPC ............. *C12P 35/00* (2013.01); *C07K 14/36* (2013.01); *C12N 15/52* (2013.01); *C12N 15/76* (2013.01)

(58) Field of Classification Search
CPC ......... C12N 15/52; C12P 35/00; C12P 114/00
See application file for complete search history.

(56) References Cited

U.S. PATENT DOCUMENTS

| | | |
|---|---|---|
| 6,183,965 B1 | 2/2001 | Verdine et al. |
| 6,372,712 B1 | 4/2002 | Briesewitz et al. |
| 6,686,454 B1 | 2/2004 | Yatscoff et al. |
| 6,713,607 B2 | 3/2004 | Caggiano et al. |
| 7,396,660 B2 | 7/2008 | Huang et al. |
| 7,851,183 B2 | 12/2010 | Zotchev et al. |
| 8,664,186 B2 | 3/2014 | Aigle et al. |
| 9,250,237 B2 | 2/2016 | Liu et al. |
| 9,260,484 B2 | 2/2016 | Briesewitz et al. |
| 9,428,845 B1 | 8/2016 | Verdine et al. |
| 9,989,535 B2 | 6/2018 | Verdine et al. |
| 10,039,839 B2 | 8/2018 | Verdine et al. |
| 10,466,249 B2 | 11/2019 | Verdine et al. |
| 2002/0110874 A1 | 8/2002 | Khosla et al. |
| 2002/0147133 A1 | 10/2002 | Briesewitz et al. |
| 2003/0153053 A1 | 8/2003 | Reid |
| 2003/0175901 A1 | 9/2003 | Reeves et al. |
| 2004/0087496 A1 | 5/2004 | Kim et al. |
| 2004/0157768 A1 | 8/2004 | Or et al. |
| 2005/0233431 A1 | 10/2005 | Ashley et al. |
| 2007/0203168 A1 | 8/2007 | Zhao |
| 2007/0218502 A1 | 9/2007 | Hahn et al. |
| 2011/0117606 A1 | 5/2011 | Jorgensen et al. |
| 2012/0142622 A1 | 6/2012 | Aigle et al. |
| 2012/0208720 A1 | 8/2012 | Kashiwagi et al. |
| 2012/0270800 A1 | 10/2012 | Verdine et al. |
| 2013/0072439 A1 | 3/2013 | Nash et al. |
| 2014/0073581 A1 | 3/2014 | Liu et al. |
| 2014/0316104 A1 | 10/2014 | Fischer et al. |
| 2015/0250896 A1 | 9/2015 | Zhao |
| 2015/0307855 A1 | 10/2015 | Yuzawa et al. |
| 2016/0199506 A1 | 7/2016 | Verdine et al. |
| 2016/0341719 A1 | 11/2016 | Verdine et al. |

FOREIGN PATENT DOCUMENTS

| | | |
|---|---|---|
| EP | 0393934 A1 | 10/1990 |
| EP | 0562853 A1 | 9/1993 |
| EP | 1079859 B1 | 7/2010 |
| JP | 2000-511063 A | 8/2000 |
| JP | 2002-536014 A | 10/2002 |
| KR | 10-2009-0041971 A | 4/2009 |
| WO | WO-86/02080 A1 | 4/1986 |
| WO | WO-95/32294 A1 | 11/1995 |
| WO | WO-96/20216 A1 | 7/1996 |
| WO | WO-98/01546 A2 | 1/1998 |
| WO | WO-98/07743 A1 | 2/1998 |
| WO | WO-98/12217 A1 | 3/1998 |
| WO | WO-99/61055 A1 | 12/1999 |
| WO | WO-00/47724 A2 | 8/2000 |
| WO | WO-01/36460 A2 | 5/2001 |

(Continued)

OTHER PUBLICATIONS

Keatinge-Clay et al., "The Structure of a Ketoreductase Determines the Organization of the β-Carbon Processing Enzymes of Modular Polyketide Synthases," Structure. 14: 737-74 (2006).
"LuxR family trancriptional regulator [Streptomyces iranensis]," NCBI Reference Sequence: WP_044578204.1 (2 pages).
Yuzawa et al., "Bio-based production of fuels and industrial chemicals by repurposing antibiotic-producing type I modular polyketide synthases: opportunities and challenges," J Antibiot. 70(4):378-385 (2017).

(Continued)

*Primary Examiner* — Tekchand Saidha
(74) *Attorney, Agent, or Firm* — Clark & Elbing LLP

(57) ABSTRACT

The present disclosure provides nucleic acids encoding a Large ATP-binding regulator of the LuxR family (LAL) of transcription factors, vectors and host cells including such nucleic acids, and methods for producing compounds (e.g., polyketides or β-lactam compounds) with such nucleic acids, vectors, and/or host cells.

19 Claims, 18 Drawing Sheets

Specification includes a Sequence Listing.

(56) References Cited

FOREIGN PATENT DOCUMENTS

| | | |
|---|---|---|
| WO | WO-01/36612 A1 | 5/2001 |
| WO | WO-01/90070 A2 | 11/2001 |
| WO | WO-2008/069824 A2 | 6/2008 |
| WO | WO-2010/031185 A1 | 3/2010 |
| WO | WO-2010/034243 A1 | 4/2010 |
| WO | WO-2010/088573 A1 | 8/2010 |
| WO | WO-2012/075048 A2 | 6/2012 |
| WO | WO-2012/174489 A2 | 12/2012 |
| WO | WO-2014/009774 A1 | 1/2014 |
| WO | WO-2014/187959 A2 | 11/2014 |
| WO | WO-2015/132784 A1 | 9/2015 |
| WO | WO-2016/112279 A1 | 7/2016 |
| WO | WO-2016/112295 A1 | 7/2016 |
| WO | WO-2016/160362 A1 | 10/2016 |
| WO | WO-2017/059207 A1 | 4/2017 |
| WO | WO-2018/081592 A2 | 5/2018 |

OTHER PUBLICATIONS

Kushnir et al., "Minimally invasive mutagenesis gives rise to a biosynthetic polyketide library," Agnew Chem Int Ed. 51 (42):10664-9 (2012).

U.S. Appl. No. 61/418,038, Johns Hopkins University.

"SMART™ Drugs: Engineering Nature's Solution to the Undruggable Target Challenge," WarpDrive Bio, 2016 (31 pages).

"Streptomyces iranensis regulatory protein LuxR," EBI Database Accession No. CDR13506 (2014) (2 pages).

"Streptomyces rapamycinicus NRRL 5491 hypothetical protein," EBI Database Accession No. AGP59507 (2014) (2 pages).

"Substructure Search Report on Specifically Substituted Macrocycles—Substances Only", prepared by Science IP, dated Dec. 17, 2014 (6177 pages).

Aebi et al., "Synthesis, Conformation, and Immunosuppressive Activities of Three Analogues of Cyclosporin A Modified in the 1-Position1," J. Med. Chem. 33(3):999-1009 (1990).

Allain et al., "Cyclophilin B mediates cyclosporin A incorporation in human blood T-lymphocytes through the specific binding of complexed drug to the cell surface," Biochem J. 317 (Pt 2):565-70 (1996).

Andrei et al., "Stabilization of protein-protein interactions in drug discovery," Expert Opin Drug Discov. 12(9):925-40 (2017) (17 pages).

Antunes et al., "A mutational analysis defines Vibrio fischeri LuxR binding sites," J Bacteriol. 190(13):4392-7 (2008).

Archibald et al., "Discovery and Evaluation of Potent, Cysteine-based alpha4beta1 Integrin Antagonists," Bioorg Med Chem Lett. 10(9):993-995 (2000).

Banaszynski et al., "Characterization of the FKBP.rapamycin.FRB ternary complex," J Am Chem Soc. 127(13):4715-21 (2005).

Baranasic et al., "Draft Genome Sequence of *Streptomyces rapamycinicus* Strain NRRL 5491, the Producer of the Immunosuppressant Rapamycin," Genome Announc. 1(4):e00581-13 (2013) (2 pages).

Bayle et al., "Rapamycin analogs with differential binding specificity permit orthogonal control of protein activity," Chem Biol. 13(1):99-107 (2006).

Benjamin et al., "Rapamycin passes the torch: a new generation of mTOR inhibitors," Nat Rev Drug Discov. 10(11):868-80 (2011).

Bhuyan et al., "Antioxidant activity of peptide-based angiotensin converting enzyme inhibitors," Org. Biomol. Chem. 10(11):2237-47 (2012).

Blodgett et al., "Unusual transformations in the biosynthesis of the antibiotic phosphinothricin tripeptide," Nat Chem Biol. 3(8):480-5 (2007).

Briesewitz et al., "Affinity modulation of small-molecule ligands by borrowing endogenous protein surfaces," Proc Natl Acad Sci U.S.A. 96(5):1953-8 (1999).

Bruce, "In vivo protein complex topologies: sights through a cross-linking lens," Proteomics. 12(10):1565-75 (2012).

Burgess et al., "Controlled translocation of palladium(II) within a 22 ring atom macrocyclic ligand," Dalton Trans. 43(45):17006-16 (2014).

Chaurasia et al., "Molecular insights into the stabilization of protein-protein interactions with small molecule: The FKBP12-rapamycin-FRB case study," Chem Phys Lett. 587:68-74 (2013).

Che et al., "Inducing protein-protein interactions with molecular glues," Bioorganic & Medicinal Chemistry Letters (2018).

Chevalier et al., "Straightforward synthesis of bioconjugatable azo dyes. Part 1: Black Hole Quencher-1 (BHQ-1) scaffold," Tetrahedron Lett. 55(50):6759-63 (2014).

Chica et al., "Semi-rational approaches to engineering enzyme activity: combining the benefits of directed evolution and rational design," Curr Opin Biotechnol. 16(4):378-84 (2005).

De Schrijver et al., "A subfamily of MalT-related ATP-dependent regulators in the LuxR family," Microbiology. 145(6):1287-8 (1999).

Ding et al. "Insights into Bacterial 6-Methylsalicylic Acid Synthase and Its Engineering to Orsellinic Acid Synthase for Spirotetronate Generation," Chem Biol. 17(5):495-503 (2010).

Eberle et al. "Preparation of Functionalized Ethers of Cyclosporin A," Tetrahedron Lett. 35(35):6477-6480 (1994).

Extended European Search Report for European Patent Application No. 17783058.5, dated Aug. 22, 2019 (15 pages).

Findlay et al., "The structure of demethoxyrapamycin," Can J Chem. 60:2046-7 (1982).

Garg et al. "Elucidation of the Cryptic Epimerase Activity of Redox-Inactive Ketoreductase Domains from Modular Polyketide Synthases by Tandem Equilibrium Isotope Exchange," J. Am. Chem. Soc. 136(29):10190-10193 (2014).

Guerra et al., "LAL regulators SCO0877 and SCO7173 as pleiotropic modulators of phosphate starvation response and actinorhodin biosynthesis in Streptomyces coelicolor," PLoS One. 7(2):e31475 (2012) (11 pages).

He et al., "The LuxR family members GdmRI and GdmRII are positive regulators of geldanamycin biosynthesis in Streptomyces hygroscopicus 17997," Arch Microbiol. 189(5):501-10 (2008).

Hong et al., "Evidence for an iterative module in chain elongation on the azalomycin polyketide synthase," Beilstein J Org Chem. 12:2164-2172 (2016).

Horn et al., "Draft Genome Sequence of Streptomyces iranensis," Genome Announc. 2(4):e00616-14 (2014) (2 Pages).

Horton et al., "Engineering hybrid genes without the use of restriction enzymes: gene splicing by overlap extension," Gene. 77(1):61-8 (1989).

Hosted et al., "Use of rpsL for dominance selection and gene replacement in *Streptomyces roseosporus*" J Bacteriol. 179(1): 180-6 (1997).

Huang et al., "Enhanced rapamycin production in *Streptomyces hygroscopicus* by integrative expression of aveR, a LAL family transcriptional regulator," World J Microbiol Biotechnol. 27:2103-9 (2011).

Hubler et al., "Synthetic routes to NEtXaa4-cyclosporin A derivatives as potential anti-HIV I drugs," Tetrahedron Lett. 41:7193-6 (2000).

International Preliminary Report on Patentability for International Application No. PCT/US2017/027215, dated Oct. 25, 2018 (7 pages).

International Search Report and Written Opinion for International Application No. PCT/US2017/027215, dated Jul. 10, 2017 (13 pages).

Ishizawa et al., "TRAP display: a high-speed selection method for the generation of functional polypeptides," J Am Chem. 135(14):5433-40 (2013).

Jones et al., "Phage p1-derived artificial chromosomes facilitate heterologous expression of the FK506 gene cluster," PLoS One. 8(7):e69319 (9 pages).

Kawakami et al., "In vitro selection of multiple libraries created by genetic code reprogramming to discover macrocyclic peptides that antagonize VEGFR2 activity in living cells," ACS Chem Biol. 8(6):1205-14 (2013).

Kendrew et al., "Recombinant strains for the enhanced production of bioengineered rapalogs," Metab Eng. 15:167-73 (2013).

(56) References Cited

OTHER PUBLICATIONS

Kuramochi et al., "Identification of Small Molecule Binding Molecules by Affinity Purification Using a Specific Ligand Immobilized on PEGA Resin," Bioconjug. Chem. 19(12):2417-26 (2008).
Laureti et al., "Identification of a bioactive 51-membered macrolide complex by activation of a silent polyketide synthase in Streptomyces ambofaciens," Proc Natl Acad Sci USA. 108(15):6258-63 (2011).
Laureti et al., Supporting Material for "Identification of a bioactive 51-membered macrolide complex by activation of a silent polyketide synthase in Streptomyces ambofaciens," Proc Natl Acad Sci U.S.A. 108(15):6258-63 (2011), accessed via <www.pnas.org/content/suppl/2011/03/24/1019077108.DCSupplemental> (41 pages).
Lee et al. "Current implications of cyclophilins in human cancers," J Exp Clin Cancer Res. 29:97 (2010) (6 pages).
Leskiw et al., "TTA codons in some genes prevent their expression in a class of developmental, antibiotic-negative, *Streptomyces* mutants," Proc Natl Acad Sci USA. 88(6):2461-5 (1991).
Li et al., "A simple and efficient route to the FKBP-binding domain from rapamycin," available in PMC Sep. 28, 2012, published in final edited form as: Tetrahedron Lett. 52(39):5070-2 (2011) (7 pages).
Luengo et al., "Structure-activity studies of rapamycin analogs: evidence that the C-7 methoxy group is part of the effector domain and positioned at the FKBP12-FRAP interface," Chem Biol. 2(7):471-81 (1995).
Majumder et al. "Interaction of aryl hydrocarbon receptor-interacting protein-like 1 with the farnesyl moiety," J Biol Chem. 288(29):21320-21328 (2013).
Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012).
Mo et al., "Interspecies Complementation of the LuxR Family Pathway-Specific Regulator Involved in Macrolide Biosynthesis," J Microbiol Biotechnol. 26(1):66-71 (2016).
Murphy et al. "Isolation and characterisation of amphotericin B analogues and truncated polyketide intermediates produced by genetic engineering of *Streptomyces nodosus*" Org Biomol Chem. 8(16):3758-70 (2010).
NCBI Reference Sequence WP_053141444.1, retrieved Apr. 22, 2021 (1 page).
Ochi et al., "New strategies for drug discovery: activation of silent or weakly expressed microbial gene clusters," Appl Microbiol Biotechnol. 97(1):87-98 (2013).
Papageorgiou et al., "Improved binding affinity for cyclophilin A by a cyclosporin derivative singly modified at its effector domain," J Med Chem. 37(22):3674-6 (1994).
Pfeifer et al., "Biosynthesis of complex polyketides in a metabolically engineered strain of *E. coli*," Science. 291 (5509):1790-2 (2001).
Power et al. "Engineered Synthesis of 7-Oxo- and 15-Deoxy-15-Oxo-Amphotericins: Insights into Structure-Activity Relationships in Polyene Antibiotics," Chem Biol. 15:78-86 (2008).
Ranganathan et al., "Knowledge-based design of bimodular and trimodular polyketide synthases based on domain and module swaps: a route to simple statin analogues," Chem Biol. 6(10):731-41 (1999).
Reid et al. "A model of structure and catalysis for ketoreductase domains in modular polyketide synthases," Biochemistry. 42(1):72-79 (2003).
Revill et al., "Genetically engineered analogs of ascomycin for nerve regeneration," J Pharmacol Exp Ther. 302(3):1 278-85 (2002).
Ruan et al., "Binding of rapamycin analogs to calcium channels and FKBP52 contributes to their neuroprotective activities," Proc Natl Acad Sci U.S.A. 105(1):33-8 (2008).
Schwecke et al., "The biosynthetic gene cluster for the polyketide immunosuppressant rapamycin," Proc Natl Acad Sci USA. 92(17)7839-43 (1995).
Sieber et al., "Novel inhibitors of the calcineurin/NFATc hub—alternatives to CsA and FK506?," Cell Common Signal. 7:25 (2009) (19 pages).
Singh et al., "Protein Engineering Approaches in the Post-Genomic Era," Curr Protein Pept Sci. 19(1):5-15(2018).
STN record of WO 2014/009774, available online Jan. 16, 2014 (4 pages).
STN record of WO 98/12217, available online Mar. 26, 1998 (6 pages).
Sun et al. "Design and structure-based study of new potential FKBP12 inhibitors," Biophys J. 85(5):3194-3201 (2003).
Supplementary Partial European Search Report for European Application No. 17863519.9, dated Jun. 15, 2020 (16 pages).
Supplementary Partial European Search Report for European Patent Application No. 17865512.2, dated May 7, 2020 (20 pages).
Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).
Takakusagi et al., "Efficient one-cycle affinity selection of binding proteins or peptides specific for a small-molecule using a T7 phage display pool," Bioorg. Med. Chem. 16(22):9837-46 (2008).
Tang et al. "Generation of New Epothilones by Genetic Engineering of a Polyketide Synthase in Myxococcus xanthus," J Antibiot (Tokyo). 58(3):178-184 (2005).
UniProtKB Accession No. A0A061A6I8, Sep. 3, 2014 (12 pages).
UniProtKB Accession No. Q54296, "Polyketide synthase," retrieved May 29, 2020 (12 pages).
UniProtKB Accession No. Q54296, Nov. 1, 1996 (12 pages).
UniProtKB Accession No. Q54297, Nov. 1, 1996 (3 pages).
Vignot et al., "mTOR-targeted therapy of cancer with rapamycin derivatives," Ann Oncol. 16(4):525-37 (2005).
Wagner et al., "New naturally occurring amino acids," Angew Chem Int Ed Engl. 22(11):816-28 (1983).
Wang et al., "Thermodynamic analysis of cyclosporin a binding to cyclophilin a in a lung tumor tissue lysate," Anal Chem. 76(15):4343-8 (2004).
Weissman et al., "Combinatorial biosynthesis of reduced polyketides," Nat Rev Microbiol. 3(12):925-36 (2005).
Weissman, "Genetic engineering of modular PKSs: from combinatorial biosynthesis to synthetic biology," Nat Prod Rep. 33(2):203-230 (2016).
Wilson et al., "Comparative X-ray structures of the major binding protein for the immunosuppressant FK506 (tacrolimus) in unliganded form and in complex with FK506 and rapamycin," Acta Cryst. D51:511-21 (1995).
Wright et al., "Multivalent binding in the design of bioactive compounds," Curr Org Chem. 5(11):1107-31 (2001).
Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).
Wu et al., "Inhibition of ras-effector interactions by cyclic peptides," Med Chem Commun. 4(2):378-82 (2013).

FIG. 1A

Promoter region 1 — LAL — X1 biosynthetic locus — Promoter region 2

FIG. 1B Conserved putative LAL binding domains extracted from FK cluster promoter regions

```
SEQ ID NO: 38 S12intergenicPIPrt   TG--GCCGGAAAACCTAGGGGGTTGCGTTGGAAAGCACGGGGGTGTTCGCT 169
SEQ ID NO: 39 S22intergenicPIPrt   TG--GCCGGAAAACCTAGGGGGTTGCGTTGGAAAGCACGGGGGTGTTCGCT 169
SEQ ID NO: 40 S9intergenicPIPrt    AG--GCAGGACGTCTAGGGGGTTGCGTGACTGCGCGCCTGAGTGTCTTCT 218
SEQ ID NO: 41 S18intergenicPIPrt   AG--GCAGGAAAGCTAGGGGGTTGCGTGACTGCGACCTGGGGTGTCTTCT 227
SEQ ID NO: 42 S1intergenicPIPrt    AG--GTACGACACCTAGGGGGTTGCGTGGCTGGCGACCC-GGTGTCT-CC 145
SEQ ID NO: 43 S21intergenicPIPrt   AG--CTCGGCCCCCTAGGGGGTTGCCCCGCTGAGGCG-GAGGTGTTTGGC 246
SEQ ID NO: 44 FK506intergenicPIPrt TG---TTGCCCATCTAGGGGGTTGCACGAATAACGTC-----ACACGTACT 217
SEQ ID NO: 45 Stacrolimicus        TG---TCATATGTCTAGGGGGTTGCACGAATACCGTC-----GCGCGTACT 170
SEQ ID NO: 46 FK520intergenicPIPrt GG---AGGTCATCTAGGGGGTTGCACGCATACGGC------GTGCGTAAT 170
SEQ ID NO: 47 S12-promoter region 2 GGGCGCCTGT--TCTAGGGGGTTGCGGGGAGTG---------GCGCGCACA 174
```

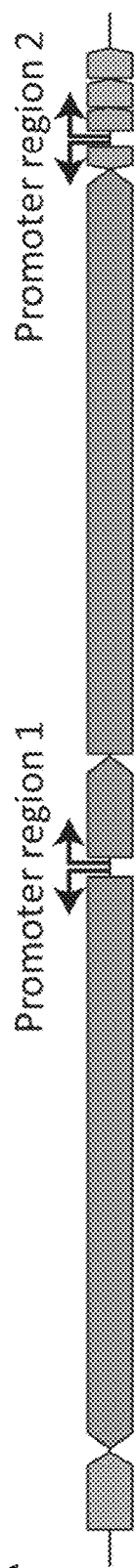

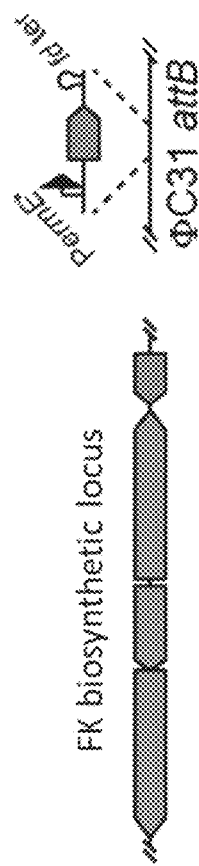

FIG. 1C Phage-integrating constitutive LAL expression scheme

Constructed integrating panel of 33 LALs under PermE*.
Test S22/LAL strains for increased WDB001-003 production Zoom in on FKs...

- Normalized mRNA levels measured by NanoString displayed as log2 values
- Probe locations denoted on cluster map

SEQUENCE LISTING

<160> NUMBER OF SEQ ID NOS: 112

<210> SEQ ID NO 1
<211> LENGTH: 914
<212> TYPE: PRT
<213> ORGANISM: Streptomyces hygroscopicus

```
<400> SEQUENCE: 1

Met Pro Ala Val Glu Ser Tyr Glu Leu Asp Ala Arg Asp Asp Glu Leu
1               5                   10                  15

Arg Arg Leu Glu Glu Ala Val Gly Gln Ala Gly Asn Gly Arg Gly Val
            20                  25                  30

Val Val Thr Ile Thr Gly Pro Ile Ala Cys Gly Lys Thr Glu Leu Leu
        35                  40                  45

Asp Ala Ala Ala Lys Ser Asp Ala Ile Thr Leu Arg Ala Val Cys
    50                  55                  60

Ser Glu Glu Glu Arg Ala Leu Pro Tyr Ala Leu Ile Gly Gln Leu Ile
65                  70                  75                  80

Asp Asn Pro Ala Val Ala Ser Gln Leu Pro Asp Pro Val Ser Met Ala
                85                  90                  95

Leu Pro Gly Glu His Leu Ser Pro Glu Ala Glu Asn Arg Leu Arg Gly
            100                 105                 110

Asp Leu Thr Arg Thr Leu Leu Ala Leu Ala Ala Glu Arg Pro Val Leu
        115                 120                 125

Ile Gly Ile Asp Asp Met His His Ala Asp Thr Ala Ser Leu Asn Cys
130                 135                 140

Leu Leu His Leu Ala Arg Arg Val Gly Pro Ala Arg Ile Ala Met Val
145                 150                 155                 160

Leu Thr Glu Leu Arg Arg Leu Thr Pro Ala His Ser Gln Phe His Ala
                165                 170                 175

Glu Leu Leu Ser Leu Gly His His Arg Glu Ile Ala Leu Arg Pro Leu
            180                 185                 190

Gly Pro Lys His Ile Ala Glu Leu Ala Arg Ala Gly Leu Gly Pro Asp
        195                 200                 205

Val Asp Glu Asp Val Leu Thr Gly Leu Tyr Arg Ala Thr Gly Gly Asn
210                 215                 220

Leu Asn Leu Gly His Gly Leu Ile Lys Asp Val Arg Glu Ala Trp Ala
225                 230                 235                 240

Thr Gly Gly Thr Gly Ile Asn Ala Gly Arg Ala Tyr Arg Leu Ala Tyr
                245                 250                 255

Leu Gly Ser Leu Tyr Arg Cys Gly Pro Val Pro Leu Arg Val Ala Arg
            260                 265                 270

Val Ala Ala Val Leu Gly Gln Ser Ala Asn Thr Thr Leu Val Arg Trp
        275                 280                 285

Ile Ser Gly Leu Asn Ala Asp Ala Val Gly Glu Ala Thr Glu Ile Leu
290                 295                 300

Thr Glu Gly Gly Leu Leu His Asp Leu Arg Phe Pro His Pro Ala Ala
305                 310                 315                 320

Arg Ser Val Val Leu Asn Asp Leu Ser Ala Arg Glu Arg Arg Leu
                325                 330                 335

His Arg Ser Ala Leu Glu Val Leu Asp Asp Val Pro Val Glu Val Val
            340                 345                 350

Ala His His Gln Ala Gly Ala Gly Phe Ile His Gly Pro Lys Ala Ala
        355                 360                 365

Glu Ile Phe Ala Lys Ala Gly Gln Glu Leu His Val Arg Gly Glu Leu
    370                 375                 380

Asp Ala Ala Ser Asp Tyr Leu Gln Leu Ala His His Ala Ser Asp Asp
385                 390                 395                 400

Ala Val Thr Arg Ala Ala Leu Arg Val Glu Ala Val Ala Ile Glu Arg
                405                 410                 415
```

```
Arg Arg Asn Pro Leu Ala Ser Ser Arg His Leu Asp Glu Leu Thr Val
            420                 425                 430

Ala Ala Arg Ala Gly Leu Leu Ser Leu Glu His Ala Ala Leu Met Ile
            435                 440                 445

Arg Trp Leu Ala Leu Gly Gly Arg Ser Gly Glu Ala Ala Glu Val Leu
            450                 455                 460

Ala Ala Gln Arg Pro Arg Ala Val Thr Asp Gln Asp Arg Ala His Leu
465                 470                 475                 480

Arg Ala Ala Glu Val Ser Leu Ala Leu Val Ser Pro Gly Ala Ser Gly
                485                 490                 495

Val Ser Pro Gly Ala Ser Gly Pro Asp Arg Arg Pro Arg Pro Leu Pro
            500                 505                 510

Pro Asp Glu Leu Ala Asn Leu Pro Lys Ala Ala Arg Leu Cys Ala Ile
            515                 520                 525

Ala Asp Asn Ala Val Ile Ser Ala Leu His Gly Arg Pro Glu Leu Ala
530                 535                 540

Ser Ala Glu Ala Glu Asn Val Leu Lys Gln Ala Asp Ser Ala Ala Asp
545                 550                 555                 560

Gly Ala Thr Ala Leu Ser Ala Leu Thr Ala Leu Leu Tyr Ala Glu Asn
            565                 570                 575

Thr Asp Thr Ala Gln Leu Trp Ala Asp Lys Leu Val Ser Glu Thr Gly
            580                 585                 590

Ala Ser Asn Glu Glu Glu Gly Ala Gly Tyr Ala Gly Pro Arg Ala Glu
            595                 600                 605

Thr Ala Leu Arg Arg Gly Asp Leu Ala Ala Ala Val Glu Ala Gly Ser
            610                 615                 620

Ala Ile Leu Asp His Arg Arg Gly Ser Leu Leu Gly Ile Thr Ala Ala
625                 630                 635                 640

Leu Pro Leu Ser Ser Ala Val Ala Ala Ala Ile Arg Leu Gly Glu Thr
            645                 650                 655

Glu Arg Ala Glu Lys Trp Leu Ala Glu Pro Leu Pro Glu Ala Ile Arg
            660                 665                 670

Asp Ser Leu Phe Gly Leu His Leu Leu Ser Ala Arg Gly Gln Tyr Cys
            675                 680                 685

Leu Ala Thr Gly Arg His Glu Ser Ala Tyr Thr Ala Phe Arg Thr Cys
            690                 695                 700

Gly Glu Arg Met Arg Asn Trp Gly Val Asp Val Pro Gly Leu Ser Leu
705                 710                 715                 720

Trp Arg Val Asp Ala Ala Glu Ala Leu Leu His Gly Arg Asp Arg Asp
                725                 730                 735

Glu Gly Arg Arg Leu Ile Asp Glu Gln Leu Thr His Ala Met Gly Pro
            740                 745                 750

Arg Ser Arg Ala Leu Thr Leu Arg Val Gln Ala Ala Tyr Ser Pro Gln
            755                 760                 765

Ala Gln Arg Val Asp Leu Leu Glu Glu Ala Ala Asp Leu Leu Leu Ser
            770                 775                 780

Cys Asn Asp Gln Tyr Glu Arg Ala Arg Val Leu Ala Asp Leu Ser Glu
785                 790                 795                 800

Ala Phe Ser Ala Leu Arg His His Ser Arg Ala Arg Gly Leu Leu Arg
                805                 810                 815

Gln Ala Arg His Leu Ala Ala Gln Cys Gly Ala Thr Pro Leu Leu Arg
            820                 825                 830
```

```
Arg Leu Gly Ala Lys Pro Gly Pro Gly Trp Leu Glu Glu Ser Gly
            835                 840                 845

Leu Pro Gln Arg Ile Lys Ser Leu Thr Asp Ala Glu Arg Arg Val Ala
    850                 855                 860

Ser Leu Ala Ala Gly Gly Gln Thr Asn Arg Val Ile Ala Asp Gln Leu
865                 870                 875                 880

Phe Val Thr Ala Ser Thr Val Glu Gln His Leu Thr Asn Val Phe Arg
                885                 890                 895

Lys Leu Gly Val Lys Gly Arg Gln His Leu Pro Ala Glu Leu Ala Asn
            900                 905                 910

Ala Glu

<210> SEQ ID NO 2
<211> LENGTH: 12
<212> TYPE: DNA
<213> ORGANISM: Artificial Sequence
<220> FEATURE:
<223> OTHER INFORMATION: synthetic construct

<400> SEQUENCE: 2 ctaggggggtt gc                                                         12

<210> SEQ ID NO 3
<211> LENGTH: 6
<212> TYPE: DNA
<213> ORGANISM: Artificial Sequence
<220> FEATURE:
<223> OTHER INFORMATION: synthetic construct

<400> SEQUENCE: 3 gggggt                                                                 6

<210> SEQ ID NO 4
<211> LENGTH: 2685
<212> TYPE: DNA
<213> ORGANISM: Streptomyces hygroscopicus

<400> SEQUENCE: 4
atgcctgccg tggagtgcta tgaactggac gcccgcgatg acgagctcag aaaactggag        60
gaggttgtga ccgggcgggc caacggccgg ggtgtggtgg tcaccatcac cggaccgatc       120
gcctgcggca agaccgaact gctcgacgca gccgccgcga aggccgacgc catcacgtta       180
cgagcggtct gctccgcgga ggaacaggca ctcccgtacg ccctgatcgg cagctcatc       240 gacaacccgg cgctcgcctc ccacgcgctg agccggcct gccgacccct ccggggcgag       300
cacctgtcgc cggaggccga gaaccggctg cgcagcgacc tcacccgtac cctgctggcg       360
ctcgccgccg aacggccggt gctgatcggc atcgacgagt cacacgcgaa cgctttgtgt       420
ctgctccacc tggcccgaag ggtcggctcg gccggatcg ccatggtcct caccgagttg       480
cgccggctca ccccggccca ctcacagttc caggccgagc tgctcagcct ggggcaccac       540
cgcgagatcg cgctgcgccc gctcagcccg aagcacaccg ccgagctggt ccgcgccggt       600
ctcggtcccg acgtcgacga ggacgtgctc acggggttgt accgggcgac cggcggcaac       660
ctgaacctca cccgcggact gatcaacgat gtgcggggagg cctgggagac gggagggacg       720
ggcatcagcg cgggccgcgc gtaccggctg gcatacctcg gttccctcta ccgctgcggc       780
ccggtcccgt tgcgggtcgc acgggtggcc gccgtgctgg ccagagcgc caacaccacc       840 ctggtgcgct ggatcagcgg gctcaacgcg gacgcggtgg gcgaggcaac cgagatcctc       900
```

```
accgaaggcg gcctgctgca cgacctgcgg ttcccgcacc cggcggcccg ttcggtggta    960
ctcaacgaca tgtccgccca ggaacgacgc cgcctgcacc ggtccgctct ggaagtgctg   1020
gacgacgtgc ccgtggaagt ggtcgcgcac caccaggtcg gcgccggtct cctgcacggc   1080
ccgaaggccg ccgagatatt cgccaaggcc ggccaggagc tgcatgtgcg cggcgagttg   1140
gacaccgcgt ccgactatct gcaactggcc caccaggcct ccgacgacgc cgtcaccggg   1200
atgcgggccg aggccgtggc gatcgagcgc cgccgcaacc cgctggcctc gagccggcac   1260
ctcgacgagc tgaccgtcgt cgcccgtgcc gggctgctct tccccgagca cacggcgctg   1320
atgatccgct ggctgggcgt cggcgggcgg tccggcgagg cagccgggct gctggcctcg   1380
cagcgccccc gtgcggtcac cgaccaggac agggcccata tgcgggccgc cgaggtatcg   1440
ctcgcgctgg tcagccccgg cacgtccggc ccgaccggc ggccgcgtcc gctcacgccg   1500
gatgagctcg cgaacctgcc gaaggcgccc cggctctgcg cgatcgccga caatgccgtc   1560
atgtcggccc tgcgcggtcg tcccgagctc gccgcggccg aggcggagaa cgtcctgcag   1620
cacgccgact cggcggcggc cggcaccacc gccctcgccg cgctgaccgc cttgctgtac   1680
gcggagaaca ccgacaccgc tcagctctgg gccgacaagc tggtctccga ccggggcg    1740
tcgaacgagg aggaggcggg ctacgcgggg ccgcgcgccg aagccgcgtt gcgtcgcggc   1800
gacctggccg cggcggtcga ggcaggcagc accgttctgg accaccggcg gctctcgacg   1860
ctcggcatca ccgccgcgct accgctgagc agcgcggtgg ccgccgccat ccggctgggc   1920
gagaccgagc gggcggagaa gtggctcgcc cagccgctgc cgcaggccat ccaggacggc   1980
ctgttcggcc tgcacctgct ctcggcgcgc ggccagtaca gcctcgccac gggccagcac   2040
gagtcggcgt acacggcgtt tcgcacctgc ggggaacgta tgcggaactg gggcgttgac   2100
gtgccgggtc tgtccctgtg cgcgcgtcga ccgccgagg gctgctgca cggccgcgac   2160
cgggacgagg gccgacggct cgtcgacgag caactcaccc gtgcgatggg accccgttcc   2220
cgcgccttga cgctgcgggt gcaggcggcg tacagcccgc cggcgaagcg ggtcgacctg   2280
ctcgatgaag cggccgacct gctgctctcc tgcaacgacc agtacgagcg ggcacgggtg   2340
ctcgccgacc tgagcgagac gttcagcgcg ctccggcacc acagccgggc gcggggactg   2400
cttcggcagg cccggcacct ggccgcccag cgcggcgcga taccgctgct cgccgactc    2460
ggggccaagc ccgaggcccc cggctggctg gaggaatccg gcctgccgca gcggatcaag   2520
tcgctgaccg acgcggagcg gcgggtggcg tcgctggccg ccggcggaca gaccaaccgc   2580
gtgatcgccg accagctctt cgtcacggcc agcacggtgg agcagcacct cacggacgtc   2640
tccactgggt caaggccgcc agcacctgcc gccgaactcg tctag                  2685

<210> SEQ ID NO 5
<211> LENGTH: 2685
<212> TYPE: DNA
<213> ORGANISM: Streptomyces hygroscopicus

<400> SEQUENCE: 5
atgcctgccg tggagtgcta tgaactggac gcccgcgatg acgagctcag aaaactggag     60
gaggttgtga ccgggcgggc caacggccgg ggtgtggtgg tcaccatcac cggaccgatc    120
gcctgcggca agaccgaact gctcgacgca gccgccgcga aggccgacgc catcacgctg    180
cgagcggtct gctccgcgga ggaacaggca ctcccgtacg ccctgatcgg cagctcatc    240
gacaacccgg cgctcgcctc ccacgcgctg agccggcct gccgaccct ccggggcgag     300
cacctgtcgc cggaggccga gaaccggctg cgcagcgacc tcacccgtac cctgctggcg    360
```

```
ctcgccgccg aacggccggt gctgatcggc atcgacgagt cacacgcgaa cgctttgtgt    420
ctgctccacc tggcccgaag ggtcggctcg gcccggatcg ccatggtcct caccgagttg    480
cgccggctca ccccggccca ctcacagttc caggccgagc tgctcagcct ggggcaccac    540
cgcgagatcg cgctgcgccc gctcagcccg aagcacaccg ccgagctggt ccgcgccggt    600
ctcggtcccg acgtcgacga ggacgtgctc acggggttgt accgggcgac cggcggcaac    660
ctgaacctca cccgcggact gatcaacgat gtgcgggagg cctgggagac gggagggacg    720
ggcatcagcg cgggccgcgc gtaccggctg catacctcg gttccctcta ccgctgcggc    780
ccggtcccgt tgcgggtcgc acgggtggcc gccgtgctgg ccagagcgc caacaccacc    840 ctggtgcgct ggatcagcgg gctcaacgcg gacgcggtgg gcgaggcaac cgagatcctc    900
accgaaggcg gcctgctgca cgacctgcgg ttcccgcacc cggcggcccg ttcggtggta    960
ctcaacgaca tgtccgccca ggaacgacgc cgcctgcacc ggtccgctct ggaagtgctg   1020
gacgacgtgc ccgtggaagt ggtcgcgcac caccaggtcg cgccggtct cctgcacggc   1080 ccgaaggccg ccgagatatt cgccaaggcc ggccaggagc tgcatgtgcg cggcgagttg   1140
gacaccgcgt ccgactatct gcaactggcc caccaggcct ccgacgacgc cgtcaccggg   1200
atgcgggccg aggccgtggc gatcgagcgc cgccgcaacc cgctggcctc gagccggcac   1260
ctcgacgagc tgaccgtcgt cgcccgtgcc gggctgctct ccccgagca cggcgctg    1320 atgatccgct ggctgggcgt cggcgggcgg tccggcgagg cagccgggct gctggcctcg   1380
cagcgccccc gtgcggtcac cgaccaggac agggcccata tgcgggccgc cgaggtatcg   1440
ctcgcgctgg tcagccccgg cacgtccggc ccggaccggc ggccgcgtcc gctcacgccg   1500
gatgagctcg cgaacctgcc gaaggcggcc cggctctgcg cgatcgccga caatgccgtc   1560
atgtcggccc tgcgcggtcg tcccgagctc gccgcggccg aggcggagaa cgtcctgcag   1620
cacgccgact cggcggcggc cggcaccacc gccctcgccg cgctgaccgc cttgctgtac   1680
gcggagaaca ccgacaccgc tcagctctgg gccgacaagc tggtctccga gaccggggcg   1740
tcgaacgagg aggaggcggg ctacgcgggg ccgcgcgccg aagccgcgtt gcgtcgcggc   1800
gacctggccg cggcggtcga ggcaggcagc accgttctgg accaccggcg gctctcgacg   1860
ctcggcatca ccgccgcgct accgctgagc agcgcggtgg ccgccgccat ccggctgggc   1920
gagaccgagc gggcggagaa gtggctcgcc cagccgctgc cgcaggccat ccaggacggc   1980
ctgttcggcc tgcacctgct ctcggcgcgc ggccagtaca gcctcgccac gggccagcac   2040
gagtcggcgt acacggcgtt tcgcacctgc ggggaacgta tgcggaactg gggcgttgac   2100
gtgccgggtc tgtccctgtg gcgcgtcgac gccgccgagg cgctgctgca cggccgcgac   2160
cgggacgagg gccgacggct cgtcgacgag caactcaccc gtgcgatggg acccgttcc    2220 cgcgccttga cgctgcgggt gcaggcggcg tacagcccgc cggcgaagcg ggtcgacctg   2280
ctcgatgaag cggccgacct gctgctctcc tgcaacgacc agtacgagcg ggcacgggtg   2340
ctcgccgacc tgagcgagac gttcagcgcg ctccggcacc acagccgggc gcggggactg   2400
cttcggcagg cccggcacct ggccgcccag cgcggcgcga taccgctgct gcgccgactc   2460
ggggccaagc ccggaggccc cggctggctg gaggaatccg gcctgccgca gcggatcaag   2520
tcgctgaccg acgcggagcg gcgggtggcg tcgctggccg ccggcggaca gaccaaccgc   2580
gtgatcgccg accagctctt cgtcacggcc agcacggtgg agcagcacct cacggacgtc   2640
tccactgggt caaggccgcc agcacctgcc gccgaactcg tctag               2685
```

<210> SEQ ID NO 6
<211> LENGTH: 2772
<212> TYPE: DNA
<213> ORGANISM: Streptomyces kanamyceticus

<400> SEQUENCE: 6

| | | | | | |
|---|---|---|---|---|---|
| gtggttcctg | aagtgcgagc | agcccccgac | gaactgatcg | cccgcgatga | cgagctgagc | 60 |
| cgcctccaac | gggcactcac | cagggcgggg | agcggaaggg | gcggcgtcgt | cgccatcacc | 120 |
| gggcccatcg | ccagcggaaa | gacggcgctg | ctcgacgccg | gagcggccaa | gtccggcttc | 180 |
| gtcgcactcc | gtgcggtgtg | ctcctgggaa | gagcgcactc | tgccgtacgg | gatgctgggc | 240 |
| cagctcttcg | accatcccga | actggccgcc | caggcgccgg | accttgccca | cttcacggct | 300 |
| tcgtgcgaga | gccctcaggc | cggtaccgac | aaccgcctgc | gggccgagtt | cacccgcacc | 360 |
| ctgctggcgc | tcgccgcgga | ctggcccgtc | ctgatcggca | tcgacgacgt | gcaccacgcc | 420 |
| gacgcggaat | cactgcgctg | tctgctccac | ctcgcccgcc | gcatcggccc | ggcccgcatc | 480 |
| gcggtcgtac | tgaccgagct | gcgcagaccg | acgcccgccg | actcccgctt | ccaggcggaa | 540 |
| ctgctgagcc | tgcgctccta | ccaggagatc | gcgctcagac | cgctcaccga | ggcgcagacc | 600 |
| ggcgaactcg | tacgtcggca | cctcggcgcg | gagacccacg | aggacgtctc | cgccgatacg | 660 |
| ttccgggcga | ccggcgggaa | cctgctcctc | gggcacggtt | tgatcaatga | catccgggag | 720 |
| gcgcggacag | cgggacggcc | ggggtcgtc | gcggggcggg | cgtaccggct | cgcgtacctc | 780 |
| agctcgctct | accgctgcgg | cccgagcgcg | ctgcgtgtcg | cccgggcgtc | cgccgtgctc | 840 |
| ggcgcgagcg | ccgaagccgt | gctcgtccag | cggatgaccg | gactgaacaa | ggacgcggtc | 900 |
| gaacaggtct | atgagcagct | gaacgaggga | cggctgctgc | agggcgagcg | gtttccgcac | 960 |
| ccggcggccc | gctccatcgt | ccttgacgac | ctgtcggccc | tggaacgcag | aaacctgcac | 1020 |
| gagtcggcgc | tggagctgct | gcgggaccac | ggcgtggccg | gcaacgtgct | cgcccgccac | 1080 |
| cagatcggcg | ccgccgggt | gcacggcgag | gaggccgtcg | agctgttcac | cggggccgca | 1140 |
| cgggagcacc | acctgcgcgg | tgaactggac | gacgcggccg | gatacctgga | actcgcccac | 1200 |
| cgtgcctccg | acgacccccgt | cacgcgcgcc | gcactacgcg | tcggcgccgc | cgcgatcgag | 1260 |
| cgcctctgca | atccggtacg | ggcaggccgg | catctgcccg | agctgctcac | cgcgtcgcgc | 1320 |
| gcggactgc | tctccagcga | gcacgccgtg | tcgctcgccg | actggctggc | gatgggcggg | 1380 |
| cgggcccgggcg | aggcggccga | ggtcctcgcg | acgcagcgtc | ccgcggccga | cagcgagcag | 1440 |
| caccgcgcac | tcctgcgcag | cggcgagttg | tccctcgcgc | tggtccaccc | cggcgcgtgg | 1500 |
| gatccgttgc | gccggaccga | tcggttcgcc | gcgggcgggc | tcggctcgct | tcccggaccc | 1560 |
| gcccggcacc | gcgcggtcgc | cgaccaagcc | gtcatcgcgg | cgctgcgtgg | acgtctcgac | 1620 |
| cgggcggacg | ccaacgcgga | gagcgttctc | cagcacaccg | acgccacggc | ggaccggacc | 1680 |
| acggccatca | tggcgttgct | ggccctgctc | tacgcggaga | acaccgatgc | tgtccagttc | 1740 |
| tgggtcgaca | aactggccgg | tgacgagggc | accaggacac | cggccgacga | ggcggtccac | 1800 |
| gcggggttca | cgccgagat | cgcgctgcgc | cgcggcgact | tgatgagagc | cgtcgagtac | 1860 |
| ggcgaggcag | cgctcggcca | ccggcacctg | cccacctggg | gaatggccgc | cgctctgccg | 1920 |
| ctgagcagca | ccgtggttgc | cgcgatccgg | ctcggcgacc | tcgacagggc | cgagcggtgg | 1980 |
| ctcgccgagc | cgctgccgca | gcagacgccg | gagagcctct | cgggctgca | cctgctctgg | 2040 |
| gcccgcgggc | agcaccacct | cgcgaccggg | cggcacgggg | cggcgtacac | ggcgttcagg | 2100 |
| gaatgcggcg | agcggatgcg | gcggtgggcc | gtcgacgtgc | cgggcctggc | cctgtggcgg | 2160 |

-continued

```
gtcgacgccg ccgaatcgct gctgctgctc ggccgtgacc gtgccgaagg actgcggctc      2220
gtctccgagc agctgtcccg gccgatgcgc cctcgcgcgc gcgtgcagac gttacgggta      2280
caggcggcct acagtccgcc gccccaacgg atcgacctgc tcgaagaggc cgccgacctg      2340
ctggtcacct gcaacgacca gtacgaactg caaacgtac tcagcgactt ggcagaggcc       2400
tccagcatgg tccggcagca cagcagggcg cggggtctgc tccgccgggc acggcacctc      2460
gccacccagt gcggcgccgt gccgctcctg cggcggctcg gcgcggaacc ctcggacatc      2520
ggcggagcct gggacgcgac gctgggacag cggatcgcgt cactgacgga gtcggagcgg      2580
cgggtggccg cgctcgccgc ggtcgggcgt acgaacaggg agatcgccga gcagctgttc      2640
gtcacggcca gcacggtgga acagcacctc acgaacgtgt ccgcaaaact ggcggtgaag      2700
ggccgccagc agcttccgaa ggaactggcc gacgtcggcg agccggcgga ccgcgaccgc      2760
cggtgcgggt ag                                                          2772

<210> SEQ ID NO 7
<211> LENGTH: 2772
<212> TYPE: DNA
<213> ORGANISM: Streptomyces kanamyceticus

<400> SEQUENCE: 7
atggttcctg aagtgcgagc agcccccgac gaactgatcg cccgcgatga cgagctgagc       60
cgcctccaac gggcactcac cagggcgggg agcggaaggg gcggcgtcgt cgccatcacc      120
gggcccatcg ccagcggaaa gacggcgctg ctcgacgccg gagcggccaa gtccggcttc      180
gtcgcactcc gtgcggtgtg ctcctgggaa gagcgcactc tgccgtacgg gatgctgggc      240
cagctcttcg accatcccga actggccgcc caggcgccgg accttgccca cttcacgggct     300 tcgtgcgaga gccctcaggc cggtaccgac aaccgcctgc gggccgagtt cacccgcacc      360
ctgctggcgc tcgccgcgga ctggcccgtc ctgatcggca tcgacgacgt gcaccacgcc      420
gacgcggaat cactgcgctg tctgctccac ctcgcccgcc gcatcggccc ggcccgcatc      480
gcggtcgtac tgaccgagct gcgcagaccg acgcccgccg actcccgctt ccaggcggaa      540
ctgctgagcc tgcgctccta ccaggagatc gcgctcagac cgctcaccga ggcgcagacc      600
ggcgaactcg tacgtcggca cctcggcgcg gagacccacg aggacgtctc cgccgatacg      660
ttccgggcga ccgcgggaa cctgctcctc gggcacggtt tgatcaatga catccggag       720 gcgcggacag cgggacggcc ggggtcgtc gcggggcggg cgtaccggct cgcgtacctc       780
agctcgctct accgctgcgg cccgagcgcg ctgcgtgtcg cccgggcgtc cgccgtgctc      840
ggcgcgagcg ccgaagccgt gctcgtccag cggatgaccg gactgaacaa ggacgcggtc      900
gaacaggtct atgagcagct gaacgaggga cggctgctgc agggcgagcg gtttccgcac      960
ccggcggccc gctccatcgt ccttgacgac ctgtcggccc tggaacgcag aaacctgcac     1020
gagtcggcgc tggagctgct gcgggaccac ggcgtggccg gcaacgtgct cgcccgccac     1080
cagatcggcg ccggccgggt gcacggcgag gaggccgtcg agctgttcac cggggccgca     1140
cgggagcacc acctgcgcgg tgaactggac gacgcggccg gatacctgga actcgcccac     1200
cgtgcctccg acgaccccgt cacgcgcgcc gcactacgcg tcggcgccgc cgcgatcgag     1260
cgcctctgca atccggtacg ggcaggccgg catctgcccg agctgctcac cgcgtcgcgc     1320 gcggactgc tctccagcga gcacgccgtg tcgctcgccg actggctggc gatgggcggg     1380
cgcccgggcg aggcggccga ggtcctcgcg acgcagcgtc ccgcggccga cagcgagcag     1440
```

| | |
|---|---:|
| caccgcgcac tcctgcgcag cggcgagttg tccctcgcgc tggtccaccc cggcgcgtgg | 1500 |
| gatccgttgc gccggaccga tcggttcgcc gcgggcgggc tcggctcgct tcccggaccc | 1560 |
| gcccggcacc gcgcggtcgc cgaccaagcc gtcatcgcgg cgctgcgtgg acgtctcgac | 1620 |
| cgggcggacg ccaacgcgga gagcgttctc cagcacaccg acgccacggc ggaccggacc | 1680 |
| acggccatca tggcgttgct ggccctgctc tacgcggaga acaccgatgc tgtccagttc | 1740 |
| tgggtcgaca aactggccgg tgacgagggc accaggacac cggccgacga ggcggtccac | 1800 |
| gcggggttca acgccgagat cgcgctgcgc cgcggcgact tgatgagagc cgtcgagtac | 1860 |
| ggcgaggcag cgctcggcca ccggcacctg cccacctggg gaatggccgc cgctctgccg | 1920 |
| ctgagcagca ccgtggttgc cgcgatccgg ctcggcgacc tcgacagggc cgagcggtgg | 1980 |
| ctcgccgagc cgctgccgca gcagacgccg gagagcctct cgggctgca cctgctctgg | 2040 |
| gcccgcgggc agcaccacct cgcgaccggg cggcacgggg cggcgtacac ggcgttcagg | 2100 |
| gaatgcggcg agcggatgcg gcggtgggcc gtcgacgtgc cgggcctggc cctgtggcgg | 2160 |
| gtcgacgccg ccgaatcgct gctgctgctc ggccgtgacc gtgccgaagg actgcggctc | 2220 |
| gtctccgagc agctgtcccg gccgatgcgc cctcgcgcgc gcgtgcagac gctgcgggta | 2280 |
| caggcggcct acagtccgcc gccccaacgg atcgacctgc tcgaagaggc cgccgacctg | 2340 |
| ctggtcacct gcaacgacca gtacgaactg caaacgtac tcagcgactt ggcagaggcc | 2400 |
| tccagcatgg tccggcagca agcagggcg cggggtctgc tccgccgggc acggcacctc | 2460 |
| gccacccagt gcggcgccgt gccgctcctg cggcggctcg gcgcggaacc ctcggacatc | 2520 |
| ggcggagcct gggacgcgac gctgggacag cggatcgcgt cactgacgga gtcggagcgg | 2580 |
| cgggtggccg cgctcgccgc ggtcgggcgt acgaacaggg agatcgccga gcagctgttc | 2640 |
| gtcacggcca gcacggtgga acagcacctc acgaacgtgt tccgcaaact ggcggtgaag | 2700 |
| ggccgccagc agcttccgaa ggaactggcc gacgtcggcg agccggcgga ccgcgaccgc | 2760 |
| cggtgcgggt ag | 2772 |

<210> SEQ ID NO 8
<211> LENGTH: 2742
<212> TYPE: DNA
<213> ORGANISM: Streptomyces ascomyceticus

<400> SEQUENCE: 8

| | |
|---|---:|
| gtgatagcgc gcttatctcc cccagacctg atcgcccgcg atgacgagtt cggttccctc | 60 |
| cacccgggcg tcacccgagc gggggcggg cggggcgtcg tcgccgccgt caccgggccg | 120 |
| atcgcctgcg gcaagaccga actcctcgac gccgccgcgg ccaaggccgg cttcgtcacc | 180 |
| cttcgcgcgg tgtgctccat ggaggagcgg gccctgccgt acggcatgct cggccagctc | 240 |
| ctcgaccagc ccgagctggc cgcccggaca ccggagctgg tccggctgac ggcatcgtgc | 300 |
| gaaaacctgc cggccgacgt cgacaaccgc ctggggaccg aactcacccg cacggtgctg | 360 |
| acgctcgccg cggagcggcc cgtactgatc ggcatcgacg acgtgcacca cgccgacgcg | 420 |
| ccgtcgctgc gctgcctgct ccacctcgcg cgccgcatca gccgggcccg tgtcgccatc | 480 |
| gtgctgaccg agctgctccg gccgacgccc gccactccc aattccgggc ggcactgctg | 540 |
| agtctgcgcc actaccagga gatcgcgctg cgcccgctca ccgaggcgca gaccaccgaa | 600 |
| ctcgtcgcgc ggcaccctcgg ccaggacgcg cacgacgacg tggtggccca ggcgttccgg | 660 |
| gcgaccggcg gcaacctgct cctcggccac ggctgatcg acgacatccg ggaggcacgg | 720 |
| acacggacct cagggtgcct ggaagtggtc gcggggcggg cgtaccggct cgcctacctc | 780 |

```
gggtcgctct atcgttgcgg cccggccgcg ctgagcgtcg cccgagcttc cgccgtgctc    840
ggcgagagtg tcgaactcac cctcgtccag cggatgaccg gcctcgacac cgaggcggtc    900
gagcaggccc acgaacagct ggtcgagggg cggctgctgc gggaagggcg gttcccgcac    960
cccgcggccc gctccgtcgt actcgacgac ctctccgccg ccgagcggcg tggcctgcac   1020
gagctggcgc tggaactgct gcgggaccgc ggcgtggcca gcaaggtgct cgcccgccac   1080
cagatgggta ccgccgggt gcacggcgcc gaggtcgccg gctgttcac cgacgccgcg    1140 cgcgagcacc acctgcgcgg cgagctcgac gaggccgtca cctacctgga gttcgcctac   1200
cgggcctccg acgaccccgc cgtccacgcc gcactgcgcg tcgacaccgc cgccatcgag   1260
cggctctgcg atcccgccag atccggccgg catgtgcccg agctgctcac cgcgtcgcgg   1320
gaacggctcc tctccagcga gcacgccgtg tcgctcgcct gctggctggc gatggacggg   1380
cggccgggcg aggccgccga ggtcctggcg gcccagcgct ccgccgcccc gagcgagcag   1440
ggccgggcgc acctgcgcgt cgcggacctg tccctcgcgc tgatctatcc cggcgcggcc   1500
gatccgccgc gtccggccga tccgccggcc gaggacgagg tcgcctcgtt ttccggagcc   1560
gtccggcacc gcgccgtcgc cgacaaggcc ctgagcaacg cgctgcgcgg ctggtccgaa   1620
caggccgagg ccaaagccga gtacgtgctc cagcactccc gggtcacgac ggaccggacc   1680
acgaccatga tggcgttgct ggccctgctc tacgccgagg acaccgatgc cgtccagtcc   1740
tgggtcgaca agctggccgg tgacgacaac atgcggaccc cggccgacga ggcggtccac   1800
gcggggttcc gcgccgaggc cgcgctgcgc gcggcgacc tgaccgccgc cgtcgaatgc   1860
ggcgaggccg cgctcgcccc ccgggtcgtg ccctcctggg ggatggccgc cgcattgccg   1920
ctgagcagca ccgtgccgc cgcgatccga ctgggcgacc tggaccgggc ggagcggtgg   1980
ctcgccgagc cgttgccgga ggagacctcc gacagcctct tcggactgca catggtctgg   2040
gcccgtgggc aacaccatct cgcggccggg cggtaccggg cggcgtacaa cgcgttccgg   2100
gactgcgggg agcggatgcg acgctggtcc gtcgacgtgc cggcctggc cctgtggcgg   2160 gtcgacgccg ccgaagcgct tctgctgctc ggccgcggcc gtgacgaggg gctgaggctc   2220
atctccgagc agctgtcccg gccgatgggg tcccgggcgc gggtgatgac gctgcgggtg   2280
caggcggcct acagtccgcc ggccaagcgg atcgaactgc tcgacgaggc cgccgatctg   2340
ctcatcatgt gccgcgacca gtacgagctg gcccgcgtcc tcgccgacat gggcgaagcg   2400
tgcggcatgc tccggcggca cagccgtgcg cggggactgt ccgccgcgc acggcacctc   2460 gcgacccagt gcggagccgt gccgctcctc cggcggctcg gtggggagtc ctcggacgcg   2520
gacggcaccc aggacgtgac gccggcgcag cggatcacat cgctgaccga ggcggagcgg   2580
cgggtggcgt cgcacgccgc ggtcgggcgc accaacaagg agatcgccag ccagctgttc   2640
gtcacctcca gcacggtgga acagcacctc accaacgtgt ccgcaagct gggggtgaag   2700 ggccgtcagc aactgcccaa ggaactgtcc gacgccggct ga                      2742
```

<210> SEQ ID NO 9
<211> LENGTH: 2742
<212> TYPE: DNA
<213> ORGANISM: Streptomyces ascomyceticus

<400> SEQUENCE: 9

```
atgatagcgc gcctgtctcc cccagacctg atcgcccgcg atgacgagtt cggttccctc     60
caccgggcgc tcacccgagc ggggggcggg cggggcgtcg tcgccgccgt caccgggccg    120
```

```
atcgcctgcg gcaagaccga actcctcgac gccgccgcgg ccaaggccgg cttcgtcacc    180
cttcgcgcgg tgtgctccat ggaggagcgg gccctgccgt acggcatgct cggccagctc    240
ctcgaccagc ccgagctggc cgcccggaca ccggagctgg tccggctgac ggcatcgtgc    300
gaaaacctgc cggccgacgt cgacaaccgc ctggggaccg aactcacccg cacggtgctg    360
acgctcgccg cggagcggcc cgtactgatc ggcatcgacg acgtgcacca cgccgacgcg    420
ccgtcgctgc gctgcctgct ccacctgcgc cgccgcatca gccgggcccg tgtcgccatc    480
gtgctgaccg agctgctccg gccgacgccc gcccactccc aattccgggc ggcactgctg    540
agtctgcgcc actaccagga gatcgcgctg cgcccgctca ccgaggcgca gaccaccgaa    600
ctcgtgcgcc ggcacctcgg ccaggacgcg cacgacgacg tggtggccca ggcgttccgg    660
gcgaccggcg gcaacctgct cctcggccac ggcctgatcg acgacatccg ggaggcacgg    720
acacggacct cagggtgcct ggaagtggtc gcggggcggg cgtaccggct cgcctacctc    780
gggtcgctct atcgttgcgg cccggccgcg ctgagcgtcg cccgagcttc gccgtgctc    840 ggcgagagtg tcgaactcac cctcgtccag cggatgaccg gcctcgacac cgaggcggtc    900
gagcaggccc acgaacagct ggtcgagggg cggctgctgc gggaagggcg gttcccgcac    960
cccgcggccc gctccgtcgt actcgacgac ctctccgccg ccgagcggcg tggcctgcac   1020
gagctggcgc tggaactgct gcgggaccgc ggcgtggcca gcaaggtgct cgcccgccac   1080
cagatgggta ccgccgggt gcacggcgcc gaggtcgccg gctgttcac cgacgccgcg   1140 cgcgagcacc acctgcgcgg cgagctcgac gaggccgtca cctacctgga gttcgcctac   1200
cgggcctccg acgaccccgc cgtccacgcc gcactgcgcg tcgacaccgc cgccatcgag   1260
cggctctgcg atcccgccag atccggccgg catgtgcccg agctgctcac cgcgtcgcgg   1320
gaacggctcc tctccagcga gcacgccgtg tcgctcgcct gctggctggc gatggacggg   1380
cggccgggcg aggccgccga ggtcctggcg gcccagcgct ccgccgcccc gagcgagcag   1440
ggccgggcgc acctgcgcgt cgcggacctg tccctcgcgc tgatctatcc cggcgcggcc   1500
gatccgccgc gtccggccga tccgccggcc gaggacgagg tcgcctcgtt ttccggagcc   1560
gtccggcacc gcgccgtcgc cgacaaggcc ctgagcaacg cgctgcgcgg ctggtccgaa   1620
caggccgagg ccaaagccga gtacgtgctc cagcactccc gggtcacgac ggaccggacc   1680
acgaccatga tggcgttgct ggccctgctc tacgccgagg acaccgatgc cgtccagtcc   1740
tgggtcgaca agctggccgg tgacgacaac atgcggaccc cggccgacga ggcggtccac   1800
gcggggttcc gcgccgaggc cgcgctgcgc gcggcgacc tgaccgccgc cgtcgaatgc   1860
ggcgaggccg cgctcgcccc ccgggtcgtg ccctcctggg ggatggccgc cgcattgccg   1920
ctgagcagca ccgtggccgc cgcgatccga ctgggcgacc tggaccgggc ggagcggtgg   1980
ctcgccgagc cgttgccgga ggagacctcc gacagcctct cggactgca catggtctgg   2040 gcccgtgggg aacaccatct cgcggccggg cggtaccggg cggcgtacaa cgcgttccgg   2100
gactgcgggg agcggatgcg acgctggtcc gtcgacgtgc cggcctggc cctgtggcgg   2160 gtcgacgccg ccgaagcgct tctgctgctc ggccgcggcc gtgacgaggg gctgaggctc   2220
atctccgagc agctgtcccg gccgatgggg tccggcgc gggtgatgac gctgcgggtg   2280
caggcggcct acagtccgcc ggccaagcgg atcgaactgc tcgacgaggc cgccgatctg   2340
ctcatcatgt gccgcgacca gtacgagctg gccgcgtcc tcgccgacat gggcgaagcg   2400
tgcggcatgc tccggcggca cagccgtgcg cggggactgt tccgccgcgc acggcacctc   2460
gcgacccagt gcggagccgt gccgctcctc cggcggctcg gtggggagtc ctcggacgcg   2520
```

-continued

| | |
|---|---|
| gacggcaccc aggacgtgac gccggcgcag cggatcacat cgctgaccga ggcggagcgg | 2580 |
| cgggtggcgt cgcacgccgc ggtcgggcgc accaacaagg agatcgccag ccagctgttc | 2640 |
| gtcacctcca gcacggtgga acagcacctc accaacgtgt ccgcaagct gggggtgaag | 2700 |
| ggccgtcagc aactgcccaa ggaactgtcc gacgccggct ga | 2742 |

<210> SEQ ID NO 10
<211> LENGTH: 2706
<212> TYPE: DNA
<213> ORGANISM: Micromonospora sp. S92-306401

<400> SEQUENCE: 10

| | |
|---|---|
| gtggagtttt acgacctggt cgcccgcgat gacgagctca gaaggttgga ccaggccctc | 60 |
| ggccgcgccg ccggcggacg gggtgtcgtg gtcaccgtca ccggaccggt cggctgcggc | 120 |
| aagaccgaac tgctggacgc ggccgcggcc gaggaggaat tcatcacgtt gcgtgcggtc | 180 |
| tgctcggccg aggagcgggc cctgccgtac gccgtgatcg ccaactcct cgaccatccc | 240 |
| gtactctccg cacgcgcgcc cgacctggcc tgcgtgacgg ctccgggccg gacgctgccg | 300 |
| gccgacaccg agaaccgcct cgccgcgac ctcacccggg ccctgctggc cctggcctcc | 360 |
| gaacgaccgg ttctgatctg catcgacgac gtgcaccagg ccgacaccgc ctcgctgaac | 420 |
| tgcctgctgc acctggcccg gcgggtcgcc tcggcccgga tcgccatgat cctcaccgag | 480 |
| ttgcgccggc tcaccccggc tcactcccgg ttcgaggcgg aactgctcag cctgcggcac | 540 |
| cgccacgaga tcgcgctgcg tcccctcggc cggccgaca ccgccgaact ggcccgcgcc | 600 |
| cggctcggcg ccggcgtcac cgccgacgag ctggcccagg tccacgaggc caccagcggg | 660 |
| aaccccaacc tggtcggagg cctggtcaac gacgtgcgag aggcctgggc ggccggtggc | 720 |
| acgggcattg cggcggggcg ggcgtaccgg ctggcgtacc tcagctccgt gtaccgctgt | 780 |
| ggtccggtcc cgttgcggat cgcccaggcg gggcggtgc tgggtcccag cgccaccgtc | 840 |
| acgctggtgc gccggatcag cgggctcgac gccgagacgg tggacgaggc gaccgcgatc | 900 |
| ctcaccgagg gcggcctgct ccgggaccac cggttcccgc atccggcggc ccgctcggtc | 960 |
| gtactcgacg acatgtccgc gcaggaacgc cgccgcctgc accggtccac gctggacgtg | 1020 |
| ctggacggcg tacccgtcga cgtgctcgcg caccaccagg ccggcgccgg tctgctgcac | 1080 |
| ggcccgcagg cggccgagat gttcgcccgg gccagccagg agctgcgggt acgcggcgag | 1140 |
| ctggacgccg cgaccgagta cctgcaactg gcctaccggg cctccgacga cgccggcgcc | 1200 |
| cgggccgccc tgcaggtgga gaccgtggcc ggcgagcgcc gccgcaaccc gctggccgcc | 1260 |
| agccggcacc tggacgagct ggccgccgcc gcccgggccg gcctgctgtc ggccgagcac | 1320 |
| gccgccctgg tcgtgcactg gctggccgac gccgacgac ccggcgaggc cgccgaggtg | 1380 |
| ctggcgctgc agcgggcgct ggccgtcacc gaccacgacc gggcccgcct gcgggcggcc | 1440 |
| gaggtgtcgc tcgcgctgtt ccaccccggc gtccccggtt cggacccgcg gcccctcgcg | 1500 |
| ccggaggagc tcgcgagcct gtccctgtcg gcccggcacg gtgtgaccgc cgacaacgcg | 1560 |
| gtgctggcgg cgctgcgcgg ccgtcccgag tcggccgccg ccgaggcgga gaacgtgctg | 1620 |
| cgcaacgccg acgccgccgc gtccggcccg accgccctgg ccgcgctgac ggccctgctc | 1680 |
| tacgccgaga acaccgacgc cgcccagctc tgggcggaca agctggccgc gggcatcggg | 1740 |
| gcgggggagg gggaggccgg ctacgcgggg ccgcggaccg tggccgccct gcgtcgcggc | 1800 |
| gacctgacca ccgcggtcca ggcggccggc gcggtcctgg accgcggccg gccgtcgtcg | 1860 |

```
ctcggcatca ccgccgtgtt gccgttgagc ggcgcggtcg ccgccgcgat ccggctgggc    1920
gagctcgagc gggccgagaa gtggctggcc gagccgctgc ccgaagccgt ccacgacagc    1980
ctgttcggcc tgcacctgct gatggcgcgg ggccgctaca gcctcgcggt gggccggcac    2040
gaggcggcgt acgccgcgtt ccgggactgc ggtgaacgga tgcgccggtg ggacgtcgac    2100
gtgcccgggc tggccctgtg gcgggtggac gcggccgagg cgctgctgcc cggcgatgac    2160
cgggcggagg gccggcggct gatcgacgag cagctcaccc ggccgatggg gccccggtca    2220
cgagccctga ccctgcgggt acgagcggcc tacgccccgc cggcgaaacg gatcgacctg    2280
ctcgacgaag cggccgacct gctgctctcc agcaacgacc agtacgagcg ggcacgggtg    2340
ctggccgacc tgagcgaggc gttcagccgc gctccggcaga acggccgggc gcgcggcatc    2400
ctgcggcagg cccggcacct ggccgcccag tgcggggcgg tccccctgct gcgccggctg    2460
ggcgtcaagg ccggccggtc cggtcggctc ggccggccgc cgcagggaat ccgctccctg    2520
accgaggccg agcgccgggt ggccacgctg ccgccgccg gcagaccaa ccgggagatc    2580 gccgaccagc tcttcgtcac cgccagcacg gtcgagcagc acctcaccaa cgtgttccgc    2640
aagctcggcg tgaagggccg ccagcaattg ccggccgagc tggccgacct gcggccgccg    2700
ggctga                                                              2706
```

<210> SEQ ID NO 11
<211> LENGTH: 2706
<212> TYPE: DNA
<213> ORGANISM: Micromonospora sp. S92-306401

<400> SEQUENCE: 11

```
atggagtttt acgacctggt cgcccgcgat gacgagctca gaaggttgga ccaggccctc      60
ggccgcgccg ccggcggacg gggtgtcgtg gtcaccgtca ccggaccggt cggctgcggc     120
aagaccgaac tgctggacgc ggccgcggcc gaggaggaat tcatcacgtt gcgtgcggtc     180
tgctcggccg aggagcgggc cctgccgtac gccgtgatcg ccaactcct cgaccatccc     240 gtactctccg cacgcgcgcc cgacctggcc tgcgtgacgg ctccggggccg gacgctgccg     300 gccgacaccg agaaccgcct gccgccgcgac ctcacccggg ccctgctggc cctggcctcc     360
gaacgaccgg ttctgatctg catcgacgac gtgcaccagg ccgacaccgc ctcgctgaac     420
tgcctgctgc acctggcccg gcgggtcgcc tcggccggga tcgccatgat cctcaccgag     480
ttgcgccggc tcaccccggc tcactcccgg ttcgaggcgg aactgctcag cctgcggcac     540
cgccacgaga tcgcgctgcg tcccctcggc ccggccgaca ccgccgaact ggcccgcgcc     600
cggctcggcg ccggcgtcac cgccgacgag ctggcccagg tccacgaggc caccagcggg     660
aaccccaacc tggtcggagg cctggtcaac gacgtgcgag aggcctgggc ggccggtggc     720
acgggcattg cggcggggcg ggcgtaccgg ctggcgtacc tcagctccgt gtaccgctgt     780
ggtccggtcc cgttgcggat cgcccaggcg gcggcggtgc tggtcccag cgccaccgtc     840 acgctggtgc gccggatcag cgggctcgac ccgagacgt ggacgaggc gaccgcgatc     900 ctcaccgagg gcggcctgct ccgggaccac cggttcccgc atccggcggc ccgctcggtc     960
gtactcgacg acatgtccgc gcaggaacgc gccgcctgc accggtccac gctgacgtg    1020 ctggacggcg taccgtcga cgtgctcgcg caccaccagg ccggcgccgg tctgctgcac    1080
ggcccgcagg cggccgagat gttcgcccgg gccagccagg agctgcgggt acgcggcgag    1140
ctggacgccg cgaccgagta cctgcaactg gcctaccggg cctccgacga cgccggcgcc    1200
cgggccgccc tgcaggtgga gaccgtggcc ggcgagcgcc gccgcaaccc gctggccgcc    1260
```

-continued

```
agccggcacc tggacgagct ggccgccgcc gcccgggccg gcctgctgtc ggccgagcac   1320
gccgccctgg tcgtgcactg gctggccgac gccggacgac ccggcgaggc cgccgaggtg   1380

ctggcgctgc agcgggcgct ggccgtcacc gaccacgacc gggcccgcct gcgggcggcc   1440
gaggtgtcgc tcgcgctgtt ccaccccggc gtccccggtt cggacccgcg gcccctcgcg   1500
ccggaggagc tcgcgagcct gtccctgtcg gcccggcacg gtgtgaccgc cgacaacgcg   1560
gtgctggcgg cgctgcgcgg ccgtcccgag tcggccgccg ccgaggcgga gaacgtgctg   1620
cgcaacgccg acgccgccgc gtccggcccg accgccctgg ccgcgctgac ggccctgctc   1680
tacgccgaga acaccgacgc cgcccagctc tgggcggaca agctggccgc gggcatcggg   1740
gcgggggagg gggaggccgg ctacgcgggg ccgcggaccg tggccgccct gcgtcgcggc   1800
gacctgacca ccgcggtcca ggcggccggc gcggtcctgg accgcggccg gccgtcgtcg   1860
ctcggcatca ccgccgtgtt gccgttgagc ggcgcggtcg ccgccgcgat ccggctgggc   1920
gagctcgagc gggccgagaa gtggctggcc gagccgctgc ccgaagccgt ccacgacagc   1980
ctgttcggcc tgcacctgct gatggcgcgg ggccgctaca gcctcgcggt gggccggcac   2040
gaggcggcgt acgccgcgtt ccgggactgc ggtgaacgga tgcgccggtg ggacgtcgac   2100
gtgcccgggc tggccctgtg gcgggtggac gcggccgagg cgctgctgcc cggcgatgac   2160
cgggcggagg gccggcggct gatcgacgag cagctcaccc ggccgatggg gccccggtca   2220
cgagccctga ccctgcgggt acgagcggcc tacgccccgc cggcgaaacg gatcgacctg   2280
ctcgacgaag cggccgacct gctgctctcc agcaacgacc agtacgagcg ggcacgggtg   2340
ctggccgacc tgagcgaggc gttcagcgcg ctccggcaga acggccgggc gcgcggcatc   2400
ctgcggcagg cccggcacct ggccgcccag tgcggggcgg tccccctgct gcgccggctg   2460
ggcgtcaagg ccggccggtc cggtcggctc ggccggccgc cgcagggaat ccgctccctg   2520
accgaggccg agcgccgggt ggccacgctg gccgccgccg ggcagaccaa ccgggagatc   2580
gccgaccagc tcttcgtcac cgccagcacg gtcgagcagc acctcaccaa cgtgttccgc   2640
aagctcggcg tgaagggccg ccagcaattg ccggccgagc tggccgacct gcggccgccg   2700
ggctga                                                              2706
```

<210> SEQ ID NO 12
<211> LENGTH: 2616
<212> TYPE: DNA
<213> ORGANISM: Streptomyces violaceusniger

<400> SEQUENCE: 12

```
gtggtcaccg tcaccggccc aatcgcctgc ggcaagacag aactgcttga cgcggctgcc     60
gcgaaggctg aggccatcat tctgcgcgcg gtctgcgcgc cagaagagcg ggctatgccg    120
tacgccatga tcgggcagct catcgacgac ccggcgctcg cgcatcgggc gccggggctg    180
gctgatcgga tagcccaggg cgggcagctg tcgctgaggg ccgagaaccg actgcgcagg    240
gatctcaccc gtgccctgct ggcgcttgcc gtcgaccggc ctgtgctgat cggcgtcgac    300
gatgtgcatc acgccgacac cgcctctttg aactgtctgc tgcatttggc gcgccgggtc    360
cgtccggccc ggatatccat gatcttcacc gagttgcgca gcctcacccc tactcagtca    420
cggttcaagg cggagctgct cagcctgccg taccaccacg agatcgcgct gcgtccgttc    480
ggaccggagc aatcggcgga gctggcccgc gccgccttcg gcccgggcct cgccgaggat    540
gtgctcgtgg ggttgtataa aacgaccagg ggcaatctga gtctcagccg tggactgatc    600
```

```
agcgatgtgc gggaggccct ggccaacgga gagagcgcct cgaggcgggg ccgcgcgttc    660
cggctggcgt acctcggctc gctctaccgc tgtggcccgg tcgcgctgcg ggtcgcccga    720
gtggctgccg tgctgggccc gagcgccacc accacgctgg tgcgccgtct aagcgggctc    780
agcgcggaga cgatagaccg ggcaaccaag atcctcaccg agggcgggct gctgctcgac    840
cagcagttcc cgcacccggc cgcccgctcg gtggtgcttg atgacatgtc cgcccaggaa    900
cgacgcggcc tgcacactct cgccctggaa ctgctggacg aggcgccggt tgaagtgctc    960
gcgcaccacc aggtcggcgc cggtctcata cacgggccca aggctgcgga gatgttcgcc   1020
aaggccggca aggctctggt cgtacgcaac gagttgggcg acgcggcaga atacctgcaa   1080
ctggctcacc gggcctccga cgatgtctcc acccgggccg ccttacgggt cgaggccgtg   1140
gcgatcgagc gccgccgcaa tccgctggcc tccagtcggc acatggacga gctgagcgcc   1200
gccggccgcg ccggtctgct ttcccccaag catgcgcgcg tggccgtctt ctggctggcc   1260
gacggcgggc gatccggcga ggcagccgag gtgctggcgt cggaacgccc gctagcgacc   1320
accgatcaga accgggccca cttgcgattt gtcgaggtga ctctcgcgct gttctctccc   1380
ggcgccttcg gatcggaccg gcgcccacct ccgctgacgc cggacgaact cgccagcctg   1440
ccgaaggcgg cctggcaatg cgcggtcgcc gacaacgcgg ccatgaccgc cttgcacggt   1500
catccagaac ttgccaccgc tcaggcggaa acagttctgc ggcaggctga ttcggcagcc   1560
gacgcgatcc ccgccgcgct gatcgccctg ttgtacgcgg agaacaccga gtccgctcat   1620
atctgggccg acaagctggg cagcacgaat ggcggggtat cgaacgaggc ggaagcgggc   1680
tacgccggcc cgtgcgccga gatcgccctg cggcgcggcg acctggccac ggcgttcgag   1740
gctggtagca ccgtcctgga cgaccggtcg ctgccgtcgc tcggcatcac cgccgcattg   1800
ctgttgagca gcaagacggc cgccgctgtc cggctgggcg aactcgagcg tgcggagaag   1860
ctgctcgccg agccgcttcc gaacggcgtc caggacagcc ttttcggtct gcacctgctc   1920
tcggcatacg gccagtacag cctcgcgatg ggccgatatg aatcggctct ccgggcgttt   1980
cacacctgcg gagaacgtat gcgcagctgg gatgttgacg tgcctggtct ggccctgtgg   2040
cgtgtcgacg ccgccgaggc gctgctcagc ctcgaccgga acgagggcca gcggctcatc   2100
gacgaacaac tcaccgtcc gatggggcct cgttccgcg cgttaacgct gcggatcaag     2160
gcggcatacc tcccgcggac gaagcggatc cccctgctcc atgaggcggc cgagctgctg   2220
ctcccctgcc ccgacccgta cgagcaagcg cgggtgctcg ccgatctggg cgacacgctc   2280
agcgcgctca gacgctatag ccgggcgcgg ggagttctcc ggcaggctcg tcacctggcc   2340
gcccagtgcg gtgctgtccc gctgctgcgc aggctcgggg gcgagcccgg ccggatcgac   2400
gacgccggcc tgccgcagcg gagcacatcg ttgaccgatg cggagcggcg ggtggcggcg   2460
ctggccgcgg ccggacagac caaccgggag atcgccaaac agctgttcgt cacggccagc   2520
acagtggaac agcacctcac aagcgtcttc cgcaaactgg gggtcaaggg tcgcaagcag   2580
ctgccgaccg cgctggccga cgtggaacag acctga                            2616

<210> SEQ ID NO 13
<211> LENGTH: 2721
<212> TYPE: DNA
<213> ORGANISM: Streptomyces violaceusniger

<400> SEQUENCE: 13
atgtatagcg gtacctgccg tgaaggatac gaactcgtcg cacgcgagga cgaactcggc      60
attctacaga ggtctctgga acaagcgagc agcggccagg gcgtcgtggt caccgtcacc     120
```

-continued

```
ggcccaatcg cctgcggcaa gacagaactg cttgacgcgg ctgccgcgaa ggctgaggcc    180
atcattctgc gcgcggtctg cgcgccagaa gagcgggcta tgccgtacgc catgatcggg    240
cagctcatcg acgacccggc gctcgcgcat cgggcgccgg gctggctga tcggatagcc     300 cagggcgggc agctgtcgct gagggccgag aaccgactgc gcaggatct cacccgtgcc     360 ctgctggcgc ttgccgtcga ccggcctgtg ctgatcggcg tcgacgatgt gcatacgcc     420 gacaccgcct ctttgaactg tctgctgcat ttggcgcgcc gggtccgtcc ggcccggata    480
tccatgatct tcaccgagtt gcgcagcctc accctactc agtcacggtt caaggcggag     540
ctgctcagcc tgccgtacca ccacgagatc gcgctgcgtc cgttcggacc ggagcaatcg    600
gcggagctgg cccgcgccgc cttcggcccg ggcctcgccg aggatgtgct cgtggggttg    660
tataaaacga ccaggggcaa tctgagtctc agccgtggac tgatcagcga tgtgcgggag    720
gccctggcca acggagagag cgccttcgag gcgggccgcg cgttccggct ggcgtacctc    780
ggctcgctct accgctgtgg cccggtcgcg ctgcgggtcg cccgagtggc tgccgtgctg    840
ggcccgagcg ccaccaccac gctggtgcgc cgtctaagcg ggctcagcgc ggagacgata    900
gaccgggcaa ccaagatcct caccgagggc gggctgctgc tcgaccagca gttcccgcac    960
ccggccgccc gctcggtggt gcttgatgac atgtccgccc aggaacgacg cggcctgcac   1020
actctcgccc tggaactgct ggacgaggcg ccggttgaag tgctcgcgca ccaccaggtc   1080
ggcgccggtc tcatacacgg gcccaaggct gcggagatgt cgccaaggc cggcaaggct    1140 ctggtcgtac gcaacgagtt gggcgacgcg gcagaatacc tgcaactggc tcaccggggcc  1200 tccgacgatg tctccacccg ggccgccctg cgggtcgagg ccgtggcgat cgagcgccgc   1260
cgcaatccgc tggcctccag tcggcacatg gacgagctga gcgccgccgg ccgcgccggt   1320
ctgctttccc ccaagcatgc ggcgctggcc gtcttctggc tggccgacgg cgggcgatcc   1380
ggcgaggcag ccgaggtgct ggcgtcggaa cgcccgctag cgaccaccga tcagaaccgg   1440
gcccacttgc gatttgtcga ggtgactctc gcgctgttct ctcccggcgc cttcggatcg   1500
gaccggcgcc cacctccgct gacgccggac gaactcgcca gcctgccgaa ggcggcctgg   1560
caatgcgcgg tcgccgacaa cgcggccatg accgccttgc acggtcatcc agaacttgcc   1620
accgctcagg cggaaacagt tctgcggcag gctgattcgg cagccgacgc gatccccgcc   1680
gcgctgatcg ccctgttgta cgcggagaac accgagtccg ctcatatctg ggccgacaag   1740
ctgggcagca cgaatggcgg ggtatcgaac gaggcggaag cgggctacgc cggcccgtgc   1800
gccgagatcg ccctgcgggcg cggcgacctg gccacgcgcgt tcgaggctgg tagcaccgtc  1860
ctggacgacc ggtcgctgcc gtcgctcggc atcaccgccg cattgctgtt gagcagcaag   1920 acggccgcc ctgtccggct gggcgaactc gagcgtgcgg agaagctgct cgccgagccg     1980
cttccgaacg gcgtccagga cagccttttc ggtctgcacc tgctctcggc atacggccag   2040
tacagcctcg cgatgggccg atatgaatcg gctctccggg cgtttcacac ctgcggagaa   2100
cgtatgcgca gctgggatgt tgacgtgcct ggtctggccc tgtggcgtgt cgacgccgcc   2160
gaggcgctgc tcagcctcga ccggaacgag ggccagcggc tcatcgacga acaactcacc   2220
cgtccgatgg ggcctcgttc ccgcgcgctg acgctgcgga tcaaggcggc atacctcccg   2280
cggacgaagc ggatccccct gctccatgag gcggccgagc tgctgctccc ctgccccgac   2340
ccgtacgagc aagcgcgggt gctcgccgat ctgggcgaca cgctcagcgc gctcagacgc   2400
tatagccggg cgcggggagt tctccggcag gctcgtcacc tggccgccca gtgcggtgct   2460
```

```
gtcccgctgc tgcgcaggct cggggggcgag cccggccgga tcgacgacgc cggcctgccg   2520
cagcggagca catcgttgac cgatgcgag cggcgggtgg cggcgctggc cgcggccgga     2580
cagaccaacc gggagatcgc caaacagctg ttcgtcacgg ccagcacagt ggaacagcac   2640
ctcacaagcg tcttccgcaa actgggggtc aagggtcgca agcagctgcc gaccgcgctg   2700
gccgacgtgg aacagacctg a                                               2721

<210> SEQ ID NO 14
<211> LENGTH: 2745
<212> TYPE: DNA
<213> ORGANISM: Streptomyces hygroscopicus

<400> SEQUENCE: 14
atgcctgccg tggagagcta tgaactggac gcccgcgatg acgagctcag aagactggag     60
gaggcggtag gccaggcggg caacggccgg ggtgtggtgg tcaccatcac cgggccgatc    120
gcctgcggca agaccgaact gctcgacgcg gccgccgcga agagcgacgc catcacatta    180
cgtgcggtct gctcccgagga ggaacgggcc ctcccgtacg ccctgatcgg gcagctcatc    240
gacaacccgg cggtcgcctc ccagctgccg gatccggtct ccatggccct cccgggcgag    300
cacctgtcgc cggaggccga gaaccggctg cgcggcgacc tcacccgtac cctgctggcg    360
ctcgccgccg aacggccggt gctgatcggc atcgacgaca tgcaccacgc cgacaccgcc    420
tctttgaact gcctgctcca cctggccagg agggtcggcc cggcccggat cgccatggtc    480
ctcaccgagc tgcgccggct caccccggcc cactcccagt tccacgccga gctgctcagc    540
ctggggcacc accgcgagat cgcgctgcgc ccgctcggcc gaagcacat cgccgagctg     600 gcccgcgccg gcctcggtcc cgatgtcgac gaggacgtgc tcacggggtt gtaccgggcg    660
accgcggcca acctgaacct cggccacgga ctgatcaagg atgtgcggga ggcctgggcg    720
acgggcggga cgggcatcaa cgcgggccgc gcgtaccggc tggcgtacct cggttccctc    780
taccgctgcg gcccggtccc gttgcgggtc gcacgggtgg ccgccgtgct gggccagagc    840
gccaacacca ccctggtgcg ctggatcagc gggctcaacg cggacgcggt gggcgaggcg    900
accgagatcc tcaccgaggg cggcctgctg cacgacctgc ggttcccgca tccgcggcc    960 cgttcggtcg tactcaacga cctgtccgcc cgggaacgcc gccgactgca ccggtccgct   1020
ctggaagtgc tggatgacgt acccgttgaa gtggtcgcgc accaccaggc cggtgccggt   1080
ttcatccacg gtcccaaggc cgccgagatc ttcgccaagg ccggccagga gctgcatgtg   1140
cgcggcgagc tggacgccgc gtccgactat ctgcaactgg cccaccacgc ctccgacgac   1200
gccgtcaccc gggccgcgct gcgggtcgag gccgtggcga tcgagcgccg ccgcaacccg   1260
ctggcctcca gccgccacct cgacgagctg accgtcgccg cccgtgccgg tctgctctcc   1320
ctcgagcacg ccgcgctgat gatccgctgg ctggctctcg gcgggcggtc cggcgaggcg   1380
gccgaggtgc tggccgcgca gcgcccgcgt gcggtcaccg accaggacag ggcccacctg   1440
cgggccgccg aggtatcgct ggcgctggtc agcccgggcg cgtccggcgt cagcccgggt   1500
gcgtccggcc cggatcggcg gccgcgtccg ctcccgccgg atgagctcgc gaacctgccg   1560
aaggcggccc ggctttgtgc gatcgccgac aacgccgtca tatcggccct gcacggtcgt   1620
cccgagcttg cctcggccga ggcggagaac gtcctgaagc aggctgactc ggcggcggac   1680
ggcgccaccg ccctctcccg gctgacggcc ttgctgtacg cggagaacac cgacaccgct   1740
cagctctggg ccgacaagct cgtctccgag accggggcgt cgaacgagga ggaaggcgcg   1800
ggctacgcgg ggccgcgcgc cgagaccgcg ttgcgccgcg gcgacctggc cgcggcggtc   1860
```

```
gaggcgggca gcgccattct ggaccaccgg cggggtcgt tgctcggcat caccgccgcg   1920
ctaccgctga gcagcgcggt agccgccgcc atcggctgg gcgagaccga gcgggcggag   1980
aagtggctcg ccgagccgct gccggaggcc attcgggaca gcctgttcgg gctgcacctg   2040
ctctcggcgc gcgccagta ctgcctcgcg acgggccggc acgagtcggc gtacacggcg   2100
ttccgcacct gcggggaacg gatgcggaac tggggcgtcg acgtgccggg tctgtccctg   2160
tggcgcgtcg acgccgccga ggcgctgctg cacggccgcg accgggacga gggccgacgg   2220
ctcatcgacg agcagctcac ccatgcgatg ggaccccgtt ccgcgctttt gacgctgcgg   2280
gtgcaggcgc gtacagccc gcaggcgcag cgggtcgacc tgctcgaaga ggcggccgac   2340
ctgctgctct cctgcaacga ccagtacgag cgggcgcggg tgctcgccga tctgagcgag   2400
gcgttcagcg cgctcaggca ccacagccgg gcgcggggac tgctccggca ggcccggcac   2460
ctggccgccc agtgcggcgc gaccccgctg ctgcgccggc tcggggccaa gcccggaggc   2520
cccggctggc tggaggaatc cggcctgccg cagcggatca gtcgctgac cgacgcggag   2580 cggcgggtgg cgtcgctggc cgccggcggc cagaccaacc gcgtgatcgc cgaccagctc   2640
ttcgtcacgg ccagcacggt ggagcagcac ctcacgaacg tcttccgcaa gctgggcgtc   2700
aagggccgcc agcacctgcc ggccgaactc gccaacgcgg aatag              2745

<210> SEQ ID NO 15
<211> LENGTH: 2745
<212> TYPE: DNA
<213> ORGANISM: Streptomyces hygroscopicus

<400> SEQUENCE: 15
atgcctgccg tggagagcta tgaactggac gcccgcgatg acgagctcag aagactggag    60
gaggcggtag gccaggcggg caacggccgg ggtgtggtgg tcaccatcac cgggccgatc   120
gcctgcggca agaccgaact gctcgacgcg ccgccgcga agagcgacgc catcacactg   180
cgtgcggtct gctccgagga ggaacgggcc ctcccgtacg ccctgatcgg gcagctcatc   240
gacaacccgg cggtcgcctc ccagctgccg gatccggtct ccatggccct cccgggcgag   300
cacctgtcgc cggaggccga gaaccggctg gcgcggccacc tcacccgtac cctgctggcg   360
ctcgccgccg aacggccggt gctgatcggc atcgacgaca tgcaccacgc cgacaccgcc   420
tctttgaact gcctgctcca cctggcccgg agggtcggcc cggccggat cgccatggtc   480 ctcaccgagc tgcgccggct cacccccggcc cactcccagt ccacgccga gctgctcagc   540 ctggggcacc accgcgagat cgcgctgcgc ccgctcggcc cgaagcacat cgccgagctg   600
gcccgcgccg gcctcggtcc cgatgtcgac gaggacgtgc tcacggggtt gtaccgggcg   660 accgcggca acctgaacct cggccacgga ctgatcaagg atgtgcggga ggcctgggcg   720
acgggcggga cgggcatcaa cgcgggccgc gcgtaccggc tggcgtacct cggttccctc   780
taccgctgcg gcccggtccc gttgcgggtc gcacgggtgg ccgccgtgct gggccagagc   840
gccaacacca ccctggtgcg ctggatcagc gggctcaacg cggacgcggt gggcgaggcg   900
accgagatcc tcaccgaggg cggcctgctg cacgacctgc ggttcccgca tccggcggcc   960
cgttcggtcg tactcaacga cctgtccgcc cgggaacgcc gccgactgca ccggtccgct  1020
ctggaagtgc tggatgacgt acccgttgaa gtggtcgcgc accaccaggc cggtgccggt  1080
ttcatccacg gtcccaaggc cgccgagatc ttcgccaagg ccggccagga gctgcatgtg  1140
cgcggcgagc tggacgccgc gtccgactat ctgcaactgg cccaccacgc ctccgacgac  1200
```

-continued

```
gccgtcaccc gggccgcgct gcgggtcgag gccgtggcga tcgagcgccg ccgcaacccg    1260
ctggcctcca gccgccacct cgacgagctg accgtcgccg cccgtgccgg tctgctctcc    1320
ctcgagcacg ccgcgctgat gatccgctgg ctggctctcg gcgggcggtc cggcgaggcg    1380
gccgaggtgc tggccgcgca cgcccgcgct gcggtcaccg accaggacag ggcccacctg    1440
cgggccgccg aggtatcgct ggcgctggtc agcccgggcg cgtccggcgt cagcccgggt    1500
gcgtccggcc cggatcggcg gccgcgtccg ctcccgccgg atgagctcgc gaacctgccg    1560
aaggcggccc ggctttgtgc gatcgccgac aacgccgtca tatcggccct gcacggtcgt    1620
cccgagcttg cctcggccga ggcggagaac gtcctgaagc aggctgactc ggcggcggac    1680
ggcgccaccg ccctctccgc gctgacggcc ttgctgtacg cggagaacac cgacaccgct    1740
cagctctggg ccgacaagct cgtctccgag accggggcgt cgaacgagga ggaaggcgcg    1800
ggctacgcgg ggccgcgcgc cgagaccgcg ttgccgccgc gcgacctggc cgcggcggtc    1860
gaggcgggca cgccattct ggaccaccgg cggggtcgt tgctcggcat caccgccgcg    1920
ctaccgctga gcagcgcgt agccgccgcc atccggctgg gcgagaccga gcgggcggag    1980
aagtggctcg ccgagccgct gccggaggcc attcgggaca gcctgttcgg gctgcacctg    2040
ctctcggcgc gcgccagta ctgcctcgcg acgggccggc acgagtcggc gtacacggcg    2100
ttccgcacct gcgggaacg gatgcggaac tggggcgtcg acgtgccggg tctgtccctg    2160
tggcgcgtcg acgccgccga ggcgctgctg cacggccgcg accgggacga gggccgacgg    2220
ctcatcgacg agcagctcac ccatgcgatg ggaccccgtt ccgcgctttt gacgctgcgg    2280
gtgcaggcgg cgtacagccc gcaggcgcag cgggtcgacc tgctcgaaga ggcggccgac    2340
ctgctgctct cctgcaacga ccagtacgag cgggcgcggg tgctcgccga tctgagcgag    2400
gcgttcagcg cgctcaggca ccacagccgg gcgcggggac tgctccggca ggcccggcac    2460
ctggccgccc agtgcggcgc gaccccgctg ctgcgccggc tcggggccaa gcccggaggc    2520
cccgctggt tggaggaatc cggcctgccg cagcggatca agtcgctgac cgacgcggag    2580
cggcgggtgg cgtcgctggc cgccggcggc cagaccaacc gcgtgatcgc cgaccagctc    2640
ttcgtcacgg ccagcacggt ggagcagcac ctcacgaacg tcttccgcaa gctgggcgtc    2700
aagggccgcc agcacctgcc ggccgaactc gccaacgcgg aatag                   2745
```

<210> SEQ ID NO 16
<211> LENGTH: 2619
<212> TYPE: DNA
<213> ORGANISM: Actinoplanes sp. N01-109

<400> SEQUENCE: 16

```
gtgaagcgca acgatctggt tgcccgcgat ggcgagctca ggtggatgca agagattctc      60
agtcaggcga gcgagggccg gggggccgtg gtcaccatca cggggggcgat cgcctgtggc    120
aagacggtgc tgctggacgc cgcggcagcc agtcaagacg tgatccaact gcgtgcggtc    180
tgctcggcga aggagcagga gctgccgtac gcgatggtcg acaactact cgacaatccg    240
gtgctcgccg cgcgagtgcc ggccctgggc aacctggctg cggcgggcga gcggctgctg    300
ccgggcaccg agaacaggat ccggcggag ctcacccgca ccctgctggc tctcgccgac    360
gaacgaccgg tgctgatcgg cgtcgacgac atgcaccatg cggaccccgc ctcgctggac    420
tgcctgctgc acctggccgc gcgggtcggc ccggccgcga tcgcgatcgt tctgaccgag    480
ttgcgccggc tcaccccggc tcactcgcgc ttccagtccg agctgctcag cctgcggtac    540
caccacgaga tcgggttgca gccgctcacc gcggagcaca ccgccgacct ggcccgcgtc    600
```

```
ggcctcggtg ccgaggtcga cgacgacgtg ctcaccgagc tctacgaggc gaccggcggc      660
aacccgagtc tgtgctgcgg cctgatcagg acgtgcggc aggactggga ggccggggtc      720
accggtatcc acgtcggccg ggcgtaccgg ctggcctatc tcagttcgct ctaccgctgc      780
ggcccggcgg cgctgcggac cgcccgcgcg gccgcggtgc tgggcgacag cgccgacgcc      840
tgcctgatcc gccgggtcag cggcctcggt acggaggccg tgggccaggc gatccagcag      900
ctcaccgagg gcggcctgct gcgtgaccag cagttcccgc acccggcggc ccgctcggtc      960
gtgctcgacg acatgtccgc gcaggaacgc cacgcgatgt atcgcagcgc ccgggaggca     1020
gccgccgaag tcaggccga ccccggcacc cgggcgagc cgcgggcggc tacggcgtac       1080
gccgggtgtg gtgagcaagc cggtgactac ccggagccgg ccggccgggc ctgcgtggac     1140
ggtgccggtc cggccgagta ctgcggcgac ccgcacggcg ccgacgacga cccggacgag     1200
ctggtcgccg cgctgggcgg gctgctgccg agccggctcg tggcgatgaa gatccggcgc     1260
ctggcggtgg ccgggcgccc cggggcggct gccgagctgc tgacctcgca gcggttgcac     1320
gcggtgacca gcgaggaccg ggccagcctg cgggccgccg aggtggcgct cgccacgctg     1380
tggccgggtg cgaccggccc ggaccggcat ccgctcacgg agcaggaggc ggcgagcctg     1440
ccggagggtc cgcgcctgct cgctgccgcc gacgatgccg tcggggccgc cctgcgcggt     1500
cgcgccgagt acgccgcggc cgaggcggag aacgtcctgc ggcacgccga tccggcagcc     1560
ggtggtgacg cctacgccgc catgatcgcc ctgctgtaca cggagcaccc cgagaacgtg     1620
ctgttctggg ccgacaagct cgacgcgggc cgccccgacg aggagaccag ttatcccggg     1680
ctgcgggccg agaccgcggt gcggctcggt gacctggaaa cggcgatgga gctgggccgc     1740
acggtgctgg accagcggcg gctgccgtcc ctgggtgtcg ccgcgggcct gctcctgggc     1800
ggcgcggtga cggccgccat ccggctcggc gacctcgacc gggcggagaa gtggctcgcc     1860
gagccgatcc ccgacgccat ccgtaccagc ctctacggcc tgcacgtgct ggccgcgcgg     1920
ggccggctcg acctggccgc gggccgctac gaggcggcgt acacggcgtt ccggctgtgt     1980
ggcgagcgga tggcaggctg ggatgccgat gtctccgggc tggcgctgtg gcgcgtcgac     2040
gccgccgagg ccctgctgtc cgcgggcatc cgcccggacg agggccgcaa gctcatcgac     2100
gaccagctca cccgtgagat gggggcccgc tcccgggcgc tgacgctgcg ggcgcaagcg     2160
gcgtacagcc tgccggtgca ccgggtgggc ctgctcgacg aggcggccgg cctgctgctc     2220
gcctgccatg acgggtacga gcgggcgcgg gtgctcgcgg acctggggga gaccctgcgc     2280
acgctgcggc acaccgacgc ggcccagcgg gtgctccggc aggccgagca ggcggccgcg     2340
cggtgcgggt cggtcccgct gctgcggcgg ctcggggccg aacccgtacg catcggcacc     2400
cggcgtggtg aacccggcct gccgcagcgg atcaggctgc tgaccgatgc cgagcggcgg     2460
gttgccgcga tggccgccgc cgggcagacc aaccgggaga tcgccggtcg gctcttcgtc     2520
acggccagca cggtggagca gcacctgacc agcgtcttcc gcaagctggg cgtcaagggc     2580
cgccggttcc tgccgaccga gctcgcccaa gccgtctga                             2619
```

<210> SEQ ID NO 17
<211> LENGTH: 2628
<212> TYPE: DNA
<213> ORGANISM: Actinoplanes sp. N01-109

<400> SEQUENCE: 17

```
atgcctgccg tgaagcgcaa cgatctggtt gcccgcgatg gcgagctcag gtggatgcaa      60
```

| | |
|---|---|
| gagattctca gtcaggcgag cgagggccgg ggggccgtgg tcaccatcac gggggcgatc | 120 |
| gcctgtggca agacggtgct gctggacgcc gcggcagcca gtcaagacgt gatccaactg | 180 |
| cgtgcggtct gctcggcgga ggagcaggag ctgccgtacg cgatggtcgg acaactactc | 240 |
| gacaatccgg tgctcgccgc gcgagtgccg gccctgggca acctggctgc ggcgggcgag | 300 |
| cggctgctgc cgggcaccga aacaggatc cggcgggagc tcacccgcac cctgctggct | 360 |
| ctcgccgacg aacgaccggt gctgatcggc gtcgacgaca tgcaccatgc ggaccccgcc | 420 |
| tcgctggact gcctgctgca cctggcccgg cgggtcggcc cggcccgcat cgcgatcgtt | 480 |
| ctgaccgagt tgcgccggct caccccggct cactcgcgct tccagtccga gctgctcagc | 540 |
| ctgcggtacc accacgagat cgggttgcag ccgctcaccg cggagcacac cgccgacctg | 600 |
| gcccgcgtcg gcctcggtgc cgaggtcgac gacgacgtgc tcaccgagct ctacgaggcg | 660 |
| accggcggca acccgagtct gtgctgcggc ctgatcaggg acgtgcggca ggactgggag | 720 |
| gccggggtca ccggtatcca cgtcggccgg gcgtaccggc tggcctatct cagttcgctc | 780 |
| taccgctgcg gccggcggc gctgcggacc ccccgcgcgg ccgcggtgct gggcgacagc | 840 |
| gccgacgcct gcctgatccg cccgggtcag ggcctcggta cggaggccgt gggccaggcg | 900 |
| atccagcagc tcaccgaggg cggcctgctg cgtgaccagc agttcccgca cccggcggcc | 960 |
| cgctcggtcg tgctcgacga catgtccgcg caggaacgcc acgcgatgta tcgcagcgcc | 1020 |
| cgggaggcag ccgccgaagg tcaggccgac cccggcaccc cgggcgagcc gcgggcggct | 1080 |
| acggcgtacg ccgggtgtgg tgagcaagcc ggtgactacc ggagccggc cggccgggcc | 1140 |
| tgcgtggacg gtgccggtcc ggccgagtac tgcggcgacc cgcacggcgc cgacgacgac | 1200 |
| ccggacgagc tggtcgccgc gctgggcggg ctgctgccga gccggctcgt ggcgatgaag | 1260 |
| atccggcgcc tggcggtggc cgggcgcccc ggggcggctg ccgagctgct gacctcgcag | 1320 |
| cggttgcacg cggtgaccag cgaggaccgg gccagcctgc gggccgccga ggtggcgctc | 1380 |
| gccacgctgt ggccgggtgc gaccggcccg gaccggcatc cgctcaccga gcaggaggcg | 1440 |
| gcgagcctgc cggagggtcc gcgcctgctc gctgccgccg acgatgccgt cggggccgcc | 1500 |
| ctgcgcggtc gcgccgagta cgccgcgcc gaggcggaga acgtcctgcg gcacgccgat | 1560 |
| ccggcagccg gtggtgacgc ctacgccgcc atgatcgccc tgctgtacac ggagcacccc | 1620 |
| gagaacgtgc tgttctgggc cgacaagctc gacgcgggcc gccccgacga ggagaccagt | 1680 |
| tatcccgggc tgcgggccga gaccgcggtg cggctcggtg acctggaaac ggcgatggag | 1740 |
| ctgggccgca cggtgctgga ccagcggcgg ctgccgtccc tgggtgtcgc cgcgggcctg | 1800 |
| ctcctgggcg gcgcggtgac ggccgccatc cggctcggcg acctcgaccg ggcggagaag | 1860 |
| tggctcgccg agccgatccc cgacgccatc cgtaccagcc tctacggcct gcacgtgctg | 1920 |
| gccgcgcggg gccggctcga cctggccgcg ggccgctacg aggcggcgta cacggcgttc | 1980 |
| cggctgtgtg gcgagcggat ggcaggctgg gatgccgatg tctccgggct ggcgctgtgg | 2040 |
| cgcgtcgacg ccgccgaggc cctgctgtcc gcgggcatcc gccggacga gggccgcaag | 2100 |
| ctcatcgacg accagctcac ccgtgagatg ggggcccgct cccgggcgct gacgctgcgg | 2160 |
| gcgcaagcgg cgtacagcct gccggtgcac cgggtgggcc tgctcgacga ggcggccggc | 2220 |
| ctgctgctcg cctgccatga cgggtacgag cgggcgcggg tgctcgcgga cctggggag | 2280 |
| accctgcgca cgctgcggca caccgacgcg cccagcgggg tgctccggca ggccgagcag | 2340 |
| gcggccgcgc ggtgcgggtc ggtcccgctg ctgcggcggg tcggggccga accgtacgc | 2400 |
| atcggcaccc ggcgtggtga accgggcctg ccgcagcgga tcaggctgct gaccgatgcc | 2460 |

```
gagcggcggg ttgccgcgat ggccgccgcc gggcagacca accgggagat cgccggtcgg    2520
ctcttcgtca cggccagcac ggtggagcag cacctgacca gcgtcttccg caagctgggc    2580
gtcaagggcc gccggttcct gccgaccgag ctcgcccaag ccgtctga                 2628
```

<210> SEQ ID NO 18
<211> LENGTH: 2616
<212> TYPE: DNA
<213> ORGANISM: Streptomyces malaysiensis

<400> SEQUENCE: 18

```
gtggtcaccg tcaccggccc aatcgcctgc ggcaagacag aactgcttga cgcggctgcc     60
gcgaaggctg aggccatcat tctgcgcgcg gtctgcgcgc cagaagagcg ggctatgccg    120
tacgccatga tcgggcagct catcgacgac ccggcgctcg cgcatcgggc gccggggctg    180
gctgatcgga tagcccaggg cgggcagctg tcgctgaggg ccgagaaccg actgcgcagg    240
gatctcaccc gtgccctgct ggcgcttgcc gtggaccggc ctgtgctgat cggcgtcgac    300
gatgtgcatc acgccgacac cgcctctttg aactgtctgc tgcatttggc ccgccgggtc    360
cgtccggccc ggatatccat gatcttcacc gagttgcgca gcctcacccc tactcagtca    420
cggttcaagg cggagctgct cagcctgcca taccaccacg agatcgcgct gcgtccattc    480
ggaccggagc aatcggcgga gctggctcgc gccgccttcg gcccgggcct cgccgaggat    540
gtgctcgcgg ggttgtataa aacgaccagg ggcaatctga gtctcagccg tggactgatc    600
agcgatgtgc gggaggccct ggccaacgga gagagcgctt cgaggcgggc cgcgcgttc     660 cggctggcgt acctcagctc gctctaccgc tgtggcccgg tcgcgctgcg ggtcgcccga    720
gtggctgccg tgctgggccc aagcgccacc accacgctgg tgcgccggct aagcgggctc    780
agcgcggaga cgatagaccg ggcaaccaag atcctcactg agggcgggct gctgctcgac    840
cagcagttcc cgcaccccgg ccgcccgctc gtggtgctcg atgacatgtc cgcccaggaa    900
cgacgcagcc tgcacactct cgccctggaa ctgctggacg aggcgccggt tgaagtgctc    960
gcgcaccacc aggtcggcgc cggtctcata cacgggccca aggctgcgga gatgttcgcc   1020
aaggccggca aggctctggt cgtacgcaac gagttgggcg acgcggccga atacctgcaa   1080
ctggctcacc gggcctccga cgatgtctcc acccgggccg ccttacgggt cgaggccgtg   1140
gccatcgagc gccgccgcaa tccgctggcc tccagtcggc acatggacga actgagcgcc   1200
gccggccgcg ccggtctgct ttccccaag catgcggcgc tggccgtctt ctggctagcc   1260
gacggcgggc gatccggcga ggcagccgaa gtgctgcgt cggaacgccc gctcgcgacc   1320
accgatcaga accgggccca cctgcgattt gtcgaggtga ctctcgcgct gttctctccc   1380
ggcgccttcg gatcggaccg gcgcccacct ccgctgacgc cggacgaact cgccagcctg   1440
ccgaaggcgg cctggcaatg cgcggtcgcc gacaacgcgg ccatgaccgc cttgcacggc   1500
catccagaac ttgccaccgc tcaggcgaaa acagttctgc ggcaggctga ttcggcagcc   1560
gacgcgatcc ccgccgcgct gatcgccctg ttgtacgcgg agaacaccga gtccgctcat   1620 atctggggccg acaagctggg cagcacgaat gccggggtat cgaacgaggc ggaagcgggc   1680
tacgccggcc cgtgcgccga gatcgccctg cggcgcggcg acctggccac ggcgttcgag   1740
gctggtagcg ccgtcctgga cgaccggtcg ctgccgtcgc tcggcatcac cgccgcattg   1800
ctgttgagca gcaagacggc cgccgctgtc cggctgggcg aactcgagcg tgcggagaag   1860
ctgctcgccg agccgcttcc gaacggcgtc caggacagcc ttttcggtct gcacctgctc   1920
```

-continued

| | |
|---|---|
| tcggcgtacg gccagtacag cctcgcgatg ggccgatatg aatcagctca ccggcgtttt | 1980 |
| cgcacctgcg gagaacgtat gcgcagctgg gatgttgacg tgcctggtct ggccctgtgg | 2040 |
| cgtgtcgacg ccgccgaggc gctgctcagc ctcgaccgga acgagggcca gcggctcatc | 2100 |
| gacgaacaac tcacccgtcc gatggggcct cgttcccacg cgttaacgct gcggatcaag | 2160 |
| gcggcatacc tcccgcggac gaagcggatc ccctgctcc atgaggcggc cgagctgctg | 2220 |
| ctcccctgcc ccgacccgta cgagcaagcc cgggtgctcg ccgatctggg cgacacgctc | 2280 |
| agcgcgctca gacgctatag ccgggcgcgg ggagttctcc ggcaggctcg tcacctggcc | 2340 |
| acccagtgcg gtgctgtccc gctgctcgcg aggctcgggg gcgagcccgg ccggatcgac | 2400 |
| gacgccggcc tgccgcagcg gagcacatcg ttgaccgatg cggagcggcg ggtggcggcg | 2460 |
| ctggccgcgg ccggacagac caaccgggag atcgccgaac agctgttcgt cacgccagc | 2520 |
| acagtggaac agcacctcac aagcgtcttc cgcaagctgg gcgtcaaggg ccgcaagcag | 2580 |
| ctgccgaccg cgctggccga cgtggaacag acctga | 2616 |

<210> SEQ ID NO 19
<211> LENGTH: 2721
<212> TYPE: DNA
<213> ORGANISM: Streptomyces malaysiensis

<400> SEQUENCE: 19

| | |
|---|---|
| atgtatagcg gtacctgccg tgaaggatac gaactcgtcg cacgcgagga cgaactcggt | 60 |
| attctacaga ggtctctgga caagcgagc agcggccagg cgtcgtggt caccgtcacc | 120 |
| ggcccaatcg cctgcggcaa gacagaactg cttgacgcgg ctgccgcgaa ggctgaggcc | 180 |
| atcattctgc gcgcggtctg cgcgccagaa gagcgggcta tgccgtacgc catgatcggg | 240 |
| cagctcatcg acgacccggc gctcgcgcat cgggcgccgg ggctggctga tcggatagcc | 300 |
| cagggcgggc agctgtcgct gagggccgag aaccgactgc gcagggatct cacccgtgcc | 360 |
| ctgctggcgc ttgccgtgga ccggcctgtg ctgatcggcg tcgacgatgt gcatcacgcc | 420 |
| gacaccgcct ctttgaactg tctgctgcat ttggcccgcc gggtccgtcc ggcccggata | 480 |
| tccatgatct tcaccgagtt gcgcagcctc accctactc agtcacggtt caaggcggag | 540 |
| ctgctcagcc tgccatacca ccacgagatc gcgctgcgtc cattcggacc ggagcaatcg | 600 |
| gcggagctgg ctcgcgccgc cttcggcccg ggcctcgccg aggatgtgct cgcggggttg | 660 |
| tataaaacga ccaggggcaa tctgagtctc agccgtggac tgatcagcga tgtgcgggag | 720 |
| gccctggcca acggagagag cgcttttcgag gcgggccgcg cgttccggct ggcgtacctc | 780 |
| agctcgctct accgctgtgg cccggtcgcg ctgcgggtcg cccgagtggc tgccgtgctg | 840 |
| ggcccaagcg ccaccaccac gctggtgcgc cggctaagcg ggctcagcgc ggagacgata | 900 |
| gaccgggcaa ccaagatcct cactgagggc gggctgctgc tcgaccagca gttcccgcac | 960 |
| ccggccgccc gctcggtggt gctcgatgac atgtccgccc aggaacgacg cagcctgcac | 1020 |
| actctcgccc tggaactgct ggacgaggcg ccggttgaag tgctcgcgca ccaccaggtc | 1080 |
| ggcgccggtc tcatacacgg gcccaaggct gcggagatgt cgccaaggc cggcaaggct | 1140 |
| ctggtcgtac gcaacgagtt gggcgacgcg ccgaatacc tgcaactggc tcaccgggcc | 1200 |
| tccgacgatg tctccacccg ggccgccctg cgggtcgagg ccgtggccat cgagcgccgc | 1260 |
| cgcaatccgc tggcctccag tcggcacatg gacgaactga gcgccgcggg ccgcgccggt | 1320 |
| ctgcttttccc ccaagcatgc ggcgctggcc gtcttctggc tagccgacgg cgggcgatcc | 1380 |
| ggcgaggcag ccgaagtgct ggcgtcggaa cgcccgctcg cgaccaccga tcagaaccgg | 1440 |

```
gcccacctgc gatttgtcga ggtgactctc gcgctgttct ctcccggcgc cttcggatcg    1500
gaccggcgcc cacctccgct gacgccggac gaactcgcca gcctgccgaa ggcggcctgg    1560
caatgcgcgg tcgccgacaa cgcggccatg accgccttgc acggccatcc agaacttgcc    1620
accgctcagg cggaaacagt tctgcggcag gctgattcgg cagccgacgc gatccccgcc    1680
gcgctgatcg ccctgttgta cgcggagaac accgagtccg ctcatatctg ggccgacaag    1740
ctgggcagca cgaatgccgg ggtatcgaac gaggcggaag cgggctacgc cggcccgtgc    1800
gccgagatcg ccctgcggcg cggcgacctg ccacggcgt tcgaggctgg tagcgccgtc    1860
ctggacgacc ggtcgctgcc gtcgctcggc atcaccgccg cattgctgtt gagcagcaag    1920
acggccgccg ctgtccggct gggcgaactc gagcgtgcgg agaagctgct cgccgagccg    1980
cttccgaacg cgtccagga cagccttttc ggtctgcacc tgctctcggc gtacggccag    2040
tacagcctcg cgatgggccg atatgaatca gctcaccggg cgtttcgcac ctgcggagaa    2100
cgtatgcgca gctgggatgt tgacgtgcct ggtctggccc tgtggcgtgt cgacgccgcc    2160
gaggcgctgc tcagcctcga ccggaacgag ggccagcggc tcatcgacga caactcacc    2220 cgtccgatgg ggcctcgttc ccacgcgctg acgctgcgga tcaaggcggc atacctcccg    2280
cggacgaagc ggatccccct gctccatgag gcggccgagc tgctgctccc ctgccccgac    2340
ccgtacgagc aagcgcgggt gctcgccgat ctgggcgaca cgctcagcgc gctcagacgc    2400
tatagccggg cgcggggagt tctccggcag gctcgtcacc tggccaccca gtgcggtgct    2460
gtcccgctgc tgcgcaggct cgggggcgag cccggccgga tcgacgacgc cggcctgccg    2520
cagcggagca catcgttgac cgatgcggag cggcgggtgg cggcgctggc cgcggccgga    2580
cagaccaacc gggagatcgc cgaacagctg ttcgtcacgg ccagcacagt ggaacagcac    2640
ctcacaagcg tcttccgcaa gctgggcgtc aagggccgca agcagctgcc gaccgcgctg    2700
gccgacgtgg aacagacctg a                                             2721

<210> SEQ ID NO 20
<211> LENGTH: 2715
<212> TYPE: DNA
<213> ORGANISM: Streptomyces violaceusniger

<400> SEQUENCE: 20
gtgtatagcg gtacctgccg tgaaggatac gaactcgtcg cccgcgagga cgaactcggc      60
attctgcaga ggtctctgga agaagcaggc agcggccagg gcgccgtggt caccgtcacc     120
ggcccgatcg cctgcggcaa gacagaactg cttgacgcgg ctgccgcgaa ggctgacgcc     180
atcattctgc gcgcggtctg cgcgcccgaa gagcgcgcta tgccgtacgc catgatcggg     240
cagctcatcg acgacccggc gctcgcgcat cgggcgccgg agctggctga tcggatagcc     300
cagggcgggc atctgtcgct gagggccgag aaccgactgc gcaggatct cacccgtgcc     360 ctgctggcgc ttgccgtcga ccggcctgtg ctgatcggcg tcgacgatgt gcatcacgcc     420
gacaccgcct ctttgaactg tctgctgcat ttagcccgcc gggtccgtcc ggcccggata     480
tccatgatct tcaccgagtt gcgcagcctc accctactc agtcacgatt caaggcggag     540
ctgctcagcc tgccgtacca ccacgagatc gcgctgcgtc cactcggacc ggagcaatcg     600
gcggagctgg cccacgccgc cttcggcccg ggcctcgccg aggatgtgct cgcggggttg     660
tatgggatga ccaggggcaa cctgagtctc agccgtggac tgatcagcga tgtgcggag     720 gcccaggcca acggagagag cgctttcgag gtgggccgcg cgttccggct ggcgtacctc     780
```

| | |
|---|---|
| agctcgctct accgctgtgg cccgatcgcg ctgcgggtcg cccgagtggc tgccgtgctg | 840 |
| ggcccaagcg ccaccaccac gctggtgcgc cgtctaagcg ggctcagcgc ggagacgata | 900 |
| gaccgggcaa ccaagatcct cactgagggc gggctgctgc tcgaccacca gttcccgcac | 960 |
| ccggccgccc gctcggtggt gctcgatgac atgtccgccc aggaacgacg cagcctgcac | 1020 |
| actctcgccc tggaactgct ggacgaggcg ccggttgaag tgctcgcgca ccaccaggtc | 1080 |
| ggcgccggtc tcatacacgg gcccaaggct gcggagatat cgccagggc tggccaggct | 1140 |
| ctggttgtac gcaacgagtt gggcgacgcg gccgaatacc tgcaactggc tcaccgagcc | 1200 |
| tccgacgatg tctccacccg ggccgcctta cgggtcgagg ccgtggcaat cgagcgccgc | 1260 |
| cgcaatccgc tggcctccag tcgtcacatg gacgagctga gcgccgccgg ccgcgccggt | 1320 |
| ctgcttttccc ccaagcatgc agcgctggct gtcttctggc tggccgacgg cgggcgatcc | 1380 |
| ggcgaggcag ccgaggtgct ggcgtcggaa cacccgctcg cgaccaccga tcagaaccga | 1440 |
| gcacacctgc gatttgccga ggtgactctc gcgctgttct gtcccggcgc cttcgggtcg | 1500 |
| gaccggcgcc cacctccgct ggcgccggac gagctcgcca gcttgccgaa ggcggcctgg | 1560 |
| caatgcgcgg tcgccgacaa cgcggtcatg acagcgttgc atgctcatcc agaacttgcc | 1620 |
| accgctcagg cggaaacagt tctgcggcag gctgattcgg cagccgacgc aatcccccgcc | 1680 |
| gcactgatcg ccctgttgta cgcagagaac accgagtccg ctcagatctg gccgacaag | 1740 |
| ctgggcagca ccaatgccgg ggtatcgaac gaggcggaag cgggctacgc cggcccgtgc | 1800 |
| gccgagatcg ccctgcggcg cggcgacctg ccacggcgt tcgaggctgg tggcaccgtc | 1860 |
| ctggacgacc ggccgctgcc gtcgctcggc atcaccgccg cattgctgtt gagcagcaag | 1920 |
| acggcagccg ctgtccgcct gggcgaactc gagcgtgcgg agaagctgct cgctgagccg | 1980 |
| cttccgaacg gtgtccagga cagccttttc ggtctgcacc tgctctcggc gcacggccag | 2040 |
| tacagcctcg cgatgggccg atatgaatcg gctcaccggg cgtttcacac ctgcggagaa | 2100 |
| cgtatgcgca gctggggtgt tgacgtgcct ggtctagccc tgtggcgtgt cgacgccgcc | 2160 |
| gaggcactgc tcagcctcga ccggaacgag ggccagcggc tcatcgacga caactcgcc | 2220 |
| cgtccgatgg gacctcgttc ccgcgcatta acgctgcgga tcaaggcggc atacctcccg | 2280 |
| cggacgaagc ggatccccct gctccatgag gcagctgagc tgctgctctc ctgccccgac | 2340 |
| ccgtacgagc aagcgcgggt gctcgccgat ctgggcgaca cgctcagcgc gctcagacgc | 2400 |
| tatagccggg cgcggggagt tctccggcag gctcgtcacc tggccaccca gtgcggtgct | 2460 |
| gtcccgctgc tgcgccgact cgggggcgag cccggccgga tcgacgacgc cggcctgccg | 2520 |
| cagcggagca catcgttgac cgatgcggag cggcgggtgt cggccctggc cgcggccgga | 2580 |
| cagaccaacc gggagatcgc caaacagcta ttcgtcacgg ccagcaccgt ggaacagcac | 2640 |
| ctcacaagcg tcttccgcaa gctgggcgtt aagggccgca ggcagctacc gaccgcgctg | 2700 |
| gccgacgtgg aatag | 2715 |

<210> SEQ ID NO 21
<211> LENGTH: 2715
<212> TYPE: DNA
<213> ORGANISM: Streptomyces violaceusniger

<400> SEQUENCE: 21

| | |
|---|---|
| atgtatagcg gtacctgccg tgaaggatac gaactcgtcg cccgcgagga cgaactcggc | 60 |
| attctgcaga ggtctctgga agaagcaggc agcggccagg gcgccgtggt caccgtcacc | 120 |
| ggcccgatcg cctgcggcaa gacagaactg cttgacgcgg ctgccgcgaa ggctgacgcc | 180 |

```
atcattctgc gcgcggtctg cgcgcccgaa gagcgcgcta tgccgtacgc catgatcggg    240
cagctcatcg acgacccggc gctcgcgcat cgggcgccgg agctggctga tcggatagcc    300
cagggcgggc atctgtcgct gagggccgag aaccgactgc gcagggatct cacccgtgcc    360
ctgctggcgc ttgccgtcga ccggcctgtg ctgatcggcg tcgacgatgt gcatcacgcc    420
gacaccgcct ctttgaactg tctgctgcat ctggcccgcc gggtccgtcc ggcccggata    480
tccatgatct tcaccgagtt gcgcagcctc acccctactc agtcacgatt caaggcggag    540
ctgctcagcc tgccgtacca ccacgagatc gcgctgcgtc cactcggacc ggagcaatcg    600
gcggagctgg cccacgccgc cttcggcccg gcctcgccg aggatgtgct cgcggggttg     660
tatgggatga ccaggggcaa cctgagtctc agccgtggac tgatcagcga tgtgcgggag    720
gcccaggcca acggagagag cgcttttcgag gtgggccgcg cgttccggct ggcgtacctc    780
agctcgctct accgctgtgg cccgatcgcg ctgcgggtcg cccgagtggc tgccgtgctg    840
ggcccaagcg ccaccaccac gctggtgcgc cgtctaagcg ggctcagcgc ggagacgata    900
gaccgggcaa ccaagatcct cactgagggc gggctgctgc tcgaccacca gttcccgcac    960
ccggccgccc gctcggtggt gctcgatgac atgtccgccc aggaacgacg cagcctgcac   1020
actctcgccc tggaactgct ggacgaggcg ccggttgaag tgctcgcgca ccaccaggtc   1080
ggcgccggtc tcatacacgg gcccaaggct gcggagatat cgccagggc tggccaggct    1140 ctggttgtac gcaacgagtt gggcgacgcg gccgaatacc tgcaactggc tcaccgagcc   1200
tccgacgatg tctccacccg ggccgccctg cgggtcgagg ccgtggcaat cgagcgccgc   1260
cgcaatccgc tggcctccag tcgtcacatg gacgagctga gcgccgccgg ccgcgccggt   1320
ctgctttccc ccaagcatgc agcgctggct gtcttctggc tggccgacgg cgggcgatcc   1380
ggcgaggcag ccgaggtgct ggcgtcggaa cacccgctcg cgaccaccga tcagaaccga   1440
gcacacctgc gatttgccga ggtgactctc gcgctgttct gtcccggcgc cttcgggtcg   1500
gaccggcgcc cacctccgct ggcgccggac gagctcgcca gcttgccgaa ggcggcctgg   1560
caatgcgcgg tcgccgacaa cgcggtcatg acagcgttgc atgctcatcc agaacttgcc   1620
accgctcagg cggaaacagt tctgcggcag gctgattcgg cagccgacgc aatccccgcc   1680
gcactgatcg ccctgttgta cgcagagaac accgagtccg ctcagatctg gccgacaag    1740 ctgggcagca ccaatgccgg ggtatcgaac gaggcggaag cgggctacgc cggcccgtgc   1800
gccgagatcg ccctgcggcg cggcgacctg gccacggcgt tcgaggctgg tggcaccgtc   1860
ctggacgacc ggccgctgcc gtcgctcggc atcaccgccg cattgctgtt gagcagcaag   1920
acggcagccg ctgtccgcct gggcgaactc gagcgtgcgg agaagctgct cgctgagccg   1980
cttccgaacg gtgtccagga cagcctttc ggtctgcacc tgctctcggc gcacggccag    2040
tacagcctcg cgatgggccg atatgaatcg gctcaccggg cgtttcacac ctgcggagaa   2100
cgtatgcgca gctgggtgt tgacgtgcct ggtctagccc tgtggcgtgt cgacgccgcc    2160
gaggcactgc tcagcctcga ccggaacgag ggccagcggc tcatcgacga caactcgcc    2220 cgtccgatgg gacctcgttc ccgcgcactg acgctgcgga tcaaggcggc atacctcccg   2280
cggacgaagc ggatcccccct gctccatgag gcagctgagc tgctgctctc ctgccccgac   2340
ccgtacgagc aagcgcgggt gctcgccgat ctgggcgaca cgctcagcgc gctcagacgc   2400
tatagccggg cgcggggagt tctccggcag gctcgtcacc tggccaccca gtgcggtgct   2460
gtcccgctgc tgcgccgact cgggggcgag cccggccgga tcgacgacgc cggcctgccg   2520
```

-continued

| | |
|---|---|
| cagcggagca catcgttgac cgatgcggag cggcgggtgt cggccctggc cgcggccgga | 2580 |
| cagaccaacc gggagatcgc caaacagcta ttcgtcacgg ccagcaccgt ggaacagcac | 2640 |
| ctcacaagcg tcttccgcaa gctgggcgtt aagggccgca ggcagctacc gaccgcgctg | 2700 |
| gccgacgtgg aatag | 2715 |

<210> SEQ ID NO 22
<211> LENGTH: 2721
<212> TYPE: DNA
<213> ORGANISM: Streptomyces Sp. NRRL F-4729

<400> SEQUENCE: 22

| | |
|---|---|
| gtgtatagcg gtacctgccg tgaaggatac gaactcgtcg cacgcgagga cgaactcggc | 60 |
| attctacaga ggtctctgga acaagcgagc agcggccagg gcgtcgtggt caccgtcacc | 120 |
| ggcccaatcg cctgcggcaa gacagaactg cttgacgcgg ctgccgcgaa ggctgaggcc | 180 |
| atcattctgc gcgcggtctg cgcgcccgaa gagcgggcta tgccgtacgc catgatcggg | 240 |
| cagctcatcg acgacccggc gctcgcgcat cgggcgccgg ggctggctga tcggatagcc | 300 |
| cagggcgggc agctgtcgct gagggccgag aaccgactgc gcaggatct cacccgtgcc | 360 |
| ctgctggcgc ttgccgtgca ccggcctgtg ctgatcggcg tcgatgatgt gcatcacgcc | 420 |
| gacaccgcct ctttgaactg tctgctgcat ttggcgcgcc gggtccgtcc ggcccggata | 480 |
| tccatgatct tcaccgagtt gcgcagcctc acccctactc agtcacgatt caaggcggag | 540 |
| ctgctcagcc tgccgtacca ccacgagatc gcgctgcgtc cattcggacc ggagcaatcg | 600 |
| gcggagctgg ctcgcgccgc cttcggcccg ggcctcgccg aggatgtgct cgcggggttg | 660 |
| tataaaacga ccaggggcaa tctgagtctc agccgtggac tgatcagcga tgtgcgggag | 720 |
| gccctggcca acggagagag cgcttcgag gcgggccgcg cgttccggct ggcgtacctc | 780 |
| agctcgctct accgctgtgg cccggtcgcg ctgcgggtcg cccgagtggc tgccgtgctg | 840 |
| ggcccaagcg ccaccaccac gctggtgcgc cggctaagcg ggctcagcgc ggagacgata | 900 |
| gaccgggcaa ccaagatcct caccgagggc gggctgctgc tcgaccagca gtttccgcac | 960 |
| ccggccgccc gctcggtggt gctcgatgac atgtccgccc aggaacgacg cggcctgcac | 1020 |
| actctcgccc tggaactgct ggacgaggcg ccggttgaag tgctcgcgca ccaccaggtc | 1080 |
| ggcgccggtc tcatacacgg gcccaaggct gcggagatgt cgccaaggc cggcaaggct | 1140 |
| ctggtcgtac gcaacgagtt gggcgacgcg gccgaatacc tgcaactggc tcaccgggcc | 1200 |
| tccgacgatg tctccacccg ggccgcctta cgggtcgagg ccgtggcgat cgagcgccgc | 1260 |
| cgcaatccgc tggcctccag tcggcacatg gacgagctga gcgccgccgg ccgcgccggt | 1320 |
| ctgctttccc ccaagcatgc ggcgctggcc gtcttctggc tggccgacgg cgggcgatcc | 1380 |
| ggcgaggcag cccaggtgct ggcgtcggaa cgcccgctcg cgaccaccga tcagaaccgg | 1440 |
| gcccacctgc gatttgtcga ggtgactctc gcgctgttct ctcccggcgc cttcggatcg | 1500 |
| gaccggcgcc cacctccgct gacgccggac gaactcgcca gcctgccgaa ggcggcctgg | 1560 |
| caatgcgcgg tcgccgacaa cgcggccatg accgccttgc acggccatcc agaacttgcc | 1620 |
| accgctcagg cggaaacagt tctgcggcag gctgattcgg cagccgacgc gatccccgcc | 1680 |
| gcgctgatcg ccctgttgta cgcggagaac accgagtccg ctcatatctg ggccgacaag | 1740 |
| ctgggcagca tgaatgccgg ggtatcgaac gaggcggaag cgggctacgc cggcccgtgc | 1800 |
| gccgagatcg ccctgcgggcg cggcgacctg gccacgcgt tcgaggctgg tagcaccgtc | 1860 |
| ctggacgacc ggtcactgcc gtcgctcggc atcaccgccg cattgctgtt gagcagcaag | 1920 |

```
acggccgccg ctgtccggct gggcgaactc gagcgtgcgg agaagctgct cgccgagccg   1980
cttccgaacg gcgtccagga cagccttttc ggtctgcacc tgctctcggc gtacggccag   2040
tacagcctcg cgatgggccg atatgaatcg gctcaccggg cgtttcgcac ctgcggagaa   2100
cgtatgcgca gctgggatgt tgacgtgcct ggtctggccc tgtggcgtgt cgacgccgcc   2160
gaggcgctgc tcagcctcga ccggaacgag ggccagcggc tcatcgacga caactcacc    2220 cgtccgatgg gacctcgttc ccgcgcgtta acgctgcgga tcaaggcggc atacctcccg   2280
cggacgaagc ggatccccct gctccatgag gcggccgagc tgctgctccc ctgccccgac   2340
ccgtacgagc aagcgcgggt gctcgccgat ctgggcgaca cgctcagcgc gctcagacgc   2400
tatagccggg cgcggggagt tctccggcag gctcgtcacc tggccaccca gtgcggtgct   2460
gtcccgctgc tgcgccgact cggggggcgag cccggccgga tcgacgacgc cggcctgccg   2520
cagcggagca catcgttgac cgatgcggag cggcgggtgg cggcgctggc cgcggccgga   2580
cagaccaacc gggagatcgc cgaacagctg ttcgtcacgg ccagcacagt ggaacagcac   2640
ctcacaagcg tcttccgcaa gctgggcgtc aagggccgca agcagctgcc gaccgcgctg   2700
gccgacgtgg aacagacctg a                                             2721

<210> SEQ ID NO 23
<211> LENGTH: 2721
<212> TYPE: DNA
<213> ORGANISM: Streptomyces Sp. NRRL F-4729

<400> SEQUENCE: 23
atgtatagcg gtacctgccg tgaaggatac gaactcgtcg cacgcgagga cgaactcggc     60
attctacaga ggtctctgga acaagcgagc agcggccagg gcgtcgtggt caccgtcacc    120
ggcccaatcg cctgcggcaa gacagaactg cttgacgcgg ctgccgcgaa ggctgaggcc    180
atcattctgc gcgcggtctg cgcgcccgaa gagcgggcta tgccgtacgc catgatcggg    240
cagctcatcg acgacccggc gctcgcgcat cgggcgccgg ggctggctga tcggatagcc    300
cagggcgggc agctgtcgct gagggccgag aaccgactgc gcaggatct cacccgtgcc    360 ctgctggcgc ttgccgtgca ccggcctgtg ctgatcggcg tcgatgatgt gcatcacgcc    420
gacaccgcct ctttgaactg tctgctgcat ttggcgcgcc gggtccgtcc ggcccggata    480
tccatgatct tcaccgagtt gcgcagcctc acccctactc agtcacgatt caaggcggag    540
ctgctcagcc tgccgtacca ccacgagatc gcgctgcgtc cattcggacc ggagcaatcg    600
gcggagctgg ctcgcgccgc cttcggcccg ggcctcgccg aggatgtgct cgcggggttg    660
tataaaacga ccaggggcaa tctgagtctc agccgtggac tgatcagcga tgtgcgggag    720
gccctggcca acggagagag cgcttttgag gcgggccgcg cgttccggct ggcgtacctc    780
agctcgctct accgctgtgg cccggtcgcg ctgcgggtcg cccgagtggc tgccgtgctg    840
ggcccaagcg ccaccaccac gctggtgcgc cggctaagcg ggctcagcgc ggagacgata    900
gaccgggcaa ccaagatcct caccgagggc gggctgctgc tcgaccagca gtttccgcac    960
ccggccgccc gctcggtggt gctcgatgac atgtccgccc aggaacgacg cggcctgcac   1020
actctcgccc tggaactgct ggacgaggcg ccggttgaag tgctcgcgca ccaccaggtc   1080
ggcgccggtc tcatacacgg gcccaaggct gcggagatgt tcgccaaggc cggcaaggct   1140
ctggtcgtac gcaacgagtt gggcgacgcg gccgaatacc tgcaactggc tcaccgggcc   1200
tccgacgatg tctccacccg ggccgccctg cgggtcgagg ccgtggcgat cgagcgccgc   1260
```

```
cgcaatccgc tggcctccag tcggcacatg acgagctga gcgccgccgg ccgcgccggt    1320
ctgctttccc ccaagcatgc ggcgctggcc gtcttctggc tggccgacgg cgggcgatcc    1380
ggcgaggcag cccaggtgct ggcgtcggaa cgcccgctcg cgaccaccga tcagaaccgg    1440
gcccacctgc gatttgtcga ggtgactctc gcgctgttct ctcccggcgc cttcggatcg    1500
gaccggcgcc cacctccgct gacgccggac gaactcgcca gcctgccgaa ggcggcctgg    1560
caatgcgcgc tcgccgacaa cgcggccatg accgccttgc acggccatcc agaacttgcc    1620
accgctcagg cggaaacagt tctgcggcag gctgattcgg cagccgacgc gatcccgcc    1680 gcgctgatcg ccctgttgta cgcggagaac accgagtccg ctcatatctg gccgacaag    1740 ctgggcagca tgaatgccgg ggtatcgaac gaggcggaag cgggctacgc cggcccgtgc    1800
gccgagatcg ccctgcggcg cggcgacctg ccacggcgt tcgaggctgg tagcaccgtc    1860
ctggacgacc ggtcactgcc gtcgctcggc atcaccgccg cattgctgtt gagcagcaag    1920
acggccgccg ctgtccggct gggcgaactc gagcgtgcgg agaagctgct cgccgagccg    1980
cttccgaacg gcgtccagga cagccttttc ggtctgcacc tgctctcggc gtacggccag    2040
tacagcctcg cgatgggccg atatgaatcg gctcaccggg cgtttcgcac ctgcggagaa    2100
cgtatgcgca gctgggatgt tgacgtgcct ggtctgcccc tgtggcgtgt cgacgccgcc    2160
gaggcgctgc tcagcctcga ccggaacgag ggccagcggc tcatcgacga caactcacc    2220 cgtccgatgg gacctcgttc ccgcgcgctg acgctgcgga tcaaggcggc atacctcccg    2280
cggacgaagc ggatccccct gctccatgag gcggccgagc tgctgctccc ctgccccgac    2340
ccgtacgagc aagcgcgggt gctcgccgat ctgggcgaca cgctcagcgc gctcagacgc    2400
tatagccggg cgcggggagt tctccggcag gctcgtcacc tggccaccca gtgcggtgct    2460
gtcccgctgc tgcgccgact cggggcgag cccggccgga tcgacgacgc cggcctgccg    2520
cagcggagca catcgttgac cgatgcggag cggcgggtgg cggcgctggc cgcggccgga    2580
cagaccaacc gggagatcgc cgaacagctg ttcgtcacgg ccagcacagt ggaacagcac    2640
ctcacaagcg tcttccgcaa gctgggcgtc aagggccgca agcagctgcc gaccgcgctg    2700
gccgacgtgg aacagacctg a                                             2721
```

<210> SEQ ID NO 24
<211> LENGTH: 2715
<212> TYPE: DNA
<213> ORGANISM: Streptomyces filamentosus

<400> SEQUENCE: 24

```
gtgcgagcta ttaatgcgtc cgacaccggt cctgaactgg tcgcccgcga agacgaactg     60
ggacgtgtac gaagtgccct gaaccgagcg aacggcggcc aaggtgtcct gatctccatt    120
accggtccga tcgcctgcgg caagaccgaa ctgcttgagg ctgccgcctc ggaagttgac    180
gccatcactc tgcgcgcggt ctgtgccgcc gaggaacggg cgataccctta tgccctgatc    240 gggcagctta tcgacaaccc cgcgctcggc attccggttc cggatccggc cggcctgacc    300
gcccagggcg gacgactgtc atcgagcgcc gagaaccgac tgcgtcgcga cctcacccgt    360
gccctgctga cgctcgccac cgaccggctg gtgctgatct gtgtcgatga cgtgcagcac    420
gccgacaacg cctcgttgag ctgccttctg tatctggccc gacggcttgt cccggctcga    480
atcgctctgg tattcaccga gttgcgagtc ctcacctcgt ctcagttacg gttcaacgcg    540
gagctgctca gcttgcggaa ccactgcgag atcgcgctgc gcccactcgg cccggggcat    600
gcggccgagc tggcccgcgc cacccctcggc cccggcctct ccgacgaaac actcacggag    660
```

```
ctgtaccggg tgaccggagg caacctgagt ctcagccgcg ggctgatcga cgatgtgcgg    720
gacgcctggg cacgagggga aacgggcgtc caggtgggcc gggcgttccg gctggcctac    780
ctcggttccc tccaccgctg tggtccgctg gcgttgcggg tcgcccgcgt agccgccgta    840
ctgggcccga gcgccaccag cgtcctggtg cgccggatca gtgggctcag gcggaggcc    900 atggcccagg cgaccgatat cctcgctgac ggcggcctcc tgcgcgacca gcggttcaca    960
catccagcgg cccgctcggt ggtgctcgac gacatgtccg ccgaggaacg acgcagcgtg   1020
cacagcctcg ccctggaact gctggacgag caccggccg agatgctcgc gcaccaccgg    1080
gtcgcgcgcc gtctcgtgca cgggccgaag gccgcggaga cattcaccgg ggccggccgg   1140
gcactggccg ttcgcggcat gctgggcgag gcagccgact acctgcaact ggcgtaccgg   1200
gcctccggcg acgccgctac caaggccgcg atacgcgtcg agtccgtggc ggtcgagcgc   1260
cgacgcaatc cgctggtcgt cagtcgccat tgggacgagc tgagcgtcgc ggcccgcgcc   1320
ggtctgctct cctgcgagca cgtgtccagg acggcccgct ggctgaccgt cggtgggcgg   1380
cccggcgagg cggccagggt gctggcgtcg caacaccgac gggtcgtcac cgatcaggac   1440
cgggcccacc tgcgggtcgc cgagttctcg ctcgcgctgc tgtacccggg tacgtccggc   1500
tcggaccggc gcccgcaccc gctcacgtcg gacgaactcg cggccctacc gactgcgacc   1560
agacactgcg cgatcgccga taacgctgtc atggctgcct tgcgtggtca tccggagctt   1620
gccaccgccg aggcagaagc cgttctgcag caagccgacg cggcggacgg cgctgctctc   1680
accgcgctga tggccctgct gtacgcggag agcatcgagg tcgctgaagt ctgggcggac   1740
aagctggcgg cagaggccgg agcatcgaac gggcaggacg cggagtacgc cggtatacgc   1800
gccgaaatcg ccctgcggcg cggcgatctg accgcggccg tcgagaccgc cggcatggtc   1860
ctggacggcc ggccgctgcc gtcgctcgac atcaccgcca cgttgctgtt ggccggcagg   1920
gcgtccgtcg ccgtccggct gggcgaactc gaccacgcgg aggagctgtt cgccgcgccg   1980
ccggaggacg ccttccagga cagcctcttc ggtctgcatc tgctctcggc gcacggccag   2040
tacagcctcg cgacaggccg gcccgagtcg gcataccggg cctttcgtgc ctgcggcgaa   2100
cgtatgcgcg attgggcctt cgacgcgccc ggtgtgccc tgtggcgcgt cggcgccgcc    2160
gaggcgctgc tcggcctcga ccggaacgag ggccgacggc tcatcgacga acagctgagc   2220
cggacgatgg cccccccggtc ccacgcgttg acgctgcgga taaaagcggc gtacatgccg   2280
gagccgaagc gggtcgacct gctctacgaa gcggctgagc tgctgctctc ctgccgggac   2340
cagtatgagc gagcgcgggt gctcgccgat ctgggcgagg cgctcagcgc gctcgggaac   2400
taccggcagg cgcgaggtgt gctccggcag gctcggcatc tggccatgcg aaccggcgcg   2460
gacccgctgc tgcgccggct cggaatcagg cccggccggc aggacgaccc cgaccgcag    2520 ccgcggagca gatcgctgac caacgctgag cggcgtgcgg cgtcgctggc cgcgaccgga   2580
ctgaccaacc gggagatcgc cgaccggctc ttcgtcaccg ccagcaccgt ggagcagcac   2640
ctcaccaacg tcttccgcaa gctgggcgtc aagggccgca agcagctgcc ggccgagttg   2700
gacgacatgg aatag                                                    2715
```

<210> SEQ ID NO 25
<211> LENGTH: 2715
<212> TYPE: DNA
<213> ORGANISM: Streptomyces filamentosus

<400> SEQUENCE: 25

```
atgcgagcta ttaatgcgtc cgacaccggt cctgaactgg tcgcccgcga agacgaactg      60
ggacgtgtac gaagtgccct gaaccgagcg aacggcggcc aaggtgtcct gatctccatt     120
accggtccga tcgcctgcgg caagaccgaa ctgcttgagg ctgccgcctc ggaagttgac     180
gccatcactc tgcgcgcggt ctgtgccgcc gaggaacggg cgataccttna tgccctgatc     240
gggcagctta tcgacaaccc cgcgctcggc attccggttc cggatccggc cggcctgacc     300
gcccagggcg gacgactgtc atcgagcgcc gagaaccgac tgcgtcgcga cctcacccgt     360
gccctgctga cgctcgccac cgaccggctg gtgctgatct gtgtcgatga cgtgcagcac     420
gccgacaacg cctcgttgag ctgccttctg tatctggccc gacggcttgt cccggctcga     480
atcgctctgg tattcaccga gttgcgagtc ctcacctcgt ctcagctgcg gttcaacgcg     540
gagctgctca gcttgcggaa ccactgcgag atcgcgctgc gcccactcgg cccggggcat     600
gcggccgagc tggcccgcgc caccctcggc cccggcctct ccgacgaaac actcacggag     660
ctgtaccggg tgaccggagg caacctgagt ctcagccgcg ggctgatcga cgatgtgcgg     720
gacgcctggg cacgagggga aacgggcgtc caggtgggcc gggcgttccg gctggcctac     780
ctcggttccc tccaccgctg tggtccgctg gcgttgcggg tcgcccgcgt agccgccgta     840
ctgggcccga gcgccaccag cgtcctggtg cgccggatca gtgggctcag cgcggaggcc     900
atggcccagg cgaccgatat cctcgctgac ggcggcctcc tgcgcgacca gcggttcaca     960
catccagcgg cccgctcggt ggtgctcgac gacatgtccg ccgaggaacg acgcagcgtg    1020
cacagcctcg ccctggaact gctggacgag gcaccggccg agatgctcgc gcaccaccgg    1080
gtcggcgccg gtctcgtgca cgggccgaag gccgcggaga cattcaccgg ggccggccgg    1140
gcactggccg ttcgcggcat gctgggcgag gcagccgact acctgcaact ggcgtaccgg    1200
gcctccggca cgccgctac caaggccgcg atacgcgtcg agtccgtggc ggtcgagcgc    1260
cgacgcaatc cgctggtcgt cagtcgccat gggacgagc tgagcgtcgc ggcccgcgcc    1320
ggtctgctct cctgcgagca cgtgtccagg acggcccgct ggctgaccgt cggtgggcgg    1380
cccggcgagg cggccagggt gctggcgtcg caacaccgac gggtcgtcac cgatcaggac    1440
cgggcccacc tgcgggtcgc cgagttctcg ctcgcgctgc tgtacccgg tacgtccggc    1500
tcggaccggc gcccgcaccc gctcacgtcg gacgaactcg cggccctacc gactgcgacc    1560
agacactgcg cgatcgccga taacgctgtc atggctgcct tgcgtggtca tccggagctt    1620
gccaccgccg aggcagaagc cgttctgcag caagccgacg cggcggacgg cgctgctctc    1680
accgcgctga tggccctgct gtacgcggag agcatcgagg tcgctgaagt ctgggcggac    1740
aagctggcgg cagaggccgg agcatcgaac gggcaggacg cggagtacgc cggtatacgc    1800
gccgaaatcg ccctgcgggcg cggcgatctg accgcggccg tcgagaccgc cggcatggtc    1860
ctggacggcc ggccgctgcc gtcgctcgac atcaccgcca cgttgctgtt ggccggcagg    1920
gcgtccgtcg ccgtccggct gggcgaactc gaccacgcgg aggagctgtt cgccgcgccg    1980
ccggaggacg ccttccagga cagcctcttc ggtctgcatc tgctctcggc gcacggccag    2040
tacagcctcg cgacaggccg gcccgagtcg gcataccggg cctttcgtgc ctgcggcgaa    2100
cgtatgcgcg attggggctt cgacgcgccc ggtgtgccc tgtggcgcgt cggcgccgcc    2160
gaggcgctgc tcggcctcga ccggaacgag ggccgacggc tcatcgacga acagctgagc    2220
cggacgatgg ccccccggtc ccacgcgttg acgctgcgga taaaagcggc gtacatgccg    2280
gagccgaagc gggtcgacct gctctacgaa gcggctgagc tgctgctctc ctgccgggac    2340
cagtatgagc gagcgcgggt gctcgccgat ctgggcgagg cgctcagcgc gctcgggaac    2400
```

```
taccggcagg cgcgaggtgt gctccggcag gctcggcatc tggccatgcg aaccggcgcg    2460
gacccgctgc tgcgccggct cggaatcagg cccggccggc aggacgaccc cgaccccgca    2520
ccgcggagca gatcgctgac caacgctgag cggcgtgcgg cgtcgctggc cgcgaccgga    2580
ctgaccaacc gggagatcgc cgaccggctc ttcgtcaccg ccagcaccgt ggagcagcac    2640
ctcaccaacg tcttccgcaa gctgggcgtc aagggccgca agcagctgcc ggccgagttg    2700
gacgacatgg aatag                                                    2715
```

<210> SEQ ID NO 26
<211> LENGTH: 894
<212> TYPE: PRT
<213> ORGANISM: Streptomyces hygroscopicus

<400> SEQUENCE: 26

```
Met Pro Ala Val Glu Cys Tyr Glu Leu Asp Ala Arg Asp Asp Glu Leu
1               5                   10                  15

Arg Lys Leu Glu Glu Val Val Thr Gly Arg Ala Asn Gly Arg Gly Val
            20                  25                  30

Val Val Thr Ile Thr Gly Pro Ile Ala Cys Gly Lys Thr Glu Leu Leu
        35                  40                  45

Asp Ala Ala Ala Lys Ala Asp Ala Ile Thr Leu Arg Ala Val Cys
    50                  55                  60

Ser Ala Glu Glu Gln Ala Leu Pro Tyr Ala Leu Ile Gly Gln Leu Ile
65                  70                  75                  80

Asp Asn Pro Ala Leu Ala Ser His Ala Leu Glu Pro Ala Cys Pro Thr
                85                  90                  95

Leu Pro Gly Glu His Leu Ser Pro Glu Ala Glu Asn Arg Leu Arg Ser
            100                 105                 110

Asp Leu Thr Arg Thr Leu Leu Ala Leu Ala Ala Glu Arg Pro Val Leu
        115                 120                 125

Ile Gly Ile Asp Glu Ser His Ala Asn Ala Leu Cys Leu Leu His Leu
    130                 135                 140

Ala Arg Arg Val Gly Ser Ala Arg Ile Ala Met Val Leu Thr Glu Leu
145                 150                 155                 160

Arg Arg Leu Thr Pro Ala His Ser Gln Phe Gln Ala Glu Leu Leu Ser
                165                 170                 175

Leu Gly His His Arg Glu Ile Ala Leu Arg Pro Leu Ser Pro Lys His
            180                 185                 190

Thr Ala Glu Leu Val Arg Ala Gly Leu Gly Pro Asp Val Asp Glu Asp
        195                 200                 205

Val Leu Thr Gly Leu Tyr Arg Ala Thr Gly Gly Asn Leu Asn Leu Thr
    210                 215                 220

Arg Gly Leu Ile Asn Asp Val Arg Glu Ala Trp Glu Thr Gly Gly Thr
225                 230                 235                 240

Gly Ile Ser Ala Gly Arg Ala Tyr Arg Leu Ala Tyr Leu Gly Ser Leu
                245                 250                 255

Tyr Arg Cys Gly Pro Val Pro Leu Arg Val Ala Arg Val Ala Ala Val
            260                 265                 270

Leu Gly Gln Ser Ala Asn Thr Thr Leu Val Arg Trp Ile Ser Gly Leu
        275                 280                 285

Asn Ala Asp Ala Val Gly Glu Ala Thr Glu Ile Leu Thr Glu Gly Gly
    290                 295                 300

Leu Leu His Asp Leu Arg Phe Pro His Pro Ala Ala Arg Ser Val Val
```

-continued

```
            305                 310                 315                 320
Leu Asn Asp Met Ser Ala Gln Glu Arg Arg Arg Leu His Arg Ser Ala
                325                 330                 335
Leu Glu Val Leu Asp Asp Val Pro Val Glu Val Ala His His Gln
            340                 345                 350
Val Gly Ala Gly Leu Leu His Gly Pro Lys Ala Ala Glu Ile Phe Ala
                355                 360                 365
Lys Ala Gly Gln Glu Leu His Val Arg Gly Glu Leu Asp Thr Ala Ser
            370                 375                 380
Asp Tyr Leu Gln Leu Ala His Gln Ala Ser Asp Ala Val Thr Gly
385                 390                 395                 400
Met Arg Ala Glu Ala Val Ala Ile Glu Arg Arg Asn Pro Leu Ala
                405                 410                 415
Ser Ser Arg His Leu Asp Glu Leu Thr Val Val Ala Arg Ala Gly Leu
            420                 425                 430
Leu Phe Pro Glu His Thr Ala Leu Met Ile Arg Trp Leu Gly Val Gly
                435                 440                 445
Gly Arg Ser Gly Glu Ala Ala Gly Leu Leu Ala Ser Gln Arg Pro Arg
            450                 455                 460
Ala Val Thr Asp Gln Asp Arg Ala His Met Arg Ala Ala Glu Val Ser
465                 470                 475                 480
Leu Ala Leu Val Ser Pro Gly Thr Ser Gly Pro Asp Arg Arg Pro Arg
                485                 490                 495
Pro Leu Thr Pro Asp Glu Leu Ala Asn Leu Pro Lys Ala Ala Arg Leu
            500                 505                 510
Cys Ala Ile Ala Asp Asn Ala Val Met Ser Ala Leu Arg Gly Arg Pro
            515                 520                 525
Glu Leu Ala Ala Ala Glu Glu Asn Val Leu Gln His Ala Asp Ser
            530                 535                 540
Ala Ala Ala Gly Thr Thr Ala Leu Ala Ala Leu Thr Ala Leu Leu Tyr
545                 550                 555                 560
Ala Glu Asn Thr Asp Thr Ala Gln Leu Trp Ala Asp Lys Leu Val Ser
                565                 570                 575
Glu Thr Gly Ala Ser Asn Glu Glu Ala Gly Tyr Ala Gly Pro Arg
                580                 585                 590
Ala Glu Ala Ala Leu Arg Arg Gly Asp Leu Ala Ala Val Glu Ala
            595                 600                 605
Gly Ser Thr Val Leu Asp His Arg Arg Leu Ser Thr Leu Gly Ile Thr
            610                 615                 620
Ala Ala Leu Pro Leu Ser Ser Ala Val Ala Ala Ile Arg Leu Gly
625                 630                 635                 640
Glu Thr Glu Arg Ala Glu Lys Trp Leu Ala Gln Pro Leu Pro Gln Ala
                645                 650                 655
Ile Gln Asp Gly Leu Phe Gly Leu His Leu Leu Ser Ala Arg Gly Gln
                660                 665                 670
Tyr Ser Leu Ala Thr Gly Gln His Glu Ser Ala Tyr Thr Ala Phe Arg
            675                 680                 685
Thr Cys Gly Glu Arg Met Arg Asn Trp Gly Val Asp Val Pro Gly Leu
            690                 695                 700
Ser Leu Trp Arg Val Asp Ala Ala Glu Ala Leu Leu His Gly Arg Asp
705                 710                 715                 720
Arg Asp Glu Gly Arg Arg Leu Val Asp Glu Gln Leu Thr Arg Ala Met
                725                 730                 735
```

Gly Pro Arg Ser Arg Ala Leu Thr Leu Arg Val Gln Ala Ala Tyr Ser
            740                 745                 750

Pro Pro Ala Lys Arg Val Asp Leu Leu Asp Glu Ala Ala Asp Leu Leu
            755                 760                 765

Leu Ser Cys Asn Asp Gln Tyr Glu Arg Ala Arg Val Leu Ala Asp Leu
770                 775                 780

Ser Glu Thr Phe Ser Ala Leu Arg His His Ser Arg Ala Arg Gly Leu
785                 790                 795                 800

Leu Arg Gln Ala Arg His Leu Ala Ala Gln Arg Gly Ala Ile Pro Leu
            805                 810                 815

Leu Arg Arg Leu Gly Ala Lys Pro Gly Gly Pro Gly Trp Leu Glu Glu
            820                 825                 830

Ser Gly Leu Pro Gln Arg Ile Lys Ser Leu Thr Asp Ala Glu Arg Arg
            835                 840                 845

Val Ala Ser Leu Ala Ala Gly Gly Gln Thr Asn Arg Val Ile Ala Asp
            850                 855                 860

Gln Leu Phe Val Thr Ala Ser Thr Val Glu Gln His Leu Thr Asp Val
865                 870                 875                 880

Ser Thr Gly Ser Arg Pro Pro Ala Pro Ala Ala Glu Leu Val
            885                 890

<210> SEQ ID NO 27
<211> LENGTH: 923
<212> TYPE: PRT
<213> ORGANISM: Streptomyces kanamyceticus

<400> SEQUENCE: 27

Met Val Pro Glu Val Arg Ala Ala Pro Asp Glu Leu Ile Ala Arg Asp
1               5                   10                  15

Asp Glu Leu Ser Arg Leu Gln Arg Ala Leu Thr Arg Ala Gly Ser Gly
            20                  25                  30

Arg Gly Gly Val Val Ala Ile Thr Gly Pro Ile Ala Ser Gly Lys Thr
            35                  40                  45

Ala Leu Leu Asp Ala Gly Ala Ala Lys Ser Gly Phe Val Ala Leu Arg
50                  55                  60

Ala Val Cys Ser Trp Glu Glu Arg Thr Leu Pro Tyr Gly Met Leu Gly
65                  70                  75                  80

Gln Leu Phe Asp His Pro Glu Leu Ala Ala Gln Ala Pro Asp Leu Ala
            85                  90                  95

His Phe Thr Ala Ser Cys Glu Ser Pro Gln Ala Gly Thr Asp Asn Arg
            100                 105                 110

Leu Arg Ala Glu Phe Thr Arg Thr Leu Leu Ala Leu Ala Ala Asp Trp
            115                 120                 125

Pro Val Leu Ile Gly Ile Asp Asp Val His Ala Asp Ala Glu Ser
130                 135                 140

Leu Arg Cys Leu Leu His Leu Ala Arg Arg Ile Gly Pro Ala Arg Ile
145                 150                 155                 160

Ala Val Val Leu Thr Glu Leu Arg Arg Pro Thr Pro Ala Asp Ser Arg
            165                 170                 175

Phe Gln Ala Glu Leu Leu Ser Leu Arg Ser Tyr Gln Glu Ile Ala Leu
            180                 185                 190

Arg Pro Leu Thr Glu Ala Gln Thr Gly Glu Leu Val Arg Arg His Leu
            195                 200                 205

Gly Ala Glu Thr His Glu Asp Val Ser Ala Asp Thr Phe Arg Ala Thr

```
              210                 215                 220
Gly Gly Asn Leu Leu Leu Gly His Gly Leu Ile Asn Asp Ile Arg Glu
225                 230                 235                 240

Ala Arg Thr Ala Gly Arg Pro Gly Val Val Ala Gly Arg Ala Tyr Arg
                245                 250                 255

Leu Ala Tyr Leu Ser Ser Leu Tyr Arg Cys Gly Pro Ser Ala Leu Arg
                260                 265                 270

Val Ala Arg Ala Ser Ala Val Leu Gly Ala Ser Ala Glu Ala Val Leu
                275                 280                 285

Val Gln Arg Met Thr Gly Leu Asn Lys Asp Ala Val Glu Gln Val Tyr
        290                 295                 300

Glu Gln Leu Asn Glu Gly Arg Leu Leu Gln Gly Glu Arg Phe Pro His
305                 310                 315                 320

Pro Ala Ala Arg Ser Ile Val Leu Asp Asp Leu Ser Ala Leu Glu Arg
                325                 330                 335

Arg Asn Leu His Glu Ser Ala Leu Glu Leu Leu Arg Asp His Gly Val
                340                 345                 350

Ala Gly Asn Val Leu Ala Arg His Gln Ile Gly Ala Gly Arg Val His
                355                 360                 365

Gly Glu Glu Ala Val Glu Leu Phe Thr Gly Ala Ala Arg Glu His His
        370                 375                 380

Leu Arg Gly Glu Leu Asp Asp Ala Ala Gly Tyr Leu Glu Leu Ala His
385                 390                 395                 400

Arg Ala Ser Asp Asp Pro Val Thr Arg Ala Ala Leu Arg Val Gly Ala
                405                 410                 415

Ala Ala Ile Glu Arg Leu Cys Asn Pro Val Arg Ala Gly Arg His Leu
                420                 425                 430

Pro Glu Leu Leu Thr Ala Ser Arg Ala Gly Leu Leu Ser Ser Glu His
                435                 440                 445

Ala Val Ser Leu Ala Asp Trp Leu Ala Met Gly Gly Arg Pro Gly Glu
        450                 455                 460

Ala Ala Glu Val Leu Ala Thr Gln Arg Pro Ala Ala Asp Ser Glu Gln
465                 470                 475                 480

His Arg Ala Leu Leu Arg Ser Gly Glu Leu Ser Leu Ala Leu Val His
                485                 490                 495

Pro Gly Ala Trp Asp Pro Leu Arg Arg Thr Asp Arg Phe Ala Ala Gly
                500                 505                 510

Gly Leu Gly Ser Leu Pro Gly Pro Ala Arg His Arg Ala Val Ala Asp
                515                 520                 525

Gln Ala Val Ile Ala Ala Leu Arg Gly Arg Leu Asp Arg Ala Asp Ala
        530                 535                 540

Asn Ala Glu Ser Val Leu Gln His Thr Asp Thr Ala Asp Arg Thr
545                 550                 555                 560

Thr Ala Ile Met Ala Leu Leu Ala Leu Leu Tyr Ala Glu Asn Thr Asp
                565                 570                 575

Ala Val Gln Phe Trp Val Asp Lys Leu Ala Gly Asp Glu Gly Thr Arg
                580                 585                 590

Thr Pro Ala Asp Glu Ala Val His Ala Gly Phe Asn Ala Glu Ile Ala
                595                 600                 605

Leu Arg Arg Gly Asp Leu Met Arg Ala Val Glu Tyr Gly Glu Ala Ala
                610                 615                 620

Leu Gly His Arg His Leu Pro Thr Trp Gly Met Ala Ala Ala Leu Pro
625                 630                 635                 640
```

Leu Ser Ser Thr Val Ala Ala Ile Arg Leu Gly Asp Leu Asp Arg
              645             650             655

Ala Glu Arg Trp Leu Ala Glu Pro Leu Pro Gln Gln Thr Pro Glu Ser
        660             665             670

Leu Phe Gly Leu His Leu Leu Trp Ala Arg Gly Gln His His Leu Ala
            675             680             685

Thr Gly Arg His Gly Ala Ala Tyr Thr Ala Phe Arg Glu Cys Gly Glu
        690             695             700

Arg Met Arg Arg Trp Ala Val Asp Val Pro Gly Leu Ala Leu Trp Arg
705             710             715             720

Val Asp Ala Ala Glu Ser Leu Leu Leu Gly Arg Asp Arg Ala Glu
              725             730             735

Gly Leu Arg Leu Val Ser Glu Gln Leu Ser Arg Pro Met Arg Pro Arg
            740             745             750

Ala Arg Val Gln Thr Leu Arg Val Gln Ala Ala Tyr Ser Pro Pro Pro
        755             760             765

Gln Arg Ile Asp Leu Leu Glu Glu Ala Ala Asp Leu Leu Val Thr Cys
    770             775             780

Asn Asp Gln Tyr Glu Leu Ala Asn Val Leu Ser Asp Leu Ala Glu Ala
785             790             795             800

Ser Ser Met Val Arg Gln His Ser Arg Ala Arg Gly Leu Leu Arg Arg
              805             810             815

Ala Arg His Leu Ala Thr Gln Cys Gly Ala Val Pro Leu Leu Arg Arg
            820             825             830

Leu Gly Ala Glu Pro Ser Asp Ile Gly Gly Ala Trp Asp Ala Thr Leu
        835             840             845

Gly Gln Arg Ile Ala Ser Leu Thr Glu Ser Glu Arg Arg Val Ala Ala
    850             855             860

Leu Ala Ala Val Gly Arg Thr Asn Arg Glu Ile Ala Glu Gln Leu Phe
865             870             875             880

Val Thr Ala Ser Thr Val Glu Gln His Leu Thr Asn Val Phe Arg Lys
              885             890             895

Leu Ala Val Lys Gly Arg Gln Gln Leu Pro Lys Glu Leu Ala Asp Val
            900             905             910

Gly Glu Pro Ala Asp Arg Asp Arg Arg Cys Gly
        915             920

<210> SEQ ID NO 28
<211> LENGTH: 913
<212> TYPE: PRT
<213> ORGANISM: Streptomyces ascomyceticus

<400> SEQUENCE: 28

Met Ile Ala Arg Leu Ser Pro Pro Asp Leu Ile Ala Arg Asp Asp Glu
1               5                   10                  15

Phe Gly Ser Leu His Arg Ala Leu Thr Arg Ala Gly Gly Arg Gly
            20                  25                  30

Val Val Ala Ala Val Thr Gly Pro Ile Ala Cys Gly Lys Thr Glu Leu
        35                  40                  45

Leu Asp Ala Ala Ala Lys Ala Gly Phe Val Thr Leu Arg Ala Val
    50                  55                  60

Cys Ser Met Glu Glu Arg Ala Leu Pro Tyr Gly Met Leu Gly Gln Leu
65                  70                  75                  80

Leu Asp Gln Pro Glu Leu Ala Ala Arg Thr Pro Glu Leu Val Arg Leu

```
                    85                  90                  95
Thr Ala Ser Cys Glu Asn Leu Pro Ala Asp Val Asp Asn Arg Leu Gly
                100                 105                 110

Thr Glu Leu Thr Arg Thr Val Leu Thr Leu Ala Ala Glu Arg Pro Val
                115                 120                 125

Leu Ile Gly Ile Asp Asp Val His His Ala Asp Ala Pro Ser Leu Arg
                130                 135                 140

Cys Leu Leu His Leu Ala Arg Arg Ile Ser Arg Ala Arg Val Ala Ile
145                 150                 155                 160

Val Leu Thr Glu Leu Leu Arg Pro Thr Pro Ala His Ser Gln Phe Arg
                165                 170                 175

Ala Ala Leu Leu Ser Leu Arg His Tyr Gln Glu Ile Ala Leu Arg Pro
                180                 185                 190

Leu Thr Glu Ala Gln Thr Thr Glu Leu Val Arg Arg His Leu Gly Gln
                195                 200                 205

Asp Ala His Asp Asp Val Val Ala Gln Ala Phe Arg Ala Thr Gly Gly
                210                 215                 220

Asn Leu Leu Leu Gly His Gly Leu Ile Asp Asp Ile Arg Glu Ala Arg
225                 230                 235                 240

Thr Arg Thr Ser Gly Cys Leu Glu Val Val Ala Gly Arg Ala Tyr Arg
                245                 250                 255

Leu Ala Tyr Leu Gly Ser Leu Tyr Arg Cys Gly Pro Ala Ala Leu Ser
                260                 265                 270

Val Ala Arg Ala Ser Ala Val Leu Gly Glu Ser Val Glu Leu Thr Leu
                275                 280                 285

Val Gln Arg Met Thr Gly Leu Asp Thr Glu Ala Val Glu Gln Ala His
                290                 295                 300

Glu Gln Leu Val Glu Gly Arg Leu Leu Arg Gly Arg Phe Pro His
305                 310                 315                 320

Pro Ala Ala Arg Ser Val Val Leu Asp Asp Leu Ser Ala Ala Glu Arg
                325                 330                 335

Arg Gly Leu His Glu Leu Ala Leu Glu Leu Leu Arg Asp Arg Gly Val
                340                 345                 350

Ala Ser Lys Val Leu Ala Arg His Gln Met Gly Thr Gly Arg Val His
                355                 360                 365

Gly Ala Glu Val Ala Gly Leu Phe Thr Asp Ala Ala Arg Glu His His
                370                 375                 380

Leu Arg Gly Glu Leu Asp Glu Ala Val Thr Tyr Leu Glu Phe Ala Tyr
385                 390                 395                 400

Arg Ala Ser Asp Asp Pro Ala Val His Ala Ala Leu Arg Val Asp Thr
                405                 410                 415

Ala Ala Ile Glu Arg Leu Cys Asp Pro Ala Arg Ser Gly Arg His Val
                420                 425                 430

Pro Glu Leu Leu Thr Ala Ser Arg Glu Arg Leu Leu Ser Ser Glu His
                435                 440                 445

Ala Val Ser Leu Ala Cys Trp Leu Ala Met Asp Gly Arg Pro Gly Glu
450                 455                 460

Ala Ala Glu Val Leu Ala Ala Gln Arg Ser Ala Pro Ser Glu Gln
465                 470                 475                 480

Gly Arg Ala His Leu Arg Val Ala Asp Leu Ser Leu Ala Leu Ile Tyr
                485                 490                 495

Pro Gly Ala Ala Asp Pro Pro Arg Pro Ala Asp Pro Pro Ala Glu Asp
                500                 505                 510
```

```
Glu Val Ala Ser Phe Ser Gly Ala Val Arg His Arg Ala Val Ala Asp
        515                 520                 525

Lys Ala Leu Ser Asn Ala Leu Arg Gly Trp Ser Glu Gln Ala Glu Ala
530                 535                 540

Lys Ala Glu Tyr Val Leu Gln His Ser Arg Val Thr Thr Asp Arg Thr
545                 550                 555                 560

Thr Thr Met Met Ala Leu Leu Ala Leu Leu Tyr Ala Glu Asp Thr Asp
                565                 570                 575

Ala Val Gln Ser Trp Val Asp Lys Leu Ala Gly Asp Asp Asn Met Arg
                580                 585                 590

Thr Pro Ala Asp Glu Ala Val His Ala Gly Phe Arg Ala Glu Ala Ala
        595                 600                 605

Leu Arg Arg Gly Asp Leu Thr Ala Ala Val Glu Cys Gly Glu Ala Ala
        610                 615                 620

Leu Ala Pro Arg Val Val Pro Ser Trp Gly Met Ala Ala Leu Pro
625                 630                 635                 640

Leu Ser Ser Thr Val Ala Ala Ile Arg Leu Gly Asp Leu Asp Arg
                645                 650                 655

Ala Glu Arg Trp Leu Ala Glu Pro Leu Pro Glu Glu Thr Ser Asp Ser
        660                 665                 670

Leu Phe Gly Leu His Met Val Trp Ala Arg Gly Gln His His Leu Ala
        675                 680                 685

Ala Gly Arg Tyr Arg Ala Ala Tyr Asn Ala Phe Arg Asp Cys Gly Glu
        690                 695                 700

Arg Met Arg Arg Trp Ser Val Asp Val Pro Gly Leu Ala Leu Trp Arg
705                 710                 715                 720

Val Asp Ala Ala Glu Ala Leu Leu Leu Gly Arg Gly Arg Asp Glu
                725                 730                 735

Gly Leu Arg Leu Ile Ser Glu Gln Leu Ser Arg Pro Met Gly Ser Arg
                740                 745                 750

Ala Arg Val Met Thr Leu Arg Val Gln Ala Ala Tyr Ser Pro Pro Ala
        755                 760                 765

Lys Arg Ile Glu Leu Leu Asp Glu Ala Ala Asp Leu Leu Ile Met Cys
        770                 775                 780

Arg Asp Gln Tyr Glu Leu Ala Arg Val Leu Ala Asp Met Gly Glu Ala
785                 790                 795                 800

Cys Gly Met Leu Arg Arg His Ser Arg Ala Arg Gly Leu Phe Arg Arg
                805                 810                 815

Ala Arg His Leu Ala Thr Gln Cys Gly Ala Val Pro Leu Leu Arg Arg
                820                 825                 830

Leu Gly Gly Glu Ser Ser Asp Ala Asp Gly Thr Gln Asp Val Thr Pro
        835                 840                 845

Ala Gln Arg Ile Thr Ser Leu Thr Glu Ala Glu Arg Arg Val Ala Ser
        850                 855                 860

His Ala Ala Val Gly Arg Thr Asn Lys Glu Ile Ala Ser Gln Leu Phe
865                 870                 875                 880

Val Thr Ser Ser Thr Val Glu Gln His Leu Thr Asn Val Phe Arg Lys
                885                 890                 895

Leu Gly Val Lys Gly Arg Gln Gln Leu Pro Lys Glu Leu Ser Asp Ala
                900                 905                 910

Gly
```

```
<210> SEQ ID NO 29
<211> LENGTH: 901
<212> TYPE: PRT
<213> ORGANISM: Micromonospora sp. S92-306401

<400> SEQUENCE: 29

Met Glu Phe Tyr Asp Leu Val Ala Arg Asp Glu Leu Arg Arg Leu
1               5                   10                  15

Asp Gln Ala Leu Gly Arg Ala Ala Gly Gly Arg Gly Val Val Thr
                20                  25                  30

Val Thr Gly Pro Val Gly Cys Gly Lys Thr Glu Leu Leu Asp Ala Ala
                35                  40                  45

Ala Ala Glu Glu Glu Phe Ile Thr Leu Arg Ala Val Cys Ser Ala Glu
        50                  55                  60

Glu Arg Ala Leu Pro Tyr Ala Val Ile Gly Gln Leu Leu Asp His Pro
65                  70                  75                  80

Val Leu Ser Ala Arg Ala Pro Asp Leu Ala Cys Val Thr Ala Pro Gly
                85                  90                  95

Arg Thr Leu Pro Ala Asp Thr Glu Asn Arg Leu Arg Arg Asp Leu Thr
                100                 105                 110

Arg Ala Leu Leu Ala Leu Ala Ser Glu Arg Pro Val Leu Ile Cys Ile
                115                 120                 125

Asp Asp Val His Gln Ala Asp Thr Ala Ser Leu Asn Cys Leu Leu His
130                 135                 140

Leu Ala Arg Arg Val Ala Ser Ala Arg Ile Ala Met Ile Leu Thr Glu
145                 150                 155                 160

Leu Arg Arg Leu Thr Pro Ala His Ser Arg Phe Glu Ala Glu Leu Leu
                165                 170                 175

Ser Leu Arg His Arg His Glu Ile Ala Leu Arg Pro Leu Gly Pro Ala
                180                 185                 190

Asp Thr Ala Glu Leu Ala Arg Ala Arg Leu Gly Ala Gly Val Thr Ala
                195                 200                 205

Asp Glu Leu Ala Gln Val His Glu Ala Thr Ser Gly Asn Pro Asn Leu
210                 215                 220

Val Gly Gly Leu Val Asn Asp Val Arg Glu Ala Trp Ala Ala Gly Gly
225                 230                 235                 240

Thr Gly Ile Ala Ala Gly Arg Ala Tyr Arg Leu Ala Tyr Leu Ser Ser
                245                 250                 255

Val Tyr Arg Cys Gly Pro Val Pro Leu Arg Ile Ala Gln Ala Ala Ala
                260                 265                 270

Val Leu Gly Pro Ser Ala Thr Val Thr Leu Val Arg Arg Ile Ser Gly
                275                 280                 285

Leu Asp Ala Glu Thr Val Asp Glu Ala Thr Ala Ile Leu Thr Glu Gly
290                 295                 300

Gly Leu Leu Arg Asp His Arg Phe Pro His Pro Ala Ala Arg Ser Val
305                 310                 315                 320

Val Leu Asp Asp Met Ser Ala Gln Glu Arg Arg Leu His Arg Ser
                325                 330                 335

Thr Leu Asp Val Leu Asp Gly Val Pro Val Asp Val Leu Ala His His
                340                 345                 350

Gln Ala Gly Ala Gly Leu Leu His Gly Pro Gln Ala Ala Glu Met Phe
                355                 360                 365

Ala Arg Ala Ser Gln Glu Leu Arg Val Arg Gly Glu Leu Asp Ala Ala
                370                 375                 380
```

```
Thr Glu Tyr Leu Gln Leu Ala Tyr Arg Ala Ser Asp Asp Ala Gly Ala
385                 390                 395                 400

Arg Ala Ala Leu Gln Val Glu Thr Val Ala Gly Glu Arg Arg Arg Asn
            405                 410                 415

Pro Leu Ala Ala Ser Arg His Leu Asp Glu Leu Ala Ala Ala Ala Arg
        420                 425                 430

Ala Gly Leu Leu Ser Ala Glu His Ala Ala Leu Val Val His Trp Leu
            435                 440                 445

Ala Asp Ala Gly Arg Pro Gly Glu Ala Ala Glu Val Leu Ala Leu Gln
        450                 455                 460

Arg Ala Leu Ala Val Thr Asp His Asp Arg Ala Arg Leu Arg Ala Ala
465                 470                 475                 480

Glu Val Ser Leu Ala Leu Phe His Pro Gly Val Pro Gly Ser Asp Pro
            485                 490                 495

Arg Pro Leu Ala Pro Glu Glu Leu Ala Ser Leu Ser Leu Ser Ala Arg
        500                 505                 510

His Gly Val Thr Ala Asp Asn Ala Val Leu Ala Ala Leu Arg Gly Arg
            515                 520                 525

Pro Glu Ser Ala Ala Ala Glu Ala Glu Asn Val Leu Arg Asn Ala Asp
        530                 535                 540

Ala Ala Ser Gly Pro Thr Ala Leu Ala Ala Leu Thr Ala Leu Leu
545                 550                 555                 560

Tyr Ala Glu Asn Thr Asp Ala Ala Gln Leu Trp Ala Asp Lys Leu Ala
            565                 570                 575

Ala Gly Ile Gly Ala Gly Glu Gly Glu Ala Gly Tyr Ala Gly Pro Arg
        580                 585                 590

Thr Val Ala Ala Leu Arg Arg Gly Asp Leu Thr Thr Ala Val Gln Ala
            595                 600                 605

Ala Gly Ala Val Leu Asp Arg Gly Arg Pro Ser Ser Leu Gly Ile Thr
        610                 615                 620

Ala Val Leu Pro Leu Ser Gly Ala Val Ala Ala Ile Arg Leu Gly
625                 630                 635                 640

Glu Leu Glu Arg Ala Glu Lys Trp Leu Ala Glu Pro Leu Pro Glu Ala
            645                 650                 655

Val His Asp Ser Leu Phe Gly Leu His Leu Leu Met Ala Arg Gly Arg
        660                 665                 670

Tyr Ser Leu Ala Val Gly Arg His Glu Ala Ala Tyr Ala Ala Phe Arg
            675                 680                 685

Asp Cys Gly Glu Arg Met Arg Arg Trp Asp Val Asp Val Pro Gly Leu
        690                 695                 700

Ala Leu Trp Arg Val Asp Ala Ala Glu Ala Leu Leu Pro Gly Asp Asp
705                 710                 715                 720

Arg Ala Glu Gly Arg Arg Leu Ile Asp Glu Gln Leu Thr Arg Pro Met
            725                 730                 735

Gly Pro Arg Ser Arg Ala Leu Thr Leu Arg Val Arg Ala Ala Tyr Ala
        740                 745                 750

Pro Pro Ala Lys Arg Ile Asp Leu Leu Asp Glu Ala Ala Asp Leu Leu
            755                 760                 765

Leu Ser Ser Asn Asp Gln Tyr Glu Arg Ala Arg Val Leu Ala Asp Leu
        770                 775                 780

Ser Glu Ala Phe Ser Ala Leu Arg Gln Asn Gly Arg Ala Arg Gly Ile
785                 790                 795                 800

Leu Arg Gln Ala Arg His Leu Ala Ala Gln Cys Gly Ala Val Pro Leu
```

```
              805                 810                 815

Leu Arg Arg Leu Gly Val Lys Ala Gly Arg Ser Gly Arg Leu Gly Arg
            820                 825                 830

Pro Pro Gln Gly Ile Arg Ser Leu Thr Glu Ala Glu Arg Arg Val Ala
            835                 840                 845

Thr Leu Ala Ala Ala Gly Gln Thr Asn Arg Glu Ile Ala Asp Gln Leu
            850                 855                 860

Phe Val Thr Ala Ser Thr Val Glu Gln His Leu Thr Asn Val Phe Arg
865                 870                 875                 880

Lys Leu Gly Val Lys Gly Arg Gln Gln Leu Pro Ala Glu Leu Ala Asp
            885                 890                 895

Leu Arg Pro Pro Gly
            900

<210> SEQ ID NO 30
<211> LENGTH: 906
<212> TYPE: PRT
<213> ORGANISM: Streptomyces violaceusniger

<400> SEQUENCE: 30

Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Glu Gln Ala Ser Ser Gly
            20                  25                  30

Gln Gly Val Val Thr Val Thr Gly Pro Ile Ala Cys Gly Lys Thr
            35                  40                  45

Glu Leu Leu Asp Ala Ala Ala Lys Ala Glu Ala Ile Ile Leu Arg
            50                  55                  60

Ala Val Cys Ala Pro Glu Glu Arg Ala Met Pro Tyr Ala Met Ile Gly
65                  70                  75                  80

Gln Leu Ile Asp Asp Pro Ala Leu Ala His Arg Ala Pro Gly Leu Ala
            85                  90                  95

Asp Arg Ile Ala Gln Gly Gly Gln Leu Ser Leu Arg Ala Glu Asn Arg
            100                 105                 110

Leu Arg Arg Asp Leu Thr Arg Ala Leu Leu Ala Leu Ala Val Asp Arg
            115                 120                 125

Pro Val Leu Ile Gly Val Asp Asp Val His His Ala Asp Thr Ala Ser
            130                 135                 140

Leu Asn Cys Leu Leu His Leu Ala Arg Arg Val Arg Pro Ala Arg Ile
145                 150                 155                 160

Ser Met Ile Phe Thr Glu Leu Arg Ser Leu Thr Pro Thr Gln Ser Arg
            165                 170                 175

Phe Lys Ala Glu Leu Leu Ser Leu Pro Tyr His His Glu Ile Ala Leu
            180                 185                 190

Arg Pro Phe Gly Pro Glu Gln Ser Ala Glu Leu Ala Arg Ala Ala Phe
            195                 200                 205

Gly Pro Gly Leu Ala Glu Asp Val Leu Val Gly Leu Tyr Lys Thr Thr
            210                 215                 220

Arg Gly Asn Leu Ser Leu Ser Arg Gly Leu Ile Ser Asp Val Arg Glu
225                 230                 235                 240

Ala Leu Ala Asn Gly Glu Ser Ala Phe Glu Ala Gly Arg Ala Phe Arg
            245                 250                 255

Leu Ala Tyr Leu Gly Ser Leu Tyr Arg Cys Gly Pro Val Ala Leu Arg
            260                 265                 270
```

```
Val Ala Arg Val Ala Ala Val Leu Gly Pro Ser Ala Thr Thr Thr Leu
            275                 280                 285
Val Arg Arg Leu Ser Gly Leu Ser Ala Glu Thr Ile Asp Arg Ala Thr
290                 295                 300
Lys Ile Leu Thr Glu Gly Gly Leu Leu Leu Asp Gln Gln Phe Pro His
305                 310                 315                 320
Pro Ala Ala Arg Ser Val Val Leu Asp Asp Met Ser Ala Gln Glu Arg
                325                 330                 335
Arg Gly Leu His Thr Leu Ala Leu Glu Leu Leu Asp Glu Ala Pro Val
            340                 345                 350
Glu Val Leu Ala His His Gln Val Gly Ala Gly Leu Ile His Gly Pro
            355                 360                 365
Lys Ala Ala Glu Met Phe Ala Lys Ala Gly Lys Ala Leu Val Val Arg
370                 375                 380
Asn Glu Leu Gly Asp Ala Ala Glu Tyr Leu Gln Leu Ala His Arg Ala
385                 390                 395                 400
Ser Asp Asp Val Ser Thr Arg Ala Ala Leu Arg Val Glu Ala Val Ala
                405                 410                 415
Ile Glu Arg Arg Arg Asn Pro Leu Ala Ser Ser Arg His Met Asp Glu
            420                 425                 430
Leu Ser Ala Ala Gly Arg Ala Gly Leu Leu Ser Pro Lys His Ala Ala
            435                 440                 445
Leu Ala Val Phe Trp Leu Ala Asp Gly Gly Arg Ser Gly Glu Ala Ala
            450                 455                 460
Glu Val Leu Ala Ser Glu Arg Pro Leu Ala Thr Thr Asp Gln Asn Arg
465                 470                 475                 480
Ala His Leu Arg Phe Val Glu Val Thr Leu Ala Leu Phe Ser Pro Gly
                485                 490                 495
Ala Phe Gly Ser Asp Arg Arg Pro Pro Leu Thr Pro Asp Glu Leu
                500                 505                 510
Ala Ser Leu Pro Lys Ala Ala Trp Gln Cys Ala Val Ala Asp Asn Ala
            515                 520                 525
Ala Met Thr Ala Leu His Gly His Pro Glu Leu Ala Thr Ala Gln Ala
            530                 535                 540
Glu Thr Val Leu Arg Gln Ala Asp Ser Ala Ala Asp Ala Ile Pro Ala
545                 550                 555                 560
Ala Leu Ile Ala Leu Leu Tyr Ala Glu Asn Thr Glu Ser Ala His Ile
                565                 570                 575
Trp Ala Asp Lys Leu Gly Ser Thr Asn Gly Gly Val Ser Asn Glu Ala
            580                 585                 590
Glu Ala Gly Tyr Ala Gly Pro Cys Ala Glu Ile Ala Leu Arg Arg Gly
            595                 600                 605
Asp Leu Ala Thr Ala Phe Glu Ala Gly Ser Thr Val Leu Asp Asp Arg
610                 615                 620
Ser Leu Pro Ser Leu Gly Ile Thr Ala Ala Leu Leu Leu Ser Ser Lys
625                 630                 635                 640
Thr Ala Ala Ala Val Arg Leu Gly Glu Leu Glu Arg Ala Glu Lys Leu
                645                 650                 655
Leu Ala Glu Pro Leu Pro Asn Gly Val Gln Asp Ser Leu Phe Gly Leu
            660                 665                 670
His Leu Leu Ser Ala Tyr Gly Gln Tyr Ser Leu Ala Met Gly Arg Tyr
            675                 680                 685
Glu Ser Ala Leu Arg Ala Phe His Thr Cys Gly Glu Arg Met Arg Ser
```

-continued

```
                690                 695                 700
Trp Asp Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
                725                 730                 735

Glu Gln Leu Thr Arg Pro Met Gly Pro Arg Ser Arg Ala Leu Thr Leu
            740                 745                 750

Arg Ile Lys Ala Ala Tyr Leu Pro Arg Thr Lys Arg Ile Pro Leu Leu
                755                 760                 765

His Glu Ala Ala Glu Leu Leu Leu Pro Cys Pro Asp Pro Tyr Glu Gln
            770                 775                 780

Ala Arg Val Leu Ala Asp Leu Gly Asp Thr Leu Ser Ala Leu Arg Arg
785                 790                 795                 800

Tyr Ser Arg Ala Arg Gly Val Leu Arg Gln Ala Arg His Leu Ala Ala
                805                 810                 815

Gln Cys Gly Ala Val Pro Leu Leu Arg Arg Leu Gly Gly Glu Pro Gly
            820                 825                 830

Arg Ile Asp Asp Ala Gly Leu Pro Gln Arg Ser Thr Ser Leu Thr Asp
            835                 840                 845

Ala Glu Arg Arg Val Ala Ala Leu Ala Ala Gly Gln Thr Asn Arg
850                 855                 860

Glu Ile Ala Lys Gln Leu Phe Val Thr Ala Ser Thr Val Glu Gln His
865                 870                 875                 880

Leu Thr Ser Val Phe Arg Lys Leu Gly Val Lys Gly Arg Lys Gln Leu
                885                 890                 895

Pro Thr Ala Leu Ala Asp Val Glu Gln Thr
            900                 905

<210> SEQ ID NO 31
<211> LENGTH: 914
<212> TYPE: PRT
<213> ORGANISM: Streptomyces hygroscopicus

<400> SEQUENCE: 31

Met Pro Ala Val Glu Ser Tyr Glu Leu Asp Ala Arg Asp Asp Glu Leu
1               5                   10                  15

Arg Arg Leu Glu Glu Ala Val Gly Gln Ala Gly Asn Gly Arg Gly Val
                20                  25                  30

Val Val Thr Ile Thr Gly Pro Ile Ala Cys Gly Lys Thr Glu Leu Leu
            35                  40                  45

Asp Ala Ala Ala Lys Ser Asp Ala Ile Thr Leu Arg Ala Val Cys
50                  55                  60

Ser Glu Glu Glu Arg Ala Leu Pro Tyr Ala Leu Ile Gly Gln Leu Ile
65                  70                  75                  80

Asp Asn Pro Ala Val Ala Ser Gln Leu Pro Asp Pro Val Ser Met Ala
                85                  90                  95

Leu Pro Gly Glu His Leu Ser Pro Glu Ala Glu Asn Arg Leu Arg Gly
            100                 105                 110

Asp Leu Thr Arg Thr Leu Leu Ala Leu Ala Ala Glu Arg Pro Val Leu
            115                 120                 125

Ile Gly Ile Asp Asp Met His His Ala Asp Thr Ala Ser Leu Asn Cys
            130                 135                 140

Leu Leu His Leu Ala Arg Arg Val Gly Pro Ala Arg Ile Ala Met Val
145                 150                 155                 160
```

```
Leu Thr Glu Leu Arg Arg Leu Thr Pro Ala His Ser Gln Phe His Ala
                165                 170                 175

Glu Leu Leu Ser Leu Gly His His Arg Glu Ile Ala Leu Arg Pro Leu
            180                 185                 190

Gly Pro Lys His Ile Ala Glu Leu Ala Arg Ala Gly Leu Gly Pro Asp
        195                 200                 205

Val Asp Glu Asp Val Leu Thr Gly Leu Tyr Arg Ala Thr Gly Gly Asn
    210                 215                 220

Leu Asn Leu Gly His Gly Leu Ile Lys Asp Val Arg Glu Ala Trp Ala
225                 230                 235                 240

Thr Gly Gly Thr Gly Ile Asn Ala Gly Arg Ala Tyr Arg Leu Ala Tyr
                245                 250                 255

Leu Gly Ser Leu Tyr Arg Cys Gly Pro Val Pro Leu Arg Val Ala Arg
            260                 265                 270

Val Ala Ala Val Leu Gly Gln Ser Ala Asn Thr Thr Leu Val Arg Trp
        275                 280                 285

Ile Ser Gly Leu Asn Ala Asp Ala Val Gly Glu Ala Thr Glu Ile Leu
    290                 295                 300

Thr Glu Gly Gly Leu Leu His Asp Leu Arg Phe Pro His Pro Ala Ala
305                 310                 315                 320

Arg Ser Val Val Leu Asn Asp Leu Ser Ala Arg Glu Arg Arg Leu
                325                 330                 335

His Arg Ser Ala Leu Glu Val Leu Asp Asp Val Pro Val Glu Val Val
                340                 345                 350

Ala His His Gln Ala Gly Ala Gly Phe Ile His Gly Pro Lys Ala Ala
            355                 360                 365

Glu Ile Phe Ala Lys Ala Gly Gln Glu Leu His Val Arg Gly Glu Leu
    370                 375                 380

Asp Ala Ala Ser Asp Tyr Leu Gln Leu Ala His His Ala Ser Asp Asp
385                 390                 395                 400

Ala Val Thr Arg Ala Ala Leu Arg Val Glu Ala Val Ala Ile Glu Arg
                405                 410                 415

Arg Arg Asn Pro Leu Ala Ser Ser Arg His Leu Asp Glu Leu Thr Val
            420                 425                 430

Ala Ala Arg Ala Gly Leu Leu Ser Leu Glu His Ala Ala Leu Met Ile
        435                 440                 445

Arg Trp Leu Ala Leu Gly Gly Arg Ser Gly Glu Ala Ala Glu Val Leu
    450                 455                 460

Ala Ala Gln Arg Pro Arg Ala Val Thr Asp Gln Asp Arg Ala His Leu
465                 470                 475                 480

Arg Ala Ala Glu Val Ser Leu Ala Leu Val Ser Pro Gly Ala Ser Gly
                485                 490                 495

Val Ser Pro Gly Ala Ser Gly Pro Asp Arg Arg Pro Arg Pro Leu Pro
            500                 505                 510

Pro Asp Glu Leu Ala Asn Leu Pro Lys Ala Ala Arg Leu Cys Ala Ile
        515                 520                 525

Ala Asp Asn Ala Val Ile Ser Ala Leu His Gly Arg Pro Glu Leu Ala
    530                 535                 540

Ser Ala Glu Ala Glu Asn Val Leu Lys Gln Ala Asp Ser Ala Ala Asp
545                 550                 555                 560

Gly Ala Thr Ala Leu Ser Ala Leu Thr Ala Leu Leu Tyr Ala Glu Asn
                565                 570                 575

Thr Asp Thr Ala Gln Leu Trp Ala Asp Lys Leu Val Ser Glu Thr Gly
```

```
                580             585             590
Ala Ser Asn Glu Glu Gly Ala Gly Tyr Ala Gly Pro Arg Ala Glu
            595                 600             605

Thr Ala Leu Arg Arg Gly Asp Leu Ala Ala Val Glu Ala Gly Ser
            610                 615             620

Ala Ile Leu Asp His Arg Arg Gly Ser Leu Leu Gly Ile Thr Ala Ala
625                 630                 635                 640

Leu Pro Leu Ser Ser Ala Val Ala Ala Ile Arg Leu Gly Glu Thr
                645                 650                 655

Glu Arg Ala Glu Lys Trp Leu Ala Glu Pro Leu Pro Glu Ala Ile Arg
                660                 665                 670

Asp Ser Leu Phe Gly Leu His Leu Leu Ser Ala Arg Gly Gln Tyr Cys
                675                 680                 685

Leu Ala Thr Gly Arg His Glu Ser Ala Tyr Thr Ala Phe Arg Thr Cys
                690                 695                 700

Gly Glu Arg Met Arg Asn Trp Gly Val Asp Val Pro Gly Leu Ser Leu
705                 710                 715                 720

Trp Arg Val Asp Ala Ala Glu Ala Leu Leu His Gly Arg Asp Arg Asp
                725                 730                 735

Glu Gly Arg Arg Leu Ile Asp Glu Gln Leu Thr His Ala Met Gly Pro
                740                 745                 750

Arg Ser Arg Ala Leu Thr Leu Arg Val Gln Ala Tyr Ser Pro Gln
755                 760                 765

Ala Gln Arg Val Asp Leu Leu Glu Glu Ala Ala Asp Leu Leu Leu Ser
770                 775                 780

Cys Asn Asp Gln Tyr Glu Arg Ala Arg Val Leu Ala Asp Leu Ser Glu
785                 790                 795                 800

Ala Phe Ser Ala Leu Arg His His Ser Arg Ala Arg Gly Leu Leu Arg
                805                 810                 815

Gln Ala Arg His Leu Ala Ala Gln Cys Gly Ala Thr Pro Leu Leu Arg
                820                 825                 830

Arg Leu Gly Ala Lys Pro Gly Gly Pro Gly Trp Leu Glu Glu Ser Gly
                835                 840                 845

Leu Pro Gln Arg Ile Lys Ser Leu Thr Asp Ala Glu Arg Arg Val Ala
                850                 855                 860

Ser Leu Ala Ala Gly Gly Gln Thr Asn Arg Val Ile Ala Asp Gln Leu
865                 870                 875                 880

Phe Val Thr Ala Ser Thr Val Glu Gln His Leu Thr Asn Val Phe Arg
                885                 890                 895

Lys Leu Gly Val Lys Gly Arg Gln His Leu Pro Ala Glu Leu Ala Asn
                900                 905                 910

Ala Glu

<210> SEQ ID NO 32
<211> LENGTH: 875
<212> TYPE: PRT
<213> ORGANISM: Actinoplanes sp. N01-109

<400> SEQUENCE: 32

Met Pro Ala Val Lys Arg Asn Asp Leu Val Ala Arg Asp Gly Glu Leu
1               5                   10                  15

Arg Trp Met Gln Glu Ile Leu Ser Gln Ala Ser Glu Gly Arg Gly Ala
                20                  25                  30

Val Val Thr Ile Thr Gly Ala Ile Ala Cys Gly Lys Thr Val Leu Leu
```

```
            35                  40                  45
Asp Ala Ala Ala Ser Gln Asp Val Ile Gln Leu Arg Ala Val Cys
 50                  55                  60

Ser Ala Glu Glu Gln Glu Leu Pro Tyr Ala Met Val Gly Gln Leu Leu
 65                  70                  75                  80

Asp Asn Pro Val Leu Ala Ala Arg Val Pro Ala Leu Gly Asn Leu Ala
                 85                  90                  95

Ala Ala Gly Glu Arg Leu Leu Pro Gly Thr Glu Asn Arg Ile Arg Arg
            100                 105                 110

Glu Leu Thr Arg Thr Leu Leu Ala Leu Ala Asp Glu Arg Pro Val Leu
            115                 120                 125

Ile Gly Val Asp Asp Met His His Ala Asp Pro Ala Ser Leu Asp Cys
            130                 135                 140

Leu Leu His Leu Ala Arg Arg Val Gly Pro Ala Arg Ile Ala Ile Val
145                 150                 155                 160

Leu Thr Glu Leu Arg Arg Leu Thr Pro Ala His Ser Arg Phe Gln Ser
                165                 170                 175

Glu Leu Leu Ser Leu Arg Tyr His His Glu Ile Gly Leu Gln Pro Leu
            180                 185                 190

Thr Ala Glu His Thr Ala Asp Leu Ala Arg Val Gly Leu Gly Ala Glu
            195                 200                 205

Val Asp Asp Asp Val Leu Thr Glu Leu Tyr Glu Ala Thr Gly Gly Asn
210                 215                 220

Pro Ser Leu Cys Cys Gly Leu Ile Arg Asp Val Arg Gln Asp Trp Glu
225                 230                 235                 240

Ala Gly Val Thr Gly Ile His Val Gly Arg Ala Tyr Arg Leu Ala Tyr
                245                 250                 255

Leu Ser Ser Leu Tyr Arg Cys Gly Pro Ala Ala Leu Arg Thr Ala Arg
            260                 265                 270

Ala Ala Ala Val Leu Gly Asp Ser Ala Asp Ala Cys Leu Ile Arg Arg
            275                 280                 285

Val Ser Gly Leu Gly Thr Glu Ala Val Gly Gln Ala Ile Gln Gln Leu
290                 295                 300

Thr Glu Gly Gly Leu Leu Arg Asp Gln Gln Phe Pro His Pro Ala Ala
305                 310                 315                 320

Arg Ser Val Val Leu Asp Asp Met Ser Ala Gln Glu Arg His Ala Met
                325                 330                 335

Tyr Arg Ser Ala Arg Glu Ala Ala Glu Gly Gln Ala Asp Pro Gly
            340                 345                 350

Thr Pro Gly Glu Pro Arg Ala Ala Thr Ala Tyr Ala Gly Cys Gly Glu
            355                 360                 365

Gln Ala Gly Asp Tyr Pro Glu Pro Ala Gly Arg Ala Cys Val Asp Gly
            370                 375                 380

Ala Gly Pro Ala Glu Tyr Cys Gly Asp Pro His Gly Ala Asp Asp
385                 390                 395                 400

Pro Asp Glu Leu Val Ala Ala Leu Gly Gly Leu Leu Pro Ser Arg Leu
                405                 410                 415

Val Ala Met Lys Ile Arg Arg Leu Ala Val Ala Gly Arg Pro Gly Ala
            420                 425                 430

Ala Ala Glu Leu Leu Thr Ser Gln Arg Leu His Ala Val Thr Ser Glu
            435                 440                 445

Asp Arg Ala Ser Leu Arg Ala Ala Glu Val Ala Leu Ala Thr Leu Trp
450                 455                 460
```

```
Pro Gly Ala Thr Gly Pro Asp Arg His Pro Leu Thr Glu Gln Glu Ala
465                 470                 475                 480

Ala Ser Leu Pro Glu Gly Pro Arg Leu Leu Ala Ala Asp Asp Ala
        485                 490                 495

Val Gly Ala Ala Leu Arg Gly Arg Ala Glu Tyr Ala Ala Ala Glu Ala
            500                 505                 510

Glu Asn Val Leu Arg His Ala Asp Pro Ala Ala Gly Gly Asp Ala Tyr
            515                 520                 525

Ala Ala Met Ile Ala Leu Leu Tyr Thr Glu His Pro Glu Asn Val Leu
            530                 535                 540

Phe Trp Ala Asp Lys Leu Asp Ala Gly Arg Pro Asp Glu Glu Thr Ser
545                 550                 555                 560

Tyr Pro Gly Leu Arg Ala Glu Thr Ala Val Arg Leu Gly Asp Leu Glu
                565                 570                 575

Thr Ala Met Glu Leu Gly Arg Thr Val Leu Asp Gln Arg Arg Leu Pro
            580                 585                 590

Ser Leu Gly Val Ala Ala Gly Leu Leu Gly Gly Ala Val Thr Ala
        595                 600                 605

Ala Ile Arg Leu Gly Asp Leu Asp Arg Ala Glu Lys Trp Leu Ala Glu
610                 615                 620

Pro Ile Pro Asp Ala Ile Arg Thr Ser Leu Tyr Gly Leu His Val Leu
625                 630                 635                 640

Ala Ala Arg Gly Arg Leu Asp Leu Ala Ala Gly Arg Tyr Glu Ala Ala
                645                 650                 655

Tyr Thr Ala Phe Arg Leu Cys Gly Glu Arg Met Ala Gly Trp Asp Ala
            660                 665                 670

Asp Val Ser Gly Leu Ala Leu Trp Arg Val Asp Ala Ala Glu Ala Leu
            675                 680                 685

Leu Ser Ala Gly Ile Arg Pro Asp Glu Gly Arg Lys Leu Ile Asp Asp
        690                 695                 700

Gln Leu Thr Arg Glu Met Gly Ala Arg Ser Arg Ala Leu Thr Leu Arg
705                 710                 715                 720

Ala Gln Ala Ala Tyr Ser Leu Pro Val His Arg Val Gly Leu Leu Asp
            725                 730                 735

Glu Ala Ala Gly Leu Leu Leu Ala Cys His Asp Gly Tyr Glu Arg Ala
        740                 745                 750

Arg Val Leu Ala Asp Leu Gly Glu Thr Leu Arg Thr Leu Arg His Thr
        755                 760                 765

Asp Ala Ala Gln Arg Val Leu Arg Gln Ala Glu Gln Ala Ala Ala Arg
        770                 775                 780

Cys Gly Ser Val Pro Leu Leu Arg Leu Gly Ala Glu Pro Val Arg
785                 790                 795                 800

Ile Gly Thr Arg Arg Gly Glu Pro Gly Leu Pro Gln Arg Ile Arg Leu
            805                 810                 815

Leu Thr Asp Ala Glu Arg Arg Val Ala Met Ala Ala Gly Gln
            820                 825                 830

Thr Asn Arg Glu Ile Ala Gly Arg Leu Phe Val Thr Ala Ser Thr Val
        835                 840                 845

Glu Gln His Leu Thr Ser Val Phe Arg Lys Leu Gly Val Lys Gly Arg
        850                 855                 860

Arg Phe Leu Pro Thr Glu Leu Ala Gln Ala Val
865                 870                 875
```

<210> SEQ ID NO 33
<211> LENGTH: 906
<212> TYPE: PRT
<213> ORGANISM: Streptomyces malaysiensis

<400> SEQUENCE: 33

```
Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Glu Gln Ala Ser Ser Gly
            20                  25                  30

Gln Gly Val Val Val Thr Val Thr Gly Pro Ile Ala Cys Gly Lys Thr
        35                  40                  45

Glu Leu Leu Asp Ala Ala Ala Lys Ala Glu Ala Ile Ile Leu Arg
50                  55                  60

Ala Val Cys Ala Pro Glu Glu Arg Ala Met Pro Tyr Ala Met Ile Gly
65                  70                  75                  80

Gln Leu Ile Asp Asp Pro Ala Leu Ala His Arg Ala Pro Gly Leu Ala
                85                  90                  95

Asp Arg Ile Ala Gln Gly Gly Gln Leu Ser Leu Arg Ala Glu Asn Arg
            100                 105                 110

Leu Arg Arg Asp Leu Thr Arg Ala Leu Leu Ala Leu Ala Val Asp Arg
        115                 120                 125

Pro Val Leu Ile Gly Val Asp Val His His Ala Asp Thr Ala Ser
    130                 135                 140

Leu Asn Cys Leu Leu His Leu Ala Arg Arg Val Arg Pro Ala Arg Ile
145                 150                 155                 160

Ser Met Ile Phe Thr Glu Leu Arg Ser Leu Thr Pro Thr Gln Ser Arg
                165                 170                 175

Phe Lys Ala Glu Leu Leu Ser Leu Pro Tyr His His Glu Ile Ala Leu
            180                 185                 190

Arg Pro Phe Gly Pro Glu Gln Ser Ala Glu Leu Ala Arg Ala Ala Phe
        195                 200                 205

Gly Pro Gly Leu Ala Glu Asp Val Leu Ala Gly Leu Tyr Lys Thr Thr
    210                 215                 220

Arg Gly Asn Leu Ser Leu Ser Arg Gly Leu Ile Ser Asp Val Arg Glu
225                 230                 235                 240

Ala Leu Ala Asn Gly Glu Ser Ala Phe Glu Ala Gly Arg Ala Phe Arg
                245                 250                 255

Leu Ala Tyr Leu Ser Ser Leu Tyr Arg Cys Gly Pro Val Ala Leu Arg
            260                 265                 270

Val Ala Arg Val Ala Ala Val Leu Gly Pro Ser Ala Thr Thr Thr Leu
        275                 280                 285

Val Arg Arg Leu Ser Gly Leu Ser Ala Glu Thr Ile Asp Arg Ala Thr
    290                 295                 300

Lys Ile Leu Thr Glu Gly Gly Leu Leu Leu Asp Gln Gln Phe Pro His
305                 310                 315                 320

Pro Ala Ala Arg Ser Val Val Leu Asp Asp Met Ser Ala Gln Glu Arg
                325                 330                 335

Arg Ser Leu His Thr Leu Ala Leu Glu Leu Leu Asp Glu Ala Pro Val
            340                 345                 350

Glu Val Leu Ala His His Gln Val Gly Ala Gly Leu Ile His Gly Pro
        355                 360                 365

Lys Ala Ala Glu Met Phe Ala Lys Ala Gly Lys Ala Leu Val Val Arg
    370                 375                 380
```

```
Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
                405                 410                 415

Ile Glu Arg Arg Arg Asn Pro Leu Ala Ser Ser Arg His Met Asp Glu
            420                 425                 430

Leu Ser Ala Ala Gly Arg Ala Gly Leu Leu Ser Pro Lys His Ala Ala
            435                 440                 445

Leu Ala Val Phe Trp Leu Ala Asp Gly Gly Arg Ser Gly Glu Ala Ala
        450                 455                 460

Glu Val Leu Ala Ser Glu Arg Pro Leu Ala Thr Thr Asp Gln Asn Arg
465                 470                 475                 480

Ala His Leu Arg Phe Val Glu Val Thr Leu Ala Leu Phe Ser Pro Gly
                485                 490                 495

Ala Phe Gly Ser Asp Arg Arg Pro Pro Leu Thr Pro Asp Glu Leu
            500                 505                 510

Ala Ser Leu Pro Lys Ala Ala Trp Gln Cys Ala Val Ala Asp Asn Ala
            515                 520                 525

Ala Met Thr Ala Leu His Gly His Pro Glu Leu Ala Thr Ala Gln Ala
            530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala His Ile
                565                 570                 575

Trp Ala Asp Lys Leu Gly Ser Thr Asn Ala Gly Val Ser Asn Glu Ala
            580                 585                 590

Glu Ala Gly Tyr Ala Gly Pro Cys Ala Glu Ile Ala Leu Arg Arg Gly
            595                 600                 605

Asp Leu Ala Thr Ala Phe Glu Ala Gly Ser Ala Val Leu Asp Asp Arg
            610                 615                 620

Ser Leu Pro Ser Leu Gly Ile Thr Ala Ala Leu Leu Leu Ser Ser Lys
625                 630                 635                 640

Thr Ala Ala Ala Val Arg Leu Gly Glu Leu Glu Arg Ala Glu Lys Leu
                645                 650                 655

Leu Ala Glu Pro Leu Pro Asn Gly Val Gln Asp Ser Leu Phe Gly Leu
            660                 665                 670

His Leu Leu Ser Ala Tyr Gly Gln Tyr Ser Leu Ala Met Gly Arg Tyr
            675                 680                 685

Glu Ser Ala His Arg Ala Phe Arg Thr Cys Gly Glu Arg Met Arg Ser
            690                 695                 700

Trp Asp Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
                725                 730                 735

Glu Gln Leu Thr Arg Pro Met Gly Pro Arg Ser His Ala Leu Thr Leu
            740                 745                 750

Arg Ile Lys Ala Ala Tyr Leu Pro Arg Thr Lys Arg Ile Pro Leu Leu
            755                 760                 765

His Glu Ala Ala Glu Leu Leu Pro Cys Pro Asp Pro Tyr Glu Gln
            770                 775                 780

Ala Arg Val Leu Ala Asp Leu Gly Asp Thr Leu Ser Ala Leu Arg Arg
785                 790                 795                 800
```

-continued

Tyr Ser Arg Ala Arg Gly Val Leu Arg Gln Ala Arg His Leu Ala Thr
                805                 810                 815

Gln Cys Gly Ala Val Pro Leu Leu Arg Arg Leu Gly Gly Glu Pro Gly
            820                 825                 830

Arg Ile Asp Asp Ala Gly Leu Pro Gln Arg Ser Thr Ser Leu Thr Asp
        835                 840                 845

Ala Glu Arg Arg Val Ala Ala Leu Ala Ala Gly Gln Thr Asn Arg
850                 855                 860

Glu Ile Ala Glu Gln Leu Phe Val Thr Ala Ser Thr Val Glu Gln His
865                 870                 875                 880

Leu Thr Ser Val Phe Arg Lys Leu Gly Val Lys Gly Arg Lys Gln Leu
                885                 890                 895

Pro Thr Ala Leu Ala Asp Val Glu Gln Thr
            900                 905

<210> SEQ ID NO 34
<211> LENGTH: 904
<212> TYPE: PRT
<213> ORGANISM: Streptomyces violaceusniger

<400> SEQUENCE: 34

Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Glu Ala Gly Ser Gly
            20                  25                  30

Gln Gly Ala Val Val Thr Val Thr Gly Pro Ile Ala Cys Gly Lys Thr
        35                  40                  45

Glu Leu Leu Asp Ala Ala Ala Lys Ala Asp Ala Ile Ile Leu Arg
50                  55                  60

Ala Val Cys Ala Pro Glu Glu Arg Ala Met Pro Tyr Ala Met Ile Gly
65                  70                  75                  80

Gln Leu Ile Asp Asp Pro Ala Leu Ala His Arg Ala Pro Glu Leu Ala
                85                  90                  95

Asp Arg Ile Ala Gln Gly Gly His Leu Ser Leu Arg Ala Glu Asn Arg
            100                 105                 110

Leu Arg Arg Asp Leu Thr Arg Ala Leu Leu Ala Leu Ala Val Asp Arg
        115                 120                 125

Pro Val Leu Ile Gly Val Asp Asp Val His His Ala Asp Thr Ala Ser
    130                 135                 140

Leu Asn Cys Leu Leu His Leu Ala Arg Arg Val Arg Pro Ala Arg Ile
145                 150                 155                 160

Ser Met Ile Phe Thr Glu Leu Arg Ser Leu Thr Pro Thr Gln Ser Arg
                165                 170                 175

Phe Lys Ala Glu Leu Leu Ser Leu Pro Tyr His His Glu Ile Ala Leu
            180                 185                 190

Arg Pro Leu Gly Pro Glu Gln Ser Ala Glu Leu Ala His Ala Ala Phe
        195                 200                 205

Gly Pro Gly Leu Ala Glu Asp Val Leu Ala Gly Leu Tyr Gly Met Thr
    210                 215                 220

Arg Gly Asn Leu Ser Leu Ser Arg Gly Leu Ile Ser Asp Val Arg Glu
225                 230                 235                 240

Ala Gln Ala Asn Gly Glu Ser Ala Phe Glu Val Gly Arg Ala Phe Arg
                245                 250                 255

Leu Ala Tyr Leu Ser Ser Leu Tyr Arg Cys Gly Pro Ile Ala Leu Arg
            260                 265                 270

```
Val Ala Arg Val Ala Ala Val Leu Gly Pro Ser Ala Thr Thr Thr Leu
        275                 280                 285

Val Arg Arg Leu Ser Gly Leu Ser Ala Glu Thr Ile Asp Arg Ala Thr
290                 295                 300

Lys Ile Leu Thr Glu Gly Gly Leu Leu Leu Asp His Gln Phe Pro His
305                 310                 315                 320

Pro Ala Ala Arg Ser Val Val Leu Asp Asp Met Ser Ala Gln Glu Arg
                325                 330                 335

Arg Ser Leu His Thr Leu Ala Leu Glu Leu Leu Asp Glu Ala Pro Val
            340                 345                 350

Glu Val Leu Ala His His Gln Val Gly Ala Gly Leu Ile His Gly Pro
                355                 360                 365

Lys Ala Ala Glu Ile Phe Ala Arg Ala Gly Gln Ala Leu Val Val Arg
370                 375                 380

Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
                405                 410                 415

Ile Glu Arg Arg Arg Asn Pro Leu Ala Ser Ser Arg His Met Asp Glu
                420                 425                 430

Leu Ser Ala Ala Gly Arg Ala Gly Leu Leu Ser Pro Lys His Ala Ala
435                 440                 445

Leu Ala Val Phe Trp Leu Ala Asp Gly Gly Arg Ser Gly Glu Ala Ala
450                 455                 460

Glu Val Leu Ala Ser Glu His Pro Leu Ala Thr Thr Asp Gln Asn Arg
465                 470                 475                 480

Ala His Leu Arg Phe Ala Glu Val Thr Leu Ala Leu Phe Cys Pro Gly
                485                 490                 495

Ala Phe Gly Ser Asp Arg Arg Pro Pro Leu Ala Pro Asp Glu Leu
                500                 505                 510

Ala Ser Leu Pro Lys Ala Ala Trp Gln Cys Ala Val Ala Asp Asn Ala
            515                 520                 525

Val Met Thr Ala Leu His Ala His Pro Glu Leu Ala Thr Ala Gln Ala
        530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala Gln Ile
                565                 570                 575

Trp Ala Asp Lys Leu Gly Ser Thr Asn Ala Gly Val Ser Asn Glu Ala
                580                 585                 590

Glu Ala Gly Tyr Ala Gly Pro Cys Ala Glu Ile Ala Leu Arg Arg Gly
            595                 600                 605

Asp Leu Ala Thr Ala Phe Glu Ala Gly Gly Thr Val Leu Asp Asp Arg
            610                 615                 620

Pro Leu Pro Ser Leu Gly Ile Thr Ala Ala Leu Leu Ser Ser Lys
625                 630                 635                 640

Thr Ala Ala Ala Val Arg Leu Gly Glu Leu Glu Arg Ala Glu Lys Leu
                645                 650                 655

Leu Ala Glu Pro Leu Pro Asn Gly Val Gln Asp Ser Leu Phe Gly Leu
                660                 665                 670

His Leu Leu Ser Ala His Gly Gln Tyr Ser Leu Ala Met Gly Arg Tyr
            675                 680                 685
```

```
Glu Ser Ala His Arg Ala Phe His Thr Cys Gly Glu Arg Met Arg Ser
690                 695                 700

Trp Gly Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
            725                 730                 735

Glu Gln Leu Ala Arg Pro Met Gly Pro Arg Ser Arg Ala Leu Thr Leu
            740                 745                 750

Arg Ile Lys Ala Ala Tyr Leu Pro Arg Thr Lys Arg Ile Pro Leu Leu
            755                 760                 765

His Glu Ala Ala Glu Leu Leu Leu Ser Cys Pro Asp Pro Tyr Glu Gln
770                 775                 780

Ala Arg Val Leu Ala Asp Leu Gly Asp Thr Leu Ser Ala Leu Arg Arg
785                 790                 795                 800

Tyr Ser Arg Ala Arg Gly Val Leu Arg Gln Ala Arg His Leu Ala Thr
                805                 810                 815

Gln Cys Gly Ala Val Pro Leu Leu Arg Arg Leu Gly Gly Glu Pro Gly
            820                 825                 830

Arg Ile Asp Asp Ala Gly Leu Pro Gln Arg Ser Thr Ser Leu Thr Asp
            835                 840                 845

Ala Glu Arg Arg Val Ser Ala Leu Ala Ala Gly Gln Thr Asn Arg
850                 855                 860

Glu Ile Ala Lys Gln Leu Phe Val Thr Ala Ser Thr Val Glu Gln His
865                 870                 875                 880

Leu Thr Ser Val Phe Arg Lys Leu Gly Val Lys Gly Arg Arg Gln Leu
                885                 890                 895

Pro Thr Ala Leu Ala Asp Val Glu
            900

<210> SEQ ID NO 35
<211> LENGTH: 906
<212> TYPE: PRT
<213> ORGANISM: Streptomyces Sp. NRRL F-4729

<400> SEQUENCE: 35

Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Gln Ala Ser Ser Gly
            20                  25                  30

Gln Gly Val Val Thr Val Thr Gly Pro Ile Ala Cys Gly Lys Thr
            35                  40                  45

Glu Leu Leu Asp Ala Ala Ala Lys Ala Glu Ala Ile Ile Leu Arg
50                  55                  60

Ala Val Cys Ala Pro Glu Arg Ala Met Pro Tyr Ala Met Ile Gly
65                  70                  75                  80

Gln Leu Ile Asp Asp Pro Ala Leu Ala His Arg Ala Pro Gly Leu Ala
            85                  90                  95

Asp Arg Ile Ala Gln Gly Gly Gln Leu Ser Leu Arg Ala Glu Asn Arg
            100                 105                 110

Leu Arg Arg Asp Leu Thr Arg Ala Leu Leu Ala Leu Ala Val His Arg
            115                 120                 125

Pro Val Leu Ile Gly Val Asp Asp Val His His Ala Asp Thr Ala Ser
130                 135                 140

Leu Asn Cys Leu Leu His Leu Ala Arg Arg Val Arg Pro Ala Arg Ile
145                 150                 155                 160
```

-continued

```
Ser Met Ile Phe Thr Glu Leu Arg Ser Leu Thr Pro Thr Gln Ser Arg
            165                 170                 175

Phe Lys Ala Glu Leu Leu Ser Leu Pro Tyr His His Glu Ile Ala Leu
            180                 185                 190

Arg Pro Phe Gly Pro Glu Gln Ser Ala Glu Leu Ala Arg Ala Ala Phe
            195                 200                 205

Gly Pro Gly Leu Ala Glu Asp Val Leu Ala Gly Leu Tyr Lys Thr Thr
            210                 215                 220

Arg Gly Asn Leu Ser Leu Ser Arg Gly Leu Ile Ser Asp Val Arg Glu
225                 230                 235                 240

Ala Leu Ala Asn Gly Glu Ser Ala Phe Glu Ala Gly Arg Ala Phe Arg
            245                 250                 255

Leu Ala Tyr Leu Ser Ser Leu Tyr Arg Cys Gly Pro Val Ala Leu Arg
            260                 265                 270

Val Ala Arg Val Ala Ala Val Leu Gly Pro Ser Ala Thr Thr Thr Leu
            275                 280                 285

Val Arg Arg Leu Ser Gly Leu Ser Ala Glu Thr Ile Asp Arg Ala Thr
            290                 295                 300

Lys Ile Leu Thr Glu Gly Gly Leu Leu Leu Asp Gln Gln Phe Pro His
305                 310                 315                 320

Pro Ala Ala Arg Ser Val Val Leu Asp Asp Met Ser Ala Gln Glu Arg
            325                 330                 335

Arg Gly Leu His Thr Leu Ala Leu Glu Leu Leu Asp Glu Ala Pro Val
            340                 345                 350

Glu Val Leu Ala His His Gln Val Gly Ala Gly Leu Ile His Gly Pro
            355                 360                 365

Lys Ala Ala Glu Met Phe Ala Lys Ala Gly Lys Ala Leu Val Val Arg
            370                 375                 380

Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
            405                 410                 415

Ile Glu Arg Arg Arg Asn Pro Leu Ala Ser Ser Arg His Met Asp Glu
            420                 425                 430

Leu Ser Ala Ala Gly Arg Ala Gly Leu Leu Ser Pro Lys His Ala Ala
            435                 440                 445

Leu Ala Val Phe Trp Leu Ala Asp Gly Gly Arg Ser Gly Glu Ala Ala
            450                 455                 460

Gln Val Leu Ala Ser Glu Arg Pro Leu Ala Thr Thr Asp Gln Asn Arg
465                 470                 475                 480

Ala His Leu Arg Phe Val Glu Val Thr Leu Ala Leu Phe Ser Pro Gly
            485                 490                 495

Ala Phe Gly Ser Asp Arg Arg Pro Pro Leu Thr Pro Asp Glu Leu
            500                 505                 510

Ala Ser Leu Pro Lys Ala Ala Trp Gln Cys Ala Val Ala Asp Asn Ala
            515                 520                 525

Ala Met Thr Ala Leu His Gly His Pro Glu Leu Ala Thr Ala Gln Ala
            530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala His Ile
            565                 570                 575
```

Trp Ala Asp Lys Leu Gly Ser Met Asn Ala Gly Val Ser Asn Glu Ala
            580                 585                 590

Glu Ala Gly Tyr Ala Gly Pro Cys Ala Glu Ile Ala Leu Arg Arg Gly
        595                 600                 605

Asp Leu Ala Thr Ala Phe Glu Ala Gly Ser Thr Val Leu Asp Asp Arg
    610                 615                 620

Ser Leu Pro Ser Leu Gly Ile Thr Ala Ala Leu Leu Leu Ser Ser Lys
625                 630                 635                 640

Thr Ala Ala Ala Val Arg Leu Gly Glu Leu Glu Arg Ala Glu Lys Leu
                645                 650                 655

Leu Ala Glu Pro Leu Pro Asn Gly Val Gln Asp Ser Leu Phe Gly Leu
            660                 665                 670

His Leu Leu Ser Ala Tyr Gly Gln Tyr Ser Leu Ala Met Gly Arg Tyr
        675                 680                 685

Glu Ser Ala His Arg Ala Phe Arg Thr Cys Gly Glu Arg Met Arg Ser
    690                 695                 700

Trp Asp Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
                725                 730                 735

Glu Gln Leu Thr Arg Pro Met Gly Pro Arg Ser Arg Ala Leu Thr Leu
            740                 745                 750

Arg Ile Lys Ala Ala Tyr Leu Pro Arg Thr Lys Arg Ile Pro Leu Leu
        755                 760                 765

His Glu Ala Ala Glu Leu Leu Leu Pro Cys Pro Asp Pro Tyr Glu Gln
    770                 775                 780

Ala Arg Val Leu Ala Asp Leu Gly Asp Thr Leu Ser Ala Leu Arg Arg
785                 790                 795                 800

Tyr Ser Arg Ala Arg Gly Val Leu Arg Gln Ala Arg His Leu Ala Thr
                805                 810                 815

Gln Cys Gly Ala Val Pro Leu Leu Arg Arg Leu Gly Gly Glu Pro Gly
            820                 825                 830

Arg Ile Asp Asp Ala Gly Leu Pro Gln Arg Ser Thr Ser Leu Thr Asp
        835                 840                 845

Ala Glu Arg Arg Val Ala Ala Leu Ala Ala Gly Gln Thr Asn Arg
    850                 855                 860

Glu Ile Ala Glu Gln Leu Phe Val Thr Ala Ser Thr Val Glu Gln His
865                 870                 875                 880

Leu Thr Ser Val Phe Arg Lys Leu Gly Val Lys Gly Arg Lys Gln Leu
                885                 890                 895

Pro Thr Ala Leu Ala Asp Val Glu Gln Thr
            900                 905

<210> SEQ ID NO 36
<211> LENGTH: 904
<212> TYPE: PRT
<213> ORGANISM: Streptomyces filamentosus

<400> SEQUENCE: 36

Met Arg Ala Ile Asn Ala Ser Asp Thr Gly Pro Glu Leu Val Ala Arg
1               5                   10                  15

Glu Asp Glu Leu Gly Arg Val Arg Ser Ala Leu Asn Arg Ala Asn Gly
            20                  25                  30

Gly Gln Gly Val Leu Ile Ser Ile Thr Gly Pro Ile Ala Cys Gly Lys
        35                  40                  45

```
Thr Glu Leu Leu Glu Ala Ala Ser Glu Val Asp Ala Ile Thr Leu
 50                  55                  60

Arg Ala Val Cys Ala Ala Glu Glu Arg Ala Ile Pro Tyr Ala Leu Ile
 65                  70                  75                  80

Gly Gln Leu Ile Asp Asn Pro Ala Leu Gly Ile Pro Val Pro Asp Pro
                 85                  90                  95

Ala Gly Leu Thr Ala Gln Gly Gly Arg Leu Ser Ser Ser Ala Glu Asn
            100                 105                 110

Arg Leu Arg Arg Asp Leu Thr Arg Ala Leu Leu Thr Leu Ala Thr Asp
        115                 120                 125

Arg Leu Val Leu Ile Cys Val Asp Asp Val Gln His Ala Asp Asn Ala
        130                 135                 140

Ser Leu Ser Cys Leu Leu Tyr Leu Ala Arg Arg Leu Val Pro Ala Arg
145                 150                 155                 160

Ile Ala Leu Val Phe Thr Glu Leu Arg Val Leu Thr Ser Ser Gln Leu
                165                 170                 175

Arg Phe Asn Ala Glu Leu Leu Ser Leu Arg Asn His Cys Glu Ile Ala
            180                 185                 190

Leu Arg Pro Leu Gly Pro Gly His Ala Ala Glu Leu Ala Arg Ala Thr
        195                 200                 205

Leu Gly Pro Gly Leu Ser Asp Glu Thr Leu Thr Glu Leu Tyr Arg Val
210                 215                 220

Thr Gly Gly Asn Leu Ser Leu Ser Arg Gly Leu Ile Asp Asp Val Arg
225                 230                 235                 240

Asp Ala Trp Ala Arg Gly Glu Thr Gly Val Gln Val Gly Arg Ala Phe
                245                 250                 255

Arg Leu Ala Tyr Leu Gly Ser Leu His Arg Cys Gly Pro Leu Ala Leu
            260                 265                 270

Arg Val Ala Arg Val Ala Ala Val Leu Gly Pro Ser Ala Thr Ser Val
        275                 280                 285

Leu Val Arg Arg Ile Ser Gly Leu Ser Ala Glu Ala Met Ala Gln Ala
        290                 295                 300

Thr Asp Ile Leu Ala Asp Gly Gly Leu Leu Arg Asp Gln Arg Phe Thr
305                 310                 315                 320

His Pro Ala Ala Arg Ser Val Val Leu Asp Asp Met Ser Ala Glu Glu
                325                 330                 335

Arg Arg Ser Val His Ser Leu Ala Leu Glu Leu Leu Asp Glu Ala Pro
            340                 345                 350

Ala Glu Met Leu Ala His His Arg Val Gly Ala Gly Leu Val His Gly
        355                 360                 365

Pro Lys Ala Ala Glu Thr Phe Thr Gly Ala Gly Arg Ala Leu Ala Val
370                 375                 380

Arg Gly Met Leu Gly Glu Ala Ala Asp Tyr Leu Gln Leu Ala Tyr Arg
385                 390                 395                 400

Ala Ser Gly Asp Ala Ala Thr Lys Ala Ala Ile Arg Val Glu Ser Val
                405                 410                 415

Ala Val Glu Arg Arg Arg Asn Pro Leu Val Val Ser Arg His Trp Asp
            420                 425                 430

Glu Leu Ser Val Ala Ala Arg Ala Gly Leu Leu Ser Cys Glu His Val
        435                 440                 445

Ser Arg Thr Ala Arg Trp Leu Thr Val Gly Gly Arg Pro Gly Glu Ala
        450                 455                 460
```

-continued

Ala Arg Val Leu Ala Ser Gln His Arg Arg Val Thr Asp Gln Asp
465                 470                 475                 480

Arg Ala His Leu Arg Val Ala Glu Phe Ser Leu Ala Leu Leu Tyr Pro
            485                 490                 495

Gly Thr Ser Gly Ser Asp Arg Arg Pro His Pro Leu Thr Ser Asp Glu
            500                 505                 510

Leu Ala Ala Leu Pro Thr Ala Thr Arg His Cys Ala Ile Ala Asp Asn
            515                 520                 525

Ala Val Met Ala Ala Leu Arg Gly His Pro Glu Leu Ala Thr Ala Glu
            530                 535                 540

Ala Glu Ala Val Leu Gln Gln Ala Asp Ala Ala Asp Gly Ala Ala Leu
545                 550                 555                 560

Thr Ala Leu Met Ala Leu Leu Tyr Ala Glu Ser Ile Glu Val Ala Glu
            565                 570                 575

Val Trp Ala Asp Lys Leu Ala Ala Glu Ala Gly Ala Ser Asn Gly Gln
            580                 585                 590

Asp Ala Glu Tyr Ala Gly Ile Arg Ala Glu Ile Ala Leu Arg Arg Gly
            595                 600                 605

Asp Leu Thr Ala Ala Val Glu Thr Ala Gly Met Val Leu Asp Gly Arg
            610                 615                 620

Pro Leu Pro Ser Leu Asp Ile Thr Ala Thr Leu Leu Leu Ala Gly Arg
625                 630                 635                 640

Ala Ser Val Ala Val Arg Leu Gly Glu Leu Asp His Ala Glu Glu Leu
            645                 650                 655

Phe Ala Ala Pro Pro Glu Asp Ala Phe Gln Asp Ser Leu Phe Gly Leu
            660                 665                 670

His Leu Leu Ser Ala His Gly Gln Tyr Ser Leu Ala Thr Gly Arg Pro
            675                 680                 685

Glu Ser Ala Tyr Arg Ala Phe Arg Ala Cys Gly Glu Arg Met Arg Asp
            690                 695                 700

Trp Gly Phe Asp Ala Pro Gly Val Ala Leu Trp Arg Val Gly Ala Ala
705                 710                 715                 720

Glu Ala Leu Leu Gly Leu Asp Arg Asn Glu Gly Arg Arg Leu Ile Asp
            725                 730                 735

Glu Gln Leu Ser Arg Thr Met Ala Pro Arg Ser His Ala Leu Thr Leu
            740                 745                 750

Arg Ile Lys Ala Ala Tyr Met Pro Glu Pro Lys Arg Val Asp Leu Leu
            755                 760                 765

Tyr Glu Ala Ala Glu Leu Leu Leu Ser Cys Arg Asp Gln Tyr Glu Arg
            770                 775                 780

Ala Arg Val Leu Ala Asp Leu Gly Glu Ala Leu Ser Ala Leu Gly Asn
785                 790                 795                 800

Tyr Arg Gln Ala Arg Gly Val Leu Arg Gln Ala Arg His Leu Ala Met
            805                 810                 815

Arg Thr Gly Ala Asp Pro Leu Leu Arg Arg Leu Gly Ile Arg Pro Gly
            820                 825                 830

Arg Gln Asp Asp Pro Asp Pro Gln Pro Arg Ser Arg Ser Leu Thr Asn
            835                 840                 845

Ala Glu Arg Arg Ala Ala Ser Leu Ala Ala Thr Gly Leu Thr Asn Arg
            850                 855                 860

Glu Ile Ala Asp Arg Leu Phe Val Thr Ala Ser Thr Val Glu Gln His
865                 870                 875                 880

Leu Thr Asn Val Phe Arg Lys Leu Gly Val Lys Gly Arg Lys Gln Leu

```
                        885                 890                 895
Pro Ala Glu Leu Asp Asp Met Glu
                900

<210> SEQ ID NO 37
<211> LENGTH: 75
<212> TYPE: DNA
<213> ORGANISM: Artificial Sequence
<220> FEATURE:
<223> OTHER INFORMATION: synthetic construct

<400> SEQUENCE: 37
caaagcgatt cggagagcgg ccggatcaga tccaggcgtg acattcatac ccttccggcg      60
aagtgcagtt caccc                                                      75

<210> SEQ ID NO 38
<211> LENGTH: 73
<212> TYPE: DNA
<213> ORGANISM: Artificial Sequence
<220> FEATURE:
<223> OTHER INFORMATION: synthetic construct

<400> SEQUENCE: 38
cgatcttctc gaaactgcac tgaggaggtt cgtcggagac tgccattcac ctctcccgga      60
aaggtattgc tcg                                                        73

<210> SEQ ID NO 39
<211> LENGTH: 429
<212> TYPE: DNA
<213> ORGANISM: Streptomyces filamentosus

<400> SEQUENCE: 39
gcgttcggca ttgacgcgaa gcaagtcatg aatcggctga atcaattccg cgcgcgacat      60
tcgcacccct tccggtgaagt gcggtattgc tcagacataa cccggatcgc aatccaacga   120
ccagccatgc actaccgata atcgaatcgg aacaatagca agctcgttga gcatattttc    180
catgcggcac cacctcggcg ccaccccta gttttgccga ccccctatgt gtatttcggc     240
aggcagacta gggggttgcg tgggccgcac ccgaggcatt cgattggcgc acggcgcact    300
cgggccatgt caccgaccgt gaatgtttca tcgctacggg tagcaatagt cctttctcgg    360
gagaagtgaa tggcttccaa aagtccccgc ccagggtccg agagagcggg ttctgcgatt    420
tcccgggca                                                           429

<210> SEQ ID NO 40
<211> LENGTH: 433
<212> TYPE: DNA
<213> ORGANISM: Streptomyces filamentosus

<400> SEQUENCE: 40
gcgttcggca ttgacgcgaa gcaagtcatg aatcggctga atcaattccg cgcgcgacat      60
tcgcacccct tccggtgaagt gcggtattgc tcagacataa cccggatcgc aatccaacga   120
ccagccatgc actaccgata atcgaatcgg aacaatagca agctcgttga gcatattttc    180
catgcggcac cacctcggcg ccaccccta gttttgccga ccccctatgt gtatttcggc     240
aggcagaaca cctaggggt tgcgtgggcc gcacccgagg cattcgattg gcgcacggcg     300
cactcgggcc atgtcaccga ccgtgaatgt tcatcgcta cggtagcaa tagtcctttc      360 tcgggagaag tgaatggctt ccaaaagtcc ccgcccaggg tccgagagag cgggttctgc    420
```

```
gatttcccgg gca                                                        433
```

<210> SEQ ID NO 41
<211> LENGTH: 432
<212> TYPE: DNA
<213> ORGANISM: Streptomyces violaceusniger

<400> SEQUENCE: 41

```
gcgttcggca ttgacgcgaa gcaagtcatg aatcggctga atcaattccg cgcgcgacat     60
tcgcatcctt ctggtgaggt gcagtattgc tgagacataa tccgggccgt aatccaacga    120
ccagccatgc gccgccgata gtcgaatccg atagtcgaat ctgaacgcta gcagctcgtc    180
gcagggctc cggggagccc aaccccctaa ttttccgcc ccctataca tatccactgc       240
aggcagaaca cctaggggt tgcgcgaacc gggcgcgcgg tatcggattt accgcacggc     300
acactcgggc gacgtcaccg accgtgaatc cttcatcgct acgggtagca cagtcctttc    360
cgggagaagt gaatggcttc caaaagtccc cgcccagggt ccgagagagc gggttctgcg    420
atttcccggg ca                                                        432
```

<210> SEQ ID NO 42
<211> LENGTH: 350
<212> TYPE: DNA
<213> ORGANISM: Streptomyces violaceusniger

<400> SEQUENCE: 42

```
gcgttcggca ttgacgcgaa gcaagtcatg aatcggctga atcaattccg cgcgcgacat     60
tcataccctt ccggcgaagt gcagttcacc cggtaatgca ttccggaccg tagcagtccg    120
atacagacgt ccgccatgcc gtgccaccct tgttttcac ccccctacgc ccgtttcgcc     180
tggccggaaa cctagggggt tgcgtggaaa gcaccggcgg gtgttcgctt gcacagcgcc    240
acctcgggca ttttctggat gcgcgagcaa tacctttccg ggagaggtga atggcttcca    300
aaagtccccg cccagggtcc gagagagcgg gttctgcgat tcccgggca               350
```

<210> SEQ ID NO 43
<211> LENGTH: 52
<212> TYPE: DNA
<213> ORGANISM: Artificial Sequence
<220> FEATURE:
<223> OTHER INFORMATION: synthetic construct

<400> SEQUENCE: 43

```
gcgcccacct taatcgcagg tgtccacgca acccctagg tttccggcca gg              52
```

<210> SEQ ID NO 44
<211> LENGTH: 59
<212> TYPE: DNA
<213> ORGANISM: Artificial Sequence
<220> FEATURE:
<223> OTHER INFORMATION: synthetic construct

<400> SEQUENCE: 44

```
gttcatagct ctccacggca ggcattcata cccttccggc gaagtgcagt tcacccggt      59
```

<210> SEQ ID NO 45
<211> LENGTH: 53
<212> TYPE: DNA
<213> ORGANISM: Artificial Sequence
<220> FEATURE:
<223> OTHER INFORMATION: synthetic construct

<400> SEQUENCE: 45

```
gcgcccacct taatcgcagg tgccaccctt gtttttcacc cccctacgcc cgt          53
```

<210> SEQ ID NO 46
<211> LENGTH: 60
<212> TYPE: DNA
<213> ORGANISM: Artificial Sequence
<220> FEATURE:
<223> OTHER INFORMATION: synthetic construct

<400> SEQUENCE: 46

```
gttcatagct ctccacggca ggcattcacc tctcccggaa aggtattgct cgtgcatcca    60
```

<210> SEQ ID NO 47
<211> LENGTH: 57
<212> TYPE: DNA
<213> ORGANISM: Artificial Sequence
<220> FEATURE:
<223> OTHER INFORMATION: synthetic construct

<400> SEQUENCE: 47

```
actgcacttc gccggaaggg tatgaatgcc tgccgtggag agctatgaac tggacgc       57
```

<210> SEQ ID NO 48
<211> LENGTH: 23
<212> TYPE: DNA
<213> ORGANISM: Artificial Sequence
<220> FEATURE:
<223> OTHER INFORMATION: synthetic construct

<400> SEQUENCE: 48

```
ccgggagggc catggagacc gga                                            23
```

<210> SEQ ID NO 49
<211> LENGTH: 57
<212> TYPE: DNA
<213> ORGANISM: Artificial Sequence
<220> FEATURE:
<223> OTHER INFORMATION: synthetic construct

<400> SEQUENCE: 49

```
agcaatacct ttccgggaga ggtgaatgcc tgccgtggag agctatgaac tggacgc       57
```

<210> SEQ ID NO 50
<211> LENGTH: 23
<212> TYPE: DNA
<213> ORGANISM: Artificial Sequence
<220> FEATURE:
<223> OTHER INFORMATION: synthetic construct

<400> SEQUENCE: 50

```
ccgggagggc catggagacc gga                                            23
```

<210> SEQ ID NO 51
<211> LENGTH: 82
<212> TYPE: DNA
<213> ORGANISM: Artificial Sequence
<220> FEATURE:
<223> OTHER INFORMATION: synthetic construct

<400> SEQUENCE: 51

```
ctacccgaat acatcgcctt ctggggccca gcccaaacca gcgccctcat ccacactcca    60
cgcaaccccc taggtttccg gc                                             82
```

<210> SEQ ID NO 52

```
<211> LENGTH: 91
<212> TYPE: DNA
<213> ORGANISM: Artificial Sequence
<220> FEATURE:
<223> OTHER INFORMATION: synthetic construct

<400> SEQUENCE: 52
gcggcccaca acgtgcacga gcgtggcgat atcggacgcg gaaagaacca gcgtgctcat    60 tcatacccti ccggcgaagt gcagttcacc c                                  91

<210> SEQ ID NO 53
<211> LENGTH: 26
<212> TYPE: DNA
<213> ORGANISM: Artificial Sequence
<220> FEATURE:
<223> OTHER INFORMATION: synthetic construct

<400> SEQUENCE: 53
cgccgtctac ccagcccaaa gccagc                                        26

<210> SEQ ID NO 54
<211> LENGTH: 26
<212> TYPE: DNA
<213> ORGANISM: Artificial Sequence
<220> FEATURE:
<223> OTHER INFORMATION: synthetic construct

<400> SEQUENCE: 54
cgggttcgtg gtgcggcatc cattcg                                        26

<210> SEQ ID NO 55
<211> LENGTH: 69
<212> TYPE: DNA
<213> ORGANISM: Artificial Sequence
<220> FEATURE:
<223> OTHER INFORMATION: synthetic construct

<400> SEQUENCE: 55
caaagcgatt cggagagcgg ccggatcaga tccaggcgtg acatggcctg gtgatgatgg    60
cgggatcgt                                                           69

<210> SEQ ID NO 56
<211> LENGTH: 74
<212> TYPE: DNA
<213> ORGANISM: Artificial Sequence
<220> FEATURE:
<223> OTHER INFORMATION: synthetic construct

<400> SEQUENCE: 56
cgatcttctc gaaactgcac tgaggaggtt cgtcggagac tgccattcat cgcagtactg    60
ttgtattcat taag                                                     74

<210> SEQ ID NO 57
<211> LENGTH: 75
<212> TYPE: DNA
<213> ORGANISM: Artificial Sequence
<220> FEATURE:
<223> OTHER INFORMATION: synthetic construct

<400> SEQUENCE: 57
caaagcgatt cggagagcgg ccggatcaga tccaggcgtg acattcatac ccttccggcg    60
aagtgcagtt caccc                                                    75
```

```
<210> SEQ ID NO 58
<211> LENGTH: 73
<212> TYPE: DNA
<213> ORGANISM: Artificial Sequence
<220> FEATURE:
<223> OTHER INFORMATION: synthetic construct

<400> SEQUENCE: 58
cgatcttctc gaaactgcac tgaggaggtt cgtcggagac tgccattcac ctctcccgga    60
aaggtattgc tcg                                                      73

<210> SEQ ID NO 59
<211> LENGTH: 98
<212> TYPE: DNA
<213> ORGANISM: Artificial Sequence
<220> FEATURE:
<223> OTHER INFORMATION: synthetic construct

<400> SEQUENCE: 59
gcaaagcgat tcggagagcg gccggatcag atccaggcgt gacatgttta aacacaacgt    60
acctttcgga caagagtgcc gcggtgcaca gcctgacc                            98

<210> SEQ ID NO 60
<211> LENGTH: 98
<212> TYPE: DNA
<213> ORGANISM: Artificial Sequence
<220> FEATURE:
<223> OTHER INFORMATION: synthetic construct

<400> SEQUENCE: 60
ggtcaggctg tgcaccgcgg cactcttgtc cgaaaggtac gttgtgttta aacatgtcac    60
gcctggatct gatccggccg ctctccgaat cgctttgc                            98

<210> SEQ ID NO 61
<211> LENGTH: 98
<212> TYPE: DNA
<213> ORGANISM: Artificial Sequence
<220> FEATURE:
<223> OTHER INFORMATION: synthetic construct

<400> SEQUENCE: 61
tccacacctc tcggttcaca aacgtccgag cataagggag gtaaagttta aacatggcag    60
tctccgacga acctcctcag tgcagtttcg agaagatc                            98

<210> SEQ ID NO 62
<211> LENGTH: 98
<212> TYPE: DNA
<213> ORGANISM: Artificial Sequence
<220> FEATURE:
<223> OTHER INFORMATION: synthetic construct

<400> SEQUENCE: 62
gatcttctcg aaactgcact gaggaggttc gtcggagact gccatgttta aactttacct    60
cccttatgct cggacgtttg tgaaccgaga ggtgtgga                            98

<210> SEQ ID NO 63
<211> LENGTH: 75
<212> TYPE: DNA
<213> ORGANISM: Artificial Sequence
<220> FEATURE:
<223> OTHER INFORMATION: synthetic construct

<400> SEQUENCE: 63
```
caaagcgatt cggagagcgg ccggatcaga tccaggcgtg acattcatac ccttccggcg    60
aagtgcagtt caccc    75

<210> SEQ ID NO 64
<211> LENGTH: 73
<212> TYPE: DNA
<213> ORGANISM: Artificial Sequence
<220> FEATURE:
<223> OTHER INFORMATION: synthetic construct

<400> SEQUENCE: 64
cgatcttctc gaaactgcac tgaggaggtt cgtcggagac tgccattcac ctctcccgga    60
aaggtattgc tcg    73

<210> SEQ ID NO 65
<211> LENGTH: 87
<212> TYPE: DNA
<213> ORGANISM: Artificial Sequence
<220> FEATURE:
<223> OTHER INFORMATION: synthetic construct

<400> SEQUENCE: 65
cccgaaccac gatgagcact tgcctatgcg gtgtagggat aacagggtaa ttaattaatg    60
acctgcgccc accttaatcg caggtgc    87

<210> SEQ ID NO 66
<211> LENGTH: 98
<212> TYPE: DNA
<213> ORGANISM: Artificial Sequence
<220> FEATURE:
<223> OTHER INFORMATION: synthetic construct

<400> SEQUENCE: 66
tactttctat ttttaattta tatatttata ttaaaaaatt taaaatataa ttattttat    60 agcacgtgat ggagcctatg gaaaaacgcc agcaacgc    98

<210> SEQ ID NO 67
<211> LENGTH: 45
<212> TYPE: DNA
<213> ORGANISM: Artificial Sequence
<220> FEATURE:
<223> OTHER INFORMATION: synthetic construct

<400> SEQUENCE: 67
ggtagtattt gttggcgatc ccctagagt cttttacatc ttcgg    45

<210> SEQ ID NO 68
<211> LENGTH: 22
<212> TYPE: DNA
<213> ORGANISM: Artificial Sequence
<220> FEATURE:
<223> OTHER INFORMATION: synthetic construct

<400> SEQUENCE: 68
agcctgcccc tcatctgtca ac    22

<210> SEQ ID NO 69
<211> LENGTH: 99
<212> TYPE: DNA
<213> ORGANISM: Artificial Sequence
<220> FEATURE:
<223> OTHER INFORMATION: synthetic construct

<400> SEQUENCE: 69

```
gttgatcgtg tggggcggcc tgccgagcag ctggtggacc cctggggcga gctggcgcat    60
tcacctgtat actgagagtg caccataaac gacattact                           99

<210> SEQ ID NO 70
<211> LENGTH: 94
<212> TYPE: DNA
<213> ORGANISM: Artificial Sequence
<220> FEATURE:
<223> OTHER INFORMATION: synthetic construct

<400> SEQUENCE: 70
gacgaccgcg gtccccacga ggacagcggc cgacgcaaca gctttgcgaa gacgagtcat    60
tcatacgtat acaggcaagt gcacaaacaa tact                                94

<210> SEQ ID NO 71
<211> LENGTH: 100
<212> TYPE: DNA
<213> ORGANISM: Artificial Sequence
<220> FEATURE:
<223> OTHER INFORMATION: synthetic construct

<400> SEQUENCE: 71
cgccggtgag gccagaccca tgagggtcag tgctgcgacc accgcgtacc tgatccgcat    60
tcacctgtta actcctgatg cggtattttc tccttacgca                         100

<210> SEQ ID NO 72
<211> LENGTH: 90
<212> TYPE: DNA
<213> ORGANISM: Artificial Sequence
<220> FEATURE:
<223> OTHER INFORMATION: synthetic construct

<400> SEQUENCE: 72
ctcggccggc agcaaggtct gctcgatcgc gatgatccgg ccgttccccc agtcgatcgt    60
gttaaccgac tacgtcgtaa ggccgtttct                                     90

<210> SEQ ID NO 73
<211> LENGTH: 102
<212> TYPE: DNA
<213> ORGANISM: Artificial Sequence
<220> FEATURE:
<223> OTHER INFORMATION: synthetic construct

<400> SEQUENCE: 73
gacgaacgcg aagtcgtcgc cgccctcctt catgcccagt ccggtggtcc agccgcggaa    60
gccgtgcgga tgcattcacc tctcccggaa aggtattgct cg                      102

<210> SEQ ID NO 74
<211> LENGTH: 102
<212> TYPE: DNA
<213> ORGANISM: Artificial Sequence
<220> FEATURE:
<223> OTHER INFORMATION: synthetic construct

<400> SEQUENCE: 74
tcgccacggg cggtcgagga actcgtcgcg gaccgccgcg accgtgttc gcgcgccgtc    60 accgccgacg cgcattcata cccttccggc gaagtgcagt tc                      102

<210> SEQ ID NO 75
<211> LENGTH: 24
<212> TYPE: DNA
```

```
<213> ORGANISM: Artificial Sequence
<220> FEATURE:
<223> OTHER INFORMATION: synthetic construct

<400> SEQUENCE: 75
ggcgtggctg gagccgaagt ggtc                                         24

<210> SEQ ID NO 76
<211> LENGTH: 33
<212> TYPE: DNA
<213> ORGANISM: Artificial Sequence
<220> FEATURE:
<223> OTHER INFORMATION: synthetic construct

<400> SEQUENCE: 76
tcttccacta ctgccatctg gcgtcataac tgc                               33

<210> SEQ ID NO 77
<211> LENGTH: 49
<212> TYPE: DNA
<213> ORGANISM: Artificial Sequence
<220> FEATURE:
<223> OTHER INFORMATION: synthetic construct

<400> SEQUENCE: 77
aggttattac tgagtagtat ttatttaagt attgtttgtg cacttgcct              49

<210> SEQ ID NO 78
<211> LENGTH: 21
<212> TYPE: DNA
<213> ORGANISM: Artificial Sequence
<220> FEATURE:
<223> OTHER INFORMATION: synthetic construct

<400> SEQUENCE: 78
actcggcggc gttggcgtgg c                                            21

<210> SEQ ID NO 79
<211> LENGTH: 19
<212> TYPE: DNA
<213> ORGANISM: Artificial Sequence
<220> FEATURE:
<223> OTHER INFORMATION: synthetic construct

<400> SEQUENCE: 79
accgtcgccc cgccgcagc                                               19

<210> SEQ ID NO 80
<211> LENGTH: 36
<212> TYPE: DNA
<213> ORGANISM: Artificial Sequence
<220> FEATURE:
<223> OTHER INFORMATION: synthetic construct

<400> SEQUENCE: 80
cgcacagatt cgtaaggaga aaataccgca tcagga                            36

<210> SEQ ID NO 81
<211> LENGTH: 32
<212> TYPE: DNA
<213> ORGANISM: Artificial Sequence
<220> FEATURE:
<223> OTHER INFORMATION: synthetic construct

<400> SEQUENCE: 81
actctgtcag aaacggcctt acgacgtagt cg                                32
```

<210> SEQ ID NO 82
<211> LENGTH: 22
<212> TYPE: DNA
<213> ORGANISM: Artificial Sequence
<220> FEATURE:
<223> OTHER INFORMATION: synthetic construct

<400> SEQUENCE: 82
cgggcggcac gcaaccgaag tg                                            22

<210> SEQ ID NO 83
<211> LENGTH: 23
<212> TYPE: DNA
<213> ORGANISM: Artificial Sequence
<220> FEATURE:
<223> OTHER INFORMATION: synthetic construct

<400> SEQUENCE: 83
gtgaagaccg ccgataccgc cgc                                           23

<210> SEQ ID NO 84
<211> LENGTH: 26
<212> TYPE: DNA
<213> ORGANISM: Artificial Sequence
<220> FEATURE:
<223> OTHER INFORMATION: synthetic construct

<400> SEQUENCE: 84
gggtgaaaaa caagggtggc acggca                                        26

<210> SEQ ID NO 85
<211> LENGTH: 26
<212> TYPE: DNA
<213> ORGANISM: Artificial Sequence
<220> FEATURE:
<223> OTHER INFORMATION: synthetic construct

<400> SEQUENCE: 85
tgccgtgcca cccttgtttt tcaccc                                        26

<210> SEQ ID NO 86
<211> LENGTH: 26
<212> TYPE: DNA
<213> ORGANISM: Artificial Sequence
<220> FEATURE:
<223> OTHER INFORMATION: synthetic construct

<400> SEQUENCE: 86
acgccaggcc cgttcacgac gaccgc                                        26

<210> SEQ ID NO 87
<211> LENGTH: 59
<212> TYPE: DNA
<213> ORGANISM: Artificial Sequence
<220> FEATURE:
<223> OTHER INFORMATION: synthetic construct

<400> SEQUENCE: 87
gctggtggac ccctggggcg agctggcgca ttcacctctc ccggaaaggt attgctcgc    59

<210> SEQ ID NO 88
<211> LENGTH: 65
<212> TYPE: DNA
<213> ORGANISM: Artificial Sequence
<220> FEATURE:

<223> OTHER INFORMATION: synthetic construct

<400> SEQUENCE: 88
aacagctttg cgaagacgag tcattcatac cattcatacc cttccggcga agtgcagttc    60
acccg    65

<210> SEQ ID NO 89
<211> LENGTH: 62
<212> TYPE: DNA
<213> ORGANISM: Artificial Sequence
<220> FEATURE:
<223> OTHER INFORMATION: synthetic construct

<400> SEQUENCE: 89
tcagtgctgc gaccaccgcg tacctgatcc gcattcacct ctcccggaaa ggtattgctc    60
gc    62

<210> SEQ ID NO 90
<211> LENGTH: 73
<212> TYPE: DNA
<213> ORGANISM: Artificial Sequence
<220> FEATURE:
<223> OTHER INFORMATION: synthetic construct

<400> SEQUENCE: 90
atcgcgatga tccggccgtt cccccagtcg atcgtccgca ttcataccct tccggcgaag    60
tgcagttcac ccg    73

<210> SEQ ID NO 91
<211> LENGTH: 49
<212> TYPE: DNA
<213> ORGANISM: Streptomyces violaceusniger

<400> SEQUENCE: 91
tggccggaaa cctaggggggt tgcgtggaaa gcaccggcgg gtgttcgct    49

<210> SEQ ID NO 92
<211> LENGTH: 49
<212> TYPE: DNA
<213> ORGANISM: Streptomyces rapamycinicus

<400> SEQUENCE: 92
aggcaggacg tctaggggggt tgcgtggact gcggcctgag gtgtcttct    49

<210> SEQ ID NO 93
<211> LENGTH: 49
<212> TYPE: DNA
<213> ORGANISM: Streptomyces hygroscopicus

<400> SEQUENCE: 93
aggcaggaag cctaggggggt tgcgtggact gcgacctggg gtgtcttct    49

<210> SEQ ID NO 94
<211> LENGTH: 47
<212> TYPE: DNA
<213> ORGANISM: Micromonospora sp. S92-306401

<400> SEQUENCE: 94
aggtacgaca cctaggggggt tgcgtcggct gcgaccccgg tgtctcc    47

<210> SEQ ID NO 95
<211> LENGTH: 48

```
<212> TYPE: DNA
<213> ORGANISM: Actinoplanes sp. N01-109

<400> SEQUENCE: 95
agctcggccc cctagggggt tgcgcccgct gaggcggagg tgtttggc                      48

<210> SEQ ID NO 96
<211> LENGTH: 43
<212> TYPE: DNA
<213> ORGANISM: Streptomyces kanamyceticus

<400> SEQUENCE: 96
tgttgcccat ctagggggtt gcacgaataa cgtcacacgt act                           43

<210> SEQ ID NO 97
<211> LENGTH: 43
<212> TYPE: DNA
<213> ORGANISM: Streptomyces tacrolimicus

<400> SEQUENCE: 97
tgtcatatgt ctagggggtt gcacgaatac cgtcgcgcgt act                           43

<210> SEQ ID NO 98
<211> LENGTH: 43
<212> TYPE: DNA
<213> ORGANISM: Streptomyces ascomyceticus

<400> SEQUENCE: 98
ggacgctcat ctagggggtt gcacgcatac cgccgtgcgt aat                           43

<210> SEQ ID NO 99
<211> LENGTH: 39
<212> TYPE: DNA
<213> ORGANISM: Streptomyces violaceusniger

<400> SEQUENCE: 99
ggcgcctgtt ctagggggtt gcggggagtg gcgcgcaca                                39

<210> SEQ ID NO 100
<211> LENGTH: 66
<212> TYPE: PRT
<213> ORGANISM: Micromonospora sp. S92-306401

<400> SEQUENCE: 100
```

Gln Gly Ile Arg Ser Leu Thr Glu Ala Glu Arg Arg Val Ala Thr Leu
1               5                   10                  15

Ala Ala Ala Gly Gln Thr Asn Arg Glu Ile Ala Asp Gln Leu Phe Val
            20                  25                  30

Thr Ala Ser Thr Val Glu Gln His Leu Thr Asn Val Phe Arg Lys Leu
        35                  40                  45

Gly Val Lys Gly Arg Gln Gln Leu Pro Ala Glu Leu Ala Asp Leu Arg
    50                  55                  60

Pro Pro
65

```
<210> SEQ ID NO 101
<211> LENGTH: 66
<212> TYPE: PRT
<213> ORGANISM: Streptomyces violaceusniger

<400> SEQUENCE: 101
```

Gln Arg Ser Thr Ser Leu Thr Asp Ala Glu Arg Arg Val Ala Ala Leu

```
                1               5                  10                 15
            Ala Ala Ala Gly Gln Thr Asn Arg Glu Ile Ala Lys Gln Leu Phe Val
                            20                  25                  30

Thr Ala Ser Thr Val Glu Gln His Leu Thr Ser Val Phe Arg Lys Leu
                            35                  40                  45

Gly Val Lys Gly Arg Lys Gln Leu Pro Thr Ala Leu Ala Asp Val Glu
                            50                  55                  60

Gln Thr
            65

<210> SEQ ID NO 102
<211> LENGTH: 58
<212> TYPE: PRT
<213> ORGANISM: Streptomyces hygroscopicus

<400> SEQUENCE: 102

Gln Arg Ile Lys Ser Leu Thr Asp Ala Glu Arg Val Ala Ser Leu
            1               5                  10                 15

Ala Ala Gly Gly Gln Thr Asn Arg Val Ile Ala Asp Gln Leu Phe Val
                            20                  25                  30

Thr Ala Ser Thr Val Glu Gln His Leu Thr Asp Val Ser Thr Gly Ser
                            35                  40                  45

Arg Pro Pro Ala Pro Ala Ala Glu Leu Val
                50                  55

<210> SEQ ID NO 103
<211> LENGTH: 64
<212> TYPE: PRT
<213> ORGANISM: Streptomyces ascomyceticus

<400> SEQUENCE: 103

Gln Arg Ile Thr Ser Leu Thr Glu Ala Glu Arg Val Ala Ser His
            1               5                  10                 15

Ala Ala Val Gly Arg Thr Asn Lys Glu Ile Ala Ser Gln Leu Phe Val
                            20                  25                  30

Thr Ser Ser Thr Val Glu Gln His Leu Thr Asn Val Phe Arg Lys Leu
                            35                  40                  45

Gly Val Lys Gly Arg Gln Gln Leu Pro Lys Glu Leu Ser Asp Ala Gly
                            50                  55                  60

<210> SEQ ID NO 104
<211> LENGTH: 74
<212> TYPE: PRT
<213> ORGANISM: Streptomyces kanamyceticus

<400> SEQUENCE: 104

Gln Arg Ile Ala Ser Leu Thr Glu Ser Glu Arg Val Ala Ala Leu
            1               5                  10                 15

Ala Ala Val Gly Arg Thr Asn Arg Glu Ile Ala Glu Gln Leu Phe Val
                            20                  25                  30

Thr Ala Ser Thr Val Glu Gln His Leu Thr Asn Val Phe Arg Lys Leu
                            35                  40                  45

Ala Val Lys Gly Arg Gln Gln Leu Pro Lys Glu Leu Ala Asp Val Gly
                            50                  55                  60

Glu Pro Ala Asp Arg Asp Arg Arg Cys Gly
            65                  70

<210> SEQ ID NO 105
```

<211> LENGTH: 71
<212> TYPE: PRT
<213> ORGANISM: Artificial Sequence
<220> FEATURE:
<223> OTHER INFORMATION: synthetic construct

<400> SEQUENCE: 105

```
Ile Arg Thr Ser Pro Leu Thr Gln Arg Glu Trp Gln Val Leu Gly Leu
1               5                   10                  15

Ile Tyr Ser Gly Tyr Ser Asn Glu Gln Ile Ala Gly Glu Leu Glu Val
            20                  25                  30

Ala Ala Thr Thr Ile Lys Thr His Ile Arg Asn Leu Tyr Gln Lys Leu
        35                  40                  45

Gly Val Ala His Arg Gln Asp Ala Val Gln His Ala Gln Gln Leu Leu
    50                  55                  60

Lys Met Met Gly Tyr Gly Val
65                  70
```

<210> SEQ ID NO 106
<211> LENGTH: 45
<212> TYPE: PRT
<213> ORGANISM: Streptomyces rapamycinicus

<400> SEQUENCE: 106

```
Leu Thr Asp Ala Glu Arg Arg Val Ala Ser Leu Ala Ala Gly Gly Gln
1               5                   10                  15

Thr Asn Arg Val Ile Ala Asp Gln Leu Phe Val Thr Ala Ser Thr Val
            20                  25                  30

Glu Gln His Leu Thr Asn Val Phe Arg Lys Leu Gly Val
        35                  40                  45
```

<210> SEQ ID NO 107
<211> LENGTH: 54
<212> TYPE: DNA
<213> ORGANISM: Streptomyces violaceusniger

<400> SEQUENCE: 107
cgcctggccg aaacctagg gggttgcgtg gaaagcaccg gcgggtgttc gctt      54

<210> SEQ ID NO 108
<211> LENGTH: 48
<212> TYPE: DNA
<213> ORGANISM: Streptomyces filamentosus

<400> SEQUENCE: 108
cggcaggcag actaggggtt gcgtgggccg cacccgaggc attcgatt      48

<210> SEQ ID NO 109
<211> LENGTH: 49
<212> TYPE: DNA
<213> ORGANISM: Streptomyces filamentosus

<400> SEQUENCE: 109
cggcaggcag actagggggt tgcgtgggcc gcacccgagg cattcgatt      49

<210> SEQ ID NO 110
<211> LENGTH: 53
<212> TYPE: DNA
<213> ORGANISM: Streptomyces filamentosus

<400> SEQUENCE: 110
cggcaggcag aacacctagg gggttgcgtg ggccgcaccc gaggcattcg att      53

```
<210> SEQ ID NO 111
<211> LENGTH: 52
<212> TYPE: DNA
<213> ORGANISM: Streptomyces violaceusniger

<400> SEQUENCE: 111
ctgcaggcag aacacctggg ggttgcgcga accgggcgcg cggtatcgga tt            52

<210> SEQ ID NO 112
<211> LENGTH: 53
<212> TYPE: DNA
<213> ORGANISM: Streptomyces violaceusniger

<400> SEQUENCE: 112
ctgcaggcag aacacctagg gggttgcgcg aaccgggcgc gcggtatcgg att           53
```

US 11,447,810 B2

COMPOSITIONS AND METHODS FOR THE PRODUCTION OF COMPOUNDS

BACKGROUND

The Large ATP-binding regulators of the LuxR family of transcriptional activators (LALs) are known transcriptional regulators of polyketides such as FK506 or rapamycin. The LAL family has been found to have an active role in the induction of expression of some types of natural product gene clusters, for example PikD for pikromycin production and RapH for rapamycin production. The LAL proteins contain three domains; a nucleotide-binding domain, an inducer-binding domain, and a helix-turn-helix (DNA binding) domain. The structure of the DNA-binding domain is a four helix bundle. The specific protein residue sequence of Helix 3 in this motif directs the LAL to specific DNA sequences contained in prokaryal transcriptional promoter regions (i.e., the LAL binding site). Binding of the LAL or multiple LALs in a complex to specific sites in the promoters of genes within a gene cluster that produces a small molecule (e.g., a polyketide synthase gene cluster or a β-lactam compound producing protein gene cluster) potentiates expression of the gene cluster and hence promotes production of the compound (e.g., a polyketide or a β-lactam compound). Thus, there is an opportunity for compositions and methods to be developed that lead to more efficient and/or increased production of compounds (e.g., polyketides or β-lactam compounds) by optimizing regulation of the corresponding gene cluster that produces a small molecule (e.g., a PKS gene cluster or a β-lactam compound gene cluster).

SUMMARY OF THE INVENTION

The present disclosure provides nucleic acids encoding a recombinant LAL, vectors and host cells including recombinant LALs, and methods of using these nucleic acids, vectors, and host cells in methods for the production of compounds (e.g., polyketides, fatty acids, terpenoids, non-ribosomal polypeptides, β-lactam compounds, and alkaloids). Accordingly, in a first aspect, the present disclosure provides a host cell (e.g., a host cell naturally lacking an LAL and/or an LAL binding site) engineered to express a recombinant LAL (e.g., a heterologous LAL). In some embodiments, the LAL is constitutively active. In some embodiments, the host cell is engineered by insertion of a LAL binding site in a nucleic acid. In some embodiments, the binding of the recombinant LAL to the LAL binding site promotes transcription of the nucleic acid (e.g., a nucleic acid encoding a compound-producing protein such as a polyketide synthase or a β-lactam compound producing protein). In some embodiments, the LAL binding site is heterologous to the LAL. In some embodiments, the LAL binding site is endogenous to the LAL. In some embodiments, the LAL binding site includes the sequence GGGGGT.

In some embodiments, the host cell includes a nucleic acid including a heterologous LAL binding site operably linked to an open reading frame such that binding of an LAL to the heterologous LAL binding site promotes expression of the open reading frame. In some embodiments, the heterologous LAL binding site is a synthetic LAL binding site. In some embodiments, the heterologous LAL binding site promotes greater expression than the endogenous LAL binding site operably linked to the open reading frame. In some embodiments, the heterologous LAL binding site includes at least 8 contiguous nucleotides of $C_1$-$T_2$-$A_3$-$G_4$-$G_5$-$G_6$-$G_7$-$G_8$-$T_9$-$T_{10}$-$G_{11}$-$C_{12}$ (SEQ ID NO: 2), wherein none or up to six nucleotides other than any three nucleotides of $G_4$, $G_5$, $G_6$, $G_7$, $G_8$, $T_9$, and $T_{10}$ (e.g., $G_4$, $G_7$, and $T_9$; $G_5$, $G_8$, and $T_{10}$; or $G_6$, $G_7$, and $G_8$) are replaced by any other nucleotide.

In some embodiments, the recombinant LAL includes a portion having at least 70% (e.g., at least 75%, at least 80%, at least 85%, at least 90%, at least 95%, at least 99%) sequence identity to the sequence of SEQ ID NO: 1. In some embodiments, the recombinant LAL includes a portion having the sequence of SEQ ID NO: 1. In some embodiments, the recombinant LAL has the amino acid sequence of SEQ ID NO: 1.

(SEQ ID NO: 1)
MPAVESYELDARDDELRRLEEAVGQAGNGRGVVVTITGPIACGKTELLDA

AAAKSDAITLRAVCSEEERALPYALIGQLIDNPAVASQLPDPVSMALPGE

HLSPEAENRLRGDLTRTLLALAAERPVLIGIDDMHHADTASLNCLLHLAR

RVGPARIAMVLTELRRLTPAHSQFHAELLSLGHHREIALRPLGPKHIAEL

ARAGLGPDVDEDVLTGLYRATGGNLNLGHGLIKDVREAWATGGTGINAGR

AYRLAYLGSLYRCGPVPLRVARVAAVLGQSANTTLVRWISGLNADAVGEA

TEILTEGGLLHDLRFPHPAARSVVLNDLSARERRRLHRSALEVLDDVPVE

VVAHHQAGAGFIHGPKAAEIFAKAGQELHVRGELDAASDYLQLAHHASDD

AVTRAALRVEAVAIERRRNPLASSRHLDELTVAARAGLLSLEHAALMIRW

LALGGRSGEAAEVLAAQRPRAVTDQDRAHLRAAEVSLALVSPGASGVSPG

ASGPDRRPRPLPPDELANLPKAARLCAIADNAVISALHGRPELASAEAEN

VLKQADSAADGATALSALTALLYAENTDTAQLWADKLVSETGASNEEEGA

GYAGPRAETALRRGDLAAAVEAGSAILDHRRGSLLGITAALPLSSAVAAA

IRLGETERAEKWLAEPLPEATRDSLFGLHLLSARGQYCLATGRHESAYTA

FRTCGERMRNWGVDVPGLSLWRVDAAEALLHGRDRDEGRRLIDEQLTHAM

GPRSRALTLRVQAAYSPQAQRVDLLEEAADLLLSCNDQYERARVLADLSE

AFSALRHHSRARGLLRQARHLAAQCGATPLLRRLGAKPGGPGWLEESGLP

QRIKSLTDAERRVASLAAGGQTNRVIADQLFVTASTVEQHLTNVERKLGV

KGRQHLPAELANAE.

In some embodiments, the host cell is a bacterium (e.g., an actinobacterium such as *Streptomyces ambofaciens*, *Streptomyces hygroscopicus*, or *Streptomyces malayensis*). In some embodiments, the actinobacterium is S1391, S1496, or S2441.

In some embodiments, the host cell has been modified to enhance expression of a compound-producing protein (e.g., a polyketide synthase or a β-lactam compound producing protein). For example, in some embodiments, the host cell has been modified to enhance expression of a compound-producing protein (e.g., a polyketide synthase or a β-lactam compound producing protein) by (i) deletion of an endogenous gene cluster which expresses a compound-producing protein (e.g., a polyketide synthase or a β-lactam compound producing protein); (ii) insertion of a heterologous gene cluster which expresses a compound-producing protein (e.g., a polyketide synthase or a β-lactam compound producing protein); (iii) exposure of said host cell to an antibiotic challenge; and/or (iv) introduction of a heterologous promoter that results in at least a two-fold increase in expression of a compound compared to the homologous promoter. An additional method to enhance the expression of a compound (e.g., a polyketide or a β-lactam compound) is to optimize media conditions for growth. This includes the specific chemical and nutrient composition of the media, whether the fermentation is conducted in liquid or solid media, the time course of the fermentation, and the volume/scale of the fermentation run.

In another aspect, the disclosure provides a nucleic acid encoding an LAL, wherein the LAL includes a portion having at least 70% (e.g., at least 75%, at least 80%, at least 85%, at least 90%, at least 95%, at least 99%) sequence identity to the amino acid sequence of SEQ ID NO: 1. In some embodiments, the LAL includes a portion having the sequence of SEQ ID NO: 1. In some embodiments, the LAL has the sequence of SEQ ID NO: 1. In some embodiments, the nucleic acid lacks a TTA regulatory codon in at least one open reading frame.

In some embodiments, the nucleic acid further comprises an LAL binding site, e.g., an LAL binding site having at least 80% (e.g., at least 85%, at least 90%, at least 95%, at least 99%) identity to the sequence of SEQ ID NO: 2 (CTAGGGGGTTGC). In some embodiments, the LAL binding site includes the sequence of SEQ ID NO: 2. In some embodiments, the LAL binding site has the sequence of SEQ ID NO: 2. In some embodiments, the LAL binding site includes the sequence SEQ ID NO: 3 (GGGGGT).

In some embodiments, the nucleic acid further includes an open reading frame positioned such that binding of the LAL to the LAL binding site promotes expression of the open reading frame. In some embodiments, the open reading frame encodes a compound-producing protein (e.g., a polyketide synthase or a β-lactam compound producing protein).

In some embodiments, the open reading frame encodes a polyketide synthase. In some embodiments, the nucleic acid further encodes a nonribosomal peptide synthase. In some embodiments, the nucleic acid further encodes a first P450 enzyme. In some embodiments, the nucleic acid further encodes a second P450 enzyme.

In some embodiments, the open reading frame encodes a β-lactam compound producing protein. In some embodiments, the open reading frame encodes two more (e.g., three or more, four or more, five or more, six or more, seven or more, or eight or more) β-lactam compound producing proteins. In some embodiments, the nucleic acid further encodes one or more tailoring proteins.

In another aspect, the disclosure provides an expression vector including any of the foregoing nucleic acids. In some embodiments, the expression vector is an artificial chromosome (e.g., a bacterial artificial chromosome).

In another aspect, the disclosure provides a host cell including any of the foregoing vectors.

In another aspect, the disclosure provides a method of producing a compound (e.g., a polyketide, a fatty acid, a terpenoid, a β-lactam compound, a non-ribosomal polypeptide, or an alkaloid). This method includes: (a) providing a host cell engineered to express a recombinant LAL and including an LAL binding site operably linked to an open reading frame such that binding of the recombinant LAL to the LAL binding site promotes expression of the open reading frame, wherein the host cell includes a nucleic acid encoding a compound-producing protein (e.g., polyketide synthase or a β-lactam compound producing protein); and (b) culturing the host cell under conditions suitable to allow expression of a compound by the compound-producing protein (e.g., polyketide synthase or a β-lactam compound producing protein); thereby producing a compound.

In another aspect, the disclosure provides a method of identifying a synthetic LAL binding site, the method including: (a) providing a plurality of synthetic nucleic acids including at least eight nucleotides; (b) contacting one or more of the plurality of nucleotides including at least eight nucleotides with one or more LALs; (c) determining the binding affinity between a nucleic acid of step (a) and an LAL of step (b), wherein a synthetic nucleic acid is identified as a synthetic LAL binding site if the synthetic binding site, when linked to a downstream gene, is capable of inducing transcription of the linked gene, as measured by at least a 2-fold increase in RNA transcription. In some embodiments, wherein a synthetic nucleic acid is identified as a synthetic LAL binding site if the affinity between the synthetic nucleic acid and an LAL is less than 500 nM (e.g., less than 250 nm, less than 100 nM, less than 50 nM, less than 20 nM or between 1-50 nM, between 5-75 nM, between 50 and 100 nM, between 75 and 250 nM).

Definitions

The term "compound-producing protein," as used herein refers to a protein such as a polyketide synthase that when expressed in a cell under suitable conditions produces a small molecule (e.g., a polyketide, a fatty acid, a terpenoid, a β-lactam compound, a non-ribosomal polypeptide, or an alkaloid)

A cell that is "engineered to contain" and/or "engineered to express" refers to a cell that has been modified to contain and/or express a protein that does not naturally occur in the cell. A cell may be engineered to contain a protein, e.g., by introducing a nucleic acid encoding the protein by introduction of a vector including the nucleic acid.

The term "gene cluster that produces a small molecule," as used herein refers to a cluster of genes which encodes one or more compound-producing proteins.

The term "heterologous," as used herein, refers to a relationship between two or more proteins, nucleic acids, compounds, and/or cell that is not present in nature. For example, the LAL having the sequence of SEQ ID NO: 1 is naturally occurring in the S18 *Streptomyces* strain and is thus homologous to that strain and would thus be heterologous to the S12 *Streptomyces* strain.

The term "homologous," as used herein, refers to a relationship between two or more proteins, nucleic acids, compounds, and/or cells that is present naturally. For example, the LAL having the sequence of SEQ ID NO: 1 is naturally occurring in the S18 *Streptomyces* strain and is thus homologous to that strain.

A "polyketide synthase" refers to an enzyme belonging to the family of multi-domain enzymes capable of producing a polyketide. A polyketide synthase may be expressed naturally in bacteria, fungi, plants, or animals.

A "β-lactam compound" refers to any compound having a structure that includes a β-lactam ring, including β-lactam antibiotics and β-lactam inhibitors. The structure of a β-lactam ring is provided in Formula I.

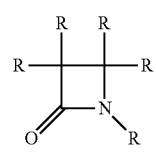

Formula I

β-lactam compounds of the invention are considered to include, at least, 5-membered unsaturated β-lactam compounds (e.g., carbapanems), 5-membered saturated β-lactam compounds (e.g., penams, such as penicillin, and clavams, such as clavulanic acid), monocyclic β-lactam compounds (e.g., nocardicins and monobactams) and 6-membered unsaturated β-lactam compounds (e.g., cephems, such as cephalosporin). Exemplary β-lactam compounds are described in Hamed, R. B., et al., The enzymes of β-lactam biosynthesis. Nat Prod Rep. 31(9):1127 (2014), the compounds of which are incorporated herein by reference.

A "β-lactam compound producing protein" refers to any protein (e.g., enzyme) in a biosynthetic pathway that produces a β-lactam compound. β-lactam compound producing enzymes may be considered to include a protein that produces the biosynthetic precursor to a β-lactam ring (e.g., ACV synthetase, carboxyethylarginine synthase), a protein that catalyzes the formation of a beta lactam ring (e.g. isopenicillin N synthetase, β-lactam synthetase, CarA, CarB, CarC, or ThnM), or any protein that modifies the β-lactam ring (e.g., a tailoring enzyme). Exemplary β-lactam producing enzymes are described in Hamed, R. B., et al., The enzymes of β-lactam biosynthesis. Nat Prod Rep. 31(9):1127 (2014), the enzymes of which are incorporated herein by reference.

A "β-lactam compound producing protein gene cluster" refers to any gene cluster that encodes the production of a β-lactam compound producing protein. In some embodiments, β-lactam compound producing protein gene clusters of the invention may encode a naturally-occurring β-lactam compound. In other embodiments, β-lactam compound producing protein gene clusters of the invention may encode an engineered variant of a naturally-occurring β-lactam compound.

The term "recombinant," as used herein, refers to a protein that is produced using synthetic methods.

BRIEF DESCRIPTION OF THE DRAWINGS

FIGS. 1A-1C are diagrams showing a strategy for use of LAL transcriptional regulators for general induction and overexpression of biosynthetic loci. FIG. 1A shows the design for the X1 biosynthetic locus, including two bidirectional promoter regions and an LAL-encoding gene. FIG. 1B shows a series of conserved putative LAL binding domains extracted from FK cluster promoter regions. FIG. 1C shows a scheme for phage-integrating constitutive LAL construction.

FIG. 17A shows the design for the biosynthetic locus, including three bidirectional X1 promoter regions (P2, P3, and P5) inserted into the WAC292 β-lactam gene cluster. FIG. 17B is a table showing the normalized mRNA levels measured by NanoString displayed as log 2 values. The NanoString analysis shows that transcripts linked to the P2, P3, and P5 promoters were significantly upregulated in WAC292-p2p3p5 as compared to WAC292-WT.

DETAILED DESCRIPTION

Figure 2:
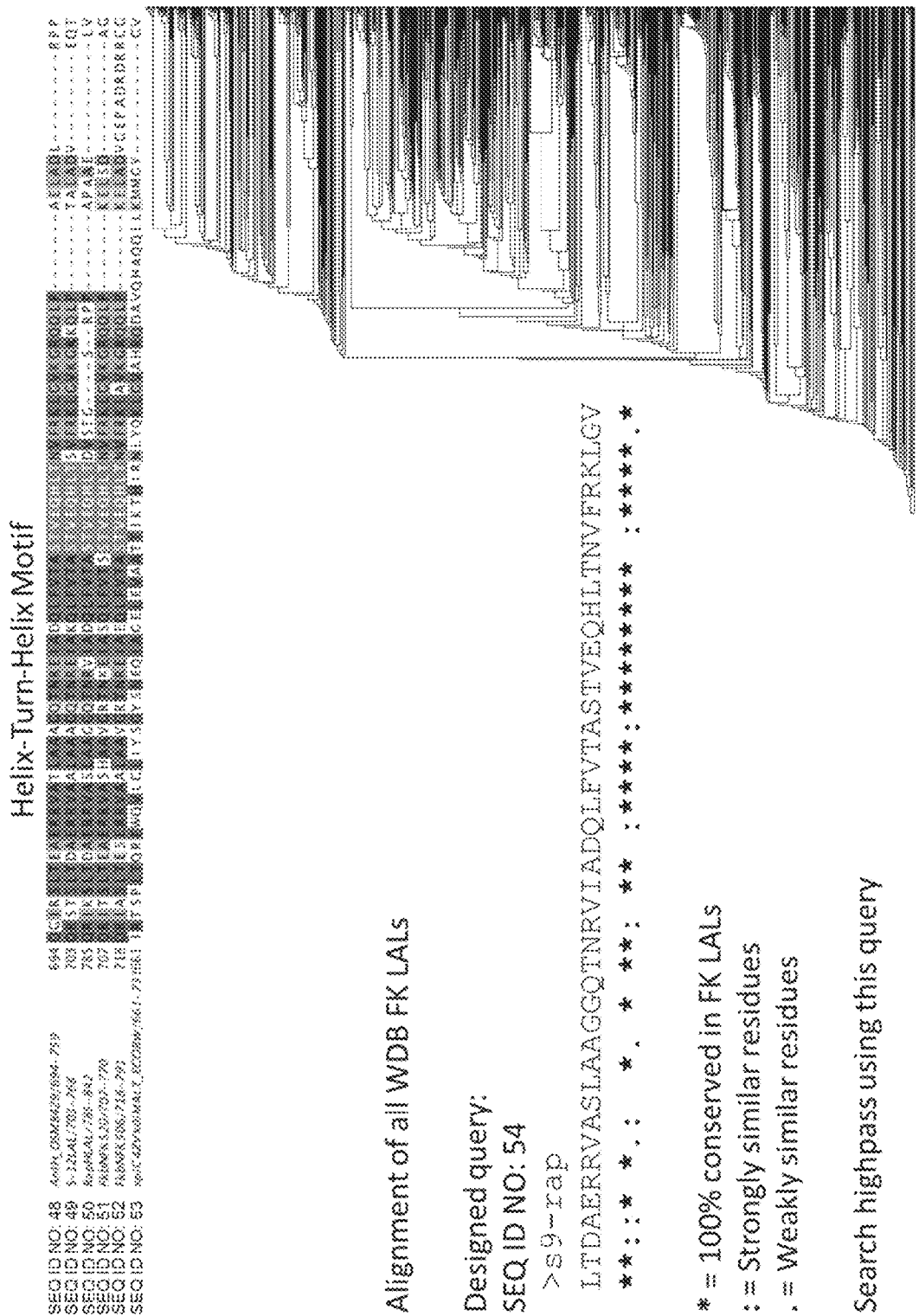
FIG. 2 is a diagram showing LAL sequence analysis based on a genomic database. The amino acid sequences of a series of FK LALs were aligned and used to design a query for clading of the LALs. Conserved residues in the designed query are indicated (*=100% conserved in FK LALs; :=strongly similar residues; .=weakly similar residues).

The present inventors discovered the amino acid sequence within helix 3 of the Helix-Turn-Helix DNA-binding motif of LALs associated with known polyketide synthases is 100% conserved. As a result of the conservation of helix 3 of the LALs, there are predictable DNA sequence motifs including likely LAL binding sites in the promoter-operator regions of genes that encode polyketide synthases. The conservation of the LAL-DNA interaction motifs at both the protein and DNA levels enables interchangeable use of the LALs for the activation of transcription of natural product gene clusters.

Compounds

Compounds that may be produced with the methods of the invention include, but are not limited to, polyketides and polyketide macrolide antibiotics such as erythromycin; hybrid polyketides/non-ribosomal peptides such as rapamycin and FK506; carbohydrates including aminoglycoside antibiotics such as gentamicin, kanamycin, neomycin, tobramycin; benzofuranoids; benzopyranoids; flavonoids; glycopeptides including vancomycin; lipopeptides including daptomycin; tannins; lignans; polycyclic aromatic natural products, terpenoids, steroids, sterols, oxazolidinones including linezolid; amino acids, peptides and peptide antibiotics including polymyxins, non-ribosomal peptides, β-lactam compounds including β-lactam antibiotics and β-lactamase inhibitors (e.g., carbapenems, cephalosporins, penicillins, clavulanic acid, monobactams, nocardicins, tabtoxins, and conjugate β-lactams); purines, pteridines, polypyrroles, tetracyclines, quinolones and fluoroquinolones; and sulfonamides.

Proteins

LALs

LALs include three domains, a nucleotide-binding domain, an inducer-binding domain, and a DNA-binding domain. A defining characteristic of the structural class of regulatory proteins that include the LALs is the presence of the AAA+ ATPase domain. Nucleotide hydrolysis is coupled to large conformational changes in the proteins and/or multimerization, and nucleotide binding and hydrolysis represents a "molecular timer" that controls the activity of the LAL (e.g., the duration of the activity of the LAL). The LAL is activated by binding of a small-molecule ligand to the inducer binding site. In most cases the allosteric inducer of the LAL is unknown. In the case of the related protein MaIT, the allosteric inducer is maltotriose. Possible inducers for LAL proteins include small molecules found in the environment that trigger compound (e.g., polyketide or a β-lactam compound) biosynthesis. The regulation of the LAL controls production of compound-producing proteins (e.g., polyketide synthases or β-lactam compound producing proteins) resulting in activation of compound (e.g., polyketide or a β-lactam compound) production in the presence of external environmental stimuli. Therefore, there are gene clusters that produce small molecules (e.g., PKS gene clusters or β-lactam compound producing protein gene clusters) which, while present in a strain, do not produce compound either because (i) the LAL has not been activated, (ii) the strain has LAL binding sites that differ from consensus, (iii) the strain lacks an LAL regulator, or (iv) the LAL regulator may be poorly expressed or not expressed under laboratory conditions. Since the DNA binding region of the LALs of the known PKS LALs are highly conserved, the known LALs may be used interchangeably to activate PKS gene clusters and other compound producing gene clusters, such as β-lactam compound producing protein gene clusters, other than those which they naturally regulate. In some embodiments, the LAL is a fusion protein.

In some embodiments, an LAL may be modified to include a non-LAL DNA-binding domain, thereby forming a fusion protein including an LAL nucleotide-binding domain and a non-LAL DNA-binding domain. In certain embodiments, the non-LAL DNA-binding domain is capable of binding to a promoter including a protein-binding site positioned such that binding of the DNA-binding domain to the protein-binding site of the promoter promotes expression of a gene of interest (e.g., a gene encoding a compound-producing protein, as described herein). The non-LAL DNA binding domain may include any DNA binding domain known in the art. In some instances, the non-LAL DNA binding domain is a transcription factor DNA binding domain. Examples of non-LAL DNA binding domains include, without limitation, a basic helix-loop-helix (bHLH) domain, leucine zipper domain (e.g., a basic leucine zipper domain), GCC box domain, helix-turn-helix domain, homeodomain, srf-like domain, paired box domain, winged helix domain, zinc finger domain, HMG-box domain, Wor3 domain, OB-fold domain, immunoglobulin domain, B3 domain, TAL effector domain, Cas9 DNA binding domain, GAL4 DNA binding domain, and any other DNA binding domain known in the art. In some instances, the promoter is positioned upstream to the gene of interest, such that the fusion protein may bind to the promoter and induce or inhibit expression of the gene of interest. In certain instances, the promoter is a heterologous promoter introduced to the nucleic acid (e.g., a chromosome, plasmid, fosmid, or any other nucleic acid construct known in the art) containing the gene of interest. In other instances, the promoter is a pre-existing promoter positioned upstream to the gene of interest. The protein-binding site within the promoter may, for example, be a non-LAL protein-binding site. In certain embodiments, the protein-binding site binds to the non-LAL DNA binding domain, thereby forming a cognate DNA binding domain/protein-binding site pair.

In some embodiments, the LAL is encoded by a nucleic acid having at least 70% (e.g., at least 75%, at least 80%, at least 85%, at least 90%, at least 95%, at least 99%) sequence identity to any one of SEQ ID Nos: 4-25 or has a sequences with at least 70% (e.g., at least 75%, at least 80%, at least 85%, at least 90%, at least 95%, at least 99%) sequence identity to any one of SEQ ID Nos: 26-36.

```
SEQ ID NO: 4:
ATGCCTGCCGTGGAGTGCTATGAACTGGACGCCCGCGATGACGAGCTCAGAAAACTGGAGGAGGTTGTGAC

CGGGCGGGCCAACGGCCGGGGTGTGGTGGTCACCATCACCGGACCGATCGCCTGCGGCAAGACCGAACTGC

TCGACGCAGCCGCCGCGAAGGCCGACGCCATCACGTTACGAGCGGTCTGCTCCGCGGAGGAACAGGCACTC

CCGTACGCCCTGATCGGGCAGCTCATCGACAACCCGGCGCTCGCCTCCCACGCGCTGGAGCCGGCCTGCCC

GACCCTCCCGGGCGAGCACCTGTCGCCGGAGGCCGAGAACCGGCTGCGCAGCGACCTCACCCGTACCCTGC

TGGCGCTCGCCGCCGAACGGCCGGTGCTGATCGGCATCGACGAGTCACACGCGAACGCTTTGTGTCTGCTC

CACCTGGCCCGAAGGGTCGGCTCGGCCCGGATCGCCATGGTCCTCACCGAGTTGCGCCGGCTCACCCCGGC

CCACTCACAGTTCCAGGCCGAGCTGCTCAGCCTGGGGCACCACCGCGAGATCGCGCTGCGCCCGCTCAGCC

CGAAGCACACCGCCGAGCTGGTCCGCGCCGGTCTCGGTCCCGACGTCGACGAGGACGTGCTCACGGGGTTG
```

-continued

TACCGGGCGACCGGCGGCAACCTGAACCTCACCCGCGGACTGATCAACGATGTGCGGGAGGCCTGGGAGAC
GGGAGGGACGGGCATCAGCGCGGGCCGCGCGTACCGGCTGGCATACCTCGGTTCCCTCTACCGCTGCGGCC
CGGTCCCGTTGCGGGTCGCACGGGTGGCCGCCGTGCTGGGCCAGAGCGCCAACACCACCCTGGTGCGCTGG
ATCAGCGGGCTCAACGCGGACGCGGTGGGCGAGGCAACCGAGATCCTCACCGAAGGCGGCCTGCTGCACGA
CCTGCGGTTCCCGCACCCGGCGGCCCGTTCGGTGGTACTCAACGACATGTCCGCCCAGGAACGACGCCGCC
TGCACCGGTCCGCTCTGGAAGTGCTGGACGACGTGCCCGTGGAAGTGGTCGCGCACCACCAGGTCGGCGCC
GGTCTCCTGCACGGCCCGAAGGCCGCCGAGATATTCGCCAAGGCCGGCCAGGAGCTGCATGTGCGCGGCGA
GTTGGACACCGCGTCCGACTATCTGCAACTGGCCCACCAGGCCTCCGACGACGCCGTCACCGGGATGCGGG
CCGAGGCCGTGGCGATCGAGCGCCGCCGCAACCCGCTGGCCTCGAGCCGGCACCTCGACGAGCTGACCGTC
GTCGCCCGTGCCGGGCTGCTCTTCCCCGAGCACACGGCGCTGATGATCCGCTGGCTGGGCGTCGGCGGGCG
GTCCGGCGAGGCAGCCGGGCTGCTGGCCTCGCAGCGCCCCCGTGCGGTCACCGACCAGGACAGGGCCCATA
TGCGGGCCGCCGAGGTATCGCTCGCGCTGGTCAGCCCCGGCACGTCCGGCCCGGACCGGCGGCCGCGTCCG
CTCACGCCGGATGAGCTCGCGAACCTGCCGAAGGCGGCCCGGCTCTGCGCGATCGCCGACAATGCCGTCAT
GTCGGCCCTGCGCGGTCGTCCCGAGCTCGCCGCGGCCGAGGCGGAGAACGTCCTGCAGCACGCCGACTCGG
CGGCGGCCGGCACCACCGCCCTCGCCGCGCTGACCGCCTTGCTGTACGCGGAGAACACCGACACCGCTCAG
CTCTGGGCCGACAAGCTGGTCTCCGAGACCGGGGCGTCGAACGAGGAGGAGGCGGGCTACGCGGGGCCGCG
CGCCGAAGCCGCGTTGCGTCGCGGCGACCTGGCCGCGGCGGTCGAGGCAGGCAGCACCGTTCTGGACCACC
GGCGGCTCTCGACGCTCGGCATCACCGCCGCGCTACCGCTGAGCAGCGCGGTGGCCGCCGCCATCCGGCTG
GGCGAGACCGAGCGGGCGGAGAAGTGGCTCGCCCAGCCGCTGCCGCAGGCCATCCAGGACGGCCTGTTCGG
CCTGCACCTGCTCTCGGCGCGCGGCCAGTACAGCCTCGCCACGGGCCAGCACGAGTCGGCGTACACGGCGT
TTCGCACCTGCGGGGAACGTATGCGGAACTGGGGCGTTGACGTGCCGGGTCTGTCCCTGTGGCGCGTCGAC
GCCGCCGAGGCGCTGCTGCACGGCCGCGACCGGGACGAGGGCCGACGGCTCGTCGACGAGCAACTCACCCG
TGCGATGGGACCCCGTTCCCGCGCCTTGACGCTGCGGGTGCAGGCGGCGTACAGCCCGCCGGCGAAGCGGG
TCGACCTGCTCGATGAAGCGGCCGACCTGCTGCTCTCCTGCAACGACCAGTACGAGCGGGCACGGGTGCTC
GCCGACCTGAGCGAGACGTTCAGCGCGCTCCGGCACCACAGCCGGGCGCGGGGACTGCTTCGGCAGGCCCG
GCACCTGGCCGCCCAGCGCGGCGCGATACCGCTGCTGCGCCGACTCGGGGCCAAGCCCGGAGGCCCCGGCT
GGCTGGAGGAATCCGGCCTGCCGCAGCGGATCAAGTCGCTGACCGACGCGGAGCGGCGGGTGGCGTCGCTG
GCCGCCGGCGGACAGACCAACCGCGTGATCGCCGACCAGCTCTTCGTCACGGCCAGCACGGTGGAGCAGCA
CCTCACGGACGTCTCCACTGGGTCAAGGCCGCCAGCACCTGCCGCCGAACTCGTCTAG

SEQ ID NO: 5
ATGCCTGCCGTGGAGTGCTATGAACTGGACGCCCGCGATGACGAGCTCAGAAAACTGGAGGAGGTTGTGAC
CGGGCGGGCCAACGGCCGGGGTGTGGTGGTCACCATCACCGGACCGATCGCCTGCGGCAAGACCGAACTGC
TCGACGCAGCCGCCGCGAAGGCCGACGCCATCACGCTGCGAGCGGTCTGCTCCGCGGAGGAACAGGCACTC
CCGTACGCCCTGATCGGGCAGCTCATCGACAACCCGGCGCTCGCCTCCCACGCGCTGGAGCCGGCCTGCCC
GACCCTCCCGGGCGAGCACCTGTCGCCGGAGGCCGAGAACCGGCTGCGCAGCGACCTCACCCGTACCCTGC
TGGCGCTCGCCGCCGAACGGCCGGTGCTGATCGGCATCGACGAGTCACACGCGAACGCTTTGTGTCTGCTC
CACCTGGCCCGAAGGGTCGGCTCGGCCCGGATCGCCATGGTCCTCACCGAGTTGCGCCGGCTCACCCCGGC
CCACTCACAGTTCCAGGCCGAGCTGCTCAGCCTGGGGCACCACCGCGAGATCGCGCTGCGCCCGCTCAGCC
CGAAGCACACCGCCGAGCTGGTCCGCGCCGGTCTCGGTCCCGACGTCGACGAGGACGTGCTCACGGGGTTG
TACCGGGCGACCGGCGGCAACCTGAACCTCACCCGCGGACTGATCAACGATGTGCGGGAGGCCTGGGAGAC
GGGAGGGACGGGCATCAGCGCGGGCCGCGCGTACCGGCTGGCATACCTCGGTTCCCTCTACCGCTGCGGCC

```
CGGTCCCGTTGCGGGTCGCACGGGTGGCCGCCGTGCTGGGCCAGAGCGCCAACACCACCCTGGTGCGCTGG
ATCAGCGGGCTCAACGCGGACGCGGTGGGCGAGGCAACCGAGATCCTCACCGAAGGCGGCCTGCTGCACGA
CCTGCGGTTCCCGCACCCGGCGGCCCGTTCGGTGGTACTCAACGACATGTCCGCCCAGGAACGACGCCGCC
TGCACCGGTCCGCTCTGGAAGTGCTGGACGACGTGCCCGTGGAAGTGGTCGCGCACCACCAGGTCGGCGCC
GGTCTCCTGCACGGCCCGAAGGCCGCCGAGATATTCGCCAAGGCCGGCCAGGAGCTGCATGTGCGCGGCGA
GTTGGACACCGCGTCCGACTATCTGCAACTGGCCCACCAGGCCTCCGACGACGCCGTCACCGGGATGCGGG
CCGAGGCCGTGGCGATCGAGCGCCGCCGCAACCCGCTGGCCTCGAGCCGGCACCTCGACGAGCTGACCGTC
GTCGCCCGTGCCGGGCTGCTCTTCCCCGAGCACACGGCGCTGATGATCCGCTGGCTGGGCGTCGGCGGGCG
GTCCGGCGAGGCAGCCGGGCTGCTGGCCTCGCAGCGCCCCGTGCGGTCACCGACCAGGACAGGGCCCATA
TGCGGGCCGCCGAGGTATCGCTCGCGCTGGTCAGCCCCGGCACGTCCGGCCCGGACCGGCGGCCGCGTCCG
CTCACGCCGGATGAGCTCGCGAACCTGCCGAAGGCGGCCCGGCTCTGCGCGATCGCCGACAATGCCGTCAT
GTCGGCCCTGCGCGGTCGTCCCGAGCTCGCCGCGGCCGAGGCGGAGAACGTCCTGCAGCACGCCGACTCGG
CGGCGGCCGGCACCACCGCCCTCGCCGCGCTGACCGCCTTGCTGTACGCGGAGAACACCGACACCGCTCAG
CTCTGGGCCGACAAGCTGGTCTCCGAGACCGGGGCGTCGAACGAGGAGGAGGCGGGCTACGCGGGGCCGCG
CGCCGAAGCCGCGTTGCGTCGCGGCGACCTGGCCGCGGCGGTCGAGGCAGGCAGCACCGTTCTGGACCACC
GGCGGCTCTCGACGCTCGGCATCACCGCCGCGCTACCGCTGAGCAGCGCGGTGGCCGCCGCCATCCGGCTG
GGCGAGACCGAGCGGGCGGAGAAGTGGCTCGCCCAGCCGCTGCCGCAGGCCATCCAGGACGGCCTGTTCGG
CCTGCACCTGCTCTCGGCGCGCGGCCAGTACAGCCTCGCCACGGGCCAGCACGAGTCGGCGTACACGGCGT
TTCGCACCTGCGGGGAACGTATGCGGAACTGGGGCGTTGACGTGCCGGGTCTGTCCCTGTGGCGCGTCGAC
GCCGCCGAGGCGCTGCTGCACGGCCGCGACCGGGACGAGGGCCGACGGCTCGTCGACGAGCAACTCACCCG
TGCGATGGGACCCCGTTCCCGCGCCTTGACGCTGCGGGTGCAGGCGGCGTACAGCCCGCCGGCGAAGCGGG
TCGACCTGCTCGATGAAGCGGCCGACCTGCTGCTCTCCTGCAACGACCAGTACGAGCGGGCACGGGTGCTC
GCCGACCTGAGCGAGACGTTCAGCGCGCTCCGGCACCACAGCCGGGCGCGGGGACTGCTTCGGCAGGCCCG
GCACCTGGCCGCCCAGCGCGGCGCGATACCGCTGCTGCGCCGACTCGGGGCCAAGCCCGGAGGCCCCGGCT
GGCTGGAGGAATCCGGCCTGCCGCAGCGGATCAAGTCGCTGACCGACGCGGAGCGGCGGGTGGCGTCGCTG
GCCGCCGGCGGACAGACCAACCGCGTGATCGCCGACCAGCTCTTCGTCACGGCCAGCACGGTGGAGCAGCA
CCTCACGGACGTCTCCACTGGGTCAAGGCCGCCAGCACCTGCCGCCGAACTCGTCTAG
SEQ ID NO: 6
GTGGTTCCTGAAGTGCGAGCAGCCCCCGACGAACTGATCGCCCGCGATGACGAGCTGAGCCGCCTCCAACG
GGCACTCACCAGGGCGGGGAGCGGAAGGGGCGGCGTCGTCGCCATCACCGGGCCCATCGCCAGCGGAAAGA
CGGCGCTGCTCGACGCCGGAGCGGCCAAGTCCGGCTTCGTCGCACTCCGTGCGGTGTGCTCCTGGGAAGAG
CGCACTCTGCCGTACGGGATGCTGGGCCAGCTCTTCGACCATCCCGAACTGGCCGCCCAGGCGCCGGACCT
TGCCCACTTCACGGCGCTTCGTGCGAGAGCCCTCAGGCCGGTACCGACAACCGCCTGCGGGCCGAGTTCACCC
GCACCCTGCTGGCGCTCGCCGCGGACTGGCCCGTCCTGATCGGCATCGACGACGTGCACCACGCCGACGCG
GAATCACTGCGCTGTCTGCTCCACCTCGCCCGCCGCATCGGCCCGGCCCGCATCGCGGTCGTACTGACCGA
GCTGCGCAGACCGACGCCCGCCGACTCCCGCTTCCAGGCGGAACTGCTGAGCCTGCGCTCCTACCAGGAGA
TCGCGCTCAGACCGCTCACCGAGGCGCAGACCGGCGAACTCGTACGTCGGCACCTCGGCGCGGAGACCCAC
GAGGACGTCTCCGCCGATACGTTCCGGGCGACCGGCGGGAACCTGCTCCTCGGGCACGGTTTGATCAATGA
CATCCGGGAGGCGCGGACAGCGGGACGGCCGGGGGTCGTCGCGGGCGGGCGTACCGGCTCGCGTACCTCA
GCTCGCTCTACCGCTGCGGCCCGAGCGCGCTGCGTGTCGCCCGGGCGTCCGCCGTGCTCGGCGCGAGCGCC
GAAGCCGTGCTCGTCCAGCGGATGACCGGACTGAACAAGGACGCGGTCGAACAGGTCTATGAGCAGCTGAA
```

```
CGAGGGACGGCTGCTGCAGGGCGAGCGGTTTCCGCACCCGGCGGCCCGCTCCATCGTCCTTGACGACCTGT
CGGCCCTGGAACGCAGAAACCTGCACGAGTCGGCGCTGGAGCTGCTGCGGGACCACGGCGTGGCCGGCAAC
GTGCTCGCCCGCCACCAGATCGGCGCCGGCCGGGTGCACGGCGAGGAGGCCGTCGAGCTGTTCACCGGGGC
CGCACGGGAGCACCACCTGCGCGGTGAACTGGACGACGCGGCCGGATACCTGGAACTCGCCCACCGTGCCT
CCGACGACCCCGTCACGCGCGCCGCACTACGCGTCGGCGCCGCCGCGATCGAGCGCCTCTGCAATCCGGTA
CGGGCAGGCCGGCATCTGCCCGAGCTGCTCACCGCGTCGCGCGCGGGACTGCTCTCCAGCGAGCACGCCGT
GTCGCTCGCCGACTGGCTGGCGATGGGCGGGCGCCCGGGCGAGGCGGCCGAGGTCCTCGCGACGCAGCGTC
CCGCGGCCGACAGCGAGCAGCACCGCGCACTCCTGCGCAGCGGCGAGTTGTCCCTCGCGCTGGTCCACCCC
GGCGCGTGGGATCCGTTGCGCCGGACCGATCGGTTCGCCGCGGGCGGGCTCGGCTCGCTTCCCGGACCCGC
CCGGCACCGCGCGGTCGCCGACCAAGCCGTCATCGCGGCGCTGCGTGGACGTCTCGACCGGGCGGACGCCA
ACGCGGAGAGCGTTCTCCAGCACACCGACGCCACGGCGGACCGGACCACGGCCATCATGGCGTTGCTGGCC
CTGCTCTACGCGGAGAACACCGATGCTGTCCAGTTCTGGGTCGACAAACTGGCCGGTGACGAGGGCACCAG
GACACCGGCCGACGAGGCGGTCCACGCGGGGTTCAACGCCGAGATCGCGCTGCGCCGCGGCGACTTGATGA
GAGCCGTCGAGTACGGCGAGGCAGCGCTCGGCCACCGGCACCTGCCCACCTGGGGAATGGCCGCCGCTCTG
CCGCTGAGCAGCACCGTGGTTGCCGCGATCCGGCTCGGCGACCTCGACAGGGCCGAGCGGTGGCTCGCCGA
GCCGCTGCCGCAGCAGACGCCGGAGAGCCTCTTCGGGCTGCACCTGCTCTGGGCCCGCGGGCAGCACCACC
TCGCGACCGGGCGGCACGGGGCGGCGTACACGGCGTTCAGGGAATGCGGCGAGCGGATGCGGCGGTGGGCC
GTCGACGTGCCGGGCCTGGCCCTGTGGCGGGTCGACGCCGCCGAATCGCTGCTGCTGCTCGGCCGTGACCG
TGCCGAAGGACTGCGGCTCGTCTCCGAGCAGCTGTCCCGGCCGATGCGCCCTCGCGCGCGCGTGCAGACGT
TACGGGTACAGGCGGCCTACAGTCCGCCGCCCCAACGGATCGACCTGCTCGAAGAGGCCGCCGACCTGCTG
GTCACCTGCAACGACCAGTACGAACTGGCAAACGTACTCAGCGACTTGGCAGAGGCCTCCAGCATGGTCCG
GCAGCACAGCAGGGCGCGGGTCTGCTCCGCCGGGCACGGCACCTCGCCCACCCAGTGCGGCGCCGTGCCGC
TCCTGCGGCGGCTCGGCGCGGAACCCTCGGACATCGGCGGAGCCTGGGACGCGACGCTGGGACAGCGGATC
GCGTCACTGACGGAGTCGGAGCGGCGGGTGGCCGCGCTCGCCGCGGTCGGGCGTACGAACAGGGAGATCGC
CGAGCAGCTGTTCGTCACGGCCAGCACGGTGGAACAGCACCTCACGAACGTGTTCCGCAAACTGGCGGTGA
AGGGCCGCCAGCAGCTTCCGAAGGAACTGGCCGACGTCGGCGAGCCGGCGGACCGCGACCGCCGGTGCGGG
TAG

SEQ ID NO: 7
ATGGTTCCTGAAGTGCGAGCAGCCCCCGACGAACTGATCGCCCGCGATGACGAGCTGAGCCGCCTCCAACG
GGCACTCACCAGGGCGGGGAGCGGAAGGGGCGGCGTCGTCGCCATCACCGGGCCCATCGCCAGCGGAAAGA
CGGCGCTGCTCGACGCCGGAGCGGCCAAGTCCGGCTTCGTCGCACTCCGTGCGGTGTGCTCCTGGGAAGAG
CGCACTCTGCCGTACGGGATGCTGGGCCAGCTCTTCGACCATCCCGAACTGGCCGCCCAGGCGCCGGACCT
TGCCCACTTCACGGCTTCGTGCGAGAGCCCTCAGGCCGGTACCGACAACGCCTGCGGGCCGAGTTCACCC
GCACCCTGCTGGCGCTCGCCGCGGACTGGCCCGTCCTGATCGGCATCGACGACGTGCACCACGCCGACGCG
GAATCACTGCGCTGTCTGCTCCACCTCGCCCGCCGCATCGGCCCGGCCCGCATCGCGGTCGTACTGACCGA
GCTGCGCAGACCGACGCCCGCCGACTCCCGCTTCCAGGCGGAACTGCTGAGCCTGCGCTCCTACCAGGAGA
TCGCGCTCAGACCGCTCACCGAGGCGCAGACCGGCGAACTCGTACGTCGGCACCTCGGCGCGGAGACCCAC
GAGGACGTCTCCGCCGATACGTTCCGGGCGACCGGCGGGAACCTGCTCCTCGGGCACGGTTTGATCAATGA
CATCCGGGAGGCGCGGACAGCGGGACGGCCGGGGGTCGTCGCGGGCGGGCGTACCGGCTCGCGTACCTCA
GCTCGCTCTACCGCTGCGGCCCGAGCGCGCTGCGTGTCGCCCGGGCGTCCGCCGTGCTCGGCGCGAGCGCC
GAAGCCGTGCTCGTCCAGCGGATGACCGGACTGAACAAGGACGCGGTCGAACAGGTCTATGAGCAGCTGAA
```

-continued

```
CGAGGGACGGCTGCTGCAGGGCGAGCGGTTTCCGCACCCGGCGGCCCGCTCCATCGTCCTTGACGACCTGT
CGGCCCTGGAACGCAGAAACCTGCACGAGTCGGCGCTGGAGCTGCTGCGGGACCACGGCGTGGCCGGCAAC
GTGCTCGCCCGCCACCAGATCGGCGCCGGCCGGGTGCACGGCGAGGAGGCCGTCGAGCTGTTCACCGGGGC
CGCACGGGAGCACCACCTGCGCGGTGAACTGGACGACGCGGCCGGATACCTGGAACTCGCCCACCGTGCCT
CCGACGACCCCGTCACGCGCGCCGCACTACGCGTCGGCGCCGCCGCGATCGAGCGCCTCTGCAATCCGGTA
CGGGCAGGCCGGCATCTGCCCGAGCTGCTCACCGCGTCGCGCGCGGGACTGCTCTCCAGCGAGCACGCCGT
GTCGCTCGCCGACTGGCTGGCGATGGGCGGGCGCCCGGGCGAGGCGGCCGAGGTCCTCGCGACGCAGCGTC
CCGCGGCCGACAGCGAGCAGCACCGCGCACTCCTGCGCAGCGGCGAGTTGTCCCTCGCGCTGGTCCACCCC
GGCGCGTGGGATCCGTTGCGCCGGACCGATCGGTTCGCCGCGGGCGGGCTCGGCTCGCTTCCCGGACCCGC
CCGGCACCGCGCGGTCGCCGACCAAGCCGTCATCGCGGCGCTGCGTGGACGTCTCGACCGGGCGGACGCCA
ACGCGGAGAGCGTTCTCCAGCACACCGACGCCACGGCGGACCGGACCACGGCCATCATGGCGTTGCTGGCC
CTGCTCTACGCGGAGAACACCGATGCTGTCCAGTTCTGGGTCGACAAACTGGCCGGTGACGAGGGCACCAG
GACACCGGCCGACGAGGCGGTCCACGCGGGGTTCAACGCCGAGATCGCGCTGCGCCGCGGCGACTTGATGA
GAGCCGTCGAGTACGGCGAGGCAGCGCTCGGCCACCGGCACCTGCCCACCTGGGGAATGGCCGCCGCTCTG
CCGCTGAGCAGCACCGTGGTTGCCGCGATCCGGCTCGGCGACCTCGACAGGGCCGAGCGGTGGCTCGCCGA
GCCGCTGCCGCAGCAGACGCCGGAGAGCCTCTTCGGGCTGCACCTGCTCTGGGCCCGCGGGCAGCACCACC
TCGCGACCGGGCGGCACGGGCGGCGTACACGGCGTTCAGGGAATGCGGCGAGCGGATGCGGCGGTGGGCC
GTCGACGTGCCGGGCCTGGCCCTGTGGCGGGTCGACGCCGCCGAATCGCTGCTGCTGCTCGGCCGTGACCG
TGCCGAAGGACTGCGGCTCGTCTCCGAGCAGCTGTCCCGGCCGATGCGCCCTCGCGCGCGCGTGCAGACGC
TGCGGGTACAGGCGGCCTACAGTCCGCCGCCCCAACGGATCGACCTGCTCGAAGAGGCCGCCGACCTGCTG
GTCACCTGCAACGACCAGTACGAACTGGCAAACGTACTCAGCGACTTGGCAGAGGCCTCCAGCATGGTCCG
GCAGCACAGCAGGGCGCGGGTCTGCTCCGCCGGGCACGGCACCTCGCCCACCCAGTGCGGCGCCGTGCCGC
TCCTGCGGCGGCTCGGCGCGGAACCCTCGGACATCGGCGGAGCCTGGACGCGACGCTGGGACAGCGGATC
GCGTCACTGACGGAGTCGGAGCGGCGGGTGGCCGCGCTCGCCGCGGTCGGGCGTACGAACAGGGAGATCGC
CGAGCAGCTGTTCGTCACGGCCAGCACGGTGGAACAGCACCTCACGAACGTGTTCCGCAAACTGGCGGTGA
AGGGCCGCCAGCAGCTTCCGAAGGAACTGGCCGACGTCGGCGAGCCGGCGGACCGCGACCGCCGGTGCGGG
TAG

SEQ ID NO: 8
GTGATAGCGCGCTTATCTCCCCCAGACCTGATCGCCCGCGATGACGAGTTCGGTTCCCTCCACCGGGCGCT
CACCCGAGCGGGGGCGGGCGGGCGTCGTCGCCGCCGTCACCGGGCCGATCGCCTGCGGCAAGACCGAAC
TCCTCGACGCCGCCGCGGCCAAGGCCGGCTTCGTCACCCTTCGCGCGGTGTGCTCCATGGAGGAGCGGGCC
CTGCCGTACGGCATGCTCGGCCAGCTCCTCGACCAGCCCGAGCTGGCCGCCCGGACACCGGAGCTGGTCCG
GCTGACGGCATCGTGCGAAAACCTGCCGGCCGACGTCGACAACCGCCTGGGGACCGAACTCACCCGCACGG
TGCTGACGCTCGCCGCGGAGCGGCCCGTACTGATCGGCATCGACGACGTGCACCACGCCGACGCGCCGTCG
CTGCGCTGCCTGCTCCACCTCGCGCGCCGCATCAGCCGGGCCCGTGTCGCCATCGTGCTGACCGAGCTGCT
CCGGCCGACGCCCGCCCACTCCCAATTCCGGGCGGCACTGCTGAGTCTGCGCCACTACCAGGAGATCGCGC
TGCGCCCGCTCACCGAGGCGCAGACCACCGAACTCGTGCGCCGGCACCTCGGCCAGGACGCGCACGACGAC
GTGGTGGCCCAGGCGTTCCGGGCGACCGGCGGCAACCTGCTCCTCGGCCACGGCCTGATCGACGACATCCG
GGAGGCACGGACACGGACCTCAGGGTGCCTGGAAGTGGTCGCGGGGCGGGCGTACCGGCTCGCCTACCTCG
GGTCGCTCTATCGTTGCGGCCCGGCCGCGCTGAGCGTCGCCCGAGCTTCCGCCGTGCTCGGCGAGAGTGTC
GAACTCACCCTCGTCCAGCGGATGACCGGCCTCGACACCGAGGCGGTCGAGCAGGCCCACGAACAGCTGGT
```

```
CGAGGGGCGGCTGCTGCGGGAAGGGCGGTTCCCGCACCCCGCGGCCCGCTCCGTCGTACTCGACGACCTCT

CCGCCGCCGAGCGGCGTGGCCTGCACGAGCTGGCGCTGGAACTGCTGCGGGACCGCGGCGTGGCCAGCAAG

GTGCTCGCCCGCCACCAGATGGGTACCGGCCGGGTGCACGGCGCCGAGGTCGCCGGGCTGTTCACCGACGC

CGCGCGCGAGCACCACCTGCGCGGCGAGCTCGACGAGGCCGTCACCTACCTGGAGTTCGCCTACCGGGCCT

CCGACGACCCCGCCGTCCACGCCGCACTGCGCGTCGACACCGCCGCCATCGAGCGGCTCTGCGATCCCGCC

AGATCCGGCCGGCATGTGCCCGAGCTGCTCACCGCGTCGCGGGAACGGCTCCTCTCCAGCGAGCACGCCGT

GTCGCTCGCCTGCTGGCTGGCGATGGACGGGCGGCCGGGCGAGGCCGCCGAGGTCCTGGCGGCCCAGCGCT

CCGCCGCCCCGAGCGAGCAGGGCCGGGCGCACCTGCGCGTCGCGGACCTGTCCCTCGCGCTGATCTATCCC

GGCGCGGCCGATCCGCCGCGTCCGGCCGATCCGCCGGCCGAGGACGAGGTCGCCTCGTTTTCCGGAGCCGT

CCGGCACCGCGCCGTCGCCGACAAGGCCCTGAGCAACGCGCTGCGCGGCTGGTCCGAACAGGCCGAGGCCA

AAGCCGAGTACGTGCTCCAGCACTCCCGGGTCACGACGGACCGGACCACGACCATGATGGCGTTGCTGGCC

CTGCTCTACGCCGAGGACACCGATGCCGTCCAGTCCTGGGTCGACAAGCTGGCCGGTGACGACAACATGCG

GACCCCGGCCGACGAGGCGGTCCACGCGGGGTTCCGCGCCGAGGCCGCGCTGCGCCGCGGCGACCTGACCG

CCGCCGTCGAATGCGGCGAGGCCGCGCTCGCCCCCCGGGTCGTGCCCTCCTGGGGGATGGCCGCCGCATTG

CCGCTGAGCAGCACCGTGGCCGCCGCGATCCGACTGGGCGACCTGGACCGGGCGGAGCGGTGGCTCGCCGA

GCCGTTGCCGGAGGAGACCTCCGACAGCCTCTTCGGACTGCACATGGTCTGGGCCCGTGGGCAACACCATC

TCGCGGCCGGGCGGTACCGGGCGGCGTACAACGCGTTCCGGGACTGCGGGGAGCGGATGCGACGCTGGTCC

GTCGACGTGCCGGGCCTGGCCCTGTGGCGGGTCGACGCCGCCGAAGCGCTTCTGCTGCTCGGCCGCGGCCG

TGACGAGGGGCTGAGGCTCATCTCCGAGCAGCTGTCCCGGCCGATGGGGTCCCGGGCGCGGGTGATGACGC

TGCGGGTGCAGGCGGCCTACAGTCCGCCGGCCAAGCGGATCGAACTGCTCGACGAGGCCGCCGATCTGCTC

ATCATGTGCCGCGACCAGTACGAGCTGGCCCGCGTCCTCGCCGACATGGGCGAAGCGTGCGGCATGCTCCG

GCGGCACAGCCGTGCGCGGGGACTGTTCCGCCGCGCACGGCACCTCGCGACCCAGTGCGGAGCCGTGCCGC

TCCTCCGGCGGCTCGGTGGGGAGTCCTCGGACGCGGACGGCACCCAGGACGTGACGCCGGCGCAGCGGATC

ACATCGCTGACCGAGGCGGAGCGGCGGGTGGCGTCGCACGCCGCGGTCGGGCGCACCAACAAGGAGATCGC

CAGCCAGCTGTTCGTCACCTCCAGCACGGTGGAACAGCACCTCACCAACGTGTTCCGCAAGCTGGGGGTGA

AGGGCCGTCAGCAACTGCCCAAGGAACTGTCCGACGCCGGCTGA

SEQ ID NO: 9
ATGATAGCGCGCCTGTCTCCCCCAGACCTGATCGCCCGCGATGACGAGTTCGGTTCCCTCCACCGGGCGCT

CACCCGAGCGGGGGCGGGCGGGGCGTCGTCGCCGCCGTCACCGGGCCGATCGCCTGCGGCAAGACCGAAC

TCCTCGACGCCGCCGCGGCCAAGGCCGGCTTCGTCACCCTTCGCGCGGTGTGCTCCATGGAGGAGCGGGCC

CTGCCGTACGGCATGCTCGGCCAGCTCCTCGACCAGCCCGAGCTGGCCGCCCGGACACCGGAGCTGGTCCG

GCTGACGGCATCGTGCGAAAACCTGCCGGCCGACGTCGACAACCGCCTGGGGACCGAACTCACCCGCACGG

TGCTGACGCTCGCCGCGGGAGCGGCCCGTACTGATCGGCATCGACGACGTGCACCACGCCGACGCGCCGTCG

CTGCGCTGCCTGCTCCACCTCGCGCGCCGCATCAGCCGGGCCCGTGTCGCCATCGTGCTGACCGAGCTGCT

CCGGCCGACGCCCGCCCACTCCCAATTCCGGGCGGCACTGCTGAGTCTGCGCCACTACCAGGAGATCGCGC

TGCGCCCGCTCACCGAGGCGCAGACCACCGAACTCGTGCGCCGGCACCTCGGCCAGGACGCGCACGACGAC

GTGGTGGCCCAGGCGTTCCGGGCGACCGGCGGCAACCTGCTCCTCGGCCACGGCCTGATCGACGACATCCG

GGAGGCACGGACACGGACCTCAGGGTGCCTGGAAGTGGTCGCGGGCGGGCGTACCGGCTCGCCTACCTCG

GGTCGCTCTATCGTTGCGGCCCGGCCGCGCTGAGCGTCGCCCGAGCTTCCGCCGTGCTCGGCGAGAGTGTC

GAACTCACCCTCGTCCAGCGGATGACCGGCCTCGACACCGAGGCGGTCGAGCAGGCCCACGAACAGCTGGT

CGAGGGGCGGCTGCTGCGGGAAGGGCGGTTCCCGCACCCCGCGGCCCGCTCCGTCGTACTCGACGACCTCT
```

-continued

CCGCCGCCGAGCGGCGTGGCCTGCACGAGCTGGCGCTGGAACTGCTGCGGGACCGCGGCGTGGCCAGCAAG

GTGCTCGCCCGCCACCAGATGGGTACCGGCCGGGTGCACGGCGCCGAGGTCGCCGGGCTGTTCACCGACGC

CGCGCGCGAGCACCACCTGCGCGGCGAGCTCGACGAGGCCGTCACCTACCTGGAGTTCGCCTACCGGGCCT

CCGACGACCCCGCCGTCCACGCCGCACTGCGCGTCGACACCGCCGCCATCGAGCGGCTCTGCGATCCCGCC

AGATCCGGCCGGCATGTGCCCGAGCTGCTCACCGCGTCGCGGGAACGGCTCCTCTCCAGCGAGCACGCCGT

GTCGCTCGCCTGCTGGCTGGCGATGGACGGGCGGCCGGGCGAGGCCGCCGAGGTCCTGGCGGCCCAGCGCT

CCGCCGCCCCGAGCGAGCAGGGCCGGGCGCACCTGCGCGTCGCGGACCTGTCCCTCGCGCTGATCTATCCC

GGCGCGGCCGATCCGCCGCGTCCGGCCGATCCGCCGGCCGAGGACGAGGTCGCCTCGTTTTCCGGAGCCGT

CCGGCACCGCGCCGTCGCCGACAAGGCCCTGAGCAACGCGCTGCGCGGCTGGTCCGAACAGGCCGAGGCCA

AAGCCGAGTACGTGCTCCAGCACTCCCGGGTCACGACGGACCGGACCACGACCATGATGGCGTTGCTGGCC

CTGCTCTACGCCGAGGACACCGATGCCGTCCAGTCCTGGGTCGACAAGCTGGCCGGTGACGACAACATGCG

GACCCCGGCCGACGAGGCGGTCCACGCGGGGTTCCGCGCCGAGGCCGCGCTGCGCCGCGGCGACCTGACCG

CCGCCGTCGAATGCGGCGAGGCCGCGCTCGCCCCCCGGGTCGTGCCCTCCTGGGGGATGGCCGCCGCATTG

CCGCTGAGCAGCACCGTGGCCGCCGCGATCCGACTGGGCGACCTGGACCGGGCGGAGCGGTGGCTCGCCGA

GCCGTTGCCGGAGGAGACCTCCGACAGCCTCTTCGGACTGCACATGGTCTGGGCCCGTGGGCAACACCATC

TCGCGGCCGGGCGGTACCGGGCGGCGTACAACGCGTTCCGGGACTGCGGGGAGCGGATGCGACGCTGGTCC

GTCGACGTGCCGGGCCTGGCCCTGTGGCGGGTCGACGCCGCCGAAGCGCTTCTGCTGCTCGGCCGCGGCCG

TGACGAGGGGCTGAGGCTCATCTCCGAGCAGCTGTCCCGGCCGATGGGGTCCCGGGCGCGGGTGATGACGC

TGCGGGTGCAGGCGGCCTACAGTCCGCCGGCCAAGCGGATCGAACTGCTCGACGAGGCCGCCGATCTGCTC

ATCATGTGCCGCGACCAGTACGAGCTGGCCCGCGTCCTCGCCGACATGGGCGAAGCGTGCGGCATGCTCCG

GCGGCACAGCCGTGCGCGGGGACTGTTCCGCCGCGCACGGCACCTCGCGACCCAGTGCGGAGCCGTGCCGC

TCCTCCGGCGGCTCGGTGGGGAGTCCTCGGACGCGGACGGCACCCAGGACGTGACGCCGGCGCAGCGGATC

ACATCGCTGACCGAGGCGGAGCGGCGGGTGGCGTCGCACGCCGCGGTCGGGCGCACCAACAAGGAGATCGC

CAGCCAGCTGTTCGTCACCTCCAGCACGGTGGAACAGCACCTCACCAACGTGTTCCGCAAGCTGGGGGTGA

AGGGCCGTCAGCAACTGCCCAAGGAACTGTCCGACGCCGGCTGA

SEQ ID NO: 10
GTGGAGTTTTACGACCTGGTCGCCCGCGATGACGAGCTCAGAAGGTTGGACCAGGCCCTCGGCCGCGCCGC

CGGCGGACGGGGTGTCGTGGTCACCGTCACCGGACCGGTCGGCTGCGGCAAGACCGAACTGCTGGACGCGG

CCGCGGCCGAGGAGGAATTCATCACGTTGCGTGCGGTCTGCTCGGCCGAGGAGCGGGCCCTGCCGTACGCC

GTGATCGGCCAACTCCTCGACCATCCCGTACTCTCCGCACGCGCGCCCGACCTGGCCTGCGTGACGGCTCC

GGGCCGGACGCTGCCGGCCGACACCGAGAACCGCCTGCGCCGCGACCTCACCCGGGCCCTGCTGGCCCTGG

CCTCCGAACGACCGGTTCTGATCTGCATCGACGACGTGCACCAGGCCGACACCGCCTCGCTGAACTGCCTG

CTGCACCTGGCCCGGCGGGTCGCCTCGGCCCGGATCGCCATGATCCTCACCGAGTTGCGCCGGCTCACCCC

GGCTCACTCCCGGTTCGAGGCGGAACTGCTCAGCCTGCGGCACCGCCACGAGATCGCGCTGCGTCCCCTCG

GCCCGGCCGACACCGCCGAACTGGCCCGCGCCCGGCTCGGCGCCGGCGTCACCGCCGACGAGCTGGCCCAG

GTCCACGAGGCCACCAGCGGGAACCCCAACCTGGTCGGAGGCCTGGTCAACGACGTGCGAGAGGCCTGGGC

GGCCGGTGGCACGGGCATTGCGGCGGGGCGGGCGTACCGGCTGGCGTACCTCAGCTCCGTGTACCGCTGTG

GTCCGGTCCCGTTGCGGATCGCCCAGGCGGCGGCGGTGCTGGGTCCCAGCGCCACCGTCACGCTGGTGCGC

CGGATCAGCGGGCTCGACGCCGAGACGGTGGACGAGGCGACCGCGATCCTCACCGAGGGCGGCCTGCTCCG

GGACCACCGGTTCCCGCATCCGGCGGCCCGCTCGGTCGTACTCGACGACATGTCCGCGCAGGAACGCCGCC

GCCTGCACCGGTCCACGCTGGACGTGCTGGACGGCGTACCCGTCGACGTGCTCGCGCACCACCAGGCCGGC

```
GCCGGTCTGCTGCACGGCCCGCAGGCGGCCGAGATGTTCGCCCGGGCCAGCCAGGAGCTGCGGGTACGCGG

CGAGCTGGACGCCGCGACCGAGTACCTGCAACTGGCCTACCGGGCCTCCGACGACGCCGGCGCCGGGCCG

CCCTGCAGGTGGAGACCGTGGCCGGCGAGCGCCGCCGCAACCCGCTGGCCGCCAGCCGGCACCTGGACGAG

CTGGCCGCCGCCCGGGCCGGCCTGCTGTCGGCCGAGCACGCCGCCCTGGTCGTGCACTGGCTGGCCGA

CGCCGGACGACCCGGCGAGGCCGCCGAGGTGCTGGCGCTGCAGCGGGCGCTGGCCGTCACCGACCACGACC

GGGCCCGCCTGCGGGCGGCCGAGGTGTCGCTCGCGCTGTTCCACCCCGGCGTCCCCGGTTCGGACCCGCGG

CCCCTCGCGCCGGAGGAGCTCGCGAGCCTGTCCCTGTCGGCCCGGCACGGTGTGACCGCCGACAACGCGGT

GCTGGCGGCGCTGCGCGGCCGTCCCGAGTCGGCCGCCGCCGAGGCGGAGAACGTGCTGCGCAACGCCGACG

CCGCCGCGTCCGGCCCGACCGCCCTGGCCGCGCTGACGGCCCTGCTCTACGCCGAGAACACCGACGCCGCC

CAGCTCTGGGCGGACAAGCTGGCCGCGGGCATCGGGGCGGGGAGGGGGAGGCCGGCTACGCGGGCCGCG

GACCGTGGCCGCCCTGCGTCGCGGCGACCTGACCACCGCGGTCCAGGCGGCCGGCGCGGTCCTGGACCGCG

GCCGGCCGTCGTCGCTCGGCATCACCGCCGTGTTGCCGTTGAGCGGCGCGGTCGCCGCCGCGATCCGGCTG

GGCGAGCTCGAGCGGGCCGAGAAGTGGCTGGCCGAGCCGCTGCCCGAAGCCGTCCACGACAGCCTGTTCGG

CCTGCACCTGCTGATGGCGCGGGGCCGCTACAGCCTCGCGGTGGGCCGGCACGAGGCGGCGTACGCCGCGT

TCCGGGACTGCGGTGAACGGATGCGCCGGTGGGACGTCGACGTGCCCGGGCTGGCCCTGTGGCGGGTGGAC

GCGGCCGAGGCGCTGCTGCCCGGCGATGACCGGGCGGAGGGCCGGCGGCTGATCGACGAGCAGCTCACCCG

GCCGATGGGGCCCCGGTCACGAGCCCTGACCCTGCGGGTACGAGCGGCCTACGCCCCGCCGGCGAAACGGA

TCGACCTGCTCGACGAAGCGGCCGACCTGCTGCTCTCCAGCAACGACCAGTACGAGCGGGCACGGGTGCTG

GCCGACCTGAGCGAGGCGTTCAGCGCGCTCCGGCAGAACGGCCGGGCGCGCGGCATCCTGCGGCAGGCCCG

GCACCTGGCCGCCCAGTGCGGGGCGGTCCCCCTGCTGCGCCGGCTGGGCGTCAAGGCCGGCCGGTCCGGTC

GGCTCGGCCGGCCGCCGCAGGGAATCCGCTCCCTGACCGAGGCCGAGCGCCGGGTGGCCACGCTGGCCGCC

GCCGGGCAGACCAACCGGGAGATCGCCGACCAGCTCTTCGTCACCGCCAGCACGGTCGAGCAGCACCTCAC

CAACGTGTTCCGCAAGCTCGGCGTGAAGGGCCGCCAGCAATTGCCGGCCGAGCTGGCCGACCTGCGGCCGC

CGGGCTGA

SEQ ID NO: 11
ATGGAGTTTTACGACCTGGTCGCCCGCGATGACGAGCTCAGAAGGTTGGACCAGGCCCTCGGCCGCGCCGC

CGGCGGACGGGGTGTCGTGGTCACCGTCACCGGACCGGTCGGCTGCGGCAAGACCGAACTGCTGGACGCGG

CCGCGGCCGAGGAGGAATTCATCACGTTGCGTGCGGTCTGCTCGGCCGAGGAGCGGGCCCTGCCGTACGCC

GTGATCGGCCAACTCCTCGACCATCCCGTACTCTCCGCACGCGCGCCCGACCTGGCCTGCGTGACGGCTCC

GGGCCGGACGCTGCCGGCCGACACCGAGAACCGCCTGCGCCGCGACCTCACCCGGGCCCTGCTGGCCCTGG

CCTCCGAACGACCGGTTCTGATCTGCATCGACGACGTGCACCAGGCCGACACCGCCTCGCTGAACTGCCTG

CTGCACCTGGCCCGGCGGGTCGCCTCGGCCCGGATCGCCATGATCCTCACCGAGTTGCGCCGGCTCACCCC

GGCTCACTCCCGGTTCGAGGCGGAACTGCTCAGCCTGCGGCACCGCCACGAGATCGCGCTGCGTCCCCTCG

GCCCGGCCGACACCGCCGAACTGGCCCGCGCCCGGCTCGGCGCCGGCGTCACCGCCGACGAGCTGGCCCAG

GTCCACGAGGCCACCAGCGGGAACCCCAACCTGGTCGGAGGCCTGGTCAACGACGTGCGAGAGGCCTGGGC

GGCCGGTGGCACGGGCATTGCGGCGGGGCGGGCGTACCGGCTGGCGTACCTCAGCTCCGTGTACCGCTGTG

GTCCGGTCCCGTTGCGGATCGCCCAGGCGGCGGCGGTGCTGGGTCCAGCGCCACCGTCACGCTGGTGCGC

CGGATCAGCGGGCTCGACGCCGAGACGGTGGACGAGGCGACCGCGATCCTCACCGAGGGCGGCCTGCTCCG

GGACCACCGGTTCCCGCATCCGGCGGCCCGCTCGGTCGTACTCGACGACATGTCCGCGCAGGAACGCCGCC

GCCTGCACCGGTCCACGCTGGACGTGCTGGACGGCGTACCCGTCGACGTGCTCGCGCACCACCAGGCCGGC

GCCGGTCTGCTGCACGGCCCGCAGGCGGCCGAGATGTTCGCCCGGGCCAGCCAGGAGCTGCGGGTACGCGG
```

-continued

```
CGAGCTGGACGCCGCGACCGAGTACCTGCAACTGGCCTACCGGGCCTCCGACGACGCCGGCGCCCGGGCCG
CCCTGCAGGTGGAGACCGTGGCCGGCGAGCGCCGCCGCAACCCGCTGGCCGCCAGCCGGCACCTGGACGAG
CTGGCCGCCGCCGCCCGGGCCGGCCTGCTGTCGGCCGAGCACGCCGCCCTGGTCGTGCACTGGCTGGCCGA
CGCCGGACGACCCGGCGAGGCCGCCGAGGTGCTGGCGCTGCAGCGGGCGCTGGCCGTCACCGACCACGACC
GGGCCCGCCTGCGGGCGGCCCGAGGTGTCGCTCGCGCTGTTCCACCCCGGCGTCCCCGGTTCGGACCCGCGG
CCCCTCGCGCCGGAGGAGCTCGCGAGCCTGTCCCTGTCGGCCCGGCACGGTGTGACCGCCGACAACGCGGT
GCTGGCGGCGCTGCGCGGCCGTCCCGAGTCGGCCGCCGCCGAGGCGGAGAACGTGCTGCGCAACGCCGACG
CCGCCGCGTCCGGCCCGACCGCCCTGGCCGCGCTGACGGCCCTGCTCTACGCCGAGAACACCGACGCCGCC
CAGCTCTGGGCGGACAAGCTGGCCGCGGGCATCGGGGCGGGGGAGGGGGAGGCCGGCTACGCGGGGCCGCG
GACCGTGGCCGCCCTGCGTCGCGGCGACCTGACCACCGCGGTCCAGGCGGCCGGCGCGGTCCTGGACCGCG
GCCGGCCGTCGTCGCTCGGCATCACCGCCGTGTTGCCGTTGAGCGGCGCGGTCGCCGCCGCGATCCGGCTG
GGCGAGCTCGAGCGGGCCGAGAAGTGGCTGGCCGAGCCGCTGCCCGAAGCCGTCCACGACAGCCTGTTCGG
CCTGCACCTGCTGATGGCGCGGGGCCGCTACAGCCTCGCGGTGGGCCGGCACGAGGCGGCGTACGCCGCGT
TCCGGGACTGCGGTGAACGGATGCGCCGGTGGGACGTCGACGTGCCCGGGCTGGCCCTGTGGCGGGTGGAC
GCGGCCGAGGCGCTGCTGCCCGGCGATGACCGGGCGGAGGGCCGGCGGCTGATCGACGAGCAGCTCACCCG
GCCGATGGGCCCCGGTCACGAGCCCTGACCCTGCGGGTACGAGCGGCCTACGCCCCGCCGGCGAAACGGA
TCGACCTGCTCGACGAAGCGGCCGACCTGCTGCTCTCCAGCAACGACCAGTACGAGCGGGCACGGGTGCTG
GCCGACCTGAGCGAGGCGTTCAGCGCGCTCCGGCAGAACGGCCGGGCGCGCGGCATCCTGCGGCAGGCCCG
GCACCTGGCCGCCCAGTGCGGGGCGGTCCCCCTGCTGCGCCGGCTGGGCGTCAAGGCCGCCGGTCCGGTC
GGCTCGGCCGGCCGCCGCAGGGAATCCGCTCCCTGACCGAGGCCGAGCGCCGGGTGGCCACGCTGGCCGCC
GCCGGGCAGACCAACCGGGAGATCGCCGACCAGCTCTTCGTCACCGCCAGCACGGTCGAGCAGCACCTCAC
CAACGTGTTCCGCAAGCTCGGCGTGAAGGGCCGCCAGCAATTGCCGGCCGAGCTGGCCGACCTGCGGCCGC
CGGGCTGA

SEQ ID NO: 12
GTGGTCACCGTCACCGGCCCAATCGCCTGCGGCAAGACAGAACTGCTTGACGCGGCTGCCGCGAAGGCTGA
GGCCATCATTCTGCGCGCGGTCTGCGCGCCAGAAGAGCGGGCTATGCCGTACGCCATGATCGGGCAGCTCA
TCGACGACCCGGCGCTCGCGCATCGGGCGCCGGGGCTGGCTGATCGGATAGCCCAGGGCGGGCAGCTGTCG
CTGAGGGCCGAGAACCGACTGCGCAGGGATCTCACCCGTGCCCTGCTGGCGCTTGCCGTCGACCGGCCTGT
GCTGATCGGCGTCGACGATGTGCATCACGCCGACACCGCCTCTTTGAACTGTCTGCTGCATTTGGCGCGCC
GGGTCCGTCCGGCCCGGATATCCATGATCTTCACCGAGTTGCGCAGCCTCACCCCTACTCAGTCACGGTTC
AAGGCGGAGCTGCTCAGCCTGCCGTACCACCACGAGATCGCGCTGCGTCCGTTCGGACCGGAGCAATCGGC
GGAGCTGGCCCGCGCCGCCTTCGGCCCGGGCCTCGCCGAGGATGTGCTCGTGGGGTTGTATAAAACGACCA
GGGGCAATCTGAGTCTCAGCCGTGGACTGATCAGCGATGTGCGGGAGGCCCTGGCCAACGGAGAGAGCGCC
TTCGAGGCGGGCCGCGCGTTCCGGCTGGCGTACCTCGGCTCGCTCTACCGCTGTGGCCCGGTCGCGCTGCG
GGTCGCCCGAGTGGCTGCCGTGCTGGGCCCGAGCGCCACCACCACGCTGGTGCGCCGTCTAAGCGGGCTCA
GCGCGGAGACGATAGACCGGGCAACCAAGATCCTCACCGAGGGCGGGCTGCTGCTCGACCAGCAGTTCCCG
CACCCGGCCGCCCGCTCGGTGGTGCTTGATGACATGTCCGCCCAGGAACGACGCGGCCTGCACACTCTCGC
CCTGGAACTGCTGGACGAGGCGCCGGTTGAAGTGCTCGCGCACCACCAGGTCGGCGCCGGTCTCATACACG
GGCCCAAGGCTGCGGAGATGTTCGCCAAGGCCGGCAAGGCTCTGGTCGTACGCAACGAGTTGGGCGACGCG
GCAGAATACCTGCAACTGGCTCACCGGGCCTCCGACGATGTCTCCACCCGGGCCGCCTTACGGGTCGAGGC
CGTGGCGATCGAGCGCCGCCGCAATCCGCTGGCCTCCAGTCGGCACATGGACGAGCTGAGCGCCGCCGGCC
```

```
GCGCCGGTCTGCTTTCCCCCAAGCATGCGGCGCTGGCCGTCTTCTGGCTGGCCGACGGCGGGCGATCCGGC
GAGGCAGCCGAGGTGCTGGCGTCGGAACGCCCGCTAGCGACCACCGATCAGAACCGGGCCCACTTGCGATT
TGTCGAGGTGACTCTCGCGCTGTTCTCTCCCGGCGCCTTCGGATCGGACCGGCGCCCACCTCCGCTGACGC
CGGACGAACTCGCCAGCCTGCCGAAGGCGGCCTGGCAATGCGCGGTCGCCGACAACGCGGCCATGACCGCC
TTGCACGGTCATCCAGAACTTGCCACCGCTCAGGCGGAAACAGTTCTGCGGCAGGCTGATTCGGCAGCCGA
CGCGATCCCCGCCGCGCTGATCGCCCTGTTGTACGCGGAGAACACCGAGTCCGCTCATATCTGGGCCGACA
AGCTGGGCAGCACGAATGGCGGGGTATCGAACGAGGCGGAAGCGGGCTACGCCGGCCCGTGCGCCGAGATC
GCCCTGCGGCGCGGCGACCTGGCCACGGCGTTCGAGGCTGGTAGCACCGTCCTGGACGACCGGTCGCTGCC
GTCGCTCGGCATCACCGCCGCATTGCTGTTGAGCAGCAAGACGGCCGCCGCTGTCCGGCTGGGCGAACTCG
AGCGTGCGGAGAAGCTGCTCGCCGAGCCGCTTCCGAACGGCGTCCAGGACAGCCTTTTCGGTCTGCACCTG
CTCTCGGCATACGGCCAGTACAGCCTCGCGATGGGCCGATATGAATCGGCTCTCCGGGCGTTTCACACCTG
CGGAGAACGTATGCGCAGCTGGGATGTTGACGTGCCTGGTCTGGCCCTGTGGCGTGTCGACGCCGCCGAGG
CGCTGCTCAGCCTCGACCGGAACGAGGGCCAGCGGCTCATCGACGAACAACTCACCCGTCCGATGGGCCT
CGTTCCCGCGCGTTAACGCTGCGGATCAAGGCGGCATACCTCCCGCGGACGAAGCGGATCCCCCTGCTCCA
TGAGGCGGCCGAGCTGCTGCTCCCCTGCCCCGACCCGTACGAGCAAGCGCGGGTGCTCGCCGATCTGGGCG
ACACGCTCAGCGCGCTCAGACGCTATAGCCGGGCGCGGGGAGTTCTCCGGCAGGCTCGTCACCTGGCCGCC
CAGTGCGGTGCTGTCCCGCTGCTGCGCAGGCTCGGGGGCGAGCCCGGCCGGATCGACGACGCCGGCCTGCC
GCAGCGGAGCACATCGTTGACCGATGCGGAGCGGCGGGTGGCGGCGCTGGCCGCGGCCGGACAGACCAACC
GGGAGATCGCCAAACAGCTGTTCGTCACGGCCAGCACAGTGGAACAGCACCTCACAAGCGTCTTCCGCAAA
CTGGGGGTCAAGGGTCGCAAGCAGCTGCCGACCGCGCTGGCCGACGTGGAACAGACCTGA

SEQ ID NO: 13
ATGTATAGCGGTACCTGCCGTGAAGGATACGAACTCGTCGCACGCGAGGACGAACTCGGCATTCTACAGAG
GTCTCTGGAACAAGCGAGCAGCGGCCAGGGCGTCGTGGTCACCGTCACCGGCCCAATCGCCTGCGGCAAGA
CAGAACTGCTTGACGCGGCTGCCGCGAAGGCTGAGGCCATCATTCTGCGCGCGGTCTGCGCGCCAGAAGAG
CGGGCTATGCCGTACGCCATGATCGGGCAGCTCATCGACGACCCGGCGCTCGCGCATCGGGCGCGGGGCT
GGCTGATCGGATAGCCCAGGGCGGGCAGCTGTCGCTGAGGGCCGAGAACCGACTGCGCAGGGATCTCACCC
GTGCCCTGCTGGCGCTTGCCGTCGACCGGCCTGTGCTGATCGGCGTCGACGATGTGCATCACGCCGACACC
GCCTCTTTGAACTGTCTGCTGCATTTGGCGCGCCGGGTCCGTCCGGCCCGGATATCCATGATCTTCACCGA
GTTGCGCAGCCTCACCCCTACTCAGTCACGGTTCAAGGCGGAGCTGCTCAGCCTGCCGTACCACCACGAGA
TCGCGCTGCGTCCGTTCGGACCGGAGCAATCGGCGGAGCTGGCCCGCGCCGCCTTCGGCCCGGGCCTCGCC
GAGGATGTGCTCGTGGGGTTGTATAAAACGACCAGGGGCAATCTGAGTCTCAGCCGTGGACTGATCAGCGA
TGTGCGGGAGGCCCTGGCCAACGGAGAGAGCGCCTTCGAGGCGGGCCGCGCGTTCCGGCTGGCGTACCTCG
GCTCGCTCTACCGCTGTGGCCCGGTCGCGCTGCGGGTCGCCCGAGTGGCTGCCGTGCTGGGCCCGAGCGCC
ACCACCACGCTGGTGCGCCGTCTAAGCGGGCTCAGCGCGGAGACGATAGACCGGGCAACCAAGATCCTCAC
CGAGGGCGGGCTGCTGCTCGACCAGCAGTTCCCGCACCCGGCCGCCCGCTCGGTGGTGCTTGATGACATGT
CCGCCCAGGAACGACGCGGCCTGCACACTCTCGCCCTGGAACTGCTGGACGAGGCGCCGGTTGAAGTGCTC
GCGCACCACCAGGTCGGCGCCGGTCTCATACACGGGCCCAAGGCTGCGGAGATGTTCGCCAAGGCCGGCAA
GGCTCTGGTCGTACGCAACGAGTTGGGCGACGCGCAGAATACCTGCAACTGGCTCACCGGGCCTCCGACG
ATGTCTCCACCCGGGCCGCCCTGCGGGTCGAGGCCGTGGCGATCGAGCGCCGCCGCAATCCGCTGGCCTCC
AGTCGGCACATGGACGAGCTGAGCGCCGCCGGCCGCGCCGGTCTGCTTTCCCCCAAGCATGCGGCGCTGGC
CGTCTTCTGGCTGGCCGACGGCGGGCGATCCGGCGAGGCAGCCGAGGTGCTGGCGTCGGAACGCCCGCTAG
```

-continued

```
CGACCACCGATCAGAACCGGGCCCACTTGCGATTTGTCGAGGTGACTCTCGCGCTGTTCTCTCCCGGCGCC

TTCGGATCGGACCGGCGCCCACCTCCGCTGACGCCGGACGAACTCGCCAGCCTGCCGAAGGCGGCCTGGCA

ATGCGCGGTCGCCGACAACGCGGCCATGACCGCCTTGCACGGTCATCCAGAACTTGCCACCGCTCAGGCGG

AAACAGTTCTGCGGCAGGCTGATTCGGCAGCCGACGCGATCCCCGCCGCGCTGATCGCCCTGTTGTACGCG

GAGAACACCGAGTCCGCTCATATCTGGGCCGACAAGCTGGGCAGCACGAATGGCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTAGCACCGTCCTGGACGACCGGTCGCTGCCGTCGCTCGGCATCACCGCCGCATTGCTGTTGAGCAGC

AAGACGGCCGCCGCTGTCCGGCTGGGCGAACTCGAGCGTGCGGAGAAGCTGCTCGCCGAGCCGCTTCCGAA

CGGCGTCCAGGACAGCCTTTTCGGTCTGCACCTGCTCTCGGCATACGGCCAGTACAGCCTCGCGATGGGCC

GATATGAATCGGCTCTCCGGGCGTTTCACACCTGCGGAGAACGTATGCGCAGCTGGGATGTTGACGTGCCT

GGTCTGGCCCTGTGGCGTGTCGACGCCGCCGAGGCGCTGCTCAGCCTCGACCGGAACGAGGGCCAGCGGCT

CATCGACGAACAACTCACCCGTCCGATGGGGCCTCGTTCCCGCGCGCTGACGCTGCGGATCAAGGCGGCAT

ACCTCCCGCGGACGAAGCGGATCCCCCTGCTCCATGAGGCGGCCGAGCTGCTGCTCCCCTGCCCCGACCCG

TACGAGCAAGCGCGGGTGCTCGCCGATCTGGGCGACACGCTCAGCGCGCTCAGACGCTATAGCCGGGCGCG

GGGAGTTCTCCGGCAGGCTCGTCACCTGGCCGCCCAGTGCGGTGCTGTCCCGCTGCTGCGCAGGCTCGGGG

GCGAGCCCGGCCGGATCGACGACGCCGGCCTGCCGCAGCGGAGCACATCGTTGACCGATGCGGAGCGGCGG

GTGGCGGCGCTGGCCGCGGCCGGACAGACCAACCGGGAGATCGCCAAACAGCTGTTCGTCACGGCCAGCAC

AGTGGAACAGCACCTCACAAGCGTCTTCCGCAAACTGGGGGTCAAGGGTCGCAAGCAGCTGCCGACCGCGC

TGGCCGACGTGGAACAGACCTGA

SEQ ID NO: 14
ATGCCTGCCGTGGAGAGCTATGAACTGGACGCCCGCGATGACGAGCTCAGAAGACTGGAGGAGGCGGTAGG

CCAGGCGGGCAACGGCCGGGGTGTGGTGGTCACCATCACCGGGCCGATCGCCTGCGGCAAGACCGAACTGC

TCGACGCGGCCGCCGCGAAGAGCGACGCCATCACATTACGTGCGGTCTGCTCCGAGGAGGAACGGGCCCTC

CCGTACGCCCTGATCGGGCAGCTCATCGACAACCCGGCGGTCGCCTCCCAGCTGCCGGATCCGGTCTCCAT

GGCCCTCCCGGGCGAGCACCTGTCGCCGGAGGCCGAGAACCGGCTGCGCGGCGACCTCACCCGTACCCTGC

TGGCGCTCGCCGCCGAACGGCCGGTGCTGATCGGCATCGACGACATGCACCACGCCGACACCGCCTCTTTG

AACTGCCTGCTCCACCTGGCCCGGAGGGTCGGCCCGGCCCGATCGCCATGGTCCTCACCGAGCTGCGCCG

GCTCACCCCGGCCCACTCCCAGTTCCACGCCGAGCTGCTCAGCCTGGGGCACCACCGCGAGATCGCGCTGC

GCCCGCTCGGCCCGAAGCACATCGCCGAGCTGGCCCGCGCCGGCCTCGGTCCCGATGTCGACGAGGACGTG

CTCACGGGGTTGTACCGGGCGACCGGCGGCAACCTGAACCTCGGCCACGGACTGATCAAGGATGTGCGGGA

GGCCTGGGCGACGGGCGGGACGGGCATCAACGCGGGCCGCGCGTACCGGCTGGCGTACCTCGGTTCCCTCT

ACCGCTGCGGCCCGGTCCCGTTGCGGGTCGCACGGGTGGCCGCCGTGCTGGGCCAGAGCGCCAACACCACC

CTGGTGCGCTGGATCAGCGGGCTCAACGCGGACGCGGTGGGCGAGGCGACCGAGATCCTCACCGAGGGCGG

CCTGCTGCACGACCTGCGGTTCCCGCATCCGGCGGCCCGTTCGGTCGTACTCAACGACCTGTCCGCCCGGG

AACGCCGCCGACTGCACCGGTCCGCTCTGGAAGTGCTGGATGACGTACCCGTTGAAGTGGTCGCGCACCAC

CAGGCCGGTGCCGGTTTCATCCACGGTCCCAAGGCCGCCGAGATCTTCGCCAAGGCCGGCCAGGAGCTGCA

TGTGCGCGGCGAGCTGGACGCCGCGTCCGACTATCTGCAACTGGCCCACCACGCCTCCGACGACGCCGTCA

CCCGGGCCGCGCTGCGGGTCGAGGCCGTGGCGATCGAGCGCCGCCGCAACCCGCTGGCCTCCAGCCGCCAC

CTCGACGAGCTGACCGTCGCCGCCCGTGCCGGTCTGCTCTCCCTCGAGCACGCCGCGCTGATGATCCGCTG

GCTGGCTCTCGCGGGCGGTCCGGCGAGGCGGCCGAGGTGCTGGCCGCGCAGCGCCCGCGTGCGGTCACCG

ACCAGGACAGGGCCCACCTGCGGGCCGCCGAGGTATCGCTGGCGCTGGTCAGCCCGGGCGCGTCCGGCGTC
```

AGCCCGGGTGCGTCCGGCCCGGATCGGCGGCCGCGTCCGCTCCCGCCGGATGAGCTCGCGAACCTGCCGAA

GGCGGCCCGGCTTTGTGCGATCGCCGACAACGCCGTCATATCGGCCCTGCACGGTCGTCCCGAGCTTGCCT

CGGCCCGAGGCGGAGAACGTCCTGAAGCAGGCTGACTCGGCGGCGGACGGCGCCACCGCCCTCTCCGCGCTG

ACGGCCTTGCTGTACGCGGAGAACACCGACACCGCTCAGCTCTGGGCCGACAAGCTCGTCTCCGAGACCGG

GGCGTCGAACGAGGAGGAAGGCGCGGGCTACGCGGGGCCGCGCGCCGAGACCGCGTTGCGCCGCGGCGACC

TGGCCGCGGCGGTCGAGGCGGGCAGCGCCATTCTGGACCACCGGCGGGGGTCGTTGCTCGGCATCACCGCC

GCGCTACCGCTGAGCAGCGCGGTAGCCGCCGCCATCCGGCTGGGCGAGACCGAGCGGGCGGAGAAGTGGCT

CGCCGAGCCGCTGCCGGAGGCCATTCGGGACAGCCTGTTCGGGCTGCACCTGCTCTCGGCGCGCGGCCAGT

ACTGCCTCGCGACGGGCCGGCACGAGTCGGCGTACACGGCGTTCCGCACCTGCGGGGAACGGATGCGGAAC

TGGGGCGTCGACGTGCCGGGTCTGTCCCTGTGGCGCGTCGACGCCGCCGAGGCGCTGCTGCACGGCCGCGA

CCGGGACGAGGGCCGACGGCTCATCGACGAGCAGCTCACCCATGCGATGGGACCCCGTTCCCGCGCTTTGA

CGCTGCGGGTGCAGGCGGCGTACAGCCCGCAGGCGCAGCGGGTCGACCTGCTCGAAGAGGCGGCCGACCTG

CTGCTCTCCTGCAACGACCAGTACGAGCGGGCGCGGGTGCTCGCCGATCTGAGCGAGGCGTTCAGCGCGCT

CAGGCACCACAGCCGGGCGCGGGGACTGCTCCGGCAGGCCCGGCACCTGGCCGCCCAGTGCGGCGCGACCC

CGCTGCTGCGCCGGCTCGGGGCCAAGCCCGGAGGCCCCGGCTGGCTGGAGGAATCCGGCCTGCCGCAGCGG

ATCAAGTCGCTGACCGACGCGGAGCGGCGGGTGGCGTCGCTGGCCGCCGGCGGCCAGACCAACCGCGTGAT

CGCCGACCAGCTCTTCGTCACGGCCAGCACGGTGGAGCAGCACCTCACGAACGTCTTCCGCAAGCTGGGCG

TCAAGGGCCGCCAGCACCTGCCGGCCGAACTCGCCAACGCGGAATAG

SEQ ID NO: 15
ATGCCTGCCGTGGAGAGCTATGAACTGGACGCCCGCGATGACGAGCTCAGAAGACTGGAGGAGGCGGTAGG

CCAGGCGGGCAACGGCCGGGGTGTGGTGGTCACCATCACCGGGCCGATCGCCTGCGGCAAGACCGAACTGC

TCGACGCGGCCGCCGCGAAGAGCGACGCCATCACACTGCGTGCGGTCTGCTCCGAGGAGGAACGGGCCCTC

CCGTACGCCCTGATCGGGCAGCTCATCGACAACCCGGCGGTCGCCTCCCAGCTGCCGGATCCGGTCTCCAT

GGCCCTCCCGGGCGAGCACCTGTCGCCGGAGGCCGAGAACCGGCTGCGCGGCGACCTCACCCGTACCCTGC

TGGCGCTCGCCGCCGAACGGCCGGTGCTGATCGGCATCGACGACATGCACCACGCCGACACCGCCTCTTTG

AACTGCCTGCTCCACCTGGCCCGGAGGGTCGGCCCGGCCCGGATCGCCATGGTCCTCACCGAGCTGCGCCG

GCTCACCCCGGCCCACTCCCAGTTCCACGCCGAGCTGCTCAGCCTGGGGCACCACCGCGAGATCGCGCTGC

GCCCGCTCGGCCCGAAGCACATCGCCGAGCTGGCCCGCGCCGGCCTCGGTCCCGATGTCGACGAGGACGTG

CTCACGGGGTTGTACCGGGCGACCGGCGGCAACCTGAACCTCGGCCACGGACTGATCAAGGATGTGCGGGA

GGCCTGGGCGACGGGCGGGACGGGCATCAACGCGGGCCGCGCGTACCGGCTGGCGTACCTCGGTTCCCTCT

ACCGCTGCGGCCCGGTCCCGTTGCGGGTCGCACGGGTGGCCGCCGTGCTGGGCCAGAGCGCCAACACCACC

CTGGTGCGCTGGATCAGCGGGCTCAACGCGGACGCGGTGGGCGAGGCGACCGAGATCCTCACCGAGGGCGG

CCTGCTGCACGACCTGCGGTTCCCGCATCCGGCGGCCCGTTCGGTCGTACTCAACGACCTGTCCGCCCGGG

AACGCCGCCGACTGCACCGGTCCGCTCTGGAAGTGCTGGATGACGTACCCGTTGAAGTGGTCGCGCACCAC

CAGGCCGGTGCCGGTTTCATCCACGGTCCCAAGGCCGCCGAGATCTTCGCCAAGGCCGGCCAGGAGCTGCA

TGTGCGGCGAGCTGGACGCCGCGTCCGACTATCTGCAACTGGCCCACCACGCCTCCGACGACGCCGTCA

CCCGGGCCGCGCTGCGGGTCGAGGCCGTGGCGATCGAGCGCCGCCGCAACCCGCTGGCCTCCAGCCGCCAC

CTCGACGAGCTGACCGTCGCCGCCCGTGCCGGTCTGCTCTCCCTCGAGCACGCCGCGCTGATGATCCGCTG

GCTGGCTCTCGGCGGGCGGTCCGGCGAGGCGGCCGAGGTGCTGGCCGCGCAGCGCCCGCGTGCGGTCACCG

ACCAGGACAGGGCCCACCTGCGGGCCGCCGAGGTATCGCTGGCGCTGGTCAGCCCGGGCGCGTCCGGCGTC

AGCCCGGGTGCGTCCGGCCCGGATCGGCGGCCGCGTCCGCTCCCGCCGGATGAGCTCGCGAACCTGCCGAA

-continued

GGCGGCCCGGCTTTGTGCGATCGCCGACAACGCCGTCATATCGGCCCTGCACGGTCGTCCCGAGCTTGCCT

CGGCCGAGGCGGAGAACGTCCTGAAGCAGGCTGACTCGGCGGCGGACGGCGCCACCGCCCTCTCCGCGCTG

ACGGCCTTGCTGTACGCGGAGAACACCGACACCGCTCAGCTCTGGGCCGACAAGCTCGTCTCCGAGACCGG

GGCGTCGAACGAGGAGGAAGGCGCGGGCTACGCGGGGCCGCGCGCCGAGACCGCGTTGCGCCGCGGCGACC

TGGCCGCGGCGGTCGAGGCGGGCAGCGCCATTCTGGACCACCGGCGGGGTCGTTGCTCGGCATCACCGCC

GCGCTACCGCTGAGCAGCGCGGTAGCCGCCGCCATCCGGCTGGGCGAGACCGAGCGGGCGGAGAAGTGGCT

CGCCGAGCCGCTGCCGGAGGCCATTCGGGACAGCCTGTTCGGGCTGCACCTGCTCTCGGCGCGCGGCCAGT

ACTGCCTCGCGACGGGCCGGCACGAGTCGGCGTACACGGCGTTCCGCACCTGCGGGGAACGGATGCGGAAC

TGGGGCGTCGACGTGCCGGGTCTGTCCCTGTGGCGCGTCGACGCCGCCGAGGCGCTGCTGCACGGCCGCGA

CCGGGACGAGGGCCGACGGCTCATCGACGAGCAGCTCACCCATGCGATGGGACCCCGTTCCCGCGCTTTGA

CGCTGCGGGTGCAGGCGGCGTACAGCCCGCAGGCGCAGCGGGTCGACCTGCTCGAAGAGGCGGCCGACCTG

CTGCTCTCCTGCAACGACCAGTACGAGCGGGCGCGGGTGCTCGCCGATCTGAGCGAGGCGTTCAGCGCGCT

CAGGCACCACAGCCGGGCGCGGGGACTGCTCCGGCAGGCCCGGCACCTGGCCGCCCAGTGCGGCGCGACCC

CGCTGCTGCGCCGGCTCGGGGCCAAGCCCGGAGGCCCCGGCTGGCTGGAGGAATCCGGCCTGCCGCAGCGG

ATCAAGTCGCTGACCGACGCGGAGCGGCGGGTGGCGTCGCTGGCCGCCGGCGGCCAGACCAACCGCGTGAT

CGCCGACCAGCTCTTCGTCACGGCCAGCACGGTGGAGCAGCACCTCACGAACGTCTTCCGCAAGCTGGGCG

TCAAGGGCCGCCAGCACCTGCCGGCCGAACTCGCCAACGCGGAATAG

SEQ ID NO: 16
GTGAAGCGCAACGATCTGGTTGCCCGCGATGGCGAGCTCAGGTGGATGCAAGAGATTCTCAGTCAGGCGAG

CGAGGGCCGGGGGCCGTGGTCACCATCACGGGGGCGATCGCCTGTGGCAAGACGGTGCTGCTGGACGCCG

CGGCAGCCAGTCAAGACGTGATCCAACTGCGTGCGGTCTGCTCGGCGGAGGAGCAGGAGCTGCCGTACGCG

ATGGTCGGACAACTACTCGACAATCCGGTGCTCGCCGCGCGAGTGCCGGCCCTGGGCAACCTGGCTGCGGC

GGGCGAGCGGCTGCTGCCGGGCACCGAGAACAGGATCCGGCGGGAGCTCACCCGCACCCTGCTGGCTCTCG

CCGACGAACGACCGGTGCTGATCGGCGTCGACGACATGCACCATGCGGACCCCGCCTCGCTGGACTGCCTG

CTGCACCTGGCCCGGCGGGTCGGCCCGGCCCGCATCGCGATCGTTCTGACCGAGTTGCGCCGGCTCACCCC

GGCTCACTCGCGCTTCCAGTCCGAGCTGCTCAGCCTGCGGTACCACCACGAGATCGGGTTGCAGCCGCTCA

CCGCGGAGCACACCGCCGACCTGGCCCGCGTCGGCCTCGGTGCCGAGGTCGACGACGACGTGCTCACCGAG

CTCTACGAGGCGACCGGCGGCAACCCGAGTCTGTGCTGCGGCCTGATCAGGGACGTGCGGCAGGACTGGGA

GGCCGGGGTCACCGGTATCCACGTCGGCCGGGCGTACCGGCTGGCCTATCTCAGTTCGCTCTACCGCTGCG

GCCCGGCGGCGCTGCGGACCGCCCGCGCGGCCGCGGTGCTGGGCGACAGCGCCGACGCCTGCCTGATCCGC

CGGGTCAGCGGCCTCGGTACGGAGGCCGTGGGCCAGGCGATCCAGCAGCTCACCGAGGGCGGCCTGCTGCG

TGACCAGCAGTTCCCGCACCCGGCGGCCCGCTCGGTCGTGCTCGACGACATGTCCGCGCAGGAACGCCACG

CGATGTATCGCAGCGCCCGGGAGGCAGCCGCCGAAGGTCAGGCCGACCCCGGCACCCCGGGCGAGCCGCGG

GCGGCTACGGCGTACGCCGGGTGTGGTGAGCAAGCCGGTGACTACCCGGAGCCGGCCGGCCGGGCCTGCGT

GGACGGTGCCGGTCCGGCCGAGTACTGCGGCGACCCGCACGGCGCCGACGACGACCCGGACGAGCTGGTCG

CCGCGCTGGGCGGGCTGCTGCCGAGCCGGCTCGTGGCGATGAAGATCCGGCGCCTGGCGGTGGCCGGGCGC

CCCGGGGCGGCTGCCGAGCTGCTGACCTCGCAGCGGTTGCACGCGGTGACCAGCGAGGACCGGGCCAGCCT

GCGGGCCGCCGAGGTGGCGCTCGCCACGCTGTGGCCGGGTGCGACCGGCCCGGACCGGCATCCGCTCACGG

AGCAGGAGGCGGCGAGCCTGCCGGAGGGTCCGCGCCTGCTCGCTGCCGCCGACGATGCCGTCGGGGCCGCC

CTGCGCGGTCGCGCCGAGTACGCCGCGGCCGAGGCGGAGAACGTCCTGCGGCACGCCGATCCGGCAGCCGG

TGGTGACGCCTACGCCGCCATGATCGCCCTGCTGTACACGGAGCACCCCGAGAACGTGCTGTTCTGGGCCG

ACAAGCTCGACGCGGGCCGCCCCGACGAGGAGACCAGTTATCCCGGGCTGCGGGCCGAGACCGCGGTGCGG

CTCGGTGACCTGGAAACGGCGATGGAGCTGGGCCGCACGGTGCTGGACCAGCGGCGGCTGCCGTCCCTGGG

TGTCGCCGCGGGCCTGCTCCTGGGCGGCGCGGTGACGGCCGCCATCCGGCTCGGCGACCTCGACCGGGCGG

AGAAGTGGCTCGCCGAGCCGATCCCCGACGCCATCCGTACCAGCCTCTACGGCCTGCACGTGCTGGCCGCG

CGGGGCCGGCTCGACCTGGCCGCGGGCCGCTACGAGGCGGCGTACACGGCGTTCCGGCTGTGTGGCGAGCG

GATGGCAGGCTGGGATGCCGATGTCTCCGGGCTGGCGCTGTGGCGCGTCGACGCCGCCGAGGCCCTGCTGT

CCGCGGGCATCCGCCCGGACGAGGGCCGCAAGCTCATCGACGACCAGCTCACCCGTGAGATGGGGGCCCGC

TCCCGGGCGCTGACGCTGCGGGCGCAAGCGGCGTACAGCCTGCCGGTGCACCGGGTGGGCCTGCTCGACGA

GGCGGCCGGCCTGCTGCTCGCCTGCCATGACGGGTACGAGCGGGCGCGGGTGCTCGCGGACCTGGGGGAGA

CCCTGCGCACGCTGCGGCACACCGACGCGGCCCAGCGGGTGCTCCGGCAGGCCGAGCAGGCGGCCGCGCGG

TGCGGGTCGGTCCCGCTGCTGCGGCGGCTCGGGGCCGAACCCGTACGCATCGGCACCCGGCGTGGTGAACC

CGGCCTGCCGCAGCGGATCAGGCTGCTGACCGATGCCGAGCGGCGGGTTGCCGCGATGGCCGCCGCCGGGC

AGACCAACCGGGAGATCGCCGGTCGGCTCTTCGTCACGGCCAGCACGGTGGAGCAGCACCTGACCAGCGTC

TTCCGCAAGCTGGGCGTCAAGGGCCGCCGGTTCCTGCCGACCGAGCTCGCCCAAGCCGTCTGA

SEQ ID NO: 17
ATGCCTGCCGTGAAGCGCAACGATCTGGTTGCCCGCGATGGCGAGCTCAGGTGGATGCAAGAGATTCTCAG

TCAGGCGAGCGAGGGCCGGGGGCCGTGGTCACCATCACGGGGGCGATCGCCTGTGGCAAGACGGTGCTGC

TGGACGCCGCGGCAGCCAGTCAAGACGTGATCCAACTGCGTGCGGTCTGCTCGGCGGAGGAGCAGGAGCTG

CCGTACGCGATGGTCGGACAACTACTCGACAATCCGGTGCTCGCCGCGCGAGTGCCGGCCCTGGGCAACCT

GGCTGCGGCGGGCGAGCGGCTGCTGCCGGGCACCGAGAACAGGATCCGGCGGGAGCTCACCCGCACCCTGC

TGGCTCTCGCCGACGAACGACCGGTGCTGATCGGCGTCGACGACATGCACCATGCGGACCCCGCCTCGCTG

GACTGCCTGCTGCACCTGGCCCGGCGGGTCGGCCCGGCCCGCATCGCGATCGTTCTGACCGAGTTGCGCCG

GCTCACCCCGGCTCACTCGCGCTTCCAGTCCGAGCTGCTCAGCCTGCGGTACCACCACGAGATCGGGTTGC

AGCCGCTCACCGCGGAGCACACCGCCGACCTGGCCCGCGTCGGCCTCGGTGCCGAGGTCGACGACGACGTG

CTCACCGAGCTCTACGAGGCGACCGGCGGCAACCCGAGTCTGTGCTGCGGCCTGATCAGGGACGTGCGGCA

GGACTGGGAGGCCGGGGTCACCGGTATCCACGTCGGCCGGGCGTACCGGCTGGCCTATCTCAGTTCGCTCT

ACCGCTGCGGCCCGGCGGCGCTGCGGACCGCCCGCGCGGCCCGCGGTGCTGGGCGACAGCGCCGACGCCTGC

CTGATCCGCCGGGTCAGCGGCCTCGGTACGGAGGCCGTGGGCCAGGCGATCCAGCAGCTCACCGAGGGCGG

CCTGCTGCGTGACCAGCAGTTCCCGCACCCGGCGGCCCGCTCGGTCGTGCTCGACGACATGTCCGCGCAGG

AACGCCACGCGATGTATCGCAGCGCCCGGGAGGCAGCCGCCGAAGGTCAGGCCGACCCCGGCACCCCGGGC

GAGCCGCGGCGGCTACGGCGTACGCCGGGTGTGGTGAGCAAGCCGGTGACTACCCGGAGCCGGCCGGCCG

GGCCTGCGTGGACGGTGCCGGTCCGGCCGAGTACTGCGGCGACCCGCACGGCGCCGACGACGACCCGGACG

AGCTGGTCGCCGCGCTGGGCGGCTGCTGCCGAGCCGGCTCGTGGCGATGAAGATCCGGCGCCTGGCGGTG

GCCGGGCGCCCCGGGGCGGCTGCCGAGCTGCTGACCTCGCAGCGGTTGCACGCGGTGACCAGCGAGGACCG

GGCCAGCCTGCGGGCCGCCGAGGTGGCGCTCGCCACGCTGTGGCCGGGTGCGACCGGCCCGGACCGGCATC

CGCTCACGGAGCAGGAGGCGGCGAGCCTGCCGGAGGGTCCGCGCCTGCTCGCTGCCGCCGACGATGCCGTC

GGGGCCGCCCTGCGCGGTCGCGCCGAGTACGCCGCGCCGAGGCGGAGAACGTCCTGCGGCACGCCGATCC

GGCAGCCGGTGGTGACGCCTACGCCGCCATGATCGCCCTGCTGTACACGGAGCACCCCGAGAACGTGCTGT

TCTGGGCCGACAAGCTCGACGCGGGCCGCCCCGACGAGGAGACCAGTTATCCCGGGCTGCGGGCCGAGACC

GCGGTGCGGCTCGGTGACCTGGAAACGGCGATGGAGCTGGGCCGCACGGTGCTGGACCAGCGGCGGCTGCC

GTCCCTGGGTGTCGCCGCGGGCCTGCTCCTGGGCGGCGCGGTGACGGCCGCCATCCGGCTCGGCGACCTCG

-continued

ACCGGGCGGAGAAGTGGCTCGCCGAGCCGATCCCCGACGCCATCCGTACCAGCCTCTACGGCCTGCACGTG
CTGGCCGCGCGGGGCCGGCTCGACCTGGCCGCGGGCCGCTACGAGGCGGCGTACACGGCGTTCCGGCTGTG
TGGCGAGCGGATGGCAGGCTGGGATGCCGATGTCTCCGGGCTGGCGCTGTGGCGCGTCGACGCCGCCGAGG
CCCTGCTGTCCGCGGGCATCCGCCCGGACGAGGGCCGCAAGCTCATCGACGACCAGCTCACCCGTGAGATG
GGGGCCCGCTCCCGGGCGCTGACGCTGCGGGCGCAAGCGGCGTACAGCCTGCCGGTGCACCGGGTGGGCCT
GCTCGACGAGGCGGCCGGCCTGCTGCTCGCCTGCCATGACGGGTACGAGCGGGCGCGGGTGCTCGCGGACC
TGGGGGAGACCCTGCGCACGCTGCGGCACACCGACGCGGCCCAGCGGGTGCTCCGGCAGGCCGAGCAGGCG
GCCGCGCGGTGCGGGTCGGTCCCGCTGCTGCGGCGGCTCGGGGCCGAACCCGTACGCATCGGCACCCGGCG
TGGTGAACCCGGCCTGCCGCAGCGGATCAGGCTGCTGACCGATGCCGAGCGGCGGGTTGCCGCGATGGCCG
CCGCCGGGCAGACCAACCGGGAGATCGCCGGTCGGCTCTTCGTCACGGCCAGCACGGTGGAGCAGCACCTG
ACCAGCGTCTTCCGCAAGCTGGGCGTCAAGGGCCGCCGGTTCCTGCCGACCGAGCTCGCCCAAGCCGTCTG
A

SEQ ID NO: 18
GTGGTCACCGTCACCGGCCCAATCGCCTGCGGCAAGACAGAACTGCTTGACGCGGCTGCCGCGAAGGCTGA
GGCCATCATTCTGCGCGCGGTCTGCGCGCCAGAAGAGCGGGCTATGCCGTACGCCATGATCGGGCAGCTCA
TCGACGACCCGGCGCTCGCGCATCGGGCGCCGGGGCTGGCTGATCGGATAGCCCAGGGCGGGCAGCTGTCG
CTGAGGGCCGAGAACCGACTGCGCAGGGATCTCACCCGTGCCCTGCTGGCGCTTGCCGTGGACCGGCCTGT
GCTGATCGGCGTCGACGATGTGCATCACGCCGACACCGCCTCTTTGAACTGTCTGCTGCATTTGGCCCGCC
GGGTCCGTCCGGCCCGGATATCCATGATCTTCACCGAGTTGCGCAGCCTCACCCCTACTCAGTCACGGTTC
AAGGCGGAGCTGCTCAGCCTGCCATACCACCACGAGATCGCGCTGCGTCCATTCGGACCGGAGCAATCGGC
GGAGCTGGCTCGCGCCGCCTTCGGCCCGGGCCTCGCCGAGGATGTGCTCGCGGGGTTGTATAAAACGACCA
GGGGCAATCTGAGTCTCAGCCGTGGACTGATCAGCGATGTGCGGGAGGCCCTGGCCAACGGAGAGAGCGCT
TTCGAGGCGGGCCGCGCGTTCCGGCTGGCGTACCTCAGCTCGCTCTACCGCTGTGGCCCGGTCGCGCTGCG
GGTCGCCCGAGTGGCTGCCGTGCTGGGCCCAAGCGCCACCACCACGCTGGTGCGCCGGCTAAGCGGGCTCA
GCGCGGAGACGATAGACCGGGCAACCAAGATCCTCACTGAGGGCGGGCTGCTGCTCGACCAGCAGTTCCCG
CACCCGGCCGCCCGCTCGGTGGTGCTCGATGACATGTCCGCCCAGGAACGACGCAGCCTGCACACTCTCGC
CCTGGAACTGCTGGACGAGGCGCCGGTTGAAGTGCTCGCGCACCACCAGGTCGGCGCCGGTCTCATACACG
GGCCCAAGGCTGCGGAGATGTTCGCCAAGGCCGGCAAGGCTCTGGTCGTACGCAACGAGTTGGGCGACGCG
GCCGAATACCTGCAACTGGCTCACCGGGCCTCCGACGATGTCTCCACCCGGGCCGCCTTACGGGTCGAGGC
CGTGGCCATCGAGCGCCGCCGCAATCCGCTGGCCTCCAGTCGGCACATGGACGAACTGAGCGCCGCCGGCC
GCGCCGGTCTGCTTTCCCCCAAGCATGCGGCGCTGGCCGTCTTCTGGCTAGCCGACGGCGGGCGATCCGGC
GAGGCAGCCGAAGTGCTGGCGTCGGAACGCCCGCTCGCGACCACCGATCAGAACCGGGCCCACCTGCGATT
TGTCGAGGTGACTCTCGCGCTGTTCTCTCCCGGCGCCTTCGGATCGGACCGGCGCCCACCTCCGCTGACGC
CGGACGAACTCGCCAGCCTGCCGAAGGCGGCCTGGCAATGCGCGGTCGCCGACAACGCGGCCATGACCGCC
TTGCACGGCCATCCAGAACTTGCCACCGCTCAGGCGGAAACAGTTCTGCGGCAGGCTGATTCGGCAGCCGA
CGCGATCCCCGCCGCGCTGATCGCCCTGTTGTACGCGGAGAACACCGAGTCCGCTCATATCTGGGCCGACA
AGCTGGGCAGCACGAATGCCGGGGTATCGAACGAGGCGGAAGCGGGCTACGCCGGCCCGTGCGCCGAGATC
GCCCTGCGGCGCGGCGACCTGGCCACGGCGTTCGAGGCTGGTAGCGCCGTCCTGGACGACCGGTCGCTGCC
GTCGCTCGGCATCACCGCCGCATTGCTGTTGAGCAGCAAGACGGCCGCCGCTGTCCGGCTGGGCGAACTCG
AGCGTGCGGAGAAGCTGCTCGCCGAGCCGCTTCCGAACGGCGTCCAGGACAGCCTTTTCGGTCTGCACCTG
CTCTCGGCGTACGGCCAGTACAGCCTCGCGATGGGCCGATATGAATCAGCTCACCGGGCGTTTCGCACCTG

-continued

CGGAGAACGTATGCGCAGCTGGGATGTTGACGTGCCTGGTCTGGCCCTGTGGCGTGTCGACGCCGCCGAGG

CGCTGCTCAGCCTCGACCGGAACGAGGGCCAGCGGCTCATCGACGAACAACTCACCCGTCCGATGGGGCCT

CGTTCCCACGCGTTAACGCTGCGGATCAAGGCGGCATACCTCCCGCGGACGAAGCGGATCCCCCTGCTCCA

TGAGGCGGCCGAGCTGCTGCTCCCCTGCCCCGACCCGTACGAGCAAGCGCGGGTGCTCGCCGATCTGGGCG

ACACGCTCAGCGCGCTCAGACGCTATAGCCGGGCGCGGGGAGTTCTCCGGCAGGCTCGTCACCTGGCCACC

CAGTGCGGTGCTGTCCCGCTGCTGCGCAGGCTCGGGGGCGAGCCCGGCCGGATCGACGACGCCGGCCTGCC

GCAGCGGAGCACATCGTTGACCGATGCGGAGCGGCGGGTGGCGGCGCTGGCCGCGGCCGGACAGACCAACC

GGGAGATCGCCGAACAGCTGTTCGTCACGGCCAGCACAGTGGAACAGCACCTCACAAGCGTCTTCCGCAAG

CTGGGCGTCAAGGGCCGCAAGCAGCTGCCGACCGCGCTGGCCGACGTGGAACAGACCTGA

SEQ ID NO: 19
ATGTATAGCGGTACCTGCCGTGAAGGATACGAACTCGTCGCACGCGAGGACGAACTCGGTATTCTACAGAG

GTCTCTGGAACAAGCGAGCAGCGGCCAGGGCGTCGTGGTCACCGTCACCGGCCCAATCGCCTGCGGCAAGA

CAGAACTGCTTGACGCGGCTGCCGCGAAGGCTGAGGCCATCATTCTGCGCGCGGTCTGCGCGCCAGAAGAG

CGGGCTATGCCGTACGCCATGATCGGGCAGCTCATCGACGACCCGGCGCTCGCGCATCGGGCGCCGGGGCT

GGCTGATCGGATAGCCCAGGGCGGGCAGCTGTCGCTGAGGGCCGAGAACCGACTGCGCAGGGATCTCACCC

GTGCCCTGCTGGCGCTTGCCGTGGACCGGCCTGTGCTGATCGGCGTCGACGATGTGCATCACGCCGACACC

GCCTCTTTGAACTGTCTGCTGCATTTGGCCCGCCGGGTCCGTCCGGCCCGGATATCCATGATCTTCACCGA

GTTGCGCAGCCTCACCCCTACTCAGTCACGGTTCAAGGCGGAGCTGCTCAGCCTGCCATACCACCACGAGA

TCGCGCTGCGTCCATTCGGACCGGAGCAATCGGCGGAGCTGGCTCGCGCCGCCTTCGGCCCGGGCCTCGCC

GAGGATGTGCTCGCGGGGTTGTATAAAACGACCAGGGGCAATCTGAGTCTCAGCCGTGGACTGATCAGCGA

TGTGCGGGAGGCCCTGGCCAACGGAGAGAGCGCTTTCGAGGCGGCCGCGCGTTCCGGCTGGCGTACCTCA

GCTCGCTCTACCGCTGTGGCCCGGTCGCGCTGCGGGTCGCCCGAGTGGCTGCCGTGCTGGGCCCAAGCGCC

ACCACCACGCTGGTGCGCCGGCTAAGCGGGCTCAGCGCGGAGACGATAGACCGGGCAACCAAGATCCTCAC

TGAGGGCGGGCTGCTGCTCGACCAGCAGTTCCCGCACCCGGCCGCCCGCTCGGTGGTGCTCGATGACATGT

CCGCCCAGGAACGACGCAGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATGTTCGCCAAGGCCGGCAA

GGCTCTGGTCGTACGCAACGAGTTGGGCGACGCGGCCGAATACCTGCAACTGGCTCACCGGGCCTCCGACG

ATGTCTCCACCCGGGCCGCCCTGCGGGTCGAGGCCGTGGCCATCGAGCGCCGCCGCAATCCGCTGGCCTCC

AGTCGGCACATGGACGAACTGAGCGCCGCCGCCGCGCCGGTCTGCTTTCCCCCAAGCATGCGGCGCTGGC

CGTCTTCTGGCTAGCCGACGGCGGGCGATCCGGCGAGGCAGCCGAAGTGCTGGCGTCGGAACGCCCGCTCG

CGACCACCGATCAGAACCGGGCCCACCTGCGATTTGTCGAGGTGACTCTCGCGCTGTTCTCTCCCGGCGCC

TTCGGATCGGACCGGCGCCCACCTCCGCTGACGCCGGACGAACTCGCCAGCCTGCCGAAGGCGGCCTGGCA

ATGCGCGGTCGCCGACAACGCGGCCATGACCGCCTTGCACGGCCATCCAGAACTTGCCACCGCTCAGGCGG

AAACAGTTCTGCGGCAGGCTGATTCGGCAGCCGACGCGATCCCCGCCGCGCTGATCGCCCTGTTGTACGCG

GAGAACACCGAGTCCGCTCATATCTGGGCCGACAAGCTGGGCAGCACGAATGCCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTAGCGCCGTCCTGGACGACCGGTCGCTGCCGTCGCTCGGCATCACCGCCGCATTGCTGTTGAGCAGC

AAGACGGCCGCCGCTGTCCGGCTGGGCGAACTCGAGCGTGCGGAGAAGCTGCTCGCCGAGCCGCTTCCGAA

CGGCGTCCAGGACAGCCTTTTCGGTCTGCACCTGCTCTCGGCGTACGGCCAGTACAGCCTCGCGATGGGCC

GATATGAATCAGCTCACCGGGCGTTTCGCACCTGCGGAGAACGTATGCGCAGCTGGGATGTTGACGTGCCT

GGTCTGGCCCTGTGGCGTGTCGACGCCGCCGAGGCGCTGCTCAGCCTCGACCGGAACGAGGGCCAGCGGCT

CATCGACGAACAACTCACCCGTCCGATGGGGCCTCGTTCCCACGCGCTGACGCTGCGGATCAAGGCGGCAT

ACCTCCCGCGGACGAAGCGGATCCCCCTGCTCCATGAGGCGGCCGAGCTGCTGCTCCCCTGCCCCGACCCG

TACGAGCAAGCGCGGGTGCTCGCCGATCTGGGCGACACGCTCAGCGCGCTCAGACGCTATAGCCGGGCGCG

GGGAGTTCTCCGGCAGGCTCGTCACCTGGCCACCCAGTGCGGTGCTGTCCCGCTGCTGCGCAGGCTCGGGG

GCGAGCCCGGCCGGATCGACGACGCCGGCCTGCCGCAGCGGAGCACATCGTTGACCGATGCGGAGCGGCGG

GTGGCGGCGCTGGCCGCGGCCGGACAGACCAACCGGGAGATCGCCGAACAGCTGTTCGTCACGGCCAGCAC

AGTGGAACAGCACCTCACAAGCGTCTTCCGCAAGCTGGGCGTCAAGGGCCGCAAGCAGCTGCCGACCGCGC

TGGCCGACGTGGAACAGACCTGA

SEQ ID NO: 20
GTGTATAGCGGTACCTGCCGTGAAGGATACGAACTCGTCGCCCGCGAGGACGAACTCGGCATTCTGCAGAG

GTCTCTGGAAGAAGCAGGCAGCGGCCAGGGCGCCGTGGTCACCGTCACCGGCCCGATCGCCTGCGGCAAGA

CAGAACTGCTTGACGCGGCTGCCGCGAAGGCTGACGCCATCATTCTGCGCGCGGTCTGCGCGCCCGAAGAG

CGCGCTATGCCGTACGCCATGATCGGGCAGCTCATCGACGACCCGGCGCTCGCGCATCGGGCGCGGAGCT

GGCTGATCGGATAGCCCAGGGCGGGCATCTGTCGCTGAGGGCCGAGAACCGACTGCGCAGGGATCTCACCC

GTGCCCTGCTGGCGCTTGCCGTCGACCGGCCTGTGCTGATCGGCGTCGACGATGTGCATCACGCCGACACC

GCCTCTTTGAACTGTCTGCTGCATTTAGCCCGCCGGGTCCGTCCGGCCCGGATATCCATGATCTTCACCGA

GTTGCGCAGCCTCACCCCTACTCAGTCACGATTCAAGGCGGAGCTGCTCAGCCTGCCGTACCACCACGAGA

TCGCGCTGCGTCCACTCGGACCGGAGCAATCGGCGGAGCTGCCCACGCCGCCTTCGGCCCGGGCCTCGCC

GAGGATGTGCTCGCGGGGTTGTATGGGATGACCAGGGGCAACCTGAGTCTCAGCCGTGGACTGATCAGCGA

TGTGCGGGAGGCCCAGGCCAACGGAGAGAGCGCTTTCGAGGTGGGCCGCGCGTTCCGGCTGGCGTACCTCA

GCTCGCTCTACCGCTGTGGCCCGATCGCGCTGCGGGTCGCCCGAGTGGCTGCCGTGCTGGGCCCAAGCGCC

ACCACCACGCTGGTGCGCCGTCTAAGCGGGCTCAGCGCGGAGACGATAGACCGGGCAACCAAGATCCTCAC

TGAGGGCGGGCTGCTGCTCGACCACCAGTTCCCGCACCCGGCCGCCCGCTCGGTGGTGCTCGATGACATGT

CCGCCCAGGAACGACGCAGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATATTCGCCAGGGCTGGCCA

GGCTCTGGTTGTACGCAACGAGTTGGGCGACGCGGCCGAATACCTGCAACTGGCTCACCGAGCCTCCGACG

ATGTCTCCACCCGGGCCGCCTTACGGGTCGAGGCCGTGGCAATCGAGCGCCGCCGCAATCCGCTGGCCTCC

AGTCGTCACATGGACGAGCTGAGCGCCGCCGGCCGCGCCGGTCTGCTTTCCCCCAAGCATGCAGCGCTGGC

TGTCTTCTGGCTGGCCGACGGCGGGCGATCCGGCGAGGCAGCCGAGGTGCTGGCGTCGGAACACCCGCTCG

CGACCACCGATCAGAACCGAGCACACCTGCGATTTGCCGAGGTGACTCTCGCGCTGTTCTGTCCCGGCGCC

TTCGGGTCGGACCGGCGCCCACCTCCGCTGGCGCCGGACGAGCTCGCCAGCTTGCCGAAGGCGGCCTGGCA

ATGCGCGGTCGCCGACAACGCGGTCATGACAGCGTTGCATGCTCATCCAGAACTTGCCACCGCTCAGGCGG

AAACAGTTCTGCGGCAGGCTGATTCGGCAGCCGACGCAATCCCCGCCGCACTGATCGCCCTGTTGTACGCA

GAGAACACCGAGTCCGCTCAGATCTGGGCCGACAAGCTGGGCAGCACCAATGCCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTGGCACCGTCCTGGACGACCGGCCGCTGCCGTCGCTCGGCATCACCGCCGCATTGCTGTTGAGCAGC

AAGACGGCAGCCGCTGTCCGCCTGGGCGAACTCGAGCGTGCGGAGAAGCTGCTCGCTGAGCCGCTTCCGAA

CGGTGTCCAGGACAGCCTTTTCGGTCTGCACCTGCTCTCGGCGCACGGCCAGTACAGCCTCGCGATGGGCC

GATATGAATCGGCTCACCGGGCGTTTCACACCTGCGGAGAACGTATGCGCAGCTGGGGTGTTGACGTGCCT

GGTCTAGCCCTGTGGCGTGTCGACGCCGCCGAGGCACTGCTCAGCCTCGACCGGAACGAGGGCCAGCGGCT

CATCGACGAACAACTCGCCCGTCCGATGGGACCTCGTTCCCGCGCATTAACGCTGCGGATCAAGGCGGCAT

ACCTCCCGCGGACGAAGCGGATCCCCCTGCTCCATGAGGCAGCTGAGCTGCTGCTCTCCTGCCCCGACCCG

TACGAGCAAGCGCGGGTGCTCGCCGATCTGGGCGACACGCTCAGCGCGCTCAGACGCTATAGCCGGGCGCG

GGGAGTTCTCCGGCAGGCTCGTCACCTGGCCACCCAGTGCGGTGCTGTCCCGCTGCTGCGCCGACTCGGGG

GCGAGCCCGGCCGGATCGACGACGCCGGCCTGCCGCAGCGGAGCACATCGTTGACCGATGCGGAGCGGCGG

GTGTCGGCCCTGGCCGCGGCCGGACAGACCAACCGGGAGATCGCCAAACAGCTATTCGTCACGGCCAGCAC

CGTGGAACAGCACCTCACAAGCGTCTTCCGCAAGCTGGGCGTTAAGGGCCGCAGGCAGCTACCGACCGCGC

TGGCCGACGTGGAATAG

SEQ ID NO: 21
ATGTATAGCGGTACCTGCCGTGAAGGATACGAACTCGTCGCCCGCGAGGACGAACTCGGCATTCTGCAGAG

GTCTCTGGAAGAAGCAGGCAGCGGCCAGGGCGCCGTGGTCACCGTCACCGGCCCGATCGCCTGCGGCAAGA

CAGAACTGCTTGACGCGGCTGCCGCGAAGGCTGACGCCATCATTCTGCGCGCGGTCTGCGCGCCCGAAGAG

CGCGCTATGCCGTACGCCATGATCGGGCAGCTCATCGACGACCCGGCGCTCGCGCATCGGGCGCCGGAGCT

GGCTGATCGGATAGCCCAGGGCGGGCATCTGTCGCTGAGGGCCGAGAACGACTGCGCAGGGATCTCACCC

GTGCCCTGCTGGCGCTTGCCGTCGACCGGCCTGTGCTGATCGGCGTCGACGATGTGCATCACGCCGACACC

GCCTCTTTGAACTGTCTGCTGCATCTGGCCCGCCGGGTCCGTCCGGCCCGGATATCCATGATCTTCACCGA

GTTGCGCAGCCTCACCCCTACTCAGTCACGATTCAAGGCGGAGCTGCTCAGCCTGCCGTACCACCACGAGA

TCGCGCTGCGTCCACTCGGACCGGAGCAATCGGCGGAGCTGGCCCACGCCGCCTTCGGCCCGGGCCTCGCC

GAGGATGTGCTCGCGGGGTTGTATGGGATGACCAGGGGCAACCTGAGTCTCAGCCGTGGACTGATCAGCGA

TGTGCGGGAGGCCCAGGCCAACGGAGAGAGCGCTTTCGAGGTGGCCGCGCGTTCCGGCTGGCGTACCTCA

GCTCGCTCTACCGCTGTGGCCCGATCGCGCTGCGGGTCGCCCGAGTGGCTGCCGTGCTGGGCCCAAGCGCC

ACCACCACGCTGGTGCGCCGTCTAAGCGGGCTCAGCGCGGAGACGATAGACCGGGCAACCAAGATCCTCAC

TGAGGGCGGGCTGCTGCTCGACCACCAGTTCCCGCACCCGGCCGCCCGCTCGGTGGTGCTCGATGACATGT

CCGCCCAGGAACGACGCAGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATATTCGCCAGGGCTGGCCA

GGCTCTGGTTGTACGCAACGAGTTGGGCGACGCGGCCGAATACCTGCAACTGGCTCACCGAGCCTCCGACG

ATGTCTCCACCCGGGCCGCCCTGCGGGTCGAGGCCGTGGCAATCGAGCGCCGCCGCAATCCGCTGGCCTCC

AGTCGTCACATGGACGAGCTGAGCGCCGCCGGCCGCGCCGGTCTGCTTTCCCCCAAGCATGCAGCGCTGGC

TGTCTTCTGGCTGGCCGACGGCGGGCGATCCGGCGAGGCAGCCGAGGTGCTGGCGTCGGAACACCCGCTCG

CGACCACCGATCAGAACCGAGCACACCTGCGATTTGCCGAGGTGACTCTCGCGCTGTTCTGTCCCGGCGCC

TTCGGGTCGGACCGGCGCCCACCTCCGCTGGCGCCGGACGAGCTCGCCAGCTTGCCGAAGGCGGCCTGGCA

ATGCGCGGTCGCCGACAACGCGGTCATGACAGCGTTGCATGCTCATCCAGAACTTGCCACCGCTCAGGCGG

AAACAGTTCTGCGGCAGGCTGATTCGGCAGCCGACGCAATCCCCGCCGCACTGATCGCCCTGTTGTACGCA

GAGAACACCGAGTCCGCTCAGATCTGGGCCGACAAGCTGGGCAGCACCAATGCCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTGGCACCGTCCTGGACGACCGGCCGCTGCCGTCGCTCGGCATCACCGCCGCATTGCTGTTGAGCAGC

AAGACGGCAGCCGCTGTCCGCCTGGGCGAACTCGAGCGTGCGGAGAAGCTGCTCGCTGAGCCGCTTCCGAA

CGGTGTCCAGGACAGCCTTTTCGGTCTGCACCTGCTCTCGGCGCACGGCCAGTACGCCTCGCGATGGGCC

GATATGAATCGGCTCACCGGGCGTTTCACACCTGCGGAGAACGTATGCGCAGCTGGGGTGTTGACGTGCCT

GGTCTAGCCCTGTGGCGTGTCGACGCCGCCGAGGCACTGCTCAGCCTCGACCGGAACGAGGGCCAGCGGCT

CATCGACGAACAACTCGCCCGTCCGATGGGACCTCGTTCCCGCGCACTGACGCTGCGGATCAAGGCGGCAT

ACCTCCCGCGGACGAAGCGGATCCCCCTGCTCCATGAGGCAGCTGAGCTGCTGCTCTCCTGCCCCGACCCG

-continued

TACGAGCAAGCGCGGGTGCTCGCCGATCTGGGCGACACGCTCAGCGCGCTCAGACGCTATAGCCGGGCGCG

GGGAGTTCTCCGGCAGGCTCGTCACCTGGCCACCCAGTGCGGTGCTGTCCCGCTGCTGCGCCGACTCGGGG

GCGAGCCCGGCCGGATCGACGACGCCGGCCTGCCGCAGCGGAGCACATCGTTGACCGATGCGGAGCGGCGG

GTGTCGGCCCTGGCCGCGGCCGGACAGACCAACCGGGAGATCGCCAAACAGCTATTCGTCACGGCCAGCAC

CGTGGAACAGCACCTCACAAGCGTCTTCCGCAAGCTGGGCGTTAAGGGCCGCAGGCAGCTACCGACCGCGC

TGGCCGACGTGGAATAG

SEQ ID NO: 22
GTGTATAGCGGTACCTGCCGTGAAGGATACGAACTCGTCGCACGCGAGGACGAACTCGGCATTCTACAGAG

GTCTCTGGAACAAGCGAGCAGCGGCCAGGGCGTCGTGGTCACCGTCACCGGCCCAATCGCCTGCGGCAAGA

CAGAACTGCTTGACGCGGCTGCCGCGAAGGCTGAGGCCATCATTCTGCGCGCGGTCTGCGCGCCCGAAGAG

CGGGCTATGCCGTACGCCATGATCGGGCAGCTCATCGACGACCCGGCGCTCGCGCATCGGGCGCGGGGCT

GGCTGATCGGATAGCCCAGGGCGGGCAGCTGTCGCTGAGGGCCGAGAACCGACTGCGCAGGGATCTCACCC

GTGCCCTGCTGGCGCTTGCCGTGCACCGGCCTGTGCTGATCGGCGTCGATGATGTGCATCACGCCGACACC

GCCTCTTTGAACTGTCTGCTGCATTTGGCGCGCCGGGTCCGTCCGGCCCGGATATCCATGATCTTCACCGA

GTTGCGCAGCCTCACCCCTACTCAGTCACGATTCAAGGCGGAGCTGCTCAGCCTGCCGTACCACCACGAGA

TCGCGCTGCGTCCATTCGGACCGGAGCAATCGGCGGAGCTGGCTCGCGCCGCCTTCGGCCCGGGCCTCGCC

GAGGATGTGCTCGCGGGGTTGTATAAAACGACCAGGGGCAATCTGAGTCTCAGCCGTGGACTGATCAGCGA

TGTGCGGGAGGCCCTGGCCAACGGAGAGAGCGCTTTCGAGGCGGGCCGCGCGTTCCGGCTGGCGTACCTCA

GCTCGCTCTACCGCTGTGGCCCGGTCGCGCTGCGGGTCGCCCGAGTGGCTGCCGTGCTGGGCCCAAGCGCC

ACCACCACGCTGGTGCGCCGGCTAAGCGGGCTCAGCGCGGAGACGATAGACCGGGCAACCAAGATCCTCAC

CGAGGGCGGGCTGCTGCTCGACCAGCAGTTTCCGCACCCGGCCGCCCGCTCGGTGGTGCTCGATGACATGT

CCGCCCAGGAACGACGCGGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATGTTCGCCAAGGCCGGCAA

GGCTCTGGTCGTACGCAACGAGTTGGGCGACGCGGCCGAATACCTGCAACTGGCTCACCGGGCCTCCGACG

ATGTCTCCACCCGGGCCGCCTTACGGGTCGAGGCCGTGGCGATCGAGCGCCGCCGCAATCCGCTGGCCTCC

AGTCGGCACATGGACGAGCTGAGCGCCGCCGGCCGCGCCGGTCTGCTTTCCCCCAAGCATGCGGCGCTGGC

CGTCTTCTGGCTGGCCGACGGCGGGCGATCCGGCGAGGCAGCCCAGGTGCTGGCGTCGGAACGCCCGCTCG

CGACCACCGATCAGAACCGGGCCCACCTGCGATTTGTCGAGGTGACTCTCGCGCTGTTCTCTCCCGGCGCC

TTCGGATCGGACCGGCGCCCACCTCCGCTGACGCCGGACGAACTCGCCAGCCTGCCGAAGGCGGCCTGGCA

ATGCGCGGTCGCCGACAACGCGGCCATGACCGCCTTGCACGGCCATCCAGAACTTGCCACCGCTCAGGCGG

AAACAGTTCTGCGGCAGGCTGATTCGGCAGCCGACGCGATCCCCGCCGCGCTGATCGCCCTGTTGTACGCG

GAGAACACCGAGTCCGCTCATATCTGGGCCGACAAGCTGGGCAGCATGAATGCCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTAGCACCGTCCTGGACGACCGGTCACTGCCGTCGCTCGGCATCACCGCCGCATTGCTGTTGAGCAGC

AAGACGGCCGCGCTGTCCGGCTGGGCGAACTCGAGCGTGCGGAGAAGCTGCTCGCCGAGCCGCTTCCGAA

CGGCGTCCAGGACAGCCTTTTCGGTCTGCACCTGCTCTCGGCGTACGGCCAGTACAGCCTCGCGATGGGCC

GATATGAATCGGCTCACCGGGCGTTTCGCACCTGCGGAGAACGTATGCGCAGCTGGGATGTTGACGTGCCT

GGTCTGGCCCTGTGGCGTGTCGACGCCGCCGAGGCGCTGCTCAGCCTCGACCGGAACGAGGGCCAGCGGCT

CATCGACGAACAACTCACCCGTCCGATGGGACCTCGTTCCCGCGCGTTAACGCTGCGGATCAAGGCGGCAT

ACCTCCCGCGGACGAAGCGGATCCCCCTGCTCCATGAGGCGGCCGAGCTGCTGCTCCCCTGCCCCGACCCG

TACGAGCAAGCGCGGGTGCTCGCCGATCTGGGCGACACGCTCAGCGCGCTCAGACGCTATAGCCGGGCGCG

-continued

GGGAGTTCTCCGGCAGGCTCGTCACCTGGCCACCCAGTGCGGTGCTGTCCCGCTGCTGCGCCGACTCGGGG

GCGAGCCCGGCCGGATCGACGACGCCGGCCTGCCGCAGCGGAGCACATCGTTGACCGATGCGGAGCGGCGG

GTGGCGGCGCTGGCCGCGGCCGGACAGACCAACCGGGAGATCGCCGAACAGCTGTTCGTCACGGCCAGCAC

AGTGGAACAGCACCTCACAAGCGTCTTCCGCAAGCTGGGCGTCAAGGGCCGCAAGCAGCTGCCGACCGCGC

TGGCCGACGTGGAACAGACCTGA

SEQ ID NO: 23
ATGTATAGCGGTACCTGCCGTGAAGGATACGAACTCGTCGCACGCGAGGACGAACTCGGCATTCTACAGAG

GTCTCTGGAACAAGCGAGCAGCGGCCAGGGCGTCGTGGTCACCGTCACCGGCCCAATCGCCTGCGGCAAGA

CAGAACTGCTTGACGCGGCTGCCGCGAAGGCTGAGGCCATCATTCTGCGCGCGGTCTGCGCGCCCGAAGAG

CGGGCTATGCCGTACGCCATGATCGGGCAGCTCATCGACGACCCGGCGCTCGCGCATCGGGCGCGGGGCT

GGCTGATCGGATAGCCCAGGGCGGGCAGCTGTCGCTGAGGGCCGAGAACCGACTGCGCAGGGATCTCACCC

GTGCCCTGCTGGCGCTTGCCGTGCACCGGCCTGTGCTGATCGGCGTCGATGATGTGCATCACGCCGACACC

GCCTCTTTGAACTGTCTGCTGCATTTGGCGCGCCGGGTCCGTCCGGCCCGGATATCCATGATCTTCACCGA

GTTGCGCAGCCTCACCCCTACTCAGTCACGATTCAAGGCGGAGCTGCTCAGCCTGCCGTACCACCACGAGA

TCGCGCTGCGTCCATTCGGACCGGAGCAATCGGCGGAGCTGGCTCGCGCCGCCTTCGGCCCGGGCCTCGCC

GAGGATGTGCTCGCGGGGTTGTATAAAACGACCAGGGGCAATCTGAGTCTCAGCCGTGGACTGATCAGCGA

TGTGCGGGAGGCCCTGGCCAACGGAGAGAGCGCTTTCGAGGCGGGCCGCGCGTTCCGGCTGGCGTACCTCA

GCTCGCTCTACCGCTGTGGCCCGGTCGCGCTGCGGGTCGCCCGAGTGGCTGCCGTGCTGGGCCCAAGCGCC

ACCACCACGCTGGTGCGCCGGCTAAGCGGGCTCAGCGCGGAGACGATAGACCGGGCAACCAAGATCCTCAC

CGAGGGCGGGCTGCTGCTCGACCAGCAGTTTCCGCACCCGGCCGCCCGCTCGGTGGTGCTCGATGACATGT

CCGCCCAGGAACGACGCGGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATGTTCGCCAAGGCCGGCAA

GGCTCTGGTCGTACGCAACGAGTTGGGCGACGCGGCCGAATACCTGCAACTGGCTCACCGGGCCTCCGACG

ATGTCTCCACCCGGGCCGCCCTGCGGGTCGAGGCCGTGGCGATCGAGCGCCGCCGCAATCCGCTGGCCTCC

AGTCGGCACATGGACGAGCTGAGCGCCGCCGGCCGCGCCGGTCTGCTTTCCCCCAAGCATGCGGCGCTGGC

CGTCTTCTGGCTGGCCGACGGCGGGCGATCCGGCGAGGCAGCCCAGGTGCTGGCGTCGGAACGCCCGCTCG

CGACCACCGATCAGAACCGGGCCCACCTGCGATTTGTCGAGGTGACTCTCGCGCTGTTCTCTCCCGGCGCC

TTCGGATCGGACCGGCGCCCACCTCCGCTGACGCCGGACGAACTCGCCAGCCTGCCGAAGGCGGCCTGGCA

ATGCGCGGTCGCCGACAACGCGGCCATGACCGCCTTGCACGGCCATCCAGAACTTGCCACCGCTCAGGCGG

AAACAGTTCTGCGGCAGGCTGATTCGGCAGCCGACGCGATCCCCGCCGCGCTGATCGCCCTGTTGTACGCG

GAGAACACCGAGTCCGCTCATATCTGGGCCGACAAGCTGGGCAGCATGAATGCCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTAGCACCGTCCTGGACGACCGGTCACTGCCGTCGCTCGGCATCACCGCCGCATTGCTGTTGAGCAGC

AAGACGGCCGCCGCTGTCCGGCTGGGCGAACTCGAGCGTGCGGAGAAGCTGCTCGCCGAGCCGCTTCCGAA

CGGCGTCCAGGACAGCCTTTTCGGTCTGCACCTGCTCTCGGCGTACGGCCAGTACGCCTCGCGATGGGCC

GATATGAATCGGCTCACCGGGCGTTTCGCACCTGCGGAGAACGTATGCGCAGCTGGGATGTTGACGTGCCT

GGTCTGGCCCTGTGGCGTGTCGACGCCGCCGAGGCGCTGCTCAGCCTCGACCGGAACGAGGGCCAGCGGCT

CATCGACGAACAACTCACCCGTCCGATGGGACCTCGTTCCCGCGCGCTGACGCTGCGGATCAAGGCGGCAT

ACCTCCCGCGGGACGAAGCGGATCCCCCTGCTCCATGAGGCGGCCGAGCTGCTGCTCCCCTGCCCCGACCCG

TACGAGCAAGCGCGGGTGCTCGCCGATCTGGGCGACACGCTCAGCGCGCTCGAGACGCTATAGCCGGGCGCG

GGGAGTTCTCCGGCAGGCTCGTCACCTGGCCACCCAGTGCGGTGCTGTCCCGCTGCTGCGCCGACTCGGGG

-continued

GCGAGCCCGGCCGGATCGACGACGCCGGCCTGCCGCAGCGGAGCACATCGTTGACCGATGCGGAGCGGCGG

GTGGCGGCGCTGGCCGCGGCCGGACAGACCAACCGGGAGATCGCCGAACAGCTGTTCGTCACGGCCAGCAC

AGTGGAACAGCACCTCACAAGCGTCTTCCGCAAGCTGGGCGTCAAGGGCCGCAAGCAGCTGCCGACCGCGC

TGGCCGACGTGGAACAGACCTGA

SEQ ID NO: 24
GTGCGAGCTATTAATGCGTCCGACACCGGTCCTGAACTGGTCGCCCGCGAAGACGAACTGGGACGTGTACG

AAGTGCCCTGAACCGAGCGAACGGCGGCCAAGGTGTCCTGATCTCCATTACCGGTCCGATCGCCTGCGGCA

AGACCGAACTGCTTGAGGCTGCCGCCTCGGAAGTTGACGCCATCACTCTGCGCGCGGTCTGTGCCGCCGAG

GAACGGGCGATACCTTATGCCCTGATCGGGCAGCTTATCGACAACCCCGCGCTCGGCATTCCGGTTCCGGA

TCCGGCCGGCCTGACCGCCCAGGGCGGACGACTGTCATCGAGCGCCGAGAACCGACTGCGTCGCGACCTCA

CCCGTGCCCTGCTGACGCTCGCCACCGACCGGCTGGTGCTGATCTGTGTCGATGACGTGCAGCACGCCGAC

AACGCCTCGTTGAGCTGCCTTCTGTATCTGGCCCGACGGCTTGTCCCGGCTCGAATCGCTCTGGTATTCAC

CGAGTTGCGAGTCCTCACCTCGTCTCAGTTACGGTTCAACGCGGAGCTGCTCAGCTTGCGGAACCACTGCG

AGATCGCGCTGCGCCCACTCGGCCCGGGGCATGCGGCCGAGCTGGCCCGCGCCACCCTCGGCCCCGGCCTC

TCCGACGAAACACTCACGGAGCTGTACCGGGTGACCGGAGGCAACCTGAGTCTCAGCCGCGGGCTGATCGA

CGATGTGCGGGACGCCTGGGCACGAGGGGAAACGGGCGTCCAGGTGGGCCGGGCGTTCCGGCTGGCCTACC

TCGGTTCCCTCCACCGCTGTGGTCCGCTGGCGTTGCGGGTCGCCCGCGTAGCCGCCGTACTGGGCCCGAGC

GCCACCAGCGTCCTGGTGCGCCGGATCAGTGGGCTCAGCGCGGAGGCCATGGCCCAGGCGACCGATATCCT

CGCTGACGGCGGCCTCCTGCGCGACCAGCGGTTCACACATCCAGCGGCCCGCTCGGTGGTGCTCGACGACA

TGTCCGCCGAGGAACGACGCAGCGTGCACAGCCTCGCCCTGGAACTGCTGGACGAGGCACCGGCCGAGATG

CTCGCGCACCACCGGGTCGGCGCCGGTCTCGTGCACGGGCCGAAGGCCGCGGAGACATTCACCGGGGCCGG

CCGGGCACTGGCCGTTCGCGGCATGCTGGGCGAGGCAGCCGACTACCTGCAACTGGCGTACCGGGCCTCCG

GCGACGCCGCTACCAAGGCCGCGATACGCGTCGAGTCCGTGGCGGTCGAGCGCCGACGCAATCCGCTGGTC

GTCAGTCGCCATTGGGACGAGCTGAGCGTCGCGGCCCGCGCCGGTCTGCTCTCCTGCGAGCACGTGTCCAG

GACGGCCCGCTGGCTGACCGTCGGTGGGCGGCCCGGCGAGGCGGCCAGGGTGCTGGCGTCGCAACACCGAC

GGGTCGTCACCGATCAGGACCGGGCCCACCTGCGGGTCGCCGAGTTCTCGCTCGCGCTGCTGTACCCCGGT

ACGTCCGGCTCGGACCGGCGCCCGCACCCGCTCACGTCGGACGAACTCGCGGCCCTACCGACTGCGACCAG

ACACTGCGCGATCGCCGATAACGCTGTCATGGCTGCCTTGCGTGGTCATCCGGAGCTTGCCACCGCCGAGG

CAGAAGCCGTTCTGCAGCAAGCCGACGCGGCGGACGGCGCTGCTCTCACCGCGCTGATGGCCCTGCTGTAC

GCGGAGAGCATCGAGGTCGCTGAAGTCTGGGCGGACAAGCTGGCGGCAGAGGCCGGAGCATCGAACGGGCA

GGACGCGGAGTACGCCGGTATACGCGCCGAAATCGCCCTGCGGCGCGGCGATCTGACCGCGGCCGTCGAGA

CCGCCGGCATGGTCCTGGACGGCCGGCCGCTGCCGTCGCTCGACATCACCGCCACGTTGCTGTTGGCCGGC

AGGGCGTCCGTCGCCGTCCGGCTGGGCGAACTCGACCACGCGGAGGAGCTGTTCGCCGCGCCGCCGGAGGA

CGCCTTCCAGGACAGCCTCTTCGGTCTGCATCTGCTCTCGGCGCACGGCCAGTACAGCCTCGCGACAGGCC

GGCCCGAGTCGGCATACCGGGCCTTTCGTGCCTGCGGCGAACGTATGCGCGATTGGGCTTCGACGCGCCC

GGTGTGGCCCTGTGGCGCGTCGGCGCCGCCGAGGCGCTGCTCGGCCTCGACCGGAACGAGGGCCGACGGCT

CATCGACGAACAGCTGAGCCGGACGATGGCCCCCCGGTCCCACGCGTTGACGCTGCGGATAAAAGCGGCGT

ACATGCCGGAGCCGAAGCGGGTCGACCTGCTCTACGAAGCGGCTGAGCTGCTGCTCTCCTGCCGGGACCAG

TATGAGCGAGCGCGGGTGCTCGCCGATCTGGGCGAGGCGCTCAGCGCGCTCGGGAACTACCGGCAGGCGCG

AGGTGTGCTCCGGCAGGCTCGGCATCTGGCCATGCGAACCGGCGCGGACCCGCTGCTGCGCCGGCTCGGAA

TCAGGCCCGGCCGGCAGGACGACCCCGACCCGCAGCCGCGGAGCAGATCGCTGACCAACGCTGAGCGGCGT

-continued

GCGGCGTCGCTGGCCGCGACCGGACTGACCAACCGGGAGATCGCCGACCGGCTCTTCGTCACCGCCAGCAC

CGTGGAGCAGCACCTCACCAACGTCTTCCGCAAGCTGGGCGTCAAGGGCCGCAAGCAGCTGCCGGCCGAGT

TGGACGACATGGAATAG

SEQ ID NO: 25
ATGCGAGCTATTAATGCGTCCGACACCGGTCCTGAACTGGTCGCCCGCGAAGACGAACTGGGACGTGTACG

AAGTGCCCTGAACCGAGCGAACGGCGGCCAAGGTGTCCTGATCTCCATTACCGGTCCGATCGCCTGCGGCA

AGACCGAACTGCTTGAGGCTGCCGCCTCGGAAGTTGACGCCATCACTCTGCGCGCGGTCTGTGCCGCCGAG

GAACGGGCGATACCTTATGCCCTGATCGGGCAGCTTATCGACAACCCCGCGCTCGGCATTCCGGTTCCGGA

TCCGGCCGGCCTGACCGCCCAGGGCGGACGACTGTCATCGAGCGCCGAGAACCGACTGCGTCGCGACCTCA

CCCGTGCCCTGCTGACGCTCGCCACCGACCGGCTGGTGCTGATCTGTGTCGATGACGTGCAGCACGCCGAC

AACGCCTCGTTGAGCTGCCTTCTGTATCTGGCCCGACGGCTTGTCCCGGCTCGAATCGCTCTGGTATTCAC

CGAGTTGCGAGTCCTCACCTCGTCTCAGCTGCGGTTCAACGCGGAGCTGCTCAGCTTGCGGAACCACTGCG

AGATCGCGCTGCGCCCACTCGGCCCGGGGCATGCGGCCGAGCTGGCCCGCGCCACCCTCGGCCCCGGCCTC

TCCGACGAAACACTCACGGAGCTGTACCGGGTGACCGGAGGCAACCTGAGTCTCAGCCGCGGGCTGATCGA

CGATGTGCGGGACGCCTGGGCACGAGGGGAAACGGGCGTCCAGGTGGGCCGGGCGTTCCGGCTGGCCTACC

TCGGTTCCCTCCACCGCTGTGGTCCGCTGGCGTTGCGGGTCGCCCGCGTAGCCGCCGTACTGGGCCCGAGC

GCCACCAGCGTCCTGGTGCGCCGGATCAGTGGGCTCAGCGCGGAGGCCATGCCCAGGCGACCGATATCCT

CGCTGACGGCGGCCTCCTGCGCGACCAGCGGTTCACACATCCAGCGGCCCGCTCGGTGGTGCTCGACGACA

TGTCCGCCGAGGAACGACGCAGCGTGCACAGCCTCGCCCTGGAACTGCTGGACGAGGCACCGGCCGAGATG

CTCGCGCACCACCGGGTCGGCGCCGGTCTCGTGCACGGGCCGAAGGCCGCGGAGACATTCACCGGGGCCGG

CCGGGCACTGGCCGTTCGCGGCATGCTGGGCGAGGCAGCCGACTACCTGCAACTGGCGTACCGGGCCTCCG

GCGACGCCGCTACCAAGGCCGCGATACGCGTCGAGTCCGTGGCGGTCGAGCGCCGACGCAATCCGCTGGTC

GTCAGTCGCCATTGGGACGAGCTGAGCGTCGCGGCCCGCGCCGGTCTGCTCTCCTGCGAGCACGTGTCCAG

GACGGCCCGCTGGCTGACCGTCGGTGGGCGGCCCGGCGAGGCGGCCAGGGTGCTGGCGTCGCAACACCGAC

GGGTCGTCACCGATCAGGACCGGGCCCACCTGCGGGTCGCCGAGTTCTCGCTCGCGCTGCTGTACCCCGGT

ACGTCCGGCTCGGACCGGCGCCCGCACCCGCTCACGTCGGACGAACTCGCGGCCCTACCGACTGCGACCAG

ACACTGCGCGATCGCCGATAACGCTGTCATGGCTGCCTTGCGTGGTCATCCGGAGCTTGCCACCGCCGAGG

CAGAAGCCGTTCTGCAGCAAGCCGACGCGGCGGACGGCGCTGCTCTCACCGCGCTGATGGCCCTGCTGTAC

GCGGAGAGCATCGAGGTCGCTGAAGTCTGGGCGGACAAGCTGGCGGCAGAGGCCGGAGCATCGAACGGGCA

GGACGCGGAGTACGCCGGTATACGCGCCGAAATCGCCCTGCGGCGCGGCGATCTGACCGCGGCCGTCGAGA

CCGCCGGCATGGTCCTGGACGGCCGGCCGCTGCCGTCGCTCGACATCACCGCCACGTTGCTGTTGGCCGGC

AGGGCGTCCGTCGCCGTCCGGCTGGGCGAACTCGACCACGCGGAGGAGCTGTTCGCCGCGCCGCGGAGGA

CGCCTTCCAGGACAGCCTCTTCGGTCTGCATCTGCTCTCGGCGCACGGCCAGTACAGCCTCGCGACAGGCC

GGCCCGAGTCGGCATACCGGGCCTTTCGTGCCTGCGGCGAACGTATGCGCGATTGGGGCTTCGACGCGCCC

GGTGTGGCCCTGTGGCGCGTCGGCGCCGCCGAGGCGCTGCTCGGCCTCGACCGGAACGAGGGCCGACGGCT

CATCGACGAACAGCTGAGCCGGACGATGGCCCCCGGTCCCACGCGTTGACGCTGCGGATAAAAGCGGCGT

ACATGCCGGAGCCGAAGCGGGTCGACCTGCTCTACGAAGCGGCTGAGCTGCTGCTCTCCTGCCGGGACCAG

TATGAGCGAGCGCGGGTGCTCGCCGATCTGGGCGAGGCGCTCAGCGCGCTCGGGAACTACCGGCAGGCGCG

AGGTGTGCTCCGGCAGGCTCGGCATCTGGCCATGCGAACCGGCGCGGACCCGCTGCTGCGCCGGCTCGGAA

TCAGGCCCGGCCGGCAGGACGACCCCGACCCGCAGCCGCGGAGCAGATCGCTGACCAACGCTGAGCGGCGT

GCGGCGTCGCTGGCCGCGACCGGACTGACCAACCGGGAGATCGCCGACCGGCTCTTCGTCACCGCCAGCAC

```
CGTGGAGCAGCACCTCACCAACGTCTTCCGCAAGCTGGGCGTCAAGGGCCGCAAGCAGCTGCCGGCCGAGT

TGGACGACATGGAATAG
```

SEQ ID NO: 26
```
MPAVECYELDARDDELRKLEEVVTGRANGRGVVVTITGPIACGKTELLDAAAAKADAITLRAVCSAEEQAL

PYALIGQLIDNPALASHALEPACPTLPGEHLSPEAENRLRSDLTRTLLALAAERPVLIGIDESHANALCLL

HLARRVGSARIAMVLTELRRLTPAHSQFQAELLSLGHHREIALRPLSPKHTAELVRAGLGPDVDEDVLTGL

YRATGGNLNLTRGLINDVREAWETGGTGISAGRAYRLAYLGSLYRCGPVPLRVARVAAVLGQSANTTLVRW

ISGLNADAVGEATEILTEGGLLHDLRFPHPAARSVVLNDMSAQERRRLHRSALEVLDDVPVEVVAHHQVGA

GLLHGPKAAEIFAKAGQELHVRGELDTASDYLQLAHQASDDAVTGMRAEAVAIERRRNPLASSRHLDELTV

VARAGLLFPEHTALMIRWLGVGGRSGEAAGLLASQRPRAVTDQDRAHMRAAEVSLALVSPGTSGPDRRPRP

LTPDELANLPKAARLCAIADNAVMSALRGRPELAAAEAENVLQHADSAAAGTTALAALTALLYAENTDTAQ

LWADKLVSETGASNEEEAGYAGPRAEAALRRGDLAAAVEAGSTVLDHRRLSTLGITAALPLSSAVAAAIRL

GETERAEKWLAQPLPQAIQDGLFGLHLLSARGQYSLATGQHESAYTAFRTCGERMRNWGVDVPGLSLWRVD

AAEALLHGRDRDEGRRLVDEQLTRAMGPRSRALTLRVQAAYSPPAKRVDLLDEAADLLLSCNDQYERARVL

ADLSETFSALRHHSRARGLLRQARHLAAQRGAIPLLRRLGAKPGGPGWLEESGLPQRIKSLTDAERRVASL

AAGGQTNRVIADQLFVTASTVEQHLTDVSTGSRPPAPAAELV
```

SEQ ID NO: 27
```
MVPEVRAAPDELIARDDELSRLQRALTRAGSGRGGVVAITGPIASGKTALLDAGAAKSGFVALRAVCSWEE

RTLPYGMLGQLFDHPELAAQAPDLAHETASCESPQAGTDNRLRAEFTRTLLALAADWPVLIGIDDVHHADA

ESLRCLLHLARRIGPARIAVVLTELRRPTPADSRFQAELLSLRSYQEIALRPLTEAQTGELVRRHLGAETH

EDVSADTFRATGGNLLLGHGLINDIREARTAGRPGVVAGRAYRLAYLSSLYRCGPSALRVARASAVLGASA

EAVLVQRMTGLNKDAVEQVYEQLNEGRLLQGERFPHPAARSIVLDDLSALERRNLHESALELLRDHGVAGN

VLARHQIGAGRVHGEEAVELFTGAAREHHLRGELDDAAGYLELAHRASDDPVTRAALRVGAAAIERLCNPV

RAGRHLPELLTASRAGLLSSEHAVSLADWLAMGGRPGEAAEVLATQRPAADSEQHRALLRSGELSLALVHP

GAWDPLRRTDRFAAGGLGSLPGPARHRAVADQAVIAALRGRLDRADANAESVLQHTDATADRTTAIMALLA

LLYAENTDAVQFWVDKLAGDEGTRTPADEAVHAGFNAEIALRRGDLMRAVEYGEAALGHRHLPTWGMAAAL

PLSSTVVAAIRLGDLDRAERWLAEPLPQQTPESLFGLHLLWARGQHHLATGRHGAAYTAFRECGERMRRWA

VDVPGLALWRVDAAESLLLLGRDRAEGLRLVSEQLSRPMRPRARVQTLRVQAAYSPPPQRIDLLEEAADLL

VTCNDQYELANVLSDLAEASSMVRQHSRARGLLRRARHLATQCGAVPLLRRLGAEPSDIGGAWDATLGQRI

ASLTESERRVAALAAVGRTNREIAEQLFVTASTVEQHLTNVERKLAVKGRQQLPKELADVGEPADRDRRCG
```

SEQ ID NO: 28
```
MIARLSPPDLIARDDEFGSLHRALTRAGGGRGVVAAVTGPIACGKTELLDAAAAKAGFVTLRAVCSMEERA

LPYGMLGQLLDQPELAARTPELVRLTASCENLPADVDNRLGTELTRTVLTLAAERPVLIGIDDVHHADAPS

LRCLLHLARRISRARVAIVLTELLRPTPAHSQFRAALLSLRHYQEIALRPLTEAQTTELVRRHLGQDAHDD

VVAQAFRATGGNLLLGHGLIDDIREARTRTSGCLEVVAGRAYRLAYLGSLYRCGPAALSVARASAVLGESV

ELTLVQRMTGLDTEAVEQAHEQLVEGRLLREGRFPHPAARSVVLDDLSAAERRGLHELALELLRDRGVASK

VLARHQMGTGRVHGAEVAGLFTDAAREHHLRGELDEAVTYLEFAYRASDDPAVHAALRVDTAAIERLCDPA

RSGRHVPELLTASRERLLSSEHAVSLACWLAMDGRPGEAAEVLAAQRSAAPSEQGRAHLRVADLSLALIYP

GAADPPRPADPPAEDEVASFSGAVRHRAVADKALSNALRGWSEQAEAKAEYVLQHSRVTTDRTTTMMALLA

LLYAEDTDAVQSWVDKLAGDDNMRTPADEAVHAGFRAEAALRRGDLTAAVECGEAALAPRVVPSWGMAAAL

PLSSTVAAAIRLGDLDRAERWLAEPLPEETSDSLFGLHMVWARGQHHLAAGRYRAAYNAFRDCGERMRRWS

VDVPGLALWRVDAAEALLLLGRGRDEGLRLISEQLSRPMGSRARVMTLRVQAAYSPPAKRIELLDEAADLL
```

-continued

IMCRDQYELARVLADMGEACGMLRRHSRARGLFRRARHLATQCGAVPLLRRLGGESSDADGTQDVTPAQRI

TSLTEAERRVASHAAVGRTNKEIASQLFVTSSTVEQHLTNVERKLGVKGRQQLPKELSDAG

SEQ ID NO: 29
MEFYDLVARDDELRRLDQALGRAAGGRGVVVTVTGPVGCGKTELLDAAAAEEEFITLRAVCSAEERALPYA

VIGQLLDHPVLSARAPDLACVTAPGRTLPADTENRLRRDLTRALLALASERPVLICIDDVHQADTASLNCL

LHLARRVASARIAMILTELRRLTPAHSRFEAELLSLRHRHEIALRPLGPADTAELARARLGAGVTADELAQ

VHEATSGNPNLVGGLVNDVREAWAAGGTGIAAGRAYRLAYLSSVYRCGPVPLRIAQAAAVLGPSATVTLVR

RISGLDAETVDEATAILTEGGLLRDHRFPHPAARSVVLDDMSAQERRRLHRSTLDVLDGVPVDVLAHHQAG

AGLLHGPQAAEMFARASQELRVRGELDAATEYLQLAYRASDDAGARAALQVETVAGERRRNPLAASRHLDE

LAAAARAGLLSAEHAALVVHWLADAGRPGEAAEVLALQRALAVTDHDRARLRAAEVSLALFHPGVPGSDPR

PLAPEELASLSLSARHGVTADNAVLAALRGRPESAAAEAENVLRNADAAASGPTALAALTALLYAENTDAA

QLWADKLAAGIGAGEGEAGYAGPRTVAALRRGDLTTAVQAAGAVLDRGRPSSLGITAVLPLSGAVAAAIRL

GELERAEKWLAEPLPEAVHDSLFGLHLLMARGRYSLAVGRHEAAYAAFRDCGERMRRWDVDVPGLALWRVD

AAEALLPGDDRAEGRRLIDEQLTRPMGPRSRALTLRVRAAYAPPAKRIDLLDEAADLLLSSNDQYERARVL

ADLSEAFSALRQNGRARGILRQARHLAAQCGAVPLLRRLGVKAGRSGRLGRPPQGIRSLTEAERRVATLAA

AGQTNREIADQLEVTASTVEQHLTNVERKLGVKGRQQLPAELADLRPPG

SEQ ID NO: 30
MYSGTCREGYELVAREDELGILQRSLEQASSGQGVVVTVTGPIACGKTELLDAAAAKAEAIILRAVCAPEE

RAMPYAMIGQLIDDPALAHRAPGLADRIAQGGQLSLRAENRLRRDLTRALLALAVDRPVLIGVDDVHHADT

ASLNCLLHLARRVRPARISMIFTELRSLTPTQSRFKAELLSLPYHHEIALRPFGPEQSAELARAAFGPGLA

EDVLVGLYKTTRGNLSLSRGLISDVREALANGESAFEAGRAFRLAYLGSLYRCGPVALRVARVAAVLGPSA

TTTLVRRLSGLSAETIDRATKILTEGGLLLDQQFPHPAARSVVLDDMSAQERRGLHTLALELLDEAPVEVL

AHHQVGAGLIHGPKAAEMFAKAGKALVVRNELGDAAEYLQLAHRASDDVSTRAALRVEAVAIERRRNPLAS

SRHMDELSAAGRAGLLSPKHAALAVFWLADGGRSGEAAEVLASERPLATTDQNRAHLRFVEVTLALFSPGA

FGSDRRPPPLTPDELASLPKAAWQCAVADNAAMTALHGHPELATAQAETVLRQADSAADAIPAALIALLYA

ENTESAHIWADKLGSTNGGVSNEAEAGYAGPCAEIALRRGDLATAFEAGSTVLDDRSLPSLGITAALLLSS

KTAAAVRLGELERAEKLLAEPLPNGVQDSLFGLHLLSAYGQYSLAMGRYESALRAFHTCGERMRSWDVDVP

GLALWRVDAAEALLSLDRNEGQRLIDEQLTRPMGPRSRALTLRIKAAYLPRTKRIPLLHEAAELLLPCPDP

YEQARVLADLGDTLSALRRYSRARGVLRQARHLAAQCGAVPLLRRLGGEPGRIDDAGLPQRSTSLTDAERR

VAALAAAGQTNREIAKQLFVTASTVEQHLTSVFRKLGVKGRKQLPTALADVEQT

SEQ ID NO: 31
MPAVESYELDARDDELRRLEEAVGQAGNGRGVVVTITGPIACGKTELLDAAAAKSDAITLRAVCSEEERAL

PYALIGQLIDNPAVSQLPDPVSMALPGEHLSPEAENRLRGDLTRTLLALAAERPVLIGIDDMHHADTASL

NCLLHLARRVGPARIAMVLTELRRLTPAHSQFHAELLSLGHHREIALRPLGPKHIAELARAGLGPDVDEDV

LTGLYRATGGNLNLGHGLIKDVREAWATGGTGINAGRAYRLAYLGSLYRCGPVPLRVARVAAVLGQSANTT

LVRWISGLNADAVGEATEILTEGGLLHDLRFPHPAARSVVLNDLSARERRRLHRSALEVLDDVPVEVVAHH

QAGAGFIHGPKAAEIFAKAGQELHVRGELDAASDYLQLAHHASDDAVTRAALRVEAVAIERRRNPLASSRH

LDELTVAARAGLLSLEHAALMIRWLALGGRSGEAAEVLAAQRPRAVTDQDRAHLRAAEVSLALVSPGASGV

SPGASGPDRRPRPLPPDELANLPKAARLCAIADNAVISALHGRPELASAEAENVLKQADSAADGATALSAL

TALLYAENTDTAQLWADKLVSETGASNEEEGAGYAGPRAETALRRGDLAAAVEAGSAILDHRRGSLLGITA

ALPLSSAVAAAIRLGETERAEKWLAEPLPEATRDSLFGLHLLSARGQYCLATGRHESAYTAFRTCGERMRN

WGVDVPGLSLWRVDAAEALLHGRDRDEGRRLIDEQLTHAMGPRSRALTLRVQAAYSPQAQRVDLLEEAADL

-continued

LLSCNDQYERARVLADLSEAFSALRHHSRARGLLRQARHLAAQCGATPLLRRLGAKPGGPGWLEESGLPQR

IKSLTDAERRVASLAAGGQTNRVIADQLFVTASTVEQHLTNVERKLGVKGRQHLPAELANAE

SEQ ID NO: 32
MPAVKRNDLVARDGELRWMQEILSQASEGRGAVVTITGAIACGKTVLLDAAAASQDVIQLRAVCSAEEQEL

PYAMVGQLLDNPVLAARVPALGNLAAAGERLLPGTENRIRRELTRTLLALADERPVLIGVDDMHHADPASL

DCLLHLARRVGPARIAIVLTELRRLTPAHSRFQSELLSLRYHHEIGLQPLTAEHTADLARVGLGAEVDDDV

LTELYEATGGNPSLCCGLIRDVRQDWEAGVTGIHVGRAYRLAYLSSLYRCGPAALRTARAAAVLGDSADAC

LIRRVSGLGTEAVGQAIQQLTEGGLLRDQQFPHPAARSVVLDDMSAQERHAMYRSAREAAAEGQADPGTPG

EPRAATAYAGCGEQAGDYPEPAGRACVDGAGPAEYCGDPHGADDDPDELVAALGGLLPSRLVAMKIRRLAV

AGRPGAAAELLTSQRLHAVTSEDRASLRAAEVALATLWPGATGPDRHPLTEQEAASLPEGPRLLAAADDAV

GAALRGRAEYAAAEAENVLRHADPAAGGDAYAAMIALLYTEHPENVLFWADKLDAGRPDEETSYPGLRAET

AVRLGDLETAMELGRTVLDQRRLPSLGVAAGLLLGGAVTAAIRLGDLDRAEKWLAEPIPDAIRTSLYGLHV

LAARGRLDLAAGRYEAAYTAFRLCGERMAGWDADVSGLALWRVDAAEALLSAGIRPDEGRKLIDDQLTREM

GARSRALTLRAQAAYSLPVHRVGLLDEAAGLLLACHDGYERARVLADLGETLRTLRHTDAAQRVLRQAEQA

AARCGSVPLLRRLGAEPVRIGTRRGEPGLPQRIRLLTDAERRVAAMAAAGQTNREIAGRLFVTASTVEQHL

TSVFRKLGVKGRRFLPTELAQAV

SEQ ID NO: 33
MYSGTCREGYELVAREDELGILQRSLEQASSGQGVVVTVTGPIACGKTELLDAAAAKAEAIILRAVCAPEE

RAMPYAMIGQLIDDPALAHRAPGLADRIAQGGQLSLRAENRLRRDLTRALLALAVDRPVLIGVDDVHHADT

ASLNCLLHLARRVRPARISMIFTELRSLTPTQSRFKAELLSLPYHHEIALRPFGPEQSAELARAAFGPGLA

EDVLAGLYKTTRGNLSLSRGLISDVREALANGESAFEAGRAFRLAYLSSLYRCGPVALRVARVAAVLGPSA

TTTLVRRLSGLSAETIDRATKILTEGGLLLDQQFPHPAARSVVLDDMSAQERRSLHTLALELLDEAPVEVL

AHHQVGAGLIHGPKAAEMFAKAGKALVVRNELGDAAEYLQLAHRASDDVSTRAALRVEAVAIERRRNPLAS

SRHMDELSAAGRAGLLSPKHAALAVFWLADGGRSGEAAEVLASERPLATTDQNRAHLRFVEVTLALFSPGA

FGSDRRPPPLTPDELASLPKAAWQCAVADNAAMTALHGHPELATAQAETVLRQADSAADAIPAALIALLYA

ENTESAHIWADKLGSTNAGVSNEAEAGYAGPCAEIALRRGDLATAFEAGSAVLDDRSLPSLGITAALLLSS

KTAAAVRLGELERAEKLLAEPLPNGVQDSLFGLHLLSAYGQYSLAMGRYESAHRAFRTCGERMRSWDVDVP

GLALWRVDAAEALLSLDRNEGQRLIDEQLTRPMGPRSHALTLRIKAAYLPRTKRIPLLHEAAELLLPCPDP

YEQARVLADLGDTLSALRRYSRARGVLRQARHLATQCGAVPLLRRLGGEPGRIDDAGLPQRSTSLTDAERR

VAALAAAGQTNREIAEQLFVTASTVEQHLTSVFRKLGVKGRKQLPTALADVEQT

SEQ ID NO: 34
MYSGTCREGYELVAREDELGILQRSLEEAGSGQGAVVTVTGPIACGKTELLDAAAAKADAIILRAVCAPEE

RAMPYAMIGQLIDDPALAHRAPELADRIAQGGHLSLRAENRLRRDLTRALLALAVDRPVLIGVDDVHHADT

ASLNCLLHLARRVRPARISMIFTELRSLTPTQSRFKAELLSLPYHHEIALRPLGPEQSAELAHAAFGPGLA

EDVLAGLYGMTRGNLSLSRGLISDVREAQANGESAFEVGRAFRLAYLSSLYRCGPIALRVARVAAVLGPSA

TTTLVRRLSGLSAETIDRATKILTEGGLLLDHQFPHPAARSVVLDDMSAQERRSLHTLALELLDEAPVEVL

AHHQVGAGLIHGPKAAEIFARAGQALVVRNELGDAAEYLQLAHRASDDVSTRAALRVEAVAIERRRNPLAS

SRHMDELSAAGRAGLLSPKHAALAVFWLADGGRSGEAAEVLASEHPLATTDQNRAHLRFAEVTLALFCPGA

FGSDRRPPPLAPDELASLPKAAWQCAVADNAVMTALHAHPELATAQAETVLRQADSAADAIPAALTALLYA

ENTESAQIWADKLGSTNAGVSNEAEAGYAGPCAEIALRRGDLATAFEAGGTVLDDRPLPSLGITAALLLSS

KTAAAVRLGELERAEKLLAEPLPNGVQDSLFGLHLLSAHGQYSLAMGRYESAHRAFHTCGERMRSWGVDVP

GLALWRVDAAEALLSLDRNEGQRLIDEQLARPMGPRSRALTLRIKAAYLPRTKRIPLLHEAAELLLSCPDP

-continued

YEQARVLADLGDTLSALRRYSRARGVLRQARHLATQCGAVPLLRRLGGEPGRIDDAGLPQRSTSLTDAERR

VSALAAAGQTNREIAKQLFVTASTVEQHLTSVFRKLGVKGRRQLPTALADVE

SEQ ID NO: 35
MYSGTCREGYELVAREDELGILQRSLEQASSGQGVVVTVTGPIACGKTELLDAAAAKAEAIILRAVCAPEE

RAMPYAMIGQLIDDPALAHRAPGLADRIAQGGQLSLRAENRLRRDLTRALLALAVHRPVLIGVDDVHHADT

ASLNCLLHLARRVRPARISMIFTELRSLTPTQSRFKAELLSLPYHHEIALRPFGPEQSAELARAAFGPGLA

EDVLAGLYKTTRGNLSLSRGLISDVREALANGESAFEAGRAFRLAYLSSLYRCGPVALRVARVAAVLGPSA

TTTLVRRLSGLSAETIDRATKILTEGGLLLDQQFPHPAARSVVLDDMSAQERRGLHTLALELLDEAPVEVL

AHHQVGAGLIHGPKAAEMFAKAGKALVVRNELGDAAEYLQLAHRASDDVSTRAALRVEAVAIERRRNPLAS

SRHMDELSAAGRAGLLSPKHAALAVFWLADGGRSGEAAQVLASERPLATTDQNRAHLRFVEVTLALFSPGA

FGSDRRPPPLTPDELASLPKAAWQCAVADNAAMTALHGHPELATAQAETVLRQADSAADAIPAALIALLYA

ENTESAHIWADKLGSMNAGVSNEAEAGYAGPCAEIALRRGDLATAFEAGSTVLDDRSLPSLGITAALLLSS

KTAAAVRLGELERAEKLLAEPLPNGVQDSLFGLHLLSAYGQYSLAMGRYESAHRAFRTCGERMRSWDVDVP

GLALWRVDAAEALLSLDRNEGQRLIDEQLTRPMGPRSRALTLRIKAAYLPRTKRIPLLHEAAELLLPCPDP

YEQARVLADLGDTLSALRRYSRARGVLRQARHLATQCGAVPLLRRLGGEPGRIDDAGLPQRSTSLTDAERR

VAALAAAGQTNREIAEQLFVTASTVEQHLTSVFRKLGVKGRKQLPTALADVEQT

SEQ ID NO: 36
MRAINASDTGPELVAREDELGRVRSALNRANGGQGVLISITGPIACGKTELLEAAASEVDAITLRAVCAAE

ERAIPYALIGQLIDNPALGIPVPDPAGLTAQGGRLSSSAENRLRRDLTRALLTLATDRLVLICVDDVQHAD

NASLSCLLYLARRLVPARIALVFTELRVLTSSQLRFNAELLSLRNHCEIALRPLGPGHAAELARATLGPGL

SDETLTELYRVTGGNLSLSRGLIDDVRDAWARGETGVQVGRAFRLAYLGSLHRCGPLALRVARVAAVLGPS

ATSVLVRRISGLSAEAMAQATDILADGGLLRDQRFTHPAARSVVLDDMSAEERRSVHSLALELLDEAPAEM

LAHHRVGAGLVHGPKAAETFTGAGRALAVRGMLGEAADYLQLAYRASGDAATKAAIRVESVAVERRRNPLV

VSRHWDELSVAARAGLLSCEHVSRTARWLTVGGRPGEAARVLASQHRRVVTDQDRAHLRVAEFSLALLYPG

TSGSDRRPHPLTSDELAALPTATRHCAIADNAVMAALRGHPELATAEAEAVLQQADAADGAALTALMALLY

AESIEVAEVWADKLAAEAGASNGQDAEYAGIRAEIALRRGDLTAAVETAGMVLDGRPLPSLDITATLLLAG

RASVAVRLGELDHAEELFAAPPEDAFQDSLFGLHLLSAHGQYSLATGRPESAYRAFRACGERMRDWGFDAP

GVALWRVGAAEALLGLDRNEGRRLIDEQLSRTMAPRSHALTLRIKAAYMPEPKRVDLLYEAAELLLSCRDQ

YERARVLADLGEALSALGNYRQARGVLRQARHLAMRTGADPLLRRLGIRPGRQDDPDPQPRSRSLTNAERR

AASLAATGLTNREIADRLFVTASTVEQHLTNVERKLGVKGRKQLPAELDDME

LAL Binding Sites

In some embodiments, a gene cluster (e.g., a PKS gene cluster or a β-lactam compound gene cluster) includes one or more promoters that include one or more LAL binding sites. The LAL binding sites may include a polynucleotide consensus LAL binding site sequence (e.g., as described herein). In some instances, the LAL binding site includes a core AGGGGG motif. In certain instances, the LAL binding site includes a sequence having at least 80% (e.g., 80%, 85%, 90%, 95%, 97%, 98%, 99%, or 100%) homology to SEQ ID NO: 2. The LAL binding site may include mutation sites that have been restored to match the sequence of a consensus or optimized LAL binding site. In some embodiments, the LAL binding site is a synthetic LAL binding site. In some embodiments, a synthetic LAL binding sites may be identified by (a) providing a plurality of synthetic nucleic acids including at least eight nucleotides; (b) contacting one or more of the plurality of nucleotides including at least eight nucleotides with one or more LALs; (c) determining the binding affinity between a nucleic acid of step (a) and an LAL of step (b), wherein a synthetic nucleic acid is identified as a synthetic LAL binding site if the affinity between the synthetic nucleic acid and an LAL is greater than X. The identified synthetic LAL binding sites may then be introduced into a host cell in a compound-producing cluster (e.g., a PKS cluster or a β-lactam compound producing protein gene cluster).

In some embodiments, a pair of LAL binding site and a heterologous LAL or a heterologous LAL binding site and an LAL that have increased expression compared a natural pair may be identified by (a) providing one or more LAL binding sites; (b) contacting one or more of the LAL binding sites with one or more LALs; (c) determining the binding affinity between a LAL binding site and an LAL, wherein a pair having increased expression is identified if the affinity between the LAL binding site and the LAL is greater than the affinity between the LAL binding site and its homologous LAL and/or the LAL at its homologous LAL binding site. In some embodiments, the binding affinity between the LAL binding site and the LAL is determined by determining the expression of a protein or compound by a cell which includes both the LAL and the LAL binding site.

Constitutively Active LALs

In some embodiments, the recombinant LAL is a constitutively active LAL. For example, the amino acid sequence of the LAL has been modified in such a way that it does not require the presence of an inducer compound for the altered LAL to engage its cognate binding site and activate transcription of a compound producing protein (e.g., polyketide synthase or a β-lactam compound producing protein). Introduction of a constitutively active LAL to a host cell would likely result in increased expression of the compound-producing protein (e.g., polyketide synthase or a β-lactam compound producing protein) and, in turn, increased production of the corresponding compound (e.g., polyketide or a β-lactam compound).

Engineering Unidirectional LALs

FkPhD gene clusters are arranged with a multicistronic architecture driven by multiple bidirectional promoter-operators that harbor conserved (in single or multiple, and inverted to each other and/or directly repeating) GGGGGT (SEQ ID NO: 3) motifs presumed to be LAL binding sites. Bidirectional LAL promoters may be converted to unidirectional ones (UniLALs) by strategically deleting one of the opposing promoters, but maintaining the tandem LAL binding sites (in case binding of LALs in the native promoter is cooperative, as was demonstrated for MaIT). Functionally this is achieved by removal of all sequences 3' of the conserved GGGGGT (SEQ ID NO: 3) motif present on the antisense strand (likely containing the −35 and −10 promoter sequences), but leaving intact the entire sequence on the sense strand. As a consequence of this deletion, transcription would be activated in one direction only. The advantages of this feed-forward circuit architecture would be to tune and/or maximize LAL expression during the complex life cycle of Streptomyces vegetative and fermentation growth conditions.

Host Cells

In some embodiments, the host cell is a bacteria such as an Actinobacterium. For example, in some embodiments, the host cell is a Streptomyces strain. In some embodiments, the host cell is Streptomyces anulatus, Streptomyces antibioticus, Streptomyces coelicolor, Streptomyces peucetius, Streptomyces sp. ATCC 700974, Streptomyces canus, Streptomyces nodosus, Streptomyces (multiple sp.), Streptoalloteicus hindustanus, Streptomyces hygroscopicus, Streptomyces avermitilis, Streptomyces viridochromogenes, Streptomyces verticillus, Streptomyces chartruensis, Streptomyces (multiple sp.), Saccharothrix mutabilis, Streptomyces halstedii, Streptomyces clavuligerus, Streptomyces venezuelae, Streptomyces roseochromogenes, Amycolatopsis orientalis, Streptomyces clavuligerus, Streptomyces rishiriensis, Streptomyces lavendulae, Streptomyces roseosporus, Nonomuraea sp., Streptomyces peucetius, Saccharopolyspora erythraea, Streptomyces filipinensis, Streptomyces hygroscopicus, Micromonospora purpurea, Streptomyces hygroscopicus, Streptomyces narbonensis, Streptomyces kanamyceticus, Streptomyces collinus, Streptomyces lasaliensis, Streptomyces lincolnensis, Dactosporangium aurantiacum, Streptomyces toxitricini, Streptomyces hygroscopicus, Streptomyces plicatus, Streptomyces lavendulae, Streptomyces ghanaensis, Streptomyces cinnamonensis, Streptomyces aureofaciens, Streptomyces natalensis, Streptomyces chattanoogensis L10, Streptomyces lydicus A02, Streptomyces fradiae, Streptomyces ambofaciens, Streptomyces tendae, Streptomyces noursei, Streptomyces avermitilis, Streptomyces rimosus, Streptomyces wedmorensis, Streptomyces cacaoi, Streptomyces pristinaespiralis, Streptomyces pristinaespiralis, Actinoplanes sp. ATCC 33076, Streptomyces hygroscopicus, Lechevalieria aerocolonegenes, Amycolatopsis mediterranei, Amycolatopsis lurida, Streptomyces albus, Streptomyces griseolus, Streptomyces spectabilis, Saccharopolyspora spinosa, Streptomyces ambofaciens, Streptomyces staurosporeus, Streptomyces griseus, Streptomyces (multiple species), Streptomyces acromogenes, Streptomyces tsukubaensis, Actinoplanes teichomyceticus, Streptomyces glaucescens, Streptomyces rimosus, Streptomyces cattleya, Streptomyces azureus, Streptoalloteicus hindustanus, Streptomyces chartreusis, Streptomyces fradiae, Streptomyces coelicolor, Streptomyces hygroscopicus, Streptomyces sp. 11861, Streptomyces virginiae, Amycolatopsis japonicum, Amycolatopsis balhimycini, Streptomyces albus J1074, Streptomyces coelicolor M1146, Streptomyces lividans, Streptomyces incarnates, Streptomyces violaceoruber, or Streptomyces griseofuscus. In some embodiments, the host cell is an Escherichia strain such as Escherichia coli. In some embodiments, the host cell is a Bacillus strain such as Bacillus subtilis. In some embodiments, the host cell is a Pseudomonas strain such as Pseudomonas putida. In some embodiments, the host cell is a Myxococcus strain such as Myxococcus xanthus.

Methods

The nucleic acids, vectors, and host cells of the invention may be used for increased and/or more efficient production of compounds (e.g., polyketides or β-lactam compounds). Introduction of recombinant and/or heterologous LALs to host cells or the introduction of heterologous binding sites to the gene clusters that produce a small molecule (e.g., PKS gene clusters or β-lactam compound producing protein gene clusters) allow for greater control of the regulations of the genes which encode the compound-producing proteins (e.g., polyketide synthases or β-lactam compound producing proteins) responsible for the production of compounds (e.g., polyketides or β-lactam compounds) of interest.

Introduction of Heterologous LAL

In some embodiments, compounds (e.g., polyketides or β-lactam compounds) are produced by introduction of a heterologous LAL to a host cell (e.g., the LAL may be introduced with an expression vector, such as an artificial chromosome, including a nucleic acid encoding the LAL). In some embodiments, the host cell naturally lacks an LAL. In some embodiments, the host cell naturally produces an LAL that is different from the introduced LAL. The introduced LAL may be any LAL with the conserved four helix bundle DNA binding region of the PKS regulating LALs. In some embodiments, the introduced LAL is a natural LAL. In some embodiments, the introduced LAL is a modified LAL, e.g., a constitutively active LAL. In some embodiments, the introduced LAL has at least 70% sequence identity to SEQ ID NO: 1. In some embodiments, the introduced LAL includes or consists of the sequence of SEQ ID NO: 1. In some embodiments in which the host cell naturally produces an LAL, the nucleic acid which expresses the natural LAL is deleted prior to introduction of the heterologous LAL. In certain embodiments, the introduced LAL is expressed from an expression vector in which the polynucleotide sequence encoding the LAL is codon optimized. For example, TTA codons, which are known to exert translational control of genes having such codons in a Streptomyces host cell, may be removed and/or replaced in the LAL coding sequence. In some embodiments, the host cell may be modified, for example, to remove a cytochrome P450 oxygenase.

Introduction of a Heterologous LAL Binding Site

In some embodiments, compounds (e.g., polyketides or β-lactam compounds) are produced by introduction of a heterologous LAL binding site to a host cell (e.g., the LAL binding site may be introduced with an expression vector, such as an artificial chromosome, including a nucleic acid having the LAL binding site or insertion via homologous recombination). In some embodiments, the host cell naturally lacks an LAL binding site. In some embodiments, the host cell naturally includes an LAL binding site that is different from the introduced LAL binding site. In some embodiments, the introduced LAL binding site has at least 80% identity to SEQ ID NO: 2. In some embodiments, the introduced LAL binding site includes or consists of the sequence of SEQ ID NO: 2. In some embodiments, the introduced LAL binding site includes the sequence GGGGGT (SEQ ID NO: 3). In some embodiments, the introduced LAL binding site results in increased production of a compound (e.g., a polyketide or a β-lactam compound). In some embodiments, the open reading frame encoding the compound-producing protein (e.g., a polyketide synthase or a β-lactam compound producing protein) is positioned such that binding of an LAL to the LAL binding site promotes expression of the biosynthetic protein(s) (e.g., a polyketide synthase or a β-lactam compound producing protein) and thus the compound (e.g., a polyketide or a β-lactam compound). In some embodiments, the LAL binding site has the sequence of SEQ ID NO: 2 and the LAL has the sequence of SEQ ID NO: 1.

In some instances, a construct may include one or more promoters including a heterologous LAL binding site. For example, a construct may include a unidirectional promoter driving the expression of one or more genes (e.g., genes in a gene cluster that produces a small molecule, such as a PKS gene cluster or a β-lactam compound producing protein gene cluster). In some instances, a construct may include a bidirectional promoter located between two sets of genes to be expressed, with one portion of the bidirectional promoter including a first LAL binding site and driving expression of one set of genes, and a second portion of the bidirectional promoter including a second LAL binding site and driving expression of the second set of genes. The two sets of genes may be oriented antiparallel relative to each other. In certain instances, a host cell may include a gene cluster under the control of a unidirectional or bidirectional promoter, as well as at least one gene encoding a heterologous LAL that is under the control of a promoter containing an LAL binding site. The gene cluster and the heterologous LAL-encoding gene may be located on the same construct, or may be located on different constructs. Expression of an LAL (e.g., an endogenous LAL or a heterologous LAL) results in expression of the heterologous LAL as well as the genes in the gene cluster. The expressed heterologous LAL may in turn further drive expression of the genes in the gene cluster and the heterologous LAL in a positive feedback loop.

Introduction of a Heterologous PKS Gene Cluster

In some embodiments, polyketides are produced by introduction of a nucleic acid encoding a heterologous PKS gene cluster to a host cell (e.g., the nucleic acid may be introduced with an expression vector, such as an artificial chromosome). In some embodiments, the nucleic acid further includes an LAL binding site. In some embodiments, the LAL binding site is heterologous to the PKS gene cluster. In some embodiments, the LAL binding site is homologous to the PKS gene cluster. In some embodiments, a heterologous LAL is also introduced to the host cell (e.g., the LAL may be introduced with an expression vector, such as an artificial chromosome, including a nucleic acid encoding the LAL). In some embodiments, the LAL is encoded by the same nucleic acid which encodes the heterologous PKS gene cluster. In some embodiments, the LAL is heterologous to the LAL binding site and/or the PKS gene cluster. In some embodiments, the LAL is homologous to the LAL binding site and/or the PKS gene cluster. In some embodiments, the polyketide synthase is not expressed in the absence of either an LAL or an LAL binding site.

A host cell may be modified to optimize production from the heterologous PKS gene cluster. In some embodiments, one or more tailoring enzymes (e.g., the cytochrome P450 oxygenase, cypB) is deleted. In some embodiments, a host cell may be modified to include a particular allele that confers resistance to an antibiotic (e.g., resistance alleles against streptomycin (e.g., rpsL), rifampicin (e.g., rpoB), and gentamicin), which may result in the production of higher secondary metabolite titers.

Introduction of a Heterologous β-Lactam Compound Producing Protein Gene Cluster

In some embodiments, β-lactam compounds are produced by introduction of a nucleic acid encoding a heterologous β-lactam compound producing protein gene cluster to a host cell (e.g., the nucleic acid may be introduced with an expression vector, such as an artificial chromosome). In some embodiments, the nucleic acid further includes an LAL binding site. In some embodiments, the LAL binding site is heterologous to the β-lactam compound producing protein gene cluster. In some embodiments, the LAL binding site is homologous to the β-lactam compound producing protein gene cluster. In some embodiments, a heterologous LAL is also introduced to the host cell (e.g., the LAL may be introduced with an expression vector, such as an artificial chromosome, including a nucleic acid encoding the LAL). In some embodiments, the LAL is encoded by the same nucleic acid which encodes the heterologous β-lactam compound producing protein gene cluster. In some embodiments, the LAL is heterologous to the LAL binding site and/or the β-lactam compound producing protein gene cluster. In some embodiments, the LAL is homologous to the LAL binding site and/or the β-lactam compound producing protein gene cluster. In some embodiments, the β-lactam compound is not expressed in the absence of either an LAL or an LAL binding site.

A host cell may be modified to optimize production from the heterologous β-lactam compound producing protein gene cluster. In some embodiments, one or more tailoring enzymes is deleted. In some embodiments, a host cell may be modified to include a particular allele that confers resistance to an antibiotic (e.g., resistance alleles against streptomycin (e.g., rpsL), rifampicin (e.g., rpoB), and gentamicin), which may result in the production of higher secondary metabolite titers.

Quantification of mRNA Transcripts by NanoString Analysis

In some embodiments, gene expression (e.g., expression of one or more genes regulated by a heterologous LAL binding site) may be quantified using the NanoString nCounter Analysis System® (Nanostring). The NanoString nCounter assay involves direct digital detection of mRNA molecules using target-specific, color-coded probe pairs. It does not require the conversion of mRNA to cDNA by reverse transcription or the amplification of the resulting cDNA by PCR. Each target gene of interest is detected using a pair of reporter and capture probes carrying 35- to 50-base target-specific sequences. In addition, each reporter probe carries a unique color code at the 5' end that enables the molecular barcoding of the genes of interest, while the capture probes all carry a biotin label at the 3' end that provides a molecular handle for attachment of target genes to facilitate downstream digital detection. After solution-phase hybridization between target mRNA and reporter-capture probe pairs, excess probes are removed and the probe/target complexes are aligned and immobilized in the nCounter cartridge, which is then placed in a digital analyzer for image acquisition and data processing. Hundreds of thousands of color codes designating mRNA targets of interest are directly imaged on the surface of the cartridge. The expression level of a gene is measured by counting the number of times the color-coded barcode for that gene is detected, and the barcode counts are then tabulated. The methodology and uses of NanoString are further described in Kulkarni, M. Curr. Protoc. Mol. Biol. 94:25B.10.1-25B.10.17 (2011).

In some embodiments, Nanostring analysis is used to determine if the expression of a locus of a gene cluster (e.g., a PKS gene cluster or a β-lactam compound producing protein gene cluster), which is located in proximity to a heterologous LAL binding site, is upregulated relative to the same locus when the locus is not located in proximity to a heterologous LAL binding site.

EXAMPLES

Methods
LAL Cloning:

LAL gene sequences from FKPHD gene clusters were obtained from the WarpDrive genome database or from public sources such as GenBank. LAL genes were modified from wild-type to remove single or multiple TTA codons, which are known to exert translational control of genes having these codons in *Streptomyces*. Synthetic EcoRI/XbaI bounded cassettes composed of the strong constitutive ermE* promoter, the TTA-less LALs, and the transcriptional terminator from phage fd were cloned into pSET152 having a PhiC31 integrase and attP site, an apramycin resistance gene, and an oriT for conjugal transfer from conjugation-proficient *Escherichia coli*. The TTA-less LAL genes were also inserted into other integrative vectors (example pWFE1), or functional equivalents, remaining under the transcriptional control of the strong constitutive promoter PermE*.

LAL gene panels cloned into pWFE1 were introduced into Actinomycete bacteria harboring genomic FKPHD gene clusters, and also having predicted LAL binding sites in the promoter-operator regions of their FKPHD biosynthetic loci, by intergeneric conjugation using donor strain JV36. Intergeneric conjugations were carried out as using standard methods on R2NSY media at 30° C. or 37° C., and conjugation plates were overlaid after 18-48 hours with 0.3-2.0 mg apramycin and 0.5-1.0 mg nalidixic acid. Actinomycete exconjugants harboring the pWFE1-LAL plasmids were streaked to fresh plates containing apramycin (30-50 mg/L) and nalidixic acid (25-30 mg/L) to remove residual *E. coli* donor and confirm stable apramycin resistance.

Recombinant Actinomycetes carrying integrated LAL plasmids were tested for FKPHD production as follows: Starter cultures of Actinomycetes were grown in 15 ml Maltose-Yeast extract-Glucose broth containing apramycin (25-50 mg/L). After 2-3 days at 29-30° C., the starter cultures plated for confluence to solid media suitable for production (e.g., Medium 2 or 8430 or others). After 6-7 days of growth at 30° C., two agar plates having confluent actinomycete growth were harvested for extraction. Briefly, agar with adherent actinomycete growth was removed from petri plates and extracted with 100% methanol. After soaking overnight in methanol, the agar was removed, and the methanol was diluted with water to 15-30% final concentration. FKPHD compounds were captured from the aqueous extract using Phenomenex C18-U SPE columns (0.5 g, 6 mL capacity). After washing columns with bound extract with 30% Methanol, remaining molecules including FKPHDs were eluted with 100% methanol.

Methanol was removed from eluates in vacuo, and resulting crudes were dissolved in DMSO. The dissolved samples were then diluted as necessary in methanol (generally 10 μL into 490 μL neat methanol), and analyzed by LC/MS. (Agilent HPLC with diode array in line with Agilent 6120 single quad mass spectrometer). Screens for improved strains were determined on a semi-quantitative using conventional analyses using Agilent MassHunter or Agilent ChemStation software, measuring area-under-curve (AUC) of ion-extracted mass chromatograms. Final assessment of strain improvement was done by scaled liquid growths, molecule purification, and measurement by weight and NMR using internal standards as compared to wild-type strains lacking pWFE1-LAL constructs.

Deletion of Biosynthetic Enzymes:

Deletion of biosynthetic enzymes to increase the titer of specific FKPHD compounds were made in the following way: First, ~1 kb regions of homology flanking the start and stop codons of genes selected for deletion were amplified by PCR. These homology arms were assembled into a single deletion cassette using overlap-extension $PC_R$, and cloned to the *E. coli*-*Streptomyces* shuttle vector pJVD52.1. Deletions were carried out as known in the art, with vectors carrying deletion cassettes being delivered into target strains using conjugation, as detailed above. Of note, pJVD52.1-based deletion strategies can make use of streptomycin counter-selection, and utilize parent strains with rpsL mutations. Bacteria spontaneously mutated in the rpsL allele are known to be isolable when strains are plated in the presence of streptomycin (10 to 100 μg/mL) on suitable media (e.g., ISP2, Becton Dickinson Co.). Putative mutant actinobacterial deletion hosts were confirmed to have desired lesions in rpsL by amplification by PCR and comparison to wild-type rpsL DNA sequences.

Resulting deletion strains in an rpsL background were then fermented as above, and fermentation extracts containing FKPHD compounds were analyzed against wild-type and rpsL parent strain extracts, confirming increased titers of specific FKPHDs are attributable to specific gene deletions (e.g., genes encoding predicted cytochrome P450 oxygenases) and not to rpsL mutations required for the gene deletion process.

Inducing rpoB/rpsL:

Actinobacteria harboring specific alleles conferring resistance to certain antibiotics can sometimes produce higher secondary metabolite titers than strains lacking these alleles. Spontaneous bacterial mutants harboring these alleles can be selected for using antibiotics including streptomycin (rpsL), rifampicin (rpoB), gentamicin, and others. These antibiotic resistance phenotypes can be useful singly, or in combination (double, triple mutants, or more). Isolation of improved FKPHD producers, in combination with LAL gene cluster activation, illustrates the utility and compatibility of combining both recombinant strategies for strain enhancement over wild-type. To isolate spontaneous rpoB mutants (rpsL described above), vegetative mycelia or spores of desired strains were spread to ISP2 plates containing rifampicin, and resulting individual colonies were cultivated in the presence of rifampicin to confirm resistance. Nucleotide lesions in rpoB leading to antibiotic resistance were confirmed by PCR amplification of the rpoB locus from resistant isolates in parallel with sensitive parent strains, and the DNA sequences of both were compared. Sequence-confirmed rpoB mutants were then compared in fermentation panels, screening for increased production against wild-type and LAL-enhanced recombinant strains without resistance alleles.

Promoter Swap and Promoter Repair:

A PAC library was prepared from the genomic DNA of the *Streptomyces* strain harboring the wild-type X15 gene cluster and cloned into the pESAC13 backbone by BioSandT (Montreal, Canada). Molecular clones with intact wild-type X15 gene clusters were identified from the library by colony PCR. The X1.1-S12 promoter was PCR amplified with the following primers (see below) from the S12 gene cluster and cloned into the X15 gene cluster.

X15_LAL_F
SEQ ID NO: 37
5'-CAAAGCGATTCGGAGAGCGGCCGGATCAGATCCAGGCGTGACATTCA
TACCCTTCCGGCGAAGTGCAGTTCACCC-3'

X15_LAL_R
SEQ ID NO: 38
5'-CGATCTTCTCGAAACTGCACTGAGGAGGTTCGTCGGAGACTGCCATT
CACCTCTCCCGGAAAGGTATTGCTCG-3'

To introduce the S18 LAL transcription factor, a Gateway acceptor vector (ThermoFisher, Grand Island, N.Y.) was first cloned into the pESAC13 backbone. The S18 LAL was transferred to the X15 PAC backbone using LR Clonase. The same approach was used to repair the non-canonical LAL promoter sequences in the X11.2 PAC. The X11.1 and X11.2 promoters with repaired LAL sites were generated by synthetic gene construction design with the DNAWorks webserver (mcl1.ncifcrf.gov/dnaworks/).

>PAC_HA_X11.1_promoter_G
SEQ ID NO: 39
5'-GCGTTCGGCATTGACGCGAAGCAAGTCATGAATCGGCTGAATCAATT
CCGCGCGCGACATTCGCACCCTTCCGGTGAAGTGCGGTATTGCTCAGACA
TAACCCGGATCGCAATCCAACGACCAGCCATGCACTACCGATAATCGAAT
CGGAACAATAGCAAGCTCGTTGAGCATATTTTCCATGCGGCACCACCTCG
GCGCCACCCCCTAGTTTTGCCGACCCCCTATGTGTATTTCGGCAGGCAGA
CTAGGGGGTTGCGTGGGCCGCACCCGAGGCATTCGATTGGCGCACGGCGC
ACTCGGGCCATGTCACCGACCGTGAATGTTTCATCGCTACGGGTAGCAAT
AGTCCTTTCTCGGGAGAAGTGAATGGCTTCCAAAAGTCCCCGCCCAGGGT
CCGAGAGAGCGGGTTCTGCGATTTCCCGGGCA-3'

>PAC_HA_X11.1_promoter_G_4 bp
SEQ ID NO: 40
5'-GCGTTCGGCATTGACGCGAAGCAAGTCATGAATCGGCTGAATCAATT
CCGCGCGCGACATTCGCACCCTTCCGGTGAAGTGCGGTATTGCTCAGACA
TAACCCGGATCGCAATCCAACGACCAGCCATGCACTACCGATAATCGAAT -continued
CGGAACAATAGCAAGCTCGTTGAGCATATTTTCCATGCGGCACCACCTCG
GCGCCACCCCCTAGTTTTGCCGACCCCCTATGTGTATTTCGGCAGGCAGA
ACACCTAGGGGGTTGCGTGGGCCGCACCCGAGGCATTCGATTGGCGCACG
GCGCACTCGGGCCATGTCACCGACCGTGAATGTTTCATCGCTACGGGTAG
CAATAGTCCTTTCTCGGGAGAAGTGAATGGCTTCCAAAAGTCCCCGCCCA
GGGTCCGAGAGAGCGGGTTCTGCGATTTCCCGGGCA-3'

>PAC_HA_X11.2_promoter_A
SEQ ID NO: 41
5'-GCGTTCGGCATTGACGCGAAGCAAGTCATGAATCGGCTGAATCAATT
CCGCGCGCGACATTCGCATCCTTCTGGTGAGGTGCAGTATTGCTGAGACA
TAATCCGGGCCGTAATCCAACGACCAGCCATGCGCCGCCGATAGTCGAAT
CCGATAGTCGAATCTGAACGCTAGCAGCTCGTCGCAGGGGCTCCGGGGAG
CCCAACCCCCTAATTTTTCCGCCCCCCTATACATATCCACTGCAGGCAGA
ACACCTAGGGGGTTGCGCGAACCGGGCGCGCGGTATCGGATTTACCGCAC
GGCACACTCGGGCGACGTCACCGACCGTGAATCCTTCATCGCTACGGGTA
GCACAGTCCTTTCCGGGAGAAGTGAATGGCTTCCAAAAGTCCCCGCCCAG
GGTCCGAGAGAGCGGGTTCTGCGATTTCCCGGGCA-3'

>PAC_HA_X11.2_S12_promoter SEQ ID NO: 42:
5'-GCGTTCGGCATTGACGCGAAGCAAGTCATGAATCGGCTGAATCAATT
CCGCGCGCGACATTCATACCCTTCCGGCGAAGTGCAGTTCACCCGGTAAT
GCATTCCGGACCGTAGCAGTCCGATACAGACGTCCGCCATGCCGTGCCAC
CCTTGTTTTTCACCCCCCTACGCCCGTTTCGCCTGGCCGGAAACCTAGGG
GGTTGCGTGGAAAGCACCGGCGGGTGTTCGCTTGCACAGCGCCACCTCGG
GCATTTTCTGGATGCGCGAGCAATACCTTTCCGGGAGAGGTGAATGGCTT
CCAAAAGTCCCCGCCCAGGGTCCGAGAGAGCGGGTTCTGCGATTTCCCGG
GCA-3'

The wild-type X2 gene cluster was prepared from *Streptomyces* genomic DNA and cloned into the modified pCC1 backbone by Intact Genomics, Inc. (St. Louis, Mo.). The UniLAL promoter was PCR amplified from the UniLAL-S18-LAL expression vector and cloned into the X2 gene cluster.

Example 1. Use of LAL Transcriptional Regulators as General Induction and Overexpression Strategy Gene clusters under the control of one or more bidirectional promoters were constructed. In particular, a set of FkPhD gene clusters was generated (FIG. 1A), each including two bidirectional promoters, shown as Promoter Region 1 and Promoter Region 2. Each promoter contained one or more LAL binding domains selected from those shown in FIG. 1B. Alignment of a set of such putative LAL binding domains extracted from FK gene cluster promoter regions revealed conserved regions. As shown in FIG. 1C, the general experimental approach involved subcloning of a codon-optimized LAL panel into an integrating vector driven by, e.g., a strong ermE* promoter.

Figure 3:
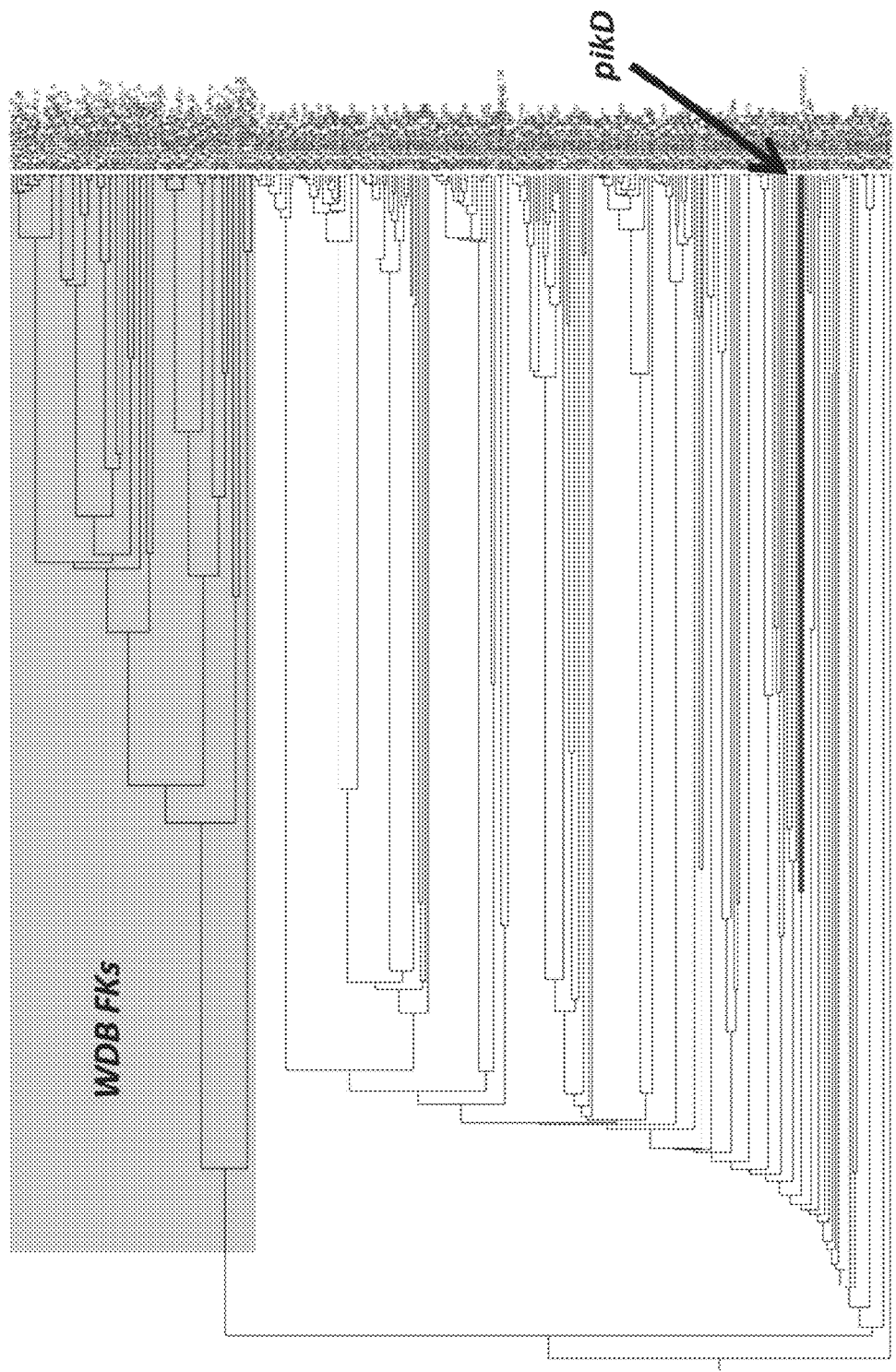
FIG. 3 is a cladogram showing that FkPhDs cluster together and are distinct from other PKS-associated LALs, such as pikD.

LALs were selected for these experiments by clading all LALs in a high pass genomic database including publication-quality assembled genomes (FIG. 2). These LALs were claded using the helix-turn-helix motif of the rapamycin LAL (S9), yielding a design query. FkPhD LALs were shown to clade together and were dissimilar on a sequence level from other Type I PKS-associated LALs, such as pikD (FIG. 3).

Figure 4:
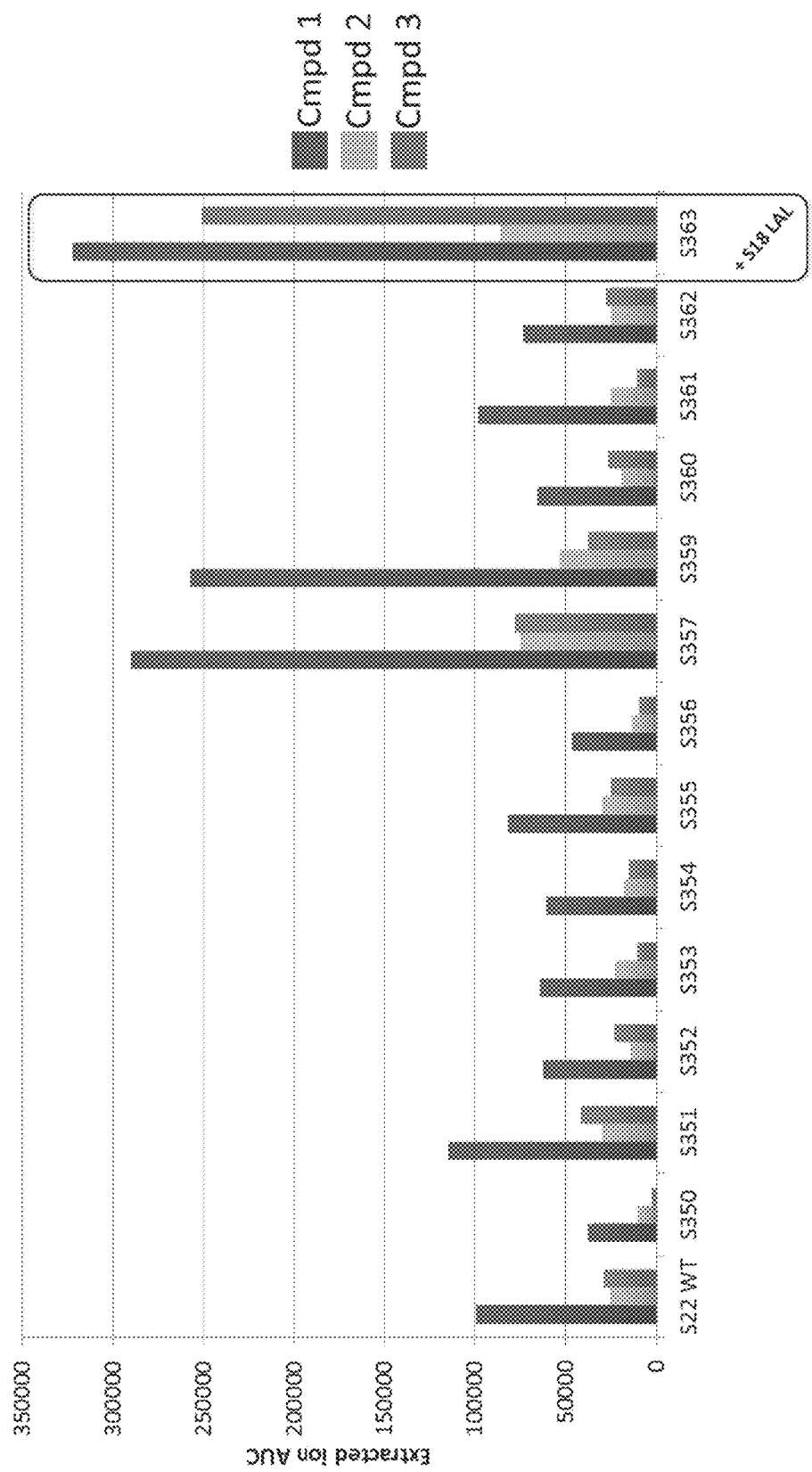
FIG. 4 is a graph showing S22/LAL exconjugants assayed for increased Compound 1, Compound 2, and Compound 3 production by LC/MS.
Figure 5:
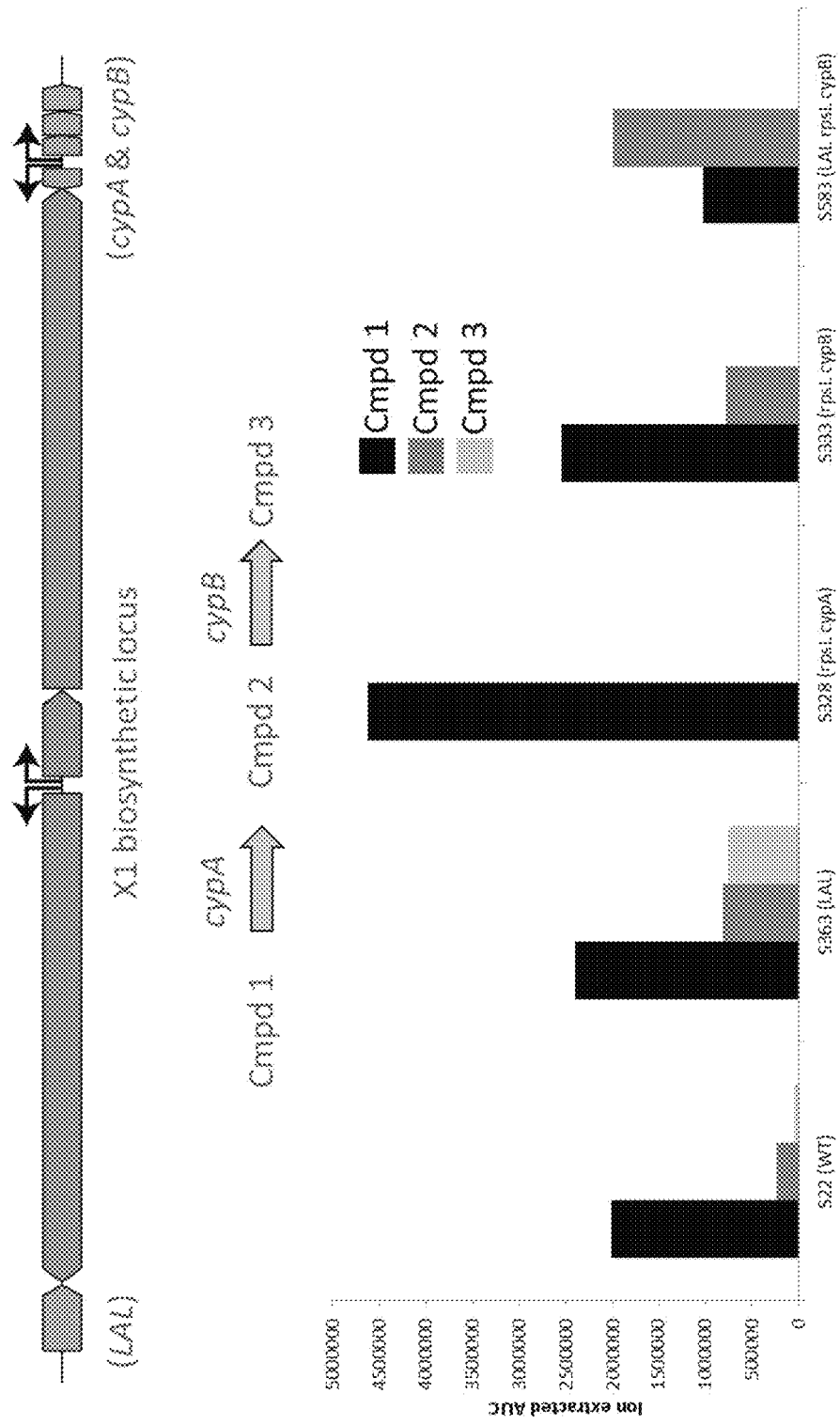
FIG. 5 is a series of diagrams showing combined LAL and cyp manipulations for increased production of Compound 1 and Compound 2 in S22.

Example 2. Expression of LALs Drives Polyketide Production from Biosynthetic Gene Clusters As presented in FIG. 4, a large panel of LALs was expressed in a native *Streptomyces* producer of the X1 family of molecules (Compound 1, Compound 2, and Compound 3). Specifically, the X1 FkPhD gene cluster was observed in the S22 native strain, and a panel of LALs were then conjugated into the S22. The resulting strains were assayed for enhanced expression of polyketides. Production of the X1 gene cluster family of products (i.e., Compound 1, Compound 2, and Compound 3) was assessed by LC/MS. The results indicated that some LALs acted as repressors and suppressed polyketide expression compared to wild-type (i.e., in the absence of LAL). In some cases, the LAL significantly increased the expression of the polyketide compared to wild-type. These results, therefore, indicated that certain LALs are constitutively active in this context. S363, the exconjugate with the integrated vector constitutively expressing the S18 LAL, produced the highest levels of Compound 1, Compound 2, and Compound 3. The production of the desired product, Compound 2, was further optimized by combining S18 overexpression with other modifications to the biosynthetic locus, including ribosomal protein rpsL mutations (e.g., induced by streptomycin) and P450 deletion (FIG. 5). The resultant strain, S583, yielded increased production of Compound 2.

Figure 6:
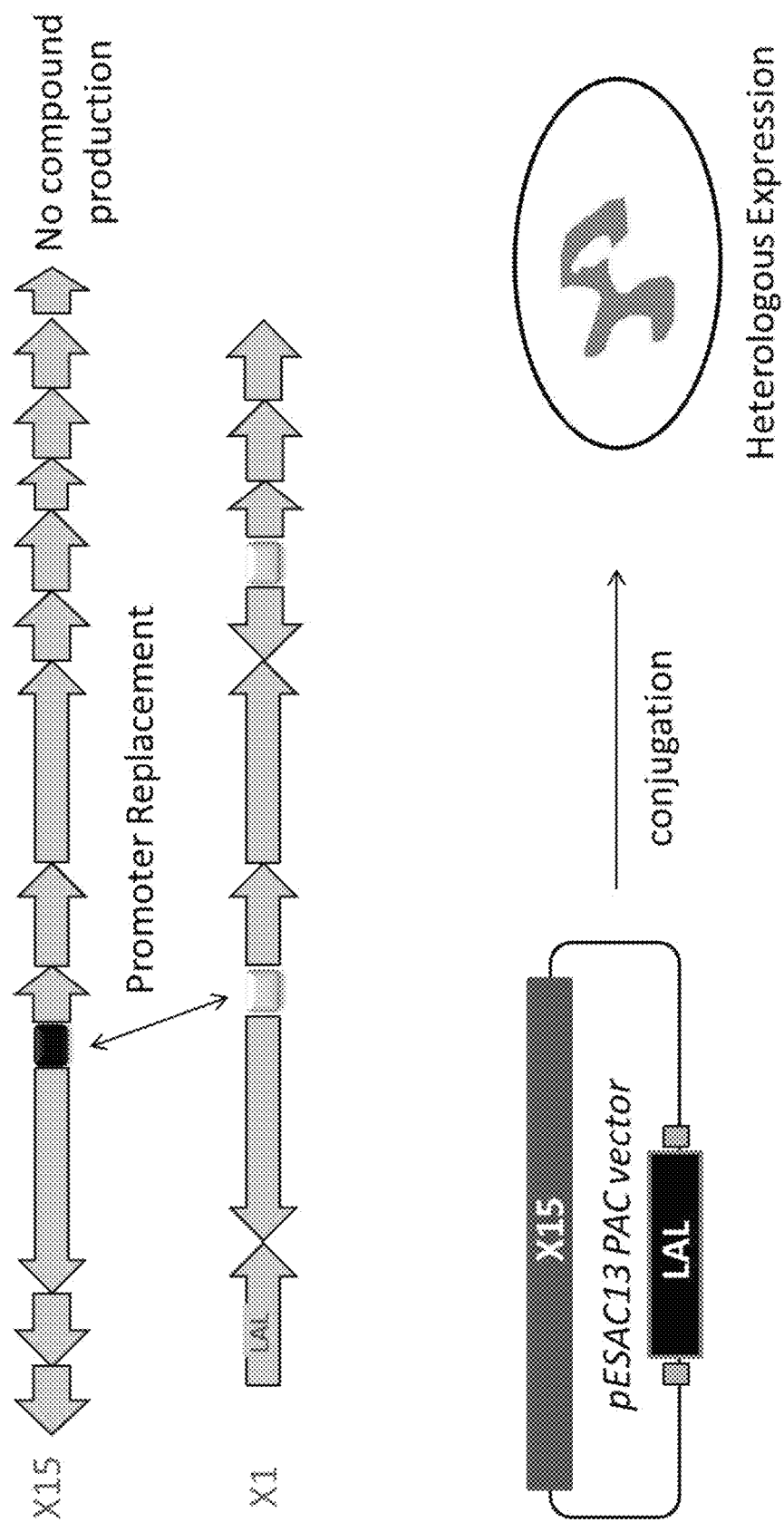
FIG. 6 is a diagram showing a strategy for replacement of the X15 promoter with an X1 promoter and introduction of a heterologous LAL-encoding locus.

Example 3. Promoter Engineering to Replace a Silent LAL Promoter in a Biosynthetic Gene Cluster The X15 gene cluster includes a silent promoter containing no canonical LAL binding sites. This promoter was replaced with the X1 promoter, which includes LAL binding sites to produce a refactored X15 gene cluster under the control of the X1 promoter (FIG. 6). A pESAC13 expression vector including the refactored X15 gene cluster was then modified by Gateway cloning to introduce a cassette where expression of the S18 LAL is under the control of the ermE* promoter. The resultant expression vector was then conjugated into S942 cells (a derivative of *Streptomyces ambofaciens*) for heterologous expression of the S18 LAL and biosynthetic genes in the X15 gene cluster.

Figure 7:
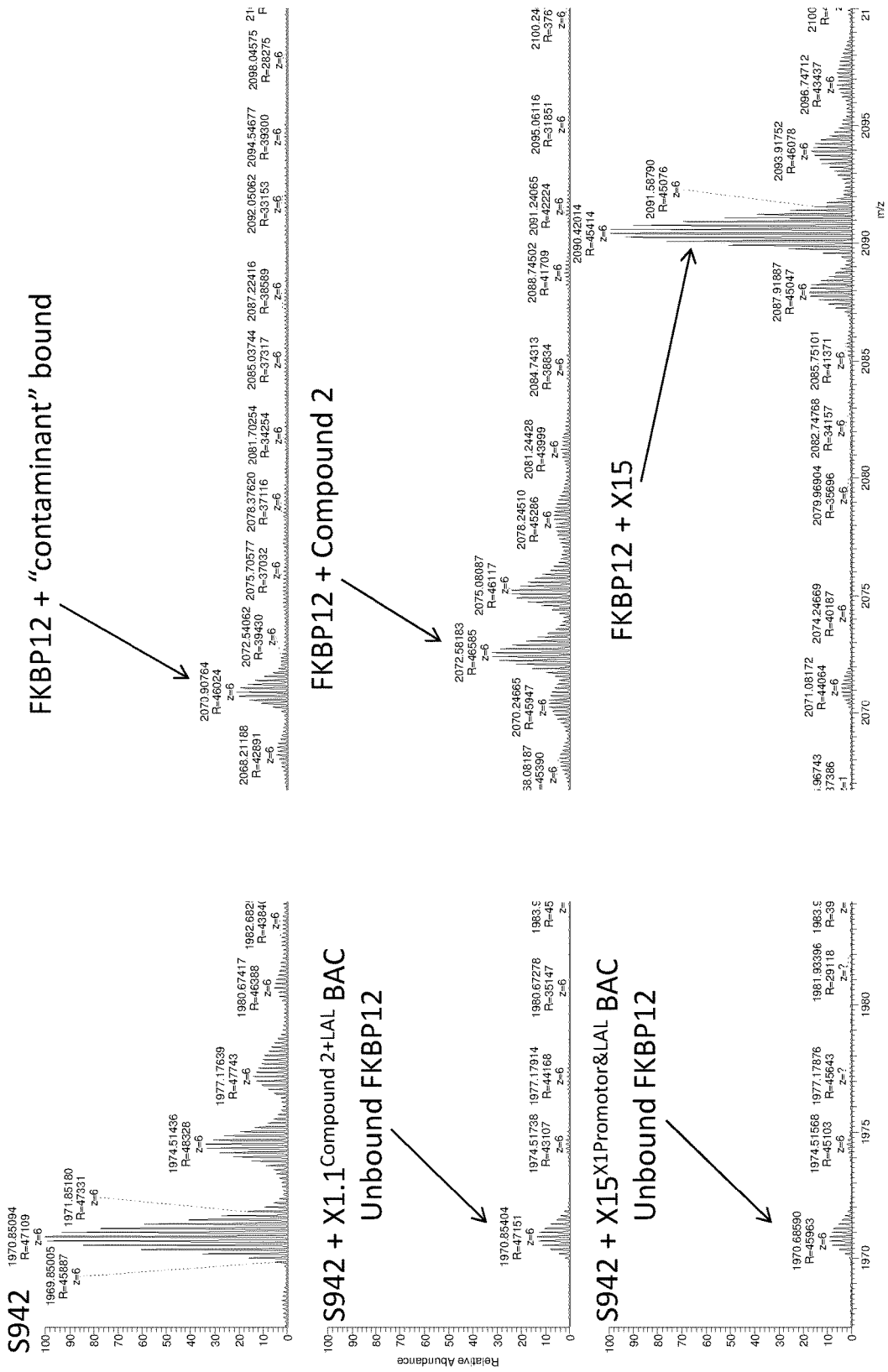
FIG. 7 is a series of graphs showing that replacement of the X15 promoter with an X1 promoter and heterologous LAL expression leads to biosynthetic production from the silent X15 cluster.

As shown in FIG. 7, re-engineering of the X15 gene cluster to replace the X15 promoter with the X1 promoter resulted in expression of X15 gene cluster genes and downstream production of X15 biosynthesis products at high levels. The top row of panels shows S942 alone as a control. The middle panel shows a strain generated by conjugating S942 to the X1 gene cluster (encoding Compound 1 and Compound 2) with the S18 LAL expressed from the vector backbone. Compound 2 expression is observed by Top-Down proteomics analysis. This data confirms that LAL expression can induce PKS expression of a strain with an intact promoter, as defined the by presence of functional LAL binding sites, in a heterologous producer strain. The bottom panels show the above-described strain generated by conjugating S942 to the X15 gene cluster with the endogenous promoter swapped with the X1 promoter and with the S18 LAL expressed from the vector backbone. These data showed that X15 production matched or exceeded that of S942 cells engineered to produce Compound 2 from an X1.1 locus. Thus, the data confirms that promoter replacement and LAL expression can induce PKS expression from a silent gene cluster in a heterologous producer.

Example 4. FK Bi-Directional Promoters

Figure 8:
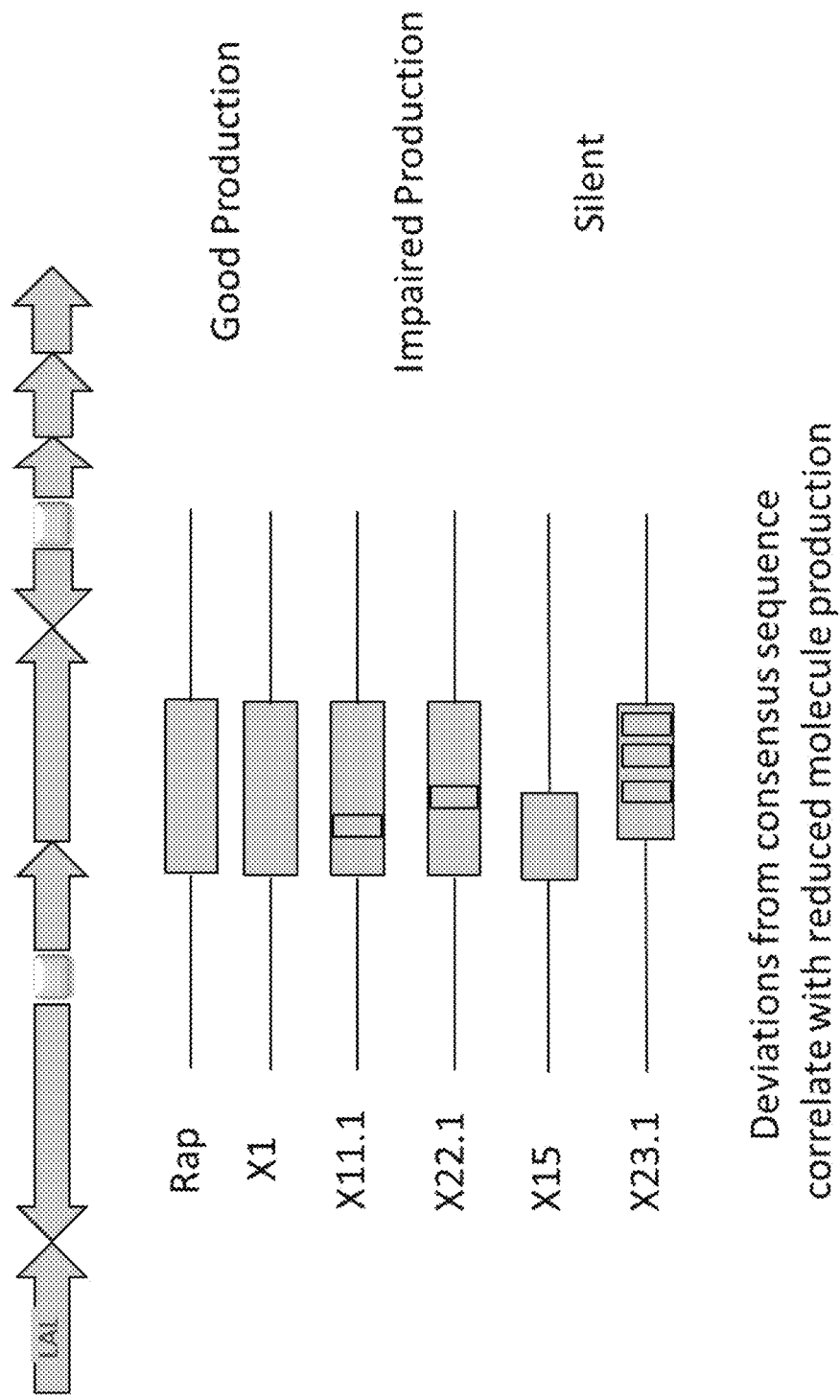
FIG. 8 is a diagram showing sequence analysis of various FK bidirectional promoters. Rap and X1 promoters were associated with good production. X11.1 and X22.1 promoters were associated with impaired production. X15 and X23.1 promoters were silent. Deviations from the consensus sequence correlated with reduced molecule production.

The sequences of the promoters from rapamycin, X1, X11.1, X22.1, X15, and X23.1 biosynthetic gene clusters were analyzed to correlate conserved sequence elements to native and/or heterologous production (FIG. 8). Three general classes of bidirectional FkPhD promoters were identified: (1) highly active promoters with intact promoter sequences including the functional LAL binding sites (e.g., rapamycin and X1), (2) less active promoters with impaired production in which mutations are observed in the core LAL binding sites (e.g., X11.1 and X22.1), and (3) silent promoters with severe deviations from the consensus sequence (e.g., X15 and X23.1). Generally, deviations from the consensus promoter sequence correlated with reduced compound production.

Figure 9:
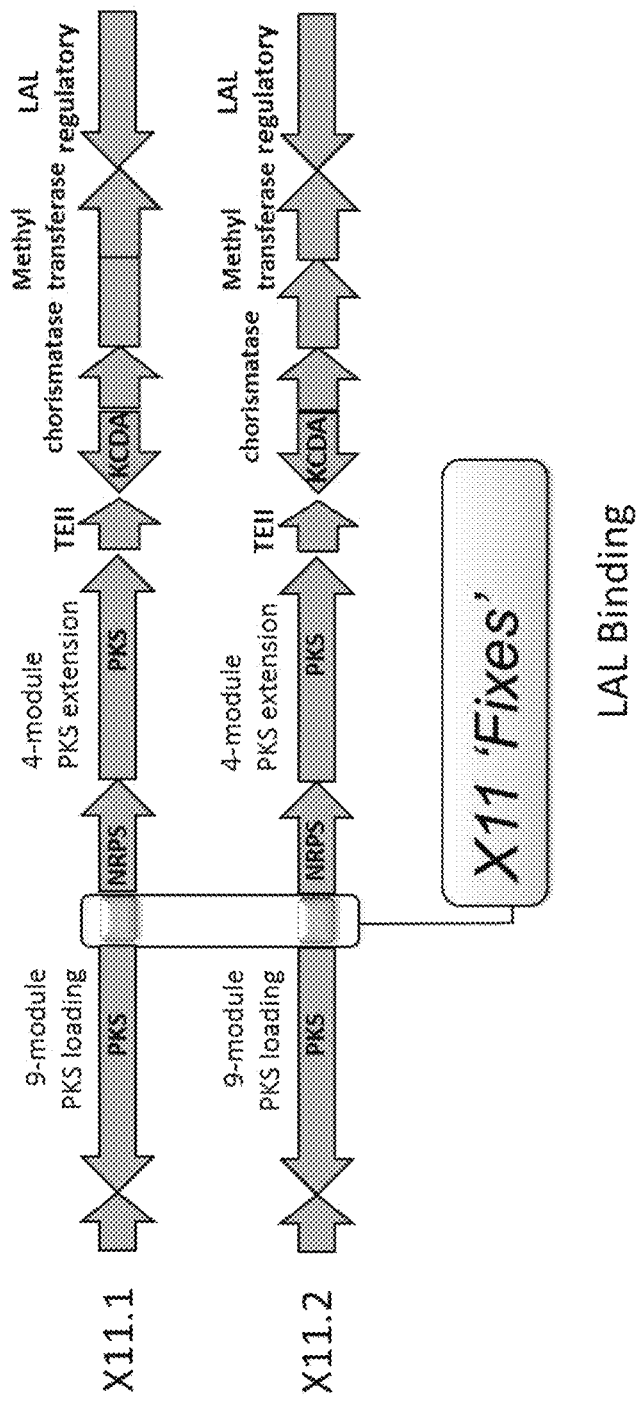
FIG. 9 is a diagram showing X11.1 and X11.2 bidirectional promoter engineering and sequence alignment of wild-type (i.e., X11.1 and X11.2) and restored (i.e., Seq1, Seq2, and Seq3) LAL binding sequences.

Sequence alignments of the LAL binding sites within the primary bi-directional promoters of two novel and related FkPhD gene clusters, X11.1 and X11.2, showed several mutations (deviations from the consensus LAL binding site) that appeared to modulate promoter strength and resultant production. For example, mutations were identified that reduced promoter strength and led to poor FkPhD expression (FIG. 9). In the case of X11.1, the wild-type promoter lacked the conserved ACAC motif and a G from a core LAL operator sequence (AGGGGG). In the case of X11.2, the wild-type promoter lacked an A from the core LAL operator sequence. We restored the X11.1 and X11.2 sequences to the consensus sequence to generate the sequences shown as Seq1, Seq2, and Seq3, and examined whether repairing these mutations impacted expression in the X11.2 gene cluster.

Figure 10:
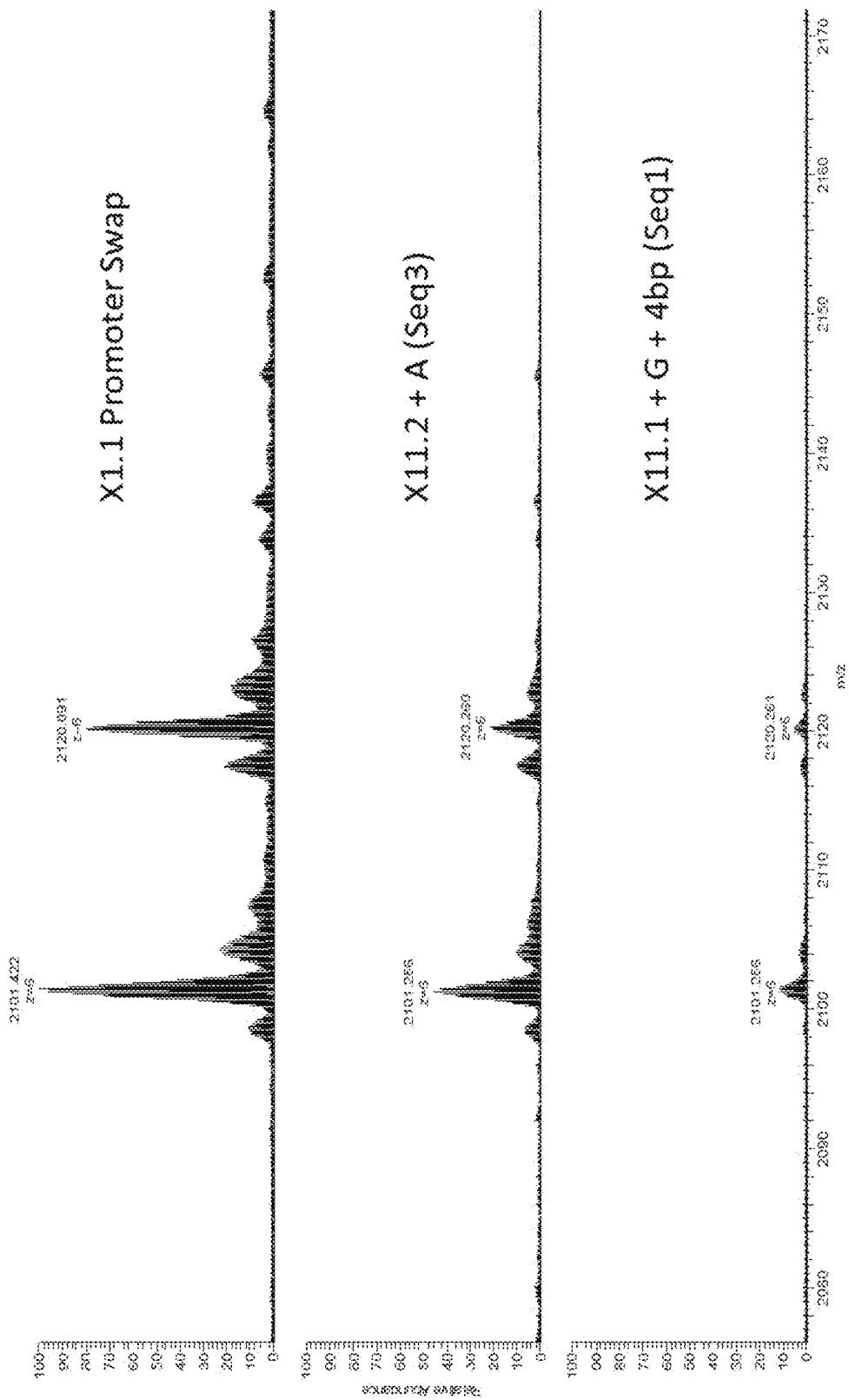
FIG. 10 is a series of graphs showing that restoration of sequence lesions in the LAL sequences yields increased PKS production.

The restored sequence lesions in the LAL binding sequence yielded increased polyketide synthase production. FIG. 10 shows a comparison of X11.2 FkPhD expression with the X1.1 promoter swap, the X11.1 promoter with the core G and ACAC motif restored (Seq2), and the X11.2 promoter with the A from the core LAL binding sequence restored (Seq3). In contrast to the wild-type (WT) 11.2, the Seq2 promoter yielded a significant increase in FkPhD production. Restoration of the A from the core LAL binding sequence (Seq3) increased FkPhD production more than the Seq2 promoter. The total X1 promoter swap yielded the greatest FkPhD production. These data show that restoring mutated conserved promoter sequences is a reliable approach for increasing FkPhD production. These data also provide support experiment support for our definition of the core LAL binding site sequence.

Example 5. UniLAL Variants

Figure 11A:
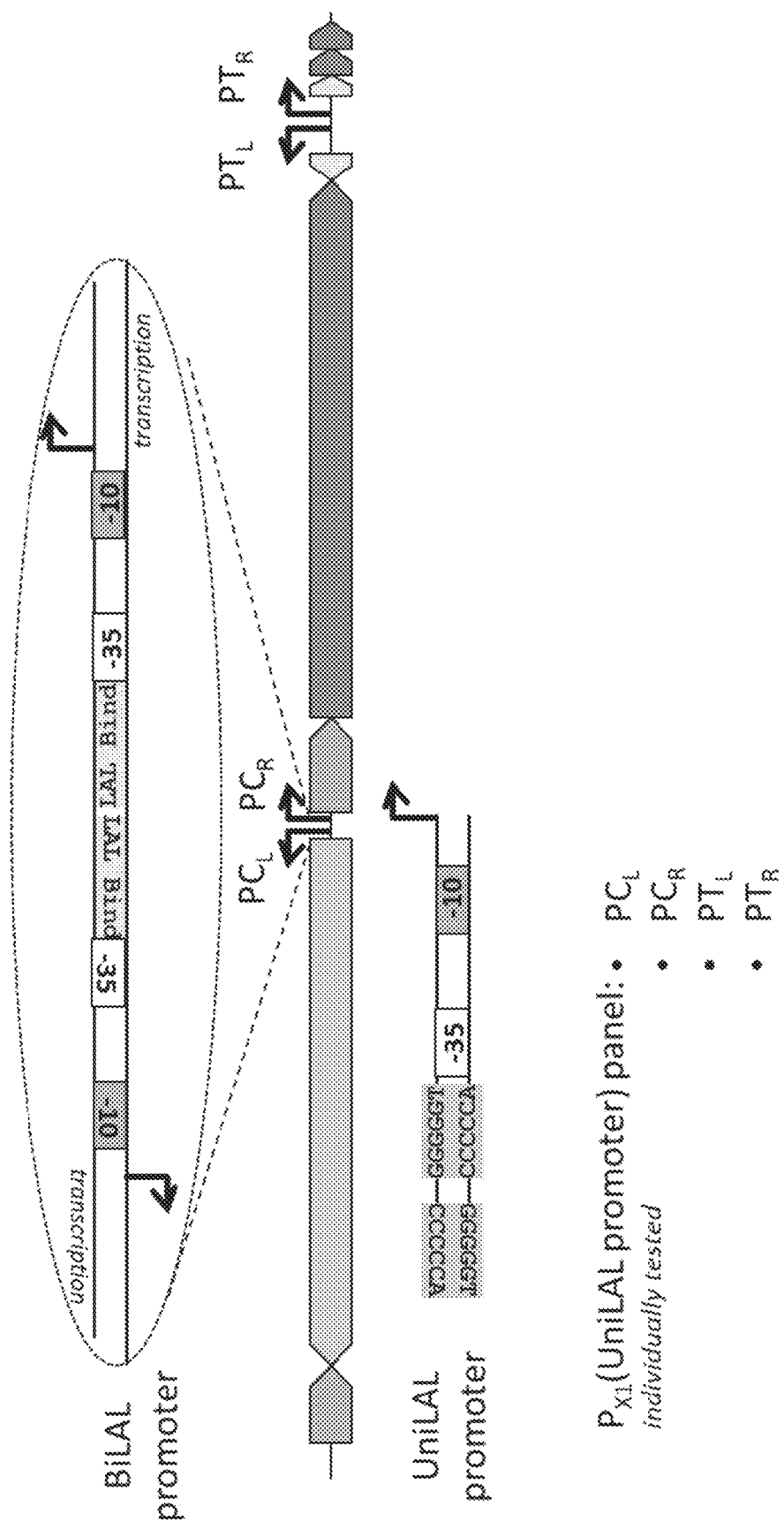
FIG. 11A is a diagram showing the dissection of the two promoter regions in a biosynthetic locus used to create the four UniLAL variants ($PC_L$, $PC_R$, $PT_L$, and $PT_R$).
Figure 11B:
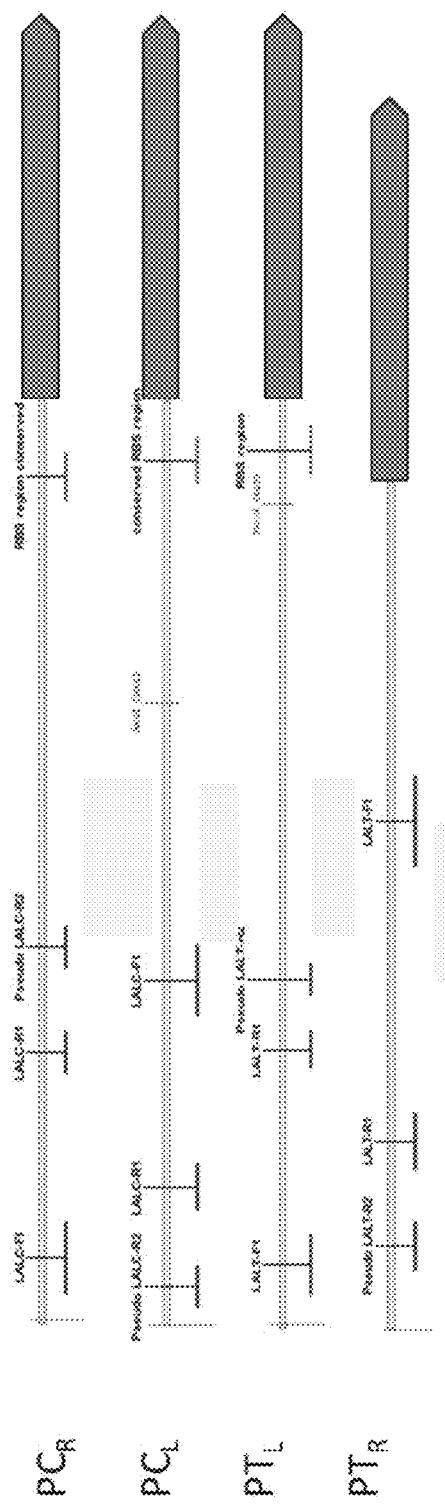
FIG. 11B is a diagram showing the nucleic acid sequence engineering strategy applied to generate the four UniLAL variants.

Promoter Region 1 and Region 2 bidirectional promoters were strategically dissected to yield four promoter designs (i.e., $PC_L$, $PC_R$, $PT_L$, $PT_R$) for subsequent functional testing (FIG. 11A) Each UniLAL variant included a −10 and −35 site as well as an LAL binding site. FIG. 11B captures the logic of UniLAL dissection. The UniLAL promoter was defined as the ribosome binding site (RBS), LAL binding sites and/or key prokaryotic promoter elements such as −10 and −35 sites. In some instances, the LAL binding site overlapped or replaced the −10 or −35 sites. In addition to the composition and sequence of these key elements, the spacing and orientation (sense/antisense) may be essential to the function of a particular design.

Figure 12:
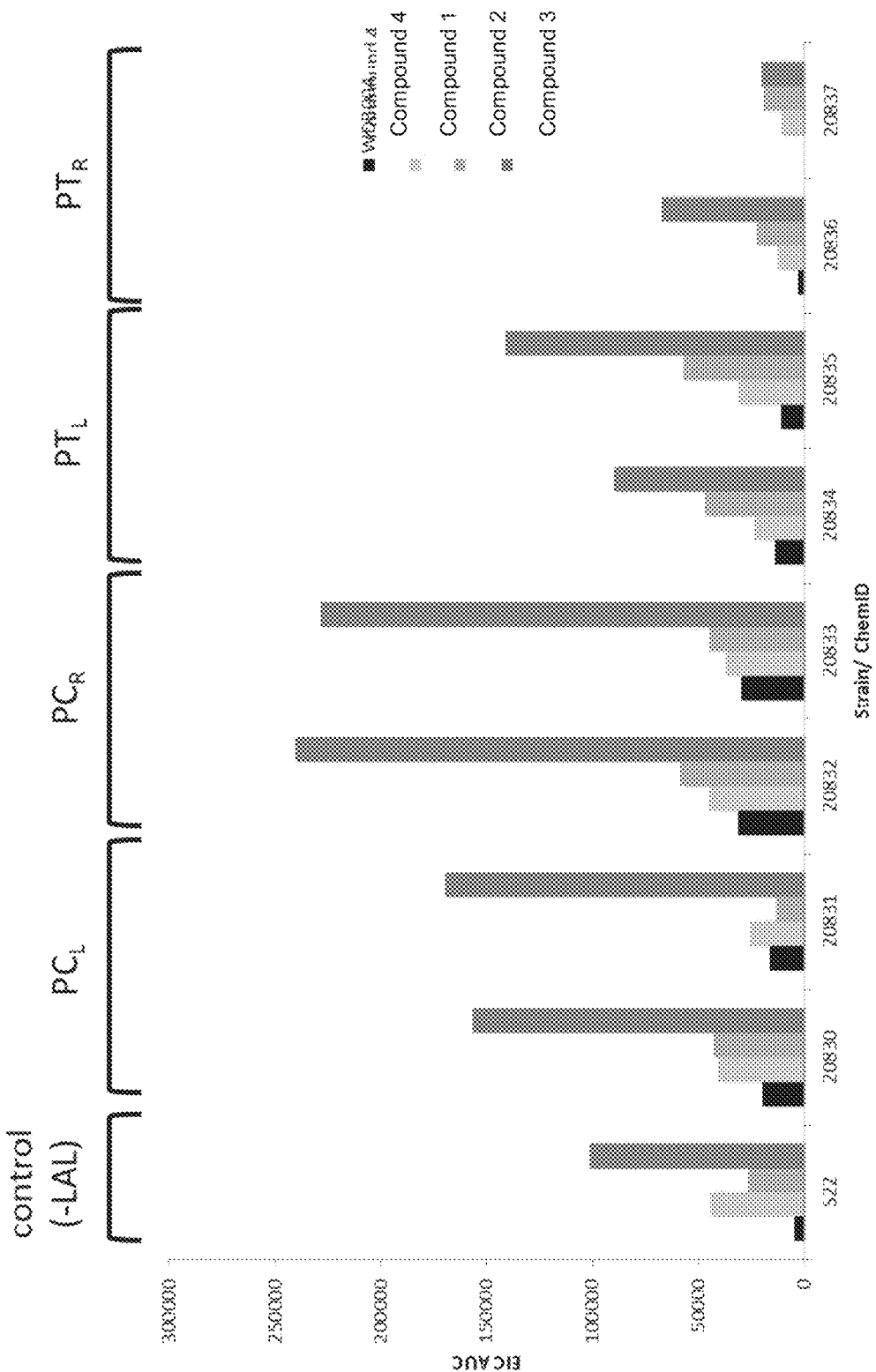
FIG. 12 is a graph showing the level of Compound 1, Compound 2, Compound 3, and Compound 4 produced in an LAL-negative S22 control and when one of each of the four UniLAL variants was subcloned in front of the S18 LAL and used to drive PKS expression in S22.

The promoter strength of each of the UniLAL variants was assessed. In order to rank order the 4 UniLAL designs ($PC_L$, $PC_R$, $PT_L$, $PT_R$), each UniLAL promoter was subcloned in front of the S18 LAL. The resulting integrative expression plasmid was conjugated to S22, which produces the Compound 2 family of compounds. As such, the Uni-LAL promoter in a particular conjugant was expected to be activated by the S18 LAL to create a feed-forward circuit to maximize LAL expression, gene cluster activation and produce an increase in Compound 2 production. Production of Compound 4, Compound 1, Compound 2, and Compound 3 induced by each of the UniLAL promoters is shown in FIG. 12. These data show that the Promoter Region 1 designs (i.e., $PC_L$, $PC_R$) are most effective for driving LAL expression and gene cluster production.

Figure 13:
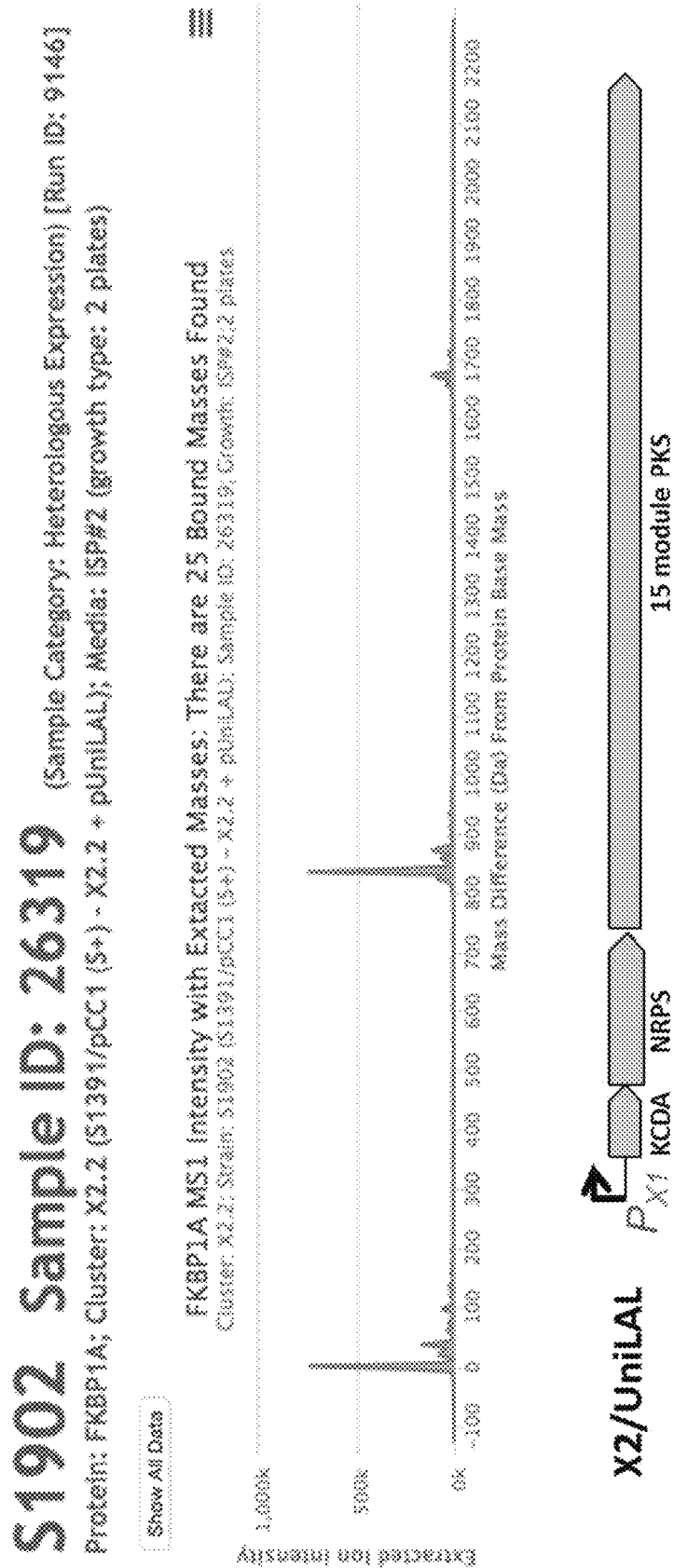
FIG. 13 is a graph showing activation of polyketide production from a transcriptionally silent biosynthetic cluster that does not naturally include an LAL regulator using a UniLAL.

This approach was also tested for ability to drive polyketide production in an ordinarily silent biosynthetic gene cluster that does not naturally include an LAL regulator (FIG. 13). When the modified X2 gene cluster was expressed in the presence of the S18 LAL, robust expression of X2 was observed by the Top-Down assay.

Example 6. Positive Feedback Overexpression Strategy

Figure 14:
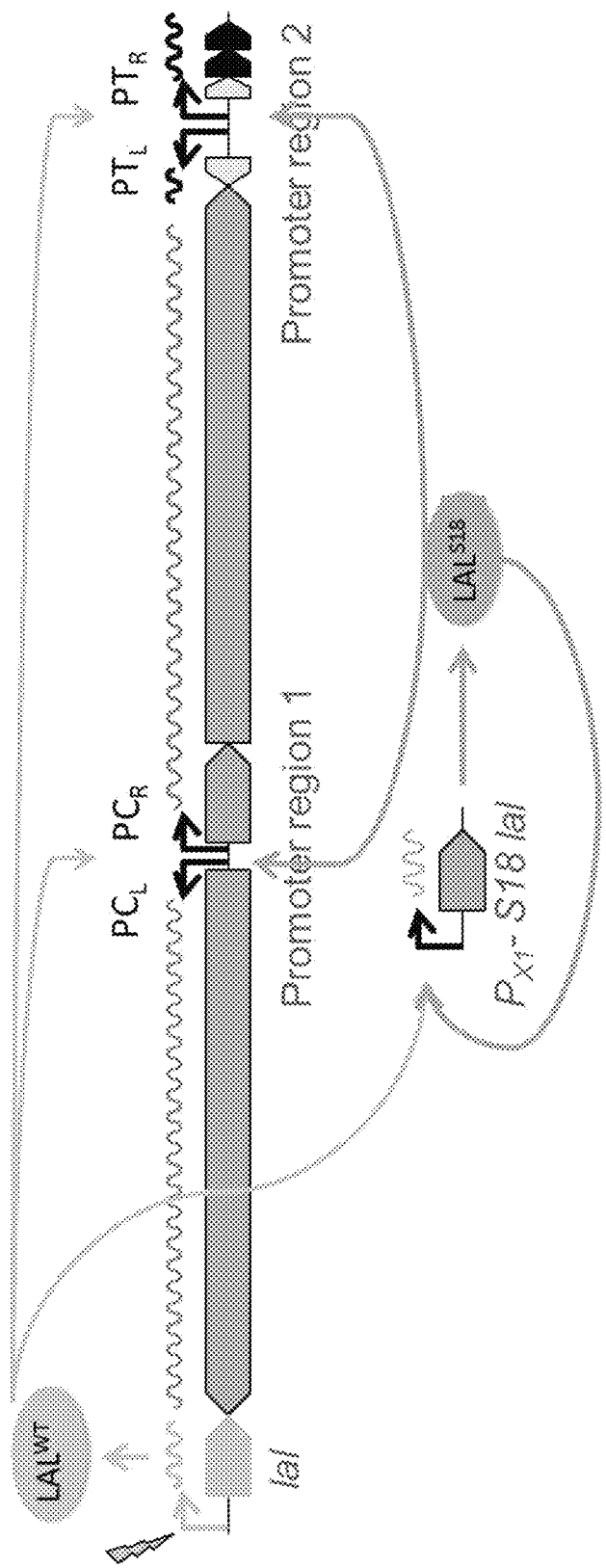
FIG. 14 is a diagram showing the use of an LAL regulon to create a positive feedback loop for overexpression from a biosynthetic cluster.
Figure 15:
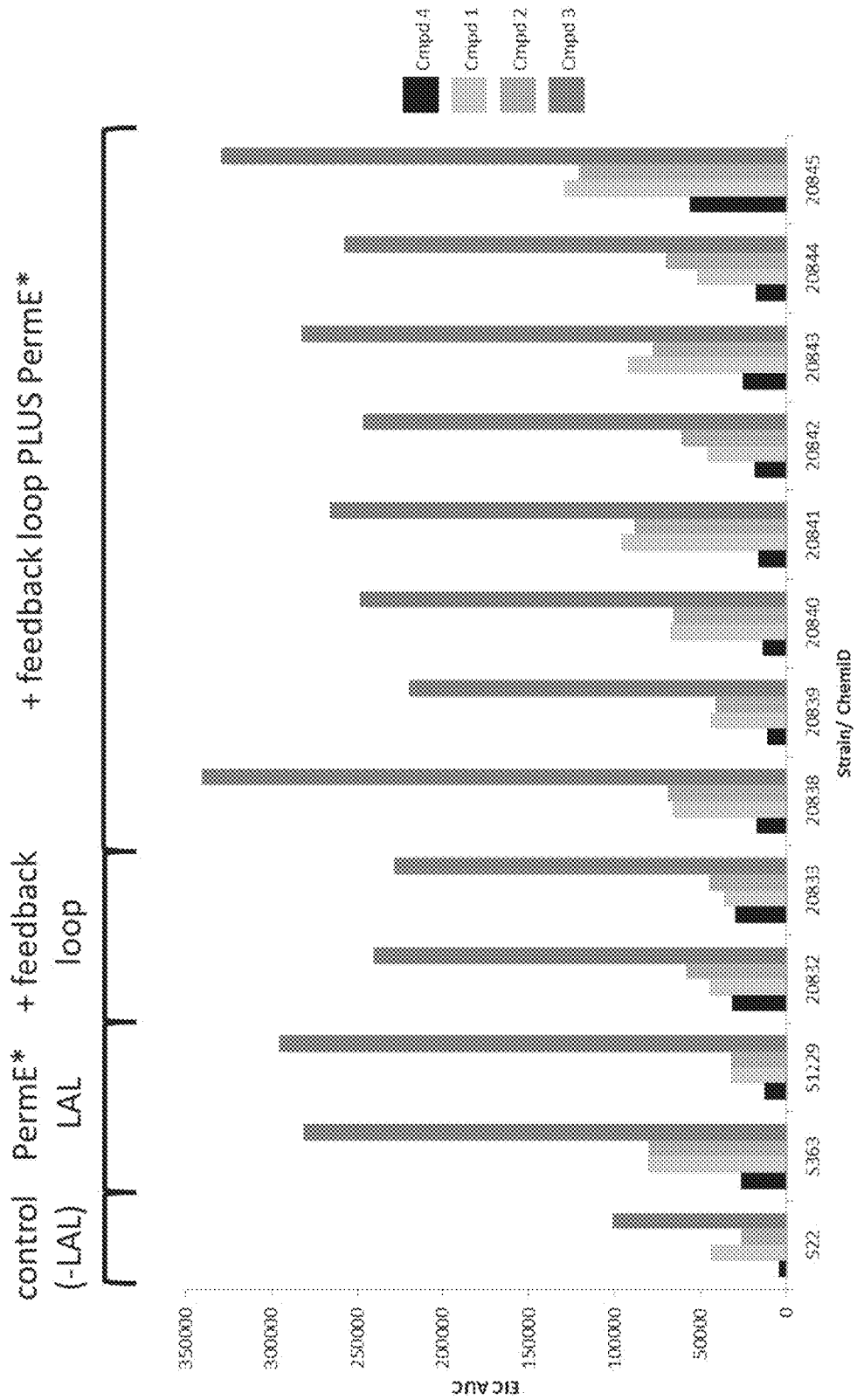
FIG. 15 is a graph showing the coupled use of a positive feedback loop and a constitutive S18 LAL.

The LAL regulon was designed to create a positive feedback loop (FIG. 14). This approach involved placement of LAL binding sites in the bi-directional promoters as well as upstream of a gene encoding an S18 LAL. As such, expression of an LAL (e.g., a wild-type LAL) could induce expression from each of the LAL binding sites: in the PKS biosynthetic gene cluster as well as those in the promoter of the S18 LAL, which can in turn further activate expression from the LAL binding sites, thereby resulting in a positive feedback loop. This may result in strong overexpression (e.g., stronger than expression driven by a PermE* promoter). Further, this strategy may permit idiophase timing according to precursor flux and/or post-translational modifications. FIG. 15 shows that the feedback loop can be used to enhance polyketide production. These data indicate that the feedback loop and/or constitutive LAL expression via the ErmE* promoter can induce PKS expression more than the native strain alone (S22). Constitutive and forward-feedback expression may yield additional PKS expression.

In one example, transcription of the single mega-cistron of the X2 biosynthetic gene cluster and the S18 LAL were placed under the control of the X1 UniLAL promoter, the latter effectively establishing an auto-regulatory operon. Transcription of the LAL would be further augmented by expression of the LAL itself. The UniLAL promoter regulated S18 LAL and X2 PKS constructs were sequentially conjugated into S1496 along with the native X2 gene cluster, to serve as a control.

Example 7. Knock-In of the X1 Promoter into a FKPHD Gene Cluster

Figure 16:
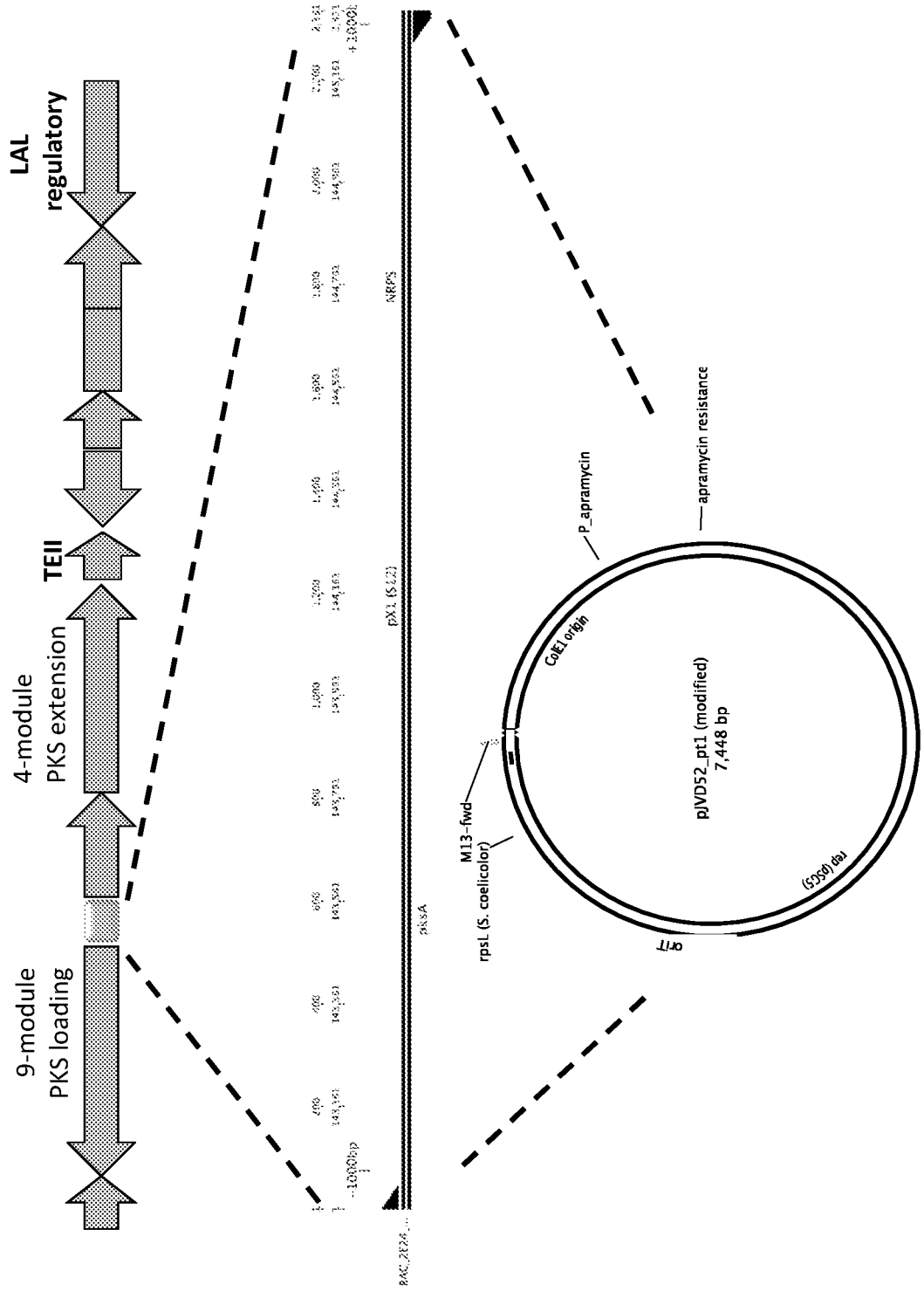
FIG. 16 is a diagram showing knock in of the X1 promoter into a FKPHD cluster in the endogenous locus for native strain expression.

Instead of inserting the X1 promoter to replace the wild-type promoter on a BAC or PAC harboring the FkPhD gene cluster for heterologous expression (e.g., as described in Example 4 above), the X1 promoter was knocked into the endogenous locus of the native strain (S61), which encodes the novel FkPhD gene cluster X11 (FIG. 16). pJVD possesses a temperature-sensitive origin of replication, an apramycin selection marker and a rpsLrplS counter-selection gene. The X1 promoter appended with 1000 bp of DNA sequence flanking the start codons of the opposing PKS mega orfs of X11 was cloned into pJVD52.1pJVD, and this vector was conjugated into S61 and selected for apramycin resistance at the permissive temperature of 30° C. Chromosomal integration was forced by growth at 39° C. and the maintenance of the apramycin selection. Cells were then passaged in the absence of apramycin, then challenged with streptomycin to bias for clones with selection for the desired resolution double crossover event, resulting in the scarless insertion of the X1 promoter precisely into the host chromosome to replace the WT X11 promoter. Colonies were confirmed as genuine pX1 knock-ins by replica plating to confirm susceptibility to apramycin and by junction PCR checking for the 5' and 3' amplicons of the expected sizes.

Example 8. Feed-Forward/UniLAL (Unidirectional LAL Sensitive) Promoter Methods

Feed-Forward Configuration of the S18 LAL

Initially the (TTA minus, synthetic) S18-derived LAL gene was put under the transcriptional control of the S12-derived "core" UniLAL-left and right promoters. The S18 LAL was substituted at the initiation codons for the left and right PKS transcripts of the S12 biosynthetic gene cluster via a two-step subcloning procedure. First, a BamHI to SpeI fragment containing all but the 5' 269 bases of the S18 LAL gene was subcloned into BamHI/XbaI digested pWFE1 cTR expression vector (which possesses the following features for conjugal delivery into Actinobacteria: the phage TG1 integrase gene and attP, an E. coli origin of transfer [oriT], and a gene that confers resistance to thiostrepton). Then the intermediate plasmid was digested with AarI and BamHI restriction endonucleases, and PCR amplicons composing either the left or right UniLAL promoter plus the missing ~269 bases of the S18 LAL from the initiation codon to the BamHI site in the gene were stitched together via a 3-part isothermal Gibson assembly using 2× Master Mix from New England Biolabs according to their instructions. To obtain the first amplicon, the UniLAL left promoter was PCR amplified and appended with the 5' end of the S18 LAL gene using the pWarp Factor 1×1 genomic TAR clone as template with the following primer pair:

```
FFcoreL_Aar_F
                              SEQ ID NO: 43
gcgcccaccttaatcgcaggtgTCCACGCAACCCCCTAGGTTTCCGGCCA

GG

C-L_S18_R
                              SEQ ID NO: 44
gttcatagctctccacggcaggcatTCATACCCTTCCGGCGAAGTGCAGT

TCACCCGGT
```

Similarly, the UniLAL right promoter was amplified and appended with the 5' end of the S18 LAL gene with the following primer pair:

```
FFcoreR_Aar_F
                              SEQ ID NO: 45
gcgcccaccttaatcgcagGTGCCACCCTTGTTTTTCACCCCCCTACGCC

CGT
```

-continued

C-R_S18_R

SEQ ID NO: 46 gttcatagctctccacggcaggcatTCACCTCTCCCGGAAAGGTATTGCT
CGTGCATCCA

For the second amplicon, 5' end of the S18 LAL gene was amplified and appended at the 5' end with either UniLAL-left or UniLAL-right sequence using pSET152 S18 LAL (TTA minus) as template with the following primer pairs:

C-L_Bam_F

SEQ ID NO: 47 actgcacttcgccggaagggtatgaATGCCTGCCGTGGAGAGCTATGAAC
TGGACGC

S18LAL_Bam_R

SEQ ID NO: 48

CCGGGAGGGCCATGGAGACCGGA or

C-R_Bam_F

SEQ ID NO: 49 agcaatacctttccgggagaggtgaATGCCTGCCGTGGAGAGCTATGAAC
TGGACGC

S18LAL_Bam_R

SEQ ID NO: 50

CCGGGAGGGCCATGGAGACCGGA

All PCR amplifications were carried out using Q5 Hot Start DNA polymerase from New England Biolabs according to their specifications (with inclusion of the GC Enhancer supplement). AarI/BamHI digested vector as well as amplicons were isolated by standard agarose electrophoresis and purified from the agarose using the Zymoclean™ Gel DNA Recovery Kit. One tenth of the Gibson assembly reaction was transformed into chemically competent NEB 10β E. coli and spread onto chloramphenicol (25 μg/mL) LB plates. After overnight incubation at 37° C., the chloramphenicol resistant colonies were picked into 5 mL cultures of Luria Bertani broth supplemented with 25 μg/mL chloramphenicol and shaken overnight at 37° C. Plasmid was isolated using the QIAprep Spin Miniprep Kit and then sent off for Sanger sequence verification at GeneWiz, Inc.

Example 9. Swapping of the "Core-Left" UniLAL Promoter for Native Promoter of the X2.1 Biosynthetic Gene Cluster Next generation sequencing (NGS) of genomic DNA from the actinomycete S17 had revealed a biosynthetic gene cluster with a polyketide synthase similar to but distinct from that of the biosynthetic gene cluster known to encode the information for the natural product meridamycin. This gene cluster was designated X2 (and later X2.1 when a second, near identical gene cluster (X2.2) was identified by NGS of S55). To obtain a molecular clone of the X2.1 biosynthetic gene cluster, S17 was liquid cultured in the presence of 0.5% w/v glycine. The mycelial biomass was frozen and sent to Lucigen Corporation who extracted and randomly sheared the genomic DNA, then used it to construct a BAC library in their shuttle vector pSMART BAC-S (which is a conventional BAC vector enabled for conjugation and integration into Streptomyces by the addition of the integrase gene and attP of phage φC31, an E. coli oriT, and a gene that confers resistance to apramycin in their host E. coli strain Replicator v2.0 (whose genotype is rpsL). The library was supplied as glycerol stocks of E. coli arrayed in 384-well plates. Clones harboring the intact X2.1 locus were identified by dual color TaqMan assays using probes designed from proximal 5'- or 3'-flanking regions of the X2.1 gene cluster that were labeled with HEX and FAM fluors respectively. Primers and probes were designed using IDT's software and then ordered from them. To identify double positive clones, 1 μL of glycerol stock was used as template in conjunction with the primer pairs and probes and TaqMan® Fast Advanced Master Mix. Cycling and real-time fluorescence monitoring took place in a Bio Rad CFX384 Touch™ Real-Time PCR Detection System. BAC DNA prepped from double positive clones was confirmed to be correct by Sanger end sequencing at Tacgen, and ultimately exhaustively checked by Illumina and PacBio NGS at the Yale YCGA.

The X1.1 UniLAL left promoter was PCR amplified (using Q5 DNA polymerase and the pWF1 X1.1 plasmid as template) and appended at the 5' and 3' ends with 60 bp of sequence upstream of and precisely downstream of the initiation codon, respectively, of the X2.1 KCDA gene. The primer pair (flanking sequences denoted as capital letters/lower case letters denote regions that anneal to the X1 Core-Left UniLAL promoter; start anticodon in bold) used was:

X2.1_ULL-Run_F

SEQ ID NO: 51

CTACCCGAATACATCGCCTTCTGGGGCCCAGCCCAAACCAGCGCCCTCAT
CCACACTccacgcaacccctaggtttccggc X2.1_ULL-Run_R

SEQ ID NO: 52 gCGGCCCACAACGTGCACGAGCGTGGCGATATCGGACGCGGAAAGAACCA
GCGTGCTCATtcataccttccggcgaagtgcagttcaccc Confirmation of insertion of the X1 Core-Left promoter precisely at the X2.1 KCDA initiation codon was obtained by performing 10 μL PCR amplifications using 0.5 μL of culture as template in conjunction with the following primer pair flanking the expected insertion site:

X2.1_HandR_cPCR_2F

SEQ ID NO: 53

CGCCGTCTACCCAGCCCAAAGCCAGC

X2.1_HandR_cPCR_2R

SEQ ID NO: 54

CGGGTTCGTGGTGCGGCATCCATTCG

Amplicons of the expected 476 bp in length were treated with ExoSAP-IT to degrade excess primer and dNTPs according to the manufacturer's conditions and sent off for Sanger sequence verification (each primer used separately for two individual reads) at GeneWiz Inc. A 250 ml LB broth culture derived from one of the clones with the exact anticipated sequence (X1 Core-Left UniLAL promoter fused to X2.1 KCDA gene at the initiation codon) was fed into the BAC XTRA purification system (according to the manufacturer's conditions) to isolate intact X2.1/Core-Left UniLAL BAC DNA. This DNA prep was used to electrotransform S181 E. coli that were allowed to recover, then selected on choramphenicol (25 μg/mL) and apramycin (100 μg/mL) LB agar plates at 37° C. overnight. Colonies were picked into 5 ml of LB broth supplemented with chloramphenicol and apramycin, grown overnight, and then used for conjugation into various heterologous production strains.

Example 10. Promoter Replacement Via dsDNA Recombineering

To replace the endogenous promoter of X15, the X15 PAC is first engineered using dsDNA recombineering to harbor a positive/negative selection cassette, thus enabling a second round of seamless DNA insertion. *E. coli* harboring the PAC with the complete X15 promoter are rendered electrocompetent, transformed with pKD46 as known in the art (e.g., as described in Wanner and Datsenko; Proc Natl Acad Sci USA. (2000) 97:6640-5) and co-selected on kanamycin (50 µg/mL) and carbenicillin (100 µg/mL) LB agar plates at 30° C. A positive/negative selection cassette is generated by PCR amplifying the plasmid template pKDCR (for the bicistronic expression of rpsL and a chloramphenicol resistance gene) using Phusion polymerase (NEB Biosystems, Beverly, Mass.) with DNA oligonucleotides containing 50 bp overhangs homologous to the X15 NRPS gene and PKS-A.

X15_rpSL_cm_F
SEQ ID NO: 55
CAAAGCGATTCGGAGAGCGGCCGGATCAGATCCAGGCGTGACATGGCCTG

GTGATGATGGCGGGATCGT

X15_rpSL_cm_R_
SEQ ID NO: 56
CGATCTTCTCGAAACTGCACTGAGGAGGTTCGTCGGAGACTGCCATTCAT

CGCAGTACTGTTGTATTCATTAAG

The amplicon from the PCR reaction is agarose gel-purified and extracted. A saturated culture of *E. coli* harboring the X15 PAC and pKD46 is diluted 1:100 into LB Lenox broth supplemented with kanamycin and carbenicillin and 1% w/v L-arabinose. The culture is shaken at 250 rpm at 30° C. until OD600 reached 0.5, at which point the cells are made electrocompetent with cold distilled dH$_2$O washes as described by Datsenko et al. 100 ng of the purified selection cassette is electroporated into *E. coli* using a Bio RAD MicroPulser™ electroporator on the "EC" setting. *E. coli* are allowed to recover in 1 mL of SOC at 30° C. for 1 hour, spread onto chloramphenicol (25 µg/mL) and carbenicillin (100 µg/mL) LB agar plates and selected overnight at 30° C. Colonies are picked into 1 mL cultures of LB broth supplemented with kanamycin, chloramphenicol, and carbenicillin and grown at 30° C. overnight. Confirmation of insertion of the positive/conditional negative selection cassette at the X15 major promoter locus is confirmed by junction PCR.

Cultures that are double positive for the expected 5' junction and 3' junction amplicons (as judge by agarose electrophoresis) are grown as above in LB Lenox with kanamycin, carbenicillin and arabinose and made electrocompetent. The S12 promoter is PCR amplified (using Q5 DNA polymerase and the pWF1.1 X1.1 plasmid as template) and appended at the 5' and 3' ends with 50 bp homology arms to the X15 NRPS gene and PKS-A.

X15_LAL_F
SEQ ID NO: 57
5'-CAAAGCGATTCGGAGAGCGGCCGGATCAGATCCAGGCGTGACATTCA

TACCCTTCCGGCGAAGTGCAGTTCACCC-3'

X15_LAL_R
SEQ ID NO: 58
5'-CGATCTTCTCGAAACTGCACTGAGGAGGTTCGTCGGAGACTGCCATT

CACCTCTCCCGGAAAGGTATTGCTCG-3'

Electroporated cells are allowed to recover in 1 mL of SOC for 1 hour at 37° C. with shaking and then selected on kanamycin (50 µg/mL)+streptomycin (250 µg/mL) LB agar plates overnight at 37° C. Colonies are picked into 1 mL cultures of LB broth supplemented with kanamycin (50 µg/mL) and apramycin (100 µg/mL) and grown at 37° C. overnight with shaking. Confirmation of insertion of the S12 promoter at the X15 major promoter locus is confirmed by junction PCR.

Example 11. Promoter Replacement Via ssDNA Recombineering and Gibson Cloning In another technique, to replace the endogenous promoter of X15, the X15 PAC is first engineered using ssDNA recombineering to introduce AT-rich PmeI restriction sites (5'-GTTTAAAC-3') flanking the endogenous X15 major promoter locus. *E. coli* harboring the PAC with the complete X15 promoter are rendered electrocompetent, transformed with pKD46β, a variant of pKD46 (Wanner and Datsenko; Proc Natl Acad Sci USA. (2000) 97:6640-5) in which the exo and gamma genes had been deleted, and co-selected on kanamycin (50 µg/mL) and carbenicillin (10 µg/mL) LB agar plates at 30° C. A saturated culture of *E. coli* harboring the X15 PAC and pKD46β is diluted 1:100 into LB Lenox broth supplemented with kanamycin and carbenicillin and 1% w/v L-arabinose. The culture is shaken at 250 rpm at 30° C. until OD600 reached 0.5, at which point the cells were made electrocompetent with cold distilled dH$_2$O washes as described by Datsenko et al. Cells are resuspended in 50 µL of a 1 µM ssDNA oligonucleotide solution and electroporated into *E. coli* using a Bio RAD MicroPulser™ electroporator on the "EC" setting. *E. coli* are allowed to recover in 1 mL of SOC at 30° C. for 1 hour, spread onto kanamycin (25 µg/mL) LB Lennox overnight to saturation. Confirmation of insertion of the PmeI site at the X15 major promoter locus is confirmed by allele-specific PCR combined with two serial rounds of a limited dilution cloning protocol that allowed the clonal selection of a successfully modified X15 PAC with a single PmeI site. This protocol is then repeated to introduce a second flanking PmeI site. Both "sense" and "antisense" oligonucleotides, which are synthesized with 5' phosphothiorate caps, are tested to define the lagging strand of the PAC.

ssDNA Oligonucleotides (PmeI Site Underlined)

5'_X15_PmeI_sense
SEQ ID NO: 59
GCAAAGCGATTCGGAGAGCGGCCGGATCAGATCCAGGCGTGACAT<u>GTTTA</u>

<u>AAC</u>ACAACGTACCTTTCGGACAAGAGTGCCGCGGTGCACAGCCTGACC

5'_X15_PmeI_antisense
SEQ ID NO: 60
GGTCAGGCTGTGCACCGCGGCACTCTTGTCCGAAAGGTACGTTGT<u>GTTTA</u>

<u>AAC</u>ATGTCACGCCTGGATCTGATCCGGCCGCTCTCCGAATCGCTTTGC

-continued

3'_X15_PmeI_sense

SEQ ID NO: 61
TCCACACCTCTCGGTTCACAAACGTCCGAGCATAAGGGAGGTAAAGTTTA

AACATGGCAGTCTCCGACGAACCTCCTCAGTGCAGTTTCGAGAAGATC

3'_X15_PmeI_antisense

SEQ ID NO: 62
GATCTTCTCGAAACTGCACTGAGGAGGTTCGTCGGAGACTGCCATGTTTA

AACTTTACCTCCCTTATGCTCGGACGTTTGTGAACCGAGAGGTGTGGA

The X15 PAC, now modified with PmeI sites, is linearized with PmeI. The S12 promoter is PCR amplified (using PQ5 DNA polymerase and the pWF1.1 X1.1 plasmid as template; primers listed below) and appended at the 5' and 3' ends with 50 bp homology arms to the X15 NRPS gene and PKS-A.

X15_LAL_F

SEQ ID NO: 63
5'-CAAAGCGATTCGGAGAGCGGCCGGATCAGATCCAGGCGTGACATTCA

TACCCTTCCGGCGAAGTGCAGTTCACCC-3'

X15_LAL_R

SEQ ID NO: 64
5'-CGATCTTCTCGAAACTGCACTGAGGAGGTTCGTCGGAGACTGCCATT

CACCTCTCCCGGAAAGGTATTGCTCG-3'

S12 promoter and the PmeI linearized X15 PAC is seamlessly cloned by Gibson cloning using the Gibson Assembly Ultra Kit (SGI-DNA, Inc.) using the recommended protocol. After electroporation, correct clones are identified as above.

Figure 17A:
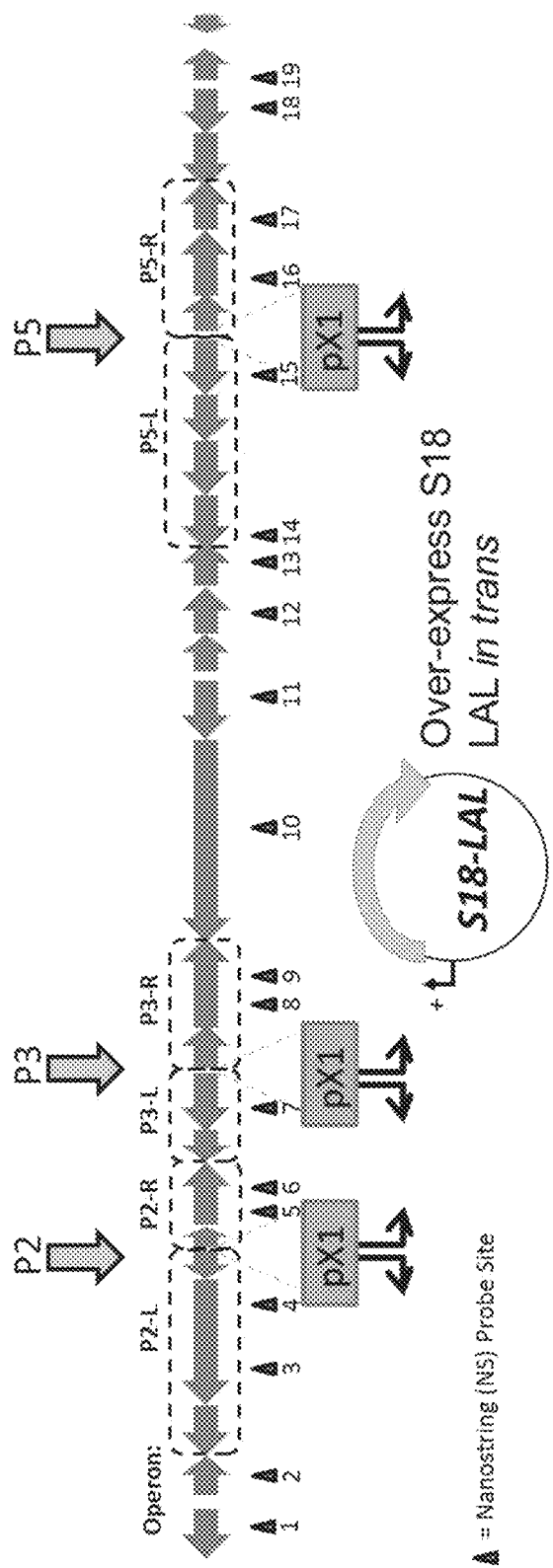
FIGS. 17A-B is a diagram showing the use of the pX1-S18 LAL system to drive the overexpression of a novel β-lactam gene cluster, WAC292.
Figure 17B:
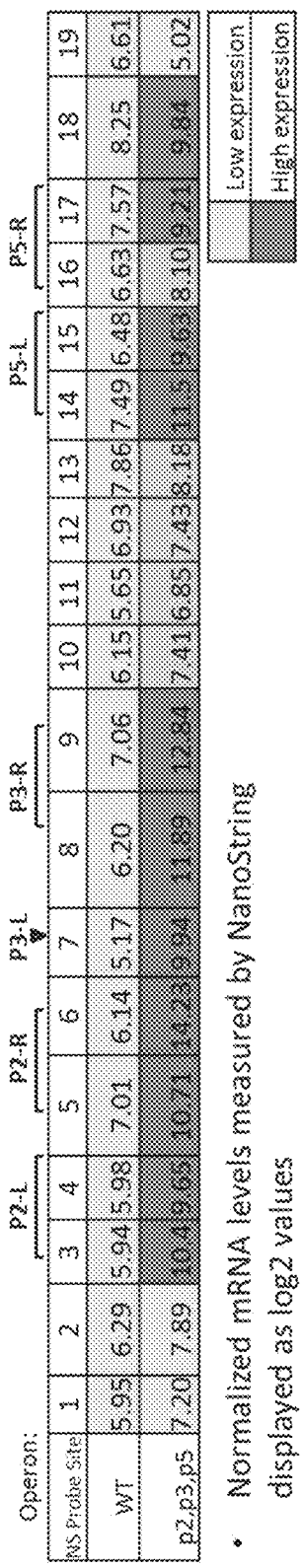

Example 12. Expression of LALs Drives β-Lactam Compound Production from a β-Lactam Gene Cluster The previously described pX1-S18 LAL system was used to drive the overexpression of a novel beta-lactam gene cluster, WAC292 (FIG. 17A). Three copies of the pX1 promoter were subcloned into WAC292 to drive the predicted core biosynthetic operons at 3 of the 5 promoter sites to generate WAC292-p2p3p5. The S18 LAL was cloned onto the backbone of WAC292-p2p3p5, and the resulting engineered BAC was conjugated to S5627, a known beta-lactam producing strain with the endogenous beta-lactam cluster deleted, thus removing any endogenous beta-lactam activity. After fermentation, WT and WAC292-p2p3p5 S5627 strains were compared to Nanostring analysis mRNA using a custom probe set designed against 19 sites of the cluster. Transcripts linked to the P2, P3, and P5 promoters were significantly upregulated in WAC292-p2p3p5 as compared to WAC292-WT (FIG. 17B).

Cloning Protocol to Generate WAC292-p2p3p5

The YAC/BAC conjugative vector pWF10 harboring the β-lactam gene cluster was linearized at the unique PacI and SwaI (NEB) sites. The S18LAL expression cassette (ermE* promoter/synthetic TTA codon minus S18 LAL gene/phage fd transcriptional terminator) was PCR amplified using pWFE1 S18LAL as template and appended at each end with ~40 bp of vector sequence 5' proximal to the PacI site and 3' proximal to the SwaI site using Q5 HotStart DNA polymerase.

LAL_N2_292_F

SEQ ID NO: 65
5'-CCCGAACCACGATGAGCACTTGCCTATGCGGTGTAGGGATAACAGGG

TAATTAATTAATGACCTGCGCCCACCTTAATCGCAGGTGC-3'

LAL_N2_292_F

SEQ ID NO: 66
5'-TACTTTCTATTTTTAATTTATATATTTATATTAAAAAATTTAAAATA

TAATTATTTTTATAGCACGTGATGGAGCCTATGGAAAAACGCCAGCAACG

C-3'

The restriction digested BAC and the PCR amplicon were mixed in a total of 5 µl and an equal volume of NEBuilder HiFi DNA Assembly 2× Master Mix added, after which the reaction proceeded for one hour at 50° C. 1.5 µl of the completed reaction was added to 70 µl of electrocompetent NEB 10-beta E. coli, mixed, the contents deposited in a Bulldog Bio 0.1 cm gap electrocuvette and transformed using a BioRad Micropulser electroporator set to the "EC1" parameters. 930 µl of SOC media was used to resuspend the electroporated cells and the entire volume pipetted into a 50 ml Falcon tube. The tube was placed in a shaking incubator set at 37° C. and the electroporated E. coli allowed to recover for 1 hour. 200 µls of recovered bacteria were spread onto five LB agar-100 µg/ml apramycin Petri dishes. The dishes were inverted and incubated overnight @37° C. Colonies were picked into 1 ml cultures of LB broth supplemented with 100 µg/ml apramycin and incubated with shaking @37° C. overnight. 1 µl of saturated bacterial culture was used as template in PCR reactions to amplify the entire S18 LAL expression cassette.

pWF10_Swa_cPCR_R

SEQ ID NO: 67
5'-GGTAGTATTTGTTGGCGATCCCCCTAGAGTCTTTTACATCTTCG

G-3' pWF10_Swa_cPCR_F

SEQ ID NO: 68
5'-AGCCTGCCCCTCATCTGTCAAC-3'

The resulting amplicons were diluted and 1:144 with dH₂O, 14.5 µls of the diluted amplicons were added to 0.5 µl of a series of 100 µM sequencing primers and sent off for Sanger verification to ensure no errors had been introduced into the S18 LAL expression cassette during the cloning process. A sequence perfect clone was grown at scale (300 ml culture prep) and the YAC/BAC purified using a Macherey Nagel Nucleobond Xtra BAC kit.

The purified YAC/BAC was concomitantly digested with three Alt-R guide crRNAs complexed with Alt-R CRISPR-Cas9 tracRNA and recombinant S. pyogenes Cas9 protein (all from Integrated DNA Technologies) for one hour @37° C. The guide cRNAs were designed to cut within bidirectional promoters 2, 3, & 5 of the β lactam biosynthetic gene cluster. The triply Cas9 digested BAC vector was ethanol precipitated and resuspended in 20 µl of 10 mM Tris pH 8.0. Meanwhile, three PCR amplicons, two yeast auxotrophic markers and a single X1 bidirectional core promoter, were generated for "gap repair" insertion at the three sites of cas9 digestion upon cotransformation into S. cerevisiae.

292_bi2_TRP-BstZ_F
SEQ ID NO: 69
5'-GTTGATCGTGTGGGGCGGCCTGCCGAGCAGCTGGTGGACCCCTGGGG
CGAGCTGGCGCATTCACCTGTATACTGAGAGTGCACCATAAACGACATTA
CT-3'

292_bi2_TRP-BstZ_R
SEQ ID NO: 70
5'-GACGACCGCGGTCCCCACGAGGACAGCGGCCGACGCAACAGCTTTGC
GAAGACGAGTCATTCATACGTATACAGGCAAGTGCACAAACAATACT-3'

292_bi3_LEU-Hpa_F
SEQ ID NO: 71
5'-CGCCGGTGAGGCCAGACCCATGAGGGTCAGTGCTGCGACCACCGCGT
ACCTGATCCGCATTCACCTGTTAACTCCTGATGCGGTATTTTCTCCTTAC
GCA-3

292_bi3_LEU-Hpa_R
SEQ ID NO: 72
5'-CTCGGCCGGCAGCAAGGTCTGCTCGATCGCGATGATCCGGCCGTTCC
CCCAGTCGATCGTGTTAACCGACTACGTCGTAAGGCCGTTTCT-3'

292_bi5_F
SEQ ID NO: 73
5'-GACGAACGCGAAGTCGTCGCCGCCCTCCTTCATGCCCAGTCCGGTGG
TCCAGCCGCGGAAGCCGTGCGGATGCATTCACCTCTCCCGGAAAGGTATT
GCTCG-3'

292_bi5_R
SEQ ID NO: 74
5'-TCGCCACGGGCGGTCGAGGAACTCGTCGCGGACCGCCGCGACCCGTG
TTCGCGCGCCGTCACCGCCGACGCGCATTCATACCCTTCCGGCGAAGTGC
AGTTC-3'

Using the above primer pairs, Q5 HotStart DNA polymerase and pRS414, pRS415, and pWF1 X1 as template, the amplicons were obtained and gel purified (using the Zymo Research Gel DNA Recovery Kit).

The three amplicons added in >10× molar excess to the triple digested β lactam YAC/BAC and transformed into BY4727 S. cerevisiae (ATCC 200889) using the lithium acetate/PEG method from the Geitz lab. Following heat shock, the transformed yeast out of the lithium/PEG/DNA mix, the yeast were pelleted @10,000×g for 30 seconds and resuspended in 1 ml of SD TRP, LEU minus broth. The yeast were then spread onto four SD TRP, LEU minus agar plates (Teknova), the plates inverted, and incubated at 30° C. until colonies were visible (four days). The YAC/BAC residing in the cells of the yeast colonies were rescued and transformed into E. coli as follows: colonies were picked into a microcentrifuge tube with 20 µl of 200 mM lithium acetate/1% SDS, five or six 100 µm diameter acid washed ceramic beads (OPS Diagnostics) added and the contents vortexed for 5 minutes at maximum rpm. 1 µl of the lysate was electroporated into electrocompetent NEB10-beta E. coli and selected on LB agar 100 µg/ml apramycin Petri dishes. Colonies were used to inoculate 1 ml cultures in LB broth supplemented with 100 µg/ml apramycin, and 1 µl from these cultures used as template in PCR (Bioline MyTaq Hotstart Red 2× master mix) to verify the presence of the expected 5' & 3' junctions for the X1 bidirectional core (P5) and TRP (P2) and LEU (P3) marker insertions.

292_Bi2_Hit_5'F
SEQ ID NO: 75
5'-GGCGTGGCTGGAGCCGAAGTGGTC-3'

TRP_5'jPCR_R
SEQ ID NO: 76
5'-TCTTCCACTACTGCCATCTGGCGTCATAACTGC-3'

TRP_3'jPCR_F
SEQ ID NO: 77
5'-AGGTTATTACTGAGTAGTATTTATTTAAGTATTGTTTGTGCACTTGC
CT-3

292_Bi2_Hit_3'R
SEQ ID NO: 78
5'-ACTCGGCGGCGTTGGCGTGGC-3'

292_Bi3_Hit_5'F
SEQ ID NO: 79
5'-ACCGTCGCCCCGCCGCAGC-3'

LEU_5'jPCR_R
SEQ ID NO: 80
5'-CGCACAGATTCGTAAGGAGAAAATACCGCATCAGGA-3'

LEU_3'jPCR_F
SEQ ID NO: 81
5'-ACTCTGTCAGAAACGGCCTTACGACGTAGTCG-3'

292_Bi3_Hit_3'R
SEQ ID NO: 82
5'-CGGGCGGCACGCAACCGAAGTG-3'

292_Bi5_Hit_5'F
SEQ ID NO: 83
5'-GTGAAGACCGCCGATACCGCCGC-3'

X1_pro_cPCR_3'
SEQ ID NO: 84
5'-GGGTGAAAAACAAGGGTGGCACGGCA-3'

X1_pro_cPCR_5'
SEQ ID NO: 85
5'-TGCCGTGCCACCCTTGTTTTTCACCC-3'

292_Bi5_Hit_3'R
SEQ ID NO: 86
5'-ACGCCAGGCCCGTTCACGACGACCGC-3'

One clone positive for the six junctions was grown at scale (300 ml culture prep) and the YAC/BAC purified, digested with an excess of BstZ17I and HpaI restriction enzymes (NEB), ethanol precipitated, and resuspended in 50 µl of 10 mM Tris pH 8.0. For multiplex insertion of X1 bidirectional core promoters, in two separate reactions the promoter was amplified and appended with ~30 bp 5' & 3' sequence proximal to the sites of BstZ17I and HpaI digestion, and gel purified.

292_bi2_Run_F
SEQ ID NO: 87
5'-GCTGGTGGACCCCTGGGGCGAGCTGGCGCATTCACCTCTCCCGGAAA
GGTATTGCTCGC-3'

292_bi2_Run_R
SEQ ID NO: 88
5'-AACAGCTTTGCGAAGACGAGTCATTCATACCATTCATACCCTTCCGG
CGAAGTGCAGTTCACCCG-3'

292_bi3_Run_F
SEQ ID NO: 89
5'-TCAGTGCTGCGACCACCGCGTACCTGATCCGCATTCACCTCTCCCGG
AAAGGTATTGCTCGC-3'

-continued

292_bi3_Run_R

SEQ ID NO: 90

5'ATCGCGATGATCCGGCCGTTCCCCCAGTCGATCGTCCGCATTCATACC

CTTCCGGCGAAGTGCAGTTCACCCG-3'

The X1 bidirectional promoter amplicons were added in tenfold molar excess to the BstZ17I/HpaI digested BAC, the mixture ethanol precipitated and resuspended in 5 µl 10 mM Tris pH 8.0. 5 µl of SGI Gibson Assembly Ultra Kit "A mix" was added, mixed, and incubated @37° C. for 5 minutes, heat killed @75° C. for 20 minutes, stepped down to 60° C. and the temperature dropped at a rate of 0.1° C./second to 4° C. 10 µl of "B mix" was then added and the reaction allowed to proceed @45° C. for 15 minutes. 1.5 µl of the completed reaction was electroporated into 70 µl of electrocompetent NEB10-beta E. coli and selected on 100 µg/ml apramycin LB agar Petri dishes. Colonies were used to inoculate 1 ml cultures in LB broth supplemented with 100 µg/ml apramycin and 1 µl used as template in PCR to confirm the presence of four new junctions indicative of insertion of the X1 bidirectional promoter in place of the native β lactam's bidirectional promoters 2 & 3.

The loci surrounding the X1 bidirectional core promoters inserted at P2, P3, and P5 were PCR amplified and used as template for Sanger sequence QC to ensure no errors had been introduced during the cloning process.

Strain Construction and Nanostring Methods

The construct WAC292-p2p3p5 was mobilized by conjugation from an E. coli donor into Streptomyces sp. S5627, a carbapenem-producing strain in which the endogenous carbapenem cluster had been deleted by homologous recombination. The resulting ex-conjugants were selected on medium containing 50 µg/ml apramycin. The resulting strain WAC292-p2p3p5-S5627 was grown in seed culture in 25 ml WDSM1 medium in a baffled 125 ml flask for 48 h before being sub-cultured (5% inoculum) into 25 ml fermentation medium FMKN1 in an unbaffled 125 ml flask for a further 48 h. A 1 ml sample was removed on ice and centrifuged to pellet the mycelium (wet weight approx. 150 mg). The pellet was resuspended in lysis buffer RA1 (Macherey-Nagal 740955.50) and transferred to a FastPrep lysing matrix B tube (MP Biomedical 116911050). The mycelium was disrupted by bead beating in a Qiagen TissueLyser II at speed 30 for 5 min. The cell debris was pelleted by centrifugation and 1 µl of the cell lysate utilized for hybridization for Nanostring analysis (following manufacturer's instructions). Nanostring probe pools were prepared and used as per manufacturer's instructions.

Nanostring Data Analysis and Normalization

RCC files were imported into nSolver 3.0 (Nanostring Inc). Raw count data was then exported to Excel. One of the following genes or the median of a set of these genes were used as the normalization factor: GAPDH, HrdB, phiC31int, AprR. Normalization was performed by dividing the measurement of interest by the normalization factor, taking the base two log of that value and adding a scaling constant of 10.

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any polynucleotide or protein encoded thereby; any method of production; any method of use) can be excluded from any one or more claims, for any reason, whether or not related to the existence of prior art.

What is claims is:

1. A method of producing a compound, the method comprising:
   (a) providing a genetically modified host cell comprising:
      (i) a nucleic acid encoding a recombinant Large ATP-binding regulator of the LuxR family (LAL) that is heterologous to the host cell; and
      (ii) a nucleic acid comprising an LAL binding site that is heterologous to the host cell, wherein the LAL binding site is operably linked to an open reading frame encoding a compound-producing protein, and wherein binding of the recombinant LAL to the LAL binding site promotes expression of the compound-producing protein; and
   (b) culturing the host cell under conditions suitable to allow expression of a compound by the compound-producing protein;
   thereby producing a compound.

2. The method of claim 1, wherein the host cell naturally lacks an LAL or the host cell naturally lacks an LAL binding site.

3. The method of claim 1, wherein the recombinant LAL comprises a portion having at least 90% sequence identity to the amino acid sequence of SEQ ID NO: 1.

4. The method of claim 1, wherein the recombinant LAL comprises a portion having the amino acid sequence of SEQ ID NO: 1.

5. The method of claim 1, wherein the recombinant LAL has the amino acid sequence of SEQ ID NO: 1.

6. The method of claim 1, wherein the host cell has been modified to enhance expression of the compound-producing protein by (i) deletion of an endogenous gene cluster which expresses an endogenous compound-producing protein; (ii) insertion of a heterologous gene cluster which expresses a heterologous compound-producing protein; (iii) exposure of the host cell to an antibiotic challenge; and/or (iv) introduction of a heterologous promoter that results in an at least 2-fold increase in expression of a compound produced by the compound-producing protein compared to the expression of the compound when the homologous promoter has not been replaced.

7. The method of claim 1, wherein:
   the nucleic acid further comprises one or more additional LAL binding sites;
   at least one of the LAL binding sites is in a promoter; or
   the nucleic acid further comprises a gene encoding an LAL.

8. The method of claim 7, wherein:
   the gene encoding an LAL is under the control of a promoter comprising an LAL binding site; or
   at least one of the LAL binding sites is in a promoter.

9. The method of claim 8, wherein at least one of the LAL binding sites is in a promoter and the promoter is a bidirectional promoter.

10. The method of claim 1, wherein the LAL binding site comprises a sequence having no more than one insertion, deletion, or substitution with respect to the nucleic acid sequence of SEQ ID NO: 2 and/or comprises the nucleic acid sequence of SEQ ID NO: 3, and wherein the LAL comprises a portion having at least 90% sequence identity to the amino acid sequence of SEQ ID NO: 1.

11. The method of claim 10, wherein the LAL comprises a portion having the amino acid sequence of SEQ ID NO: 1.

12. The method of claim 10, wherein the LAL has the amino acid sequence of SEQ ID NO: 1.

13. The method of claim 10, wherein the LAL binding site comprises the nucleic acid sequence of SEQ ID NO:2.

14. The method of claim 10, wherein the LAL binding site comprises the nucleic acid sequence of SEQ ID NO:3.

15. The method of claim 10, wherein:
   the nucleic acid further comprises one or more additional LAL binding sites; or
   the gene encoding the LAL is under the control of a promoter comprising an LAL binding site.

16. The method of claim 15, wherein at least one of the LAL binding sites is in a promoter.

17. The method of claim 16, wherein the promoter is a bidirectional promoter.

18. The method of claim 1, wherein the compound-producing protein is a polyketide synthase, a β-lactam compound-producing protein, or a non-ribosomal peptide synthase.

19. The method of claim 1, wherein the compound is a polyketide, a β-lactam compound, or a non-ribosomal peptide.

* * * * *